United States Patent
Nie et al.

(10) Patent No.: US 12,419,874 B2
(45) Date of Patent: Sep. 23, 2025

(54) GLP-1R AGONIST COMPOUND AND USE THEREOF

(71) Applicants: Chongqing Pharmaceutical Research Institute Co., Ltd., Chongqing (CN); Yaopharma Co., Ltd., Chongqing (CN)

(72) Inventors: Wei Nie, Chongqing (CN); Xiaolong Kerri Yan, Chongqing (CN); Haoying Xu, Chongqing (CN); Qiang Liu, Chongqing (CN); Zhichao Xu, Chongqing (CN); Hongkun Qin, Chongqing (CN); Xiang Li, Chongqing (CN); Hongyi Liu, Chongqing (CN); Yaming Cao, Chongqing (CN); Xiaoqing Bai, Chongqing (CN)

(73) Assignees: Chongqing Pharmaceutical Research Institute Co., Ltd., Chongqing (CN); Yaopharma Co., Ltd., Chongqing (CN)

( * ) Notice: Subject to any disclaimer, the term of this patent is extended or adjusted under 35 U.S.C. 154(b) by 0 days.

(21) Appl. No.: 19/054,180

(22) Filed: Feb. 14, 2025

(65) Prior Publication Data

US 2025/0195481 A1    Jun. 19, 2025

Related U.S. Application Data

(63) Continuation of application No. PCT/CN2024/105741, filed on Jul. 16, 2024.

(51) Int. Cl.
  *C07D 471/10* (2006.01)
  *A61K 31/437* (2006.01)
  *A61K 31/438* (2006.01)

(52) U.S. Cl.
  CPC .......... *A61K 31/437* (2013.01); *C07D 471/10* (2013.01)

(58) Field of Classification Search
  CPC .. C07D 471/10; A61K 31/438; A61K 31/437; A61P 3/08; A61P 3/04; A61P 3/10
  USPC ............................................ 546/18; 514/278
  See application file for complete search history.

(56) References Cited

U.S. PATENT DOCUMENTS

| 10,858,356 | B2 | 12/2020 | Yoshino |
| 12,234,236 | B1 | 2/2025 | Liang |
| 12,291,530 | B1 | 5/2025 | Liang |

FOREIGN PATENT DOCUMENTS

| CN | 116003403 A | 4/2023 |
| CN | 117069743 A | 11/2023 |
| CN | 119306743 A | 1/2025 |
| CN | 119431365 A | 2/2025 |
| CN | 119528907 A | 2/2025 |
| JP | 2019099571 A | 6/2019 |
| WO | 2018056453 A1 | 3/2018 |
| WO | 2021155841 A1 | 8/2021 |
| WO | 2022017338 A1 | 1/2022 |
| WO | 2022048665 A1 | 3/2022 |
| WO | 2022052958 A1 | 3/2022 |
| WO | 2023016546 A1 | 2/2023 |
| WO | 2023169456 A1 | 9/2023 |
| WO | 2024153070 A1 | 7/2024 |
| WO | 2024169952 A1 | 8/2024 |
| WO | 2025002250 A1 | 1/2025 |
| WO | 2025002326 A1 | 1/2025 |
| WO | 2025006921 A1 | 1/2025 |
| WO | 2025011664 A1 | 1/2025 |
| WO | 2025026436 A1 | 2/2025 |
| WO | 2025045208 A1 | 3/2025 |

(Continued)

OTHER PUBLICATIONS

Kawai T, Sun B, Yoshino H, et al. Structural basis for GLP-1 receptor activation by LY3502970, an orally active nonpeptide agonist. Proc Natl Acad Sci U S A. 2020; 117(47):29959-29967.

(Continued)

*Primary Examiner* — Charanjit Aulakh
(74) *Attorney, Agent, or Firm* — Ice Miller LLP

(57) ABSTRACT

The present disclosure relates to a GLP-1R agonist compound and use thereof, and specifically provides a compound represented by Formula I, or an isotope-labelled compound, a stereoisomer, or a pharmaceutically acceptable salt thereof, and use thereof as a medicament. The compound exhibits excellent agonistic effects and pharmacodynamic properties on GLP-1R and, as a modulator, is useful for manufacturing a medicament for the treatment, amelioration, or prevention of metabolic diseases and related diseases, thus having broad application prospects.

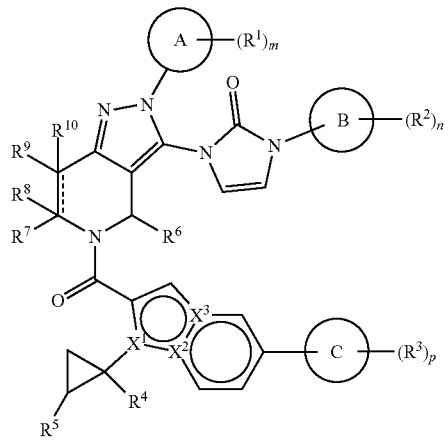

20 Claims, No Drawings

(56) References Cited

FOREIGN PATENT DOCUMENTS

| | | | |
|---|---|---|---|
| WO | 2025057134 | A2 | 3/2025 |
| WO | 2025026270 | A1 | 7/2025 |

OTHER PUBLICATIONS

International Search Report issued Sep. 19, 2024 in PCT/CN2024/105741.

GLP-1R AGONIST COMPOUND AND USE THEREOF

CROSS-REFERENCE TO RELATED APPLICATION

This application is a continuation of International Application No. PCT/CN2024/105741 filed Jul. 16, 2024, which claims priority to Chinese patent application No. 202311497272.2 filed on Nov. 10, 2023, and Chinese patent application No. 202410084261.X filed on Jan. 19, 2024, the disclosures of which are incorporated herein by reference in their entireties.

TECHNICAL FIELD

The present disclosure pertains to the technical field of medicine, and relates to a compound, or a stereoisomer or pharmaceutically acceptable salt thereof, which can bind to and activate the Glucagon-Like Peptide-1 Receptor (GLP-1R) and may be useful for treating metabolic disorders and related diseases including, but not limited to, type-II diabetes mellitus (T2DM), obesity, and non-alcoholic steatohepatitis (NASH).

BACKGROUND

Glucagon-Like Peptide-1 (GLP-1) is a peptide hormone secreted primarily by intestinal L cells postprandially. GLP-1 plays a crucial role in reducing the glucose concentration by enhancing insulin secretion and inhibiting glucagon release. Other functions of GLP-1 include delaying gastric emptying, suppressing appetite, and promoting β-cell proliferation. GLP-1 effect is mediated by binding to GLP-1R which is a glucose-dependent family-B G protein-coupled receptor. The binding of GLP-1 to GLP-1R activates the heterotrimeric G proteins and subsequently enhances the activity of adenylate cyclase, which results in an increased level of cyclic adenosine monophosphate (cAMP) in the cells, thereby enhancing glucose-stimulated insulin secretion (Pflugers Arch. 1998, 435, 583-594; Basic Clin. Pharmacol. Toxicol. 2004, 95, 252-262). GLP-1, due to its short half-life, is stable for only 2 to 3 minutes in the blood circulation and is inactivated by dipeptidyl peptidase 4 (DPP4).

GLP-1R agonists have been widely developed for treating T2DM, obesity, and related metabolic diseases. According to the pharmacological properties, GLP-1R agonists may be classified as short-acting GLP-1R stimulants (exenatide and lixisenatide) or long-acting GLP-1R stimulants (exenatide-LAR, liraglutide, albiglutide, and dulaglutide). However, the aforementioned GLP-1R agonists are mainly administered by subcutaneous injection. Oral GLP-1R agonists are easier to be administered, but the clinical options thereof are quite limited. Semaglutide, approved by the U.S. Food and Drug Administration in 2019, is the solely oral GLP-1R agonist required to be taken only once daily.

Therefore, there is an urgent need for a novel GLP-1R agonist as an alternative for treating metabolic disorders and related diseases including, but not limited to, T2DM, obesity, and NASH.

SUMMARY

In one aspect, the present disclosure provides a series of new compounds, or isotope-labelled compounds, stereoisomers, or pharmaceutically acceptable salts thereof. More specifically, the compound provided herein has a structure represented by Formula I:

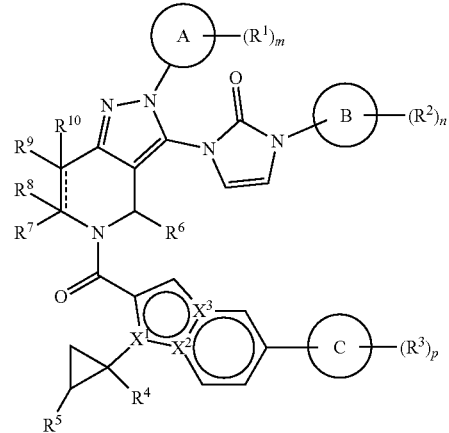

I wherein
$X^1$, $X^2$, and $X^3$ are independently selected from the group consisting of N and C;
rings A, B, and C are independently selected from the group consisting of $C_{3-10}$ cycloalkyl, heterocyclyl, aryl, and heteroaryl;
each $R^1$ is independently selected from the group consisting of hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A1}$R$^{B1}$, —OR$^{A1}$, —C(O)R$^{A1}$, —C(O)OR$^{A1}$, —OC(O)R$^{A1}$, —C(O)NR$^{A1}$R$^{B1}$, —NR$^{A1}$C(O)R$^{B1}$, —OC(O)NR$^{A1}$R$^{B1}$, —S(O)$_r$R$^{A1}$, —S(O)$_2$OR$^{A1}$, —OS(O)$_2$R$^{A1}$, —NR$^{A1}$S(O)$_r$R$^{B1}$, —S(O)$_r$NR$^{A1}$R$^{B1}$, —P(O)R$^{A1}$R$^{B1}$, and —P(O)(OR$^{A1}$)(OR$^{B1}$), wherein each of the alkyl, alkenyl, alkynyl, cycloalkyl, heterocyclyl, aryl, and heteroaryl is unsubstituted or substituted independently with at least one $R^{X1}$;
each $R^2$ is independently selected from the group consisting of hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —(CH$_2$)$_s$CF$_3$, —CN, —NO$_2$, —NR$^{A2}$R$^{B2}$, —OR$^{A2}$, —C(O)R$^{A2}$, —C(O)OR$^{A2}$, —OC(O)R$^{A2}$, —C(O)NR$^{A2}$R$^{B2}$, —NR$^{A2}$C(O)R$^{B2}$, —OC(O)NR$^{A2}$R$^{B2}$, —NR$^{A2}$C(O)OR$^{B2}$, —S(O)$_r$R$^{A2}$, —P(O)R$^{A2}$R$^{B2}$, —S(O)$_r$NR$^{A2}$R$^{B2}$, and —P(O)(OR$^{A2}$)(OR$^{B2}$), wherein each of the alkyl, alkenyl, alkynyl, cycloalkyl, heterocyclyl, aryl, and heteroaryl is unsubstituted or substituted independently with at least one $R^{X2}$;
each $R^3$ is independently selected from the group consisting of hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A3}$R$^{B3}$, —OR$^{A3}$, and —C(O)R$^{A3}$, wherein each of the alkyl, alkenyl, alkynyl, cycloalkyl, heterocyclyl, aryl, and heteroaryl is unsubstituted or substituted independently with at least one $R^{X3}$; or
two $R^3$, together with the atom(s) to which they are attached, form a $C_{3-10}$ cycloalkyl or 4- to 12-membered heterocyclyl containing 1, 2, or 3 heteroatoms, wherein the heteroatoms are independently selected from the group consisting of oxygen, sulfur, nitrogen, and phosphorus, and the ring thereof is unsubstituted or substituted independently with 1, 2, or 3 $R^{X3}$;

$R^4$ is selected from the group consisting of —C(O)OH, heterocyclyl, and heteroaryl;

$R^5$ is selected from the group consisting of hydrogen and $C_{1-6}$ alkyl;

$R^6$ is selected from the group consisting of hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —NR$^{A4}$R$^{B4}$, —OR$^{A4}$, and —C(O)R$^{A4}$, wherein each of the alkyl, alkenyl, alkynyl, cycloalkyl, heterocyclyl, aryl, and heteroaryl is unsubstituted or substituted independently with at least one $R^{X4}$;

$R^7$ and $R^8$, together with the atom to which they are attached, form a fragment

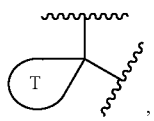

and $R^9$ and $R^{10}$ are independently selected from the group consisting of hydrogen, halogen, and $C_{1-3}$ alkyl; or $R^9$ and $R^{10}$, together with the atom to which they are attached, form a fragment

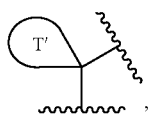

and $R^7$ and $R^8$ are independently selected from the group consisting of hydrogen, halogen, and $C_{1-3}$ alkyl; or $R^8$ and $R^9$, together with the carbon atoms to which they are attached, form a fragment

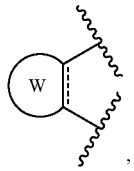

and $R^7$ and $R^{10}$ are independently selected from the group consisting of hydrogen, halogen, and $C_{1-3}$ alkyl;

rings T, T', and W are independently selected from the group consisting of $C_{3-10}$ cycloalkyl, $C_{3-8}$ cycloalkenyl, 3- to 12-membered heterocyclyl, and 5- to 6-membered heteroaryl, and the rings are unsubstituted or substituted independently with 1, 2, or 3 $R^X$;

" ═══ " is a single bond or a double bond; or $R^8$ and $R^6$, together with the atoms to which they are attached, form a $C_{3-10}$ cycloalkyl or 4- to 12-membered heterocyclyl containing 1, 2, or 3 heteroatoms, wherein the heteroatoms are independently selected from the group consisting of oxygen, sulfur, nitrogen, and phosphorus, and the ring thereof is unsubstituted or substituted with 1, 2, or 3 $R^X$; and $R^7$, $R^9$, and $R^{10}$ are each independently selected from the group consisting of hydrogen, halogen, and $C_{1-3}$ alkyl; or $R^9$ and $R^6$, together with the atoms to which they are attached, form a $C_{3-10}$ cycloalkyl or 4- to 12-membered heterocyclyl containing 1, 2, or 3 heteroatoms, wherein the heteroatoms are independently selected from the group consisting of oxygen, sulfur, nitrogen, and phosphorus, and the ring thereof is unsubstituted or substituted independently with 1, 2, or 3 $R^X$; and $R^7$, $R^8$, and $R^{10}$ are each independently selected from the group consisting of hydrogen, halogen, and $C_{1-3}$ alkyl;

each of $R^{A1}$, $R^{A2}$, $R^{A3}$, $R^{A4}$, $R^{B1}$, $R^{B2}$, $R^{B3}$, and $R^{B4}$ is independently selected from the group consisting of hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein each of the alkyl, alkenyl, alkynyl, cycloalkyl, heterocyclyl, aryl, and heteroaryl is unsubstituted or substituted with at least one substituent independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen; or "$R^{A1}$ and $R^{B1}$" or "$R^{A2}$ and $R^{B2}$" or "$R^{A3}$ and $R^{B3}$", together with single or multiple atom(s) to which they are attached, form a 4- to 12-membered heterocyclic ring containing 0, 1, or 2 additional heteroatoms independently selected from the group consisting of oxygen, sulfur, nitrogen, and phosphorus, and the ring is unsubstituted or substituted with 1, 2, or 3 substituents selected from the group consisting of hydroxyl, oxo, $C_{1-6}$ alkyl, $C_2$-6 alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen;

each of $R^X$, $R^{X1}$, $R^{X2}$, $R^{X3}$, and $R^{X4}$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen;

m, n, and p are independently selected from the group consisting of 0, 1, 2, and 3; and r and s are independently selected from the group consisting of 0, 1, and 2.

In some embodiments, provided herein is the compound of Formula I, or the isotope-labelled compound, stereoisomer, or pharmaceutically acceptable salt thereof, wherein $R^7$ and $R^8$, together with the atom to which they are both attached, form a fragment

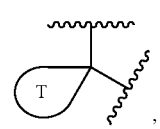

and $R^9$ and $R^{10}$ are independently selected from the group consisting of hydrogen, halogen, and $C_{1-3}$ alkyl; or $R^9$ and $R^{10}$, together with the atom to which they are attached, form a fragment

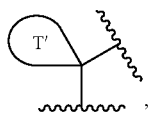

and $R^7$ and $R^5$ are independently selected from the group consisting of hydrogen, halogen, and $C_{1-3}$ alkyl.

Furthermore, in the above-mentioned compound, the rings T and T' are independently selected from the group consisting of cyclopropyl, cyclobutyl, cyclopentyl, cyclohexyl, and oxocyclobutyl; or the rings T and T' are independently selected from the group consisting of oxiranyl, oxetanyl, oxolanyl, oxanyl, aziridinyl, azetidinyl, azinanyl, and thietanyl. The cyclopropyl, cyclobutyl, cyclopentyl, cyclohexyl, oxocyclobutyl, oxiranyl, oxetanyl, oxolanyl, oxanyl, aziridinyl, azetidinyl, azinanyl, and thietanyl are unsubstituted or substituted independently with 1 to 3 (e.g. 1, 2, or 3) $R^X$, and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen.

Alternatively, in the above-mentioned compound, the rings T and T' are independently any one of the following structures:

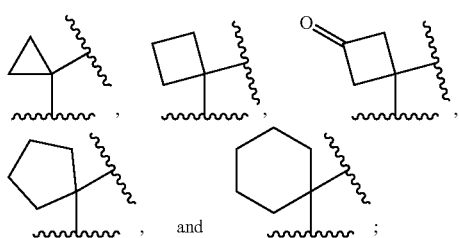

or ring T and ring T' are independently any one of the following structures:

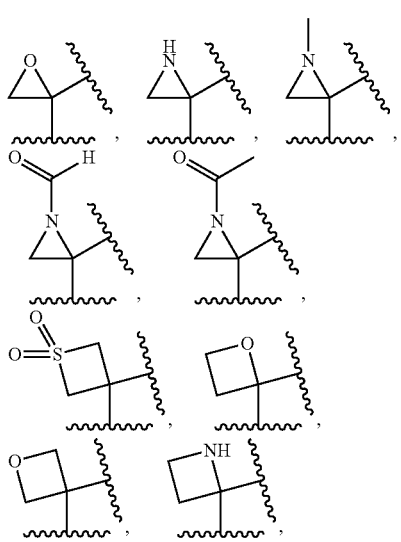

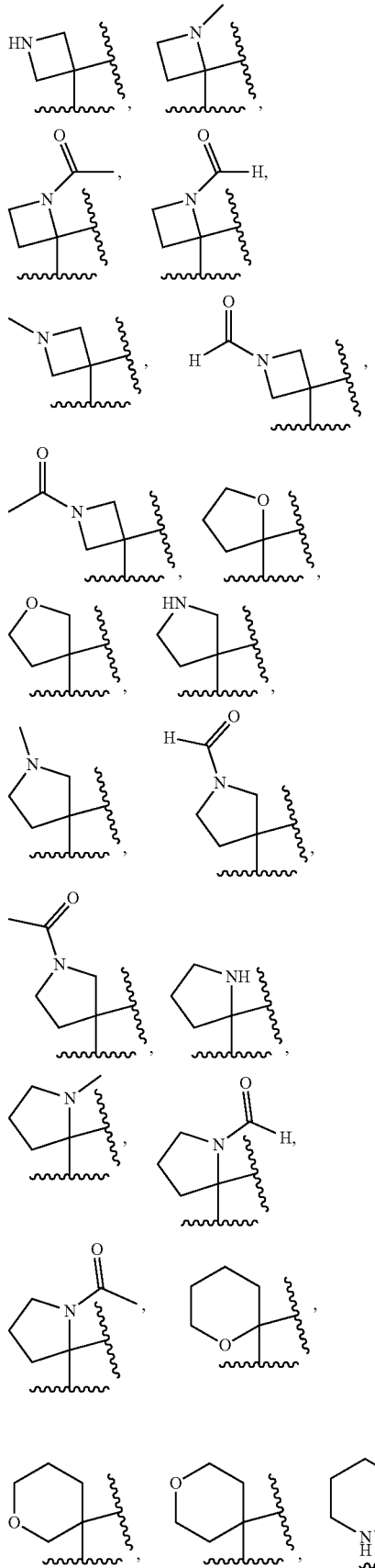

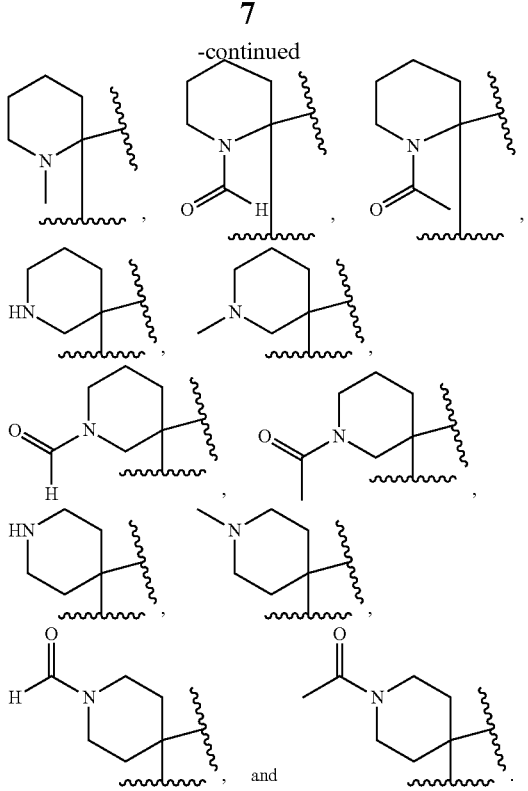

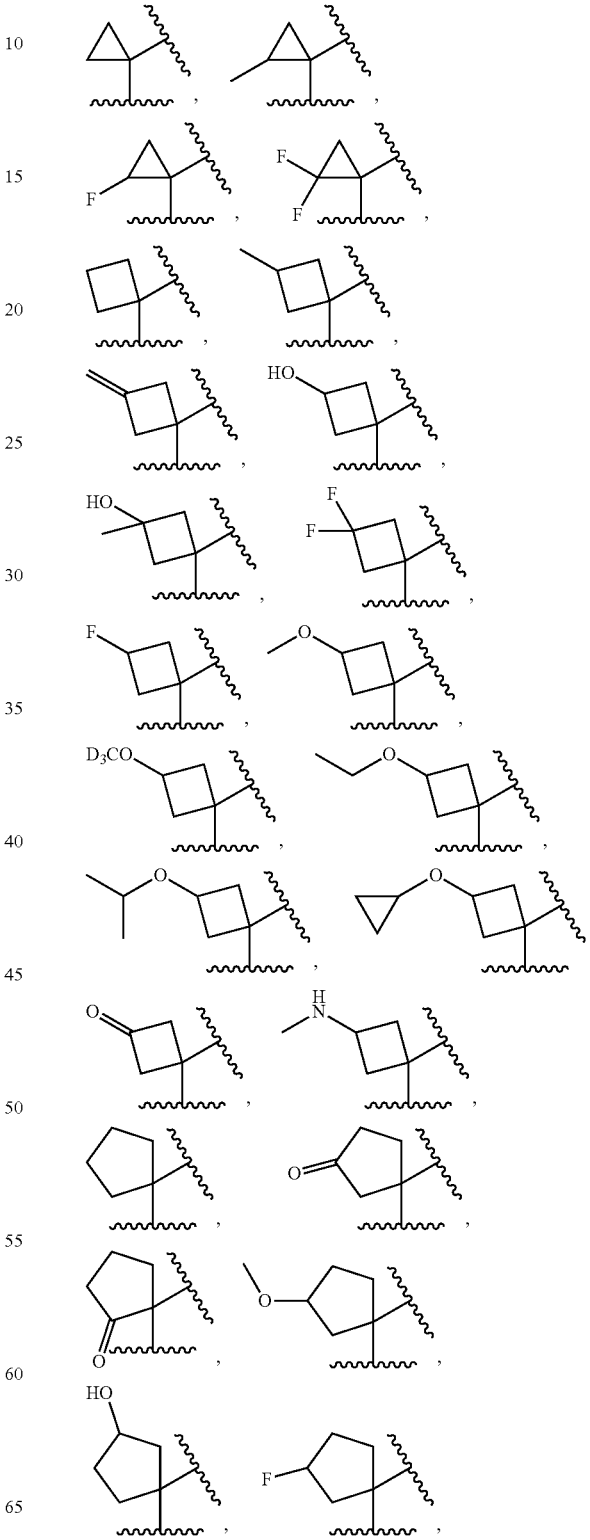

$C_{1-6}$ alkyl-$C_{1-6}$ alkoxy, —C(O)— haloalkyl, —C(O)—$C_{1-6}$ alkoxy, —C(O)—$C_{1-6}$ alkylamino, —C(O)-aminoalkyl, —C(O)NH$_2$, sulfonyl, and halogen.

Preferably, in the above-mentioned compound, the ring T' is any one of the following structures:

In some embodiments, provided herein is the compound of Formula I, or the isotope-labelled compound, stereoisomer, or pharmaceutically acceptable salt thereof, wherein $R^9$ and $R^{10}$, together with the atom to which they are attached, form a fragment

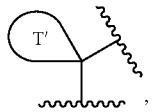

and $R^7$ and $R^5$ are independently selected from the group consisting of hydrogen, halogen, and $C_{1-3}$ alkyl.

Furthermore, in the above-mentioned compound, the ring T' is selected from the group consisting of cyclopropyl, cyclobutyl, cyclopentyl, cyclohexyl, and $C_{4-8}$ cycloalkenyl. The cyclopropyl, cyclobutyl, cyclopentyl, cyclohexyl, and $C_{4-8}$ cycloalkenyl are unsubstituted or substituted independently with 1 to 3 (e.g. 1, 2, or 3) $R^X$, and each $R^X$ is independently selected from the group consisting of hydroxyl, oxo, $C_{1-6}$ alkyl, $C_{2-6}$ alkenyl, alkylamino, —O—$C_{1-6}$ alkyl, —O—$C_{1-6}$ cycloalkyl, and halogen, or each $R^X$ is independently selected from the group consisting of hydroxyl, oxo, $C_{1-6}$ alkyl, —O—$C_{1-6}$ alkyl, —O—$C_{1-6}$ cycloalkyl, and halogen.

Alternatively, in the above-mentioned compound, the ring T' is selected from the group consisting of oxiranyl, oxetanyl, oxolanyl, oxanyl, aziridinyl, azetidinyl, azinanyl, azolidinyl, thietanyl, thiolanyl, and thianyl. The oxiranyl, oxetanyl, oxolanyl, oxanyl, aziridinyl, azetidinyl, azolidinyl, azinanyl, thietanyl, thiolanyl, and thianyl are unsubstituted or substituted independently with 1 to 3 (e.g. 1, 2, or 3) $R^X$, and each $R^X$ is independently selected from the group consisting of hydroxyl, oxo, $C_{1-6}$ alkyl, alkoxy, —C(O)H, —C(O)—$C_{1-6}$ alkyl, —C(O)—$C_{1-6}$ cycloalkyl, —C(O)—

-continued
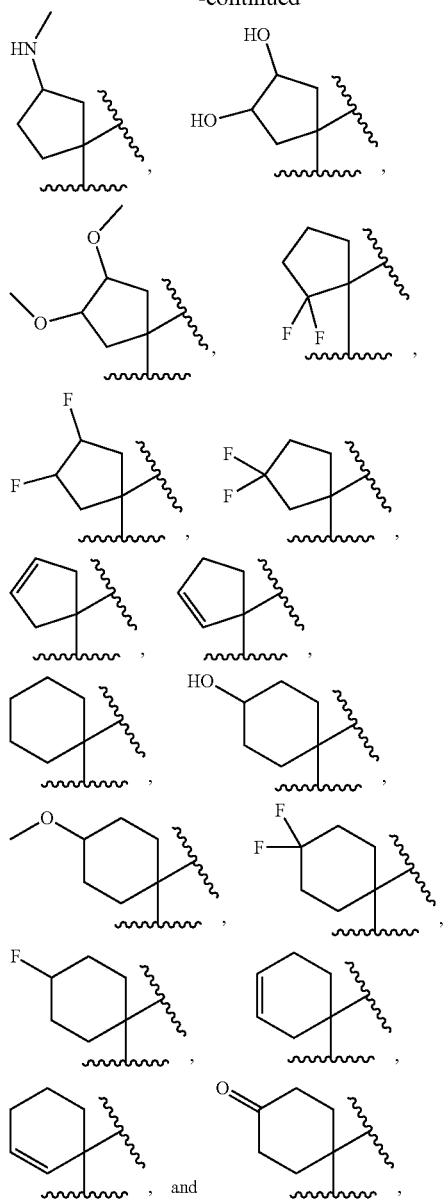
or
the ring T' is any one of the following structures:
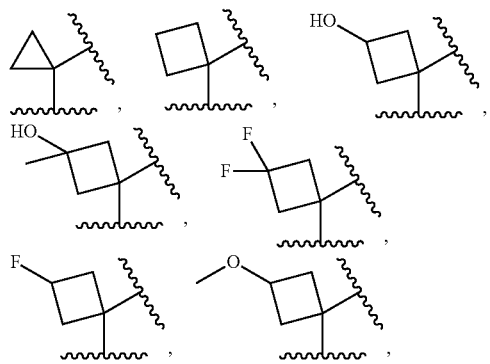
-continued
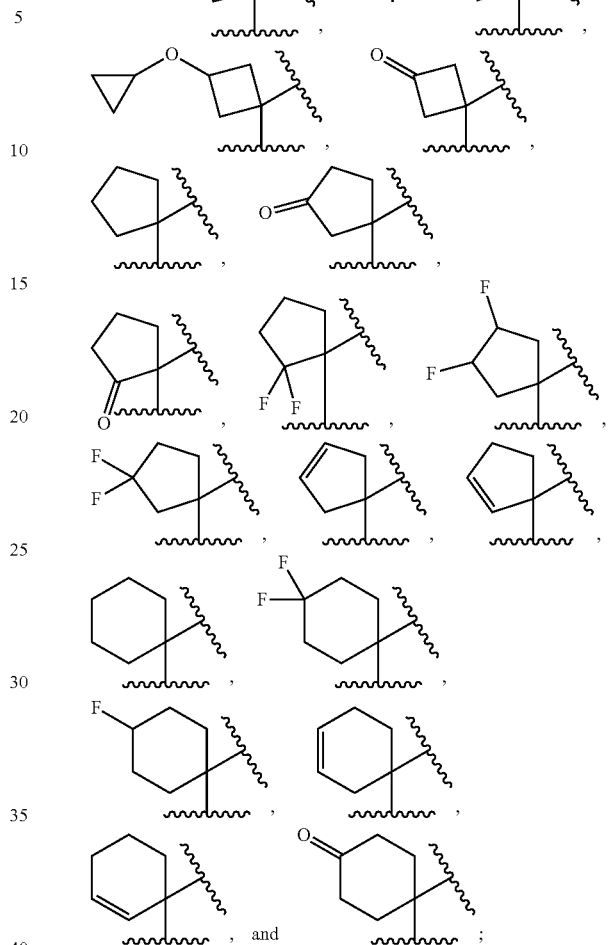
or
the ring T' is any one of the following structures:
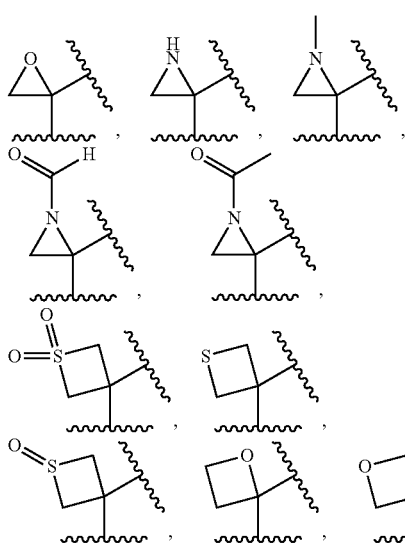

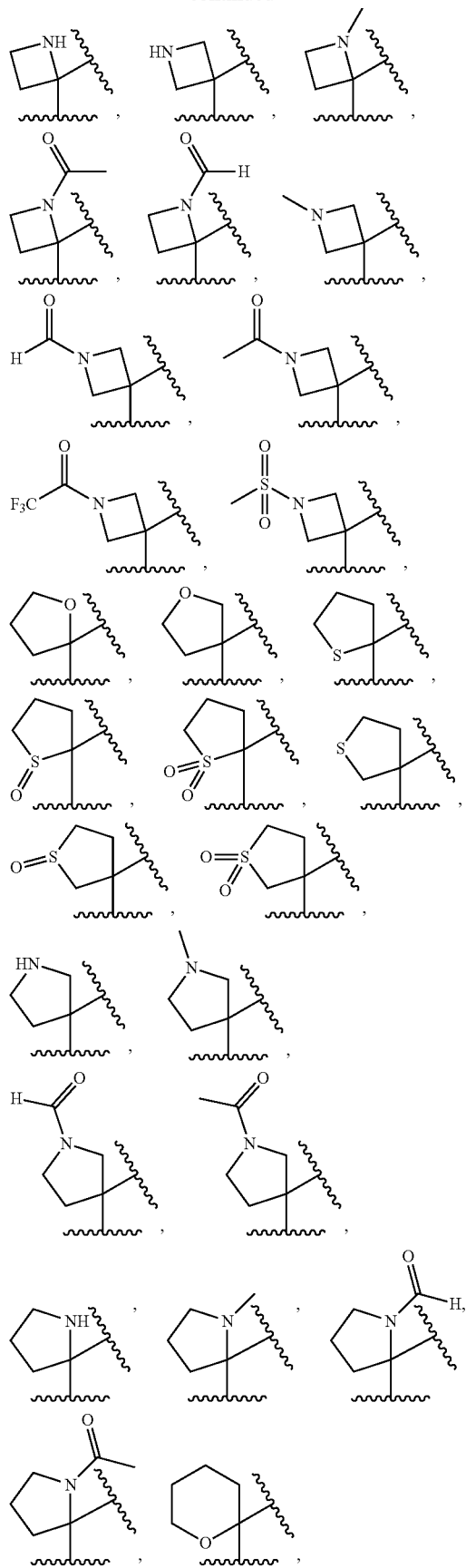
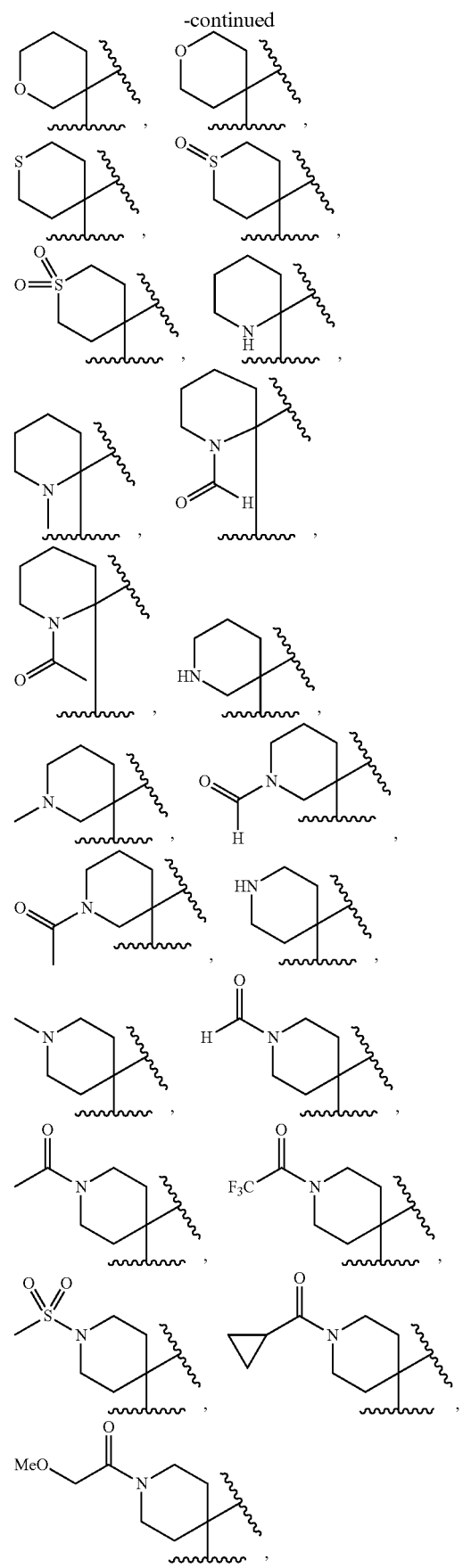

-continued

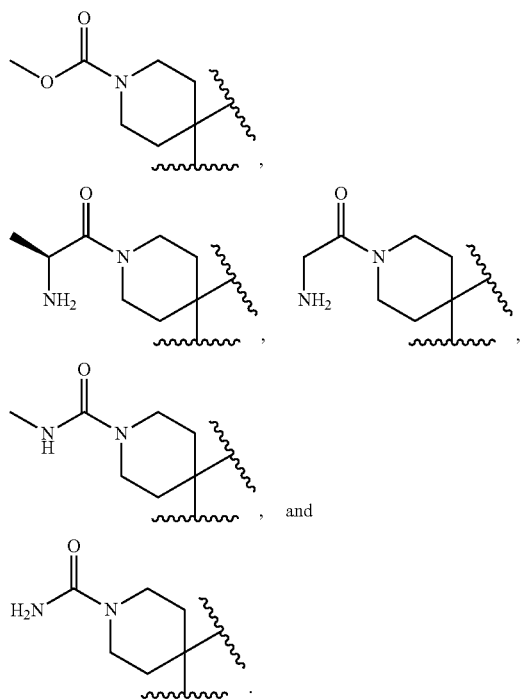

In some embodiments, provided herein is the compound of Formula I, or the isotope-labelled compound, stereoisomer, or pharmaceutically acceptable salt thereof, wherein $R^8$ and $R^9$, together with the carbon atoms to which they are attached, form a fragment

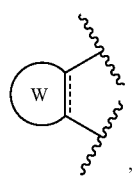

, and $R^7$ and $R^{10}$ are independently selected from the group consisting of hydrogen, halogen, and $C_{1-3}$ alkyl.

Furthermore, ring W is selected from the group consisting of cyclopropyl, cyclobutyl, cyclopentyl, cyclohexyl, oxocyclohexyl, cyclohexenyl, and oxocyclohexenyl; or ring W is selected from the group consisting of oxiranyl, oxetanyl, oxolanyl, oxanyl, aziridinyl, azetidinyl, and azinanyl; or ring W is selected from the group consisting of furanyl, pyrrolyl, imidazolyl, pyrazolyl, triazolyl, oxazolyl, pyridinyl, pyridazinyl, pyrazinyl, and pyrimidinyl, and the cyclopropyl, cyclobutyl, cyclopentyl, cyclohexyl, oxocyclohexyl, cyclohexenyl, oxocyclohexenyl, oxiranyl, oxetanyl, oxolanyl, oxanyl, aziridinyl, azetidinyl, azinanyl, furanyl, pyrrolyl, imidazolyl, pyrazolyl, triazolyl, oxazolyl, pyridinyl, pyridazinyl, pyrazinyl, and pyrimidinyl are unsubstituted or substituted independently with 1 to 3 (e.g. 1, 2, or 3) $R^X$, and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen. " ----- " is a single bond or a double bond.

Preferably, in the above-mentioned compound, the ring W is any one of the following structures:

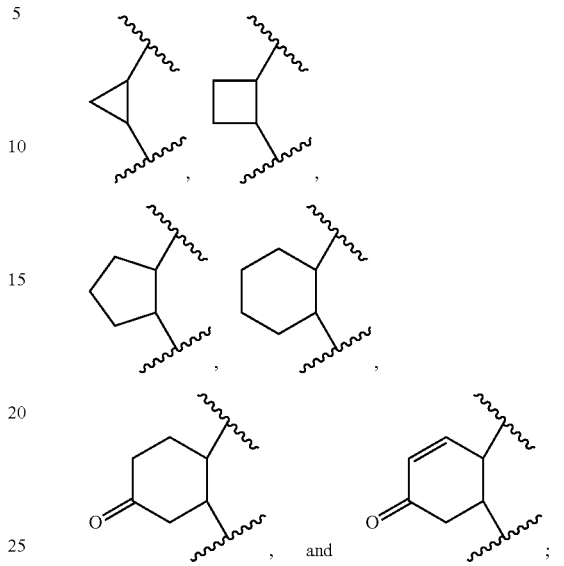

or
the ring W is any one of the following structures:

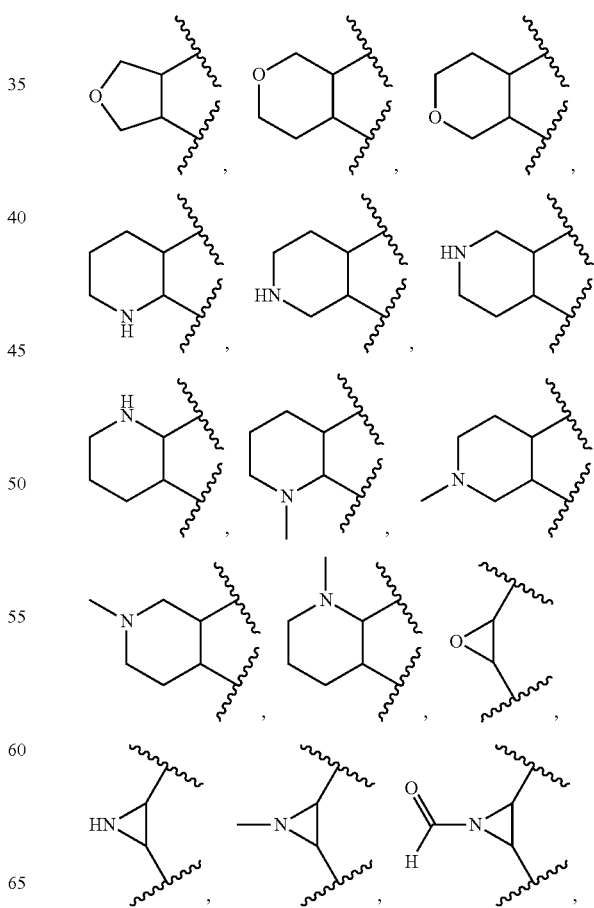

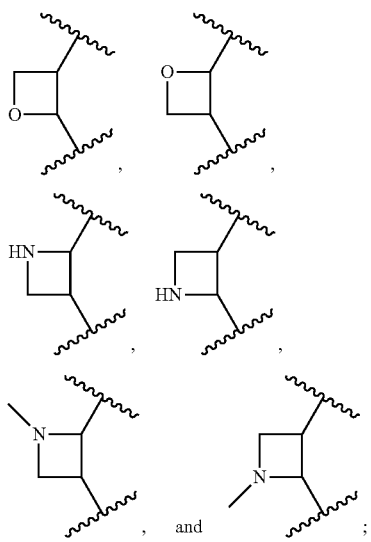

or
the ring W is any one of the following structures:

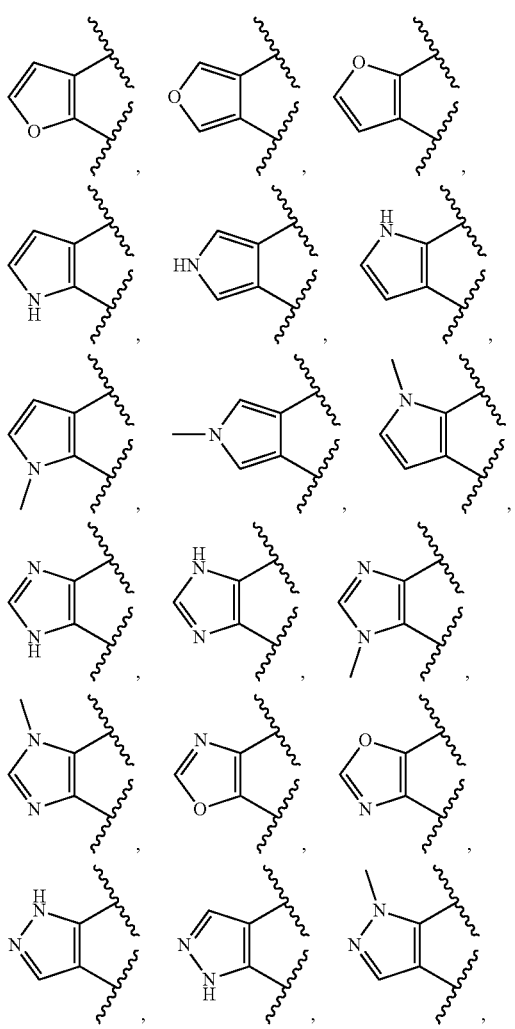

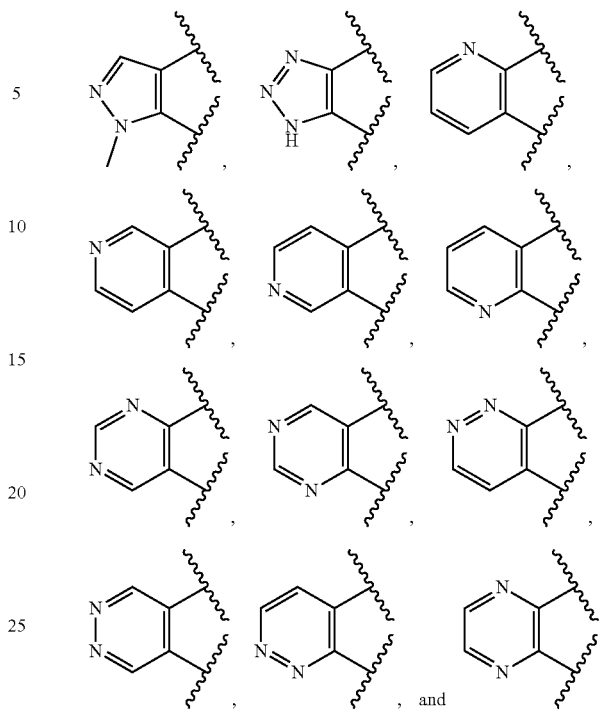

In some embodiments, provided herein is the compound of Formula I, or the isotope-labelled compound, stereoisomer, or pharmaceutically acceptable salt thereof, wherein $R^8$ and $R^6$, together with the atoms to which they are attached, form a $C_{3-8}$ cycloalkyl or 4- to 8-membered heterocyclyl containing 1, 2, or 3 heteroatoms, wherein the heteroatoms are independently selected from the group consisting of oxygen, sulfur, nitrogen, and phosphorus; and $R^7$, $R^9$, and $R^{10}$ are each independently selected from the group consisting of hydrogen, halogen, and $C_{1-3}$ alkyl; or $R^9$ and $R^6$, together with the atoms to which they are attached, form a $C_{3-8}$ cycloalkyl or 4- to 8-membered heterocyclyl containing 1, 2, or 3 heteroatoms, wherein the heteroatoms are independently selected from the group consisting of oxygen, sulfur, nitrogen, and phosphorus; and $R^7$, $R^8$, and $R^{10}$ are each independently selected from the group consisting of hydrogen, halogen, and $C_{1-3}$ alkyl. The ring thereof is unsubstituted or substituted independently with 1 to 3 (e.g. 1, 2, or 3) $R^X$, and each $R^X$ is independently selected from the group consisting of hydroxyl, oxo, $C_1$-6 alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen.

In some embodiments, provided above is the compound of Formula I, or the isotope-labelled compound, stereoisomer, or pharmaceutically acceptable salt thereof, wherein $X^1$, $X^2$, and $X^3$ are independently selected from the group consisting of N and C, wherein only one is N and the other two are C.

In some embodiments, provided above is the compound of Formula I, or the isotope-labelled compound, stereoisomer, or pharmaceutically acceptable salt thereof, wherein ring A is aryl or heteroaryl, preferably

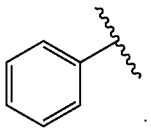 [SMILES: *c1ccccc1]

In some embodiments, provided above is the compound of Formula I, or the isotope-labelled compound, stereoisomer, or pharmaceutically acceptable salt thereof, wherein each $R^1$ is independently selected from the group consisting of hydrogen, halogen, $C_{1-4}$ alkyl, $C_{3-6}$ cycloalkyl, and $C_{1-4}$ alkoxy, and m is selected from the group consisting of 1, 2, and 3; each $R^1$ is independently preferably hydrogen, fluorine, methyl, or cyclopropyl, or preferably fluorine, methyl, or cyclopropyl, and m is preferably 2 or 3.

In some embodiments, provided above is the compound of Formula I, or the isotope-labelled compound, stereoisomer, or pharmaceutically acceptable salt thereof, wherein ring B is selected from the group consisting of

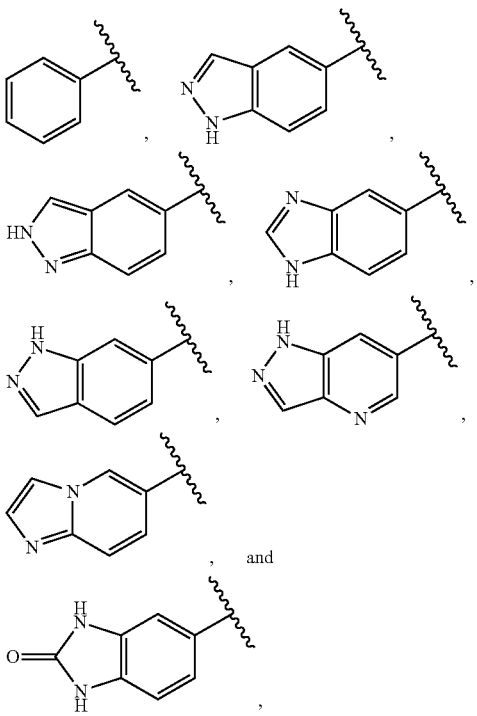

preferably is

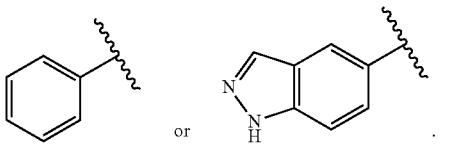 [SMILES: *c1ccccc1 ; *c1ccc2[nH]ncc2c1]

In some embodiments, provided above is the compound of Formula I, or the isotope-labelled compound, stereoisomer, or pharmaceutically acceptable salt thereof, wherein each $R^2$ is independently selected from the group consisting of hydrogen, halogen, $C_{1-4}$ alkyl, $C_{1-4}$ alkoxy, $C_{1-4}$ alkylamino, $C_{3-6}$ cycloalkyl, —$CH_2CF_3$, —$S(O)_2NR^{A2}R^{B2}$, —$S(O)_2R^{A2}$ and —$P(O)R^{A2}R^{B2}$; each of $R^{A2}$ and $R^{B2}$ is independently selected from the group consisting of $C_{1-4}$ alkyl and $C_{3-6}$ cycloalkyl, and n is 1, 2, or 3, or n is 1 or 2; or each $R^2$ is independently selected from the group consisting of hydrogen, fluorine, methyl, —$CH_2CH_3$, —$CH_2CF_3$, —$P(O)(CH_3)_2$, —$P(O)(CH_2CH_3)_2$, —$NHCH_3$, —$OCH_3$, —$CH_2S(O)_2CH_3$, and

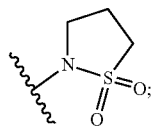 [SMILES: *N1CCCS1(=O)=O]

or each $R^2$ is independently hydrogen, fluorine, methyl, —$CH_2CF_3$, —$P(O)(CH_3)_2$, —$P(O)(CH_2CH_3)_2$, —$NHCH_3$, —$OCH_3$, —$CH_2S(O)_2CH_3$, or

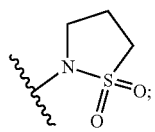 [SMILES: *N1CCCS1(=O)=O]

or each $R^2$ is independently fluorine, methyl, —$CH_2CH_3$, —$CH_2CF_3$, —$P(O)(CH_3)_2$, —$P(O)(CH_2CH_3)_2$, —$NHCH_3$, —$OCH_3$, —$CH_2S(O)_2CH_3$, or

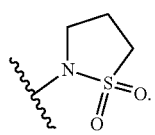

In some embodiments, provided above is the compound of Formula I, or the isotope-labelled compound, stereoisomer, or pharmaceutically acceptable salt thereof, wherein ring C is selected from the group consisting of heterocyclyl and heteroaryl; each $R^3$ is independently selected from the group consisting of hydrogen, halogen, $C_{1-4}$ alkyl, $C_{1-4}$ alkoxy, and $C_{3-6}$ cycloalkyl; and p is 0, 1, 2, or 3, and when p≥2, any two $R^3$, optionally together with the atom(s) to which they are attached, form $C_{3-10}$ cycloalkyl. Furthermore, in the above-mentioned compound, ring C is

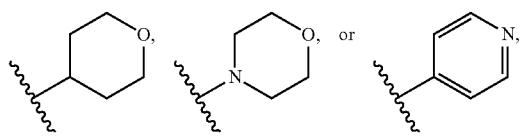

or ring C is

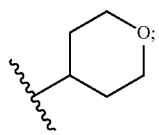 [SMILES: *C1CCOCC1]

p is preferably 0; or p is preferably 2, and $R^3$ is preferably methyl; or p is preferably 2, and two $R^3$, together with the atom(s) to which they are attached, form cyclopropyl.

In some embodiments, provided above is the compound of Formula I, or the isotope-labelled compound, stereoisomer, or pharmaceutically acceptable salt thereof, wherein $R^4$ is selected from the group consisting of

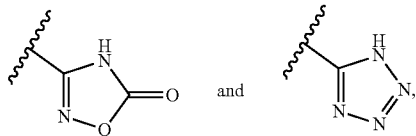 [SMILES: *c1noc(=O)[nH]1 ; *c1nnn[nH]1]

or $R^4$ is

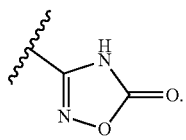 [SMILES: *c1noc(=O)[nH]1]

In some embodiments, provided above is the compound of Formula I, or the isotope-labelled compound, stereoisomer, or pharmaceutically acceptable salt thereof, wherein $R^5$ is selected from the group consisting of hydrogen and $C_{1-3}$ alkyl, or $R^5$ is hydrogen or methyl.

In some embodiments, provided above is the compound of Formula I, or the isotope-labelled compound, stereoisomer, or pharmaceutically acceptable salt thereof, wherein $R^6$ is selected from the group consisting of hydrogen and $C_{1-3}$ alkyl, or $R^6$ is methyl.

In some embodiments, the compound of Formula I provided above has any one of the following structures:

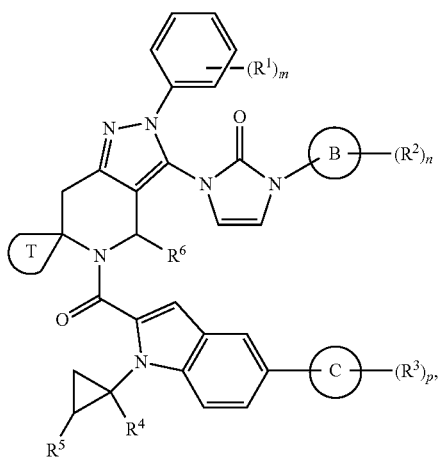

(I-1)

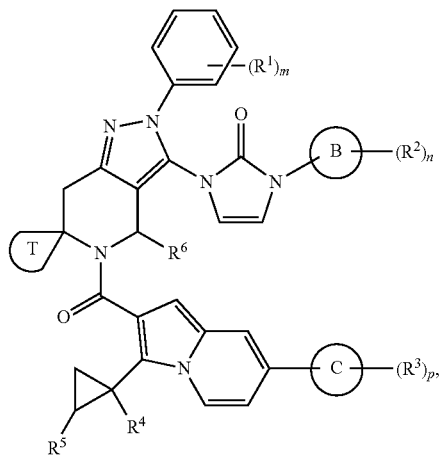

(I-2)

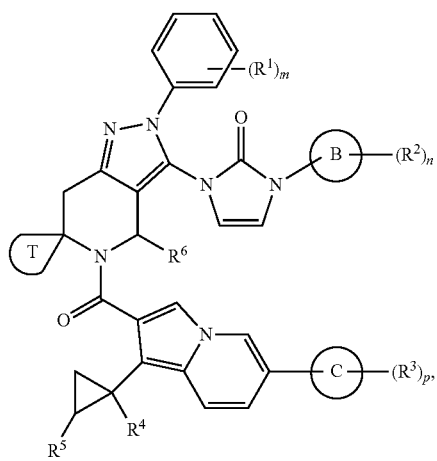

(I-3)

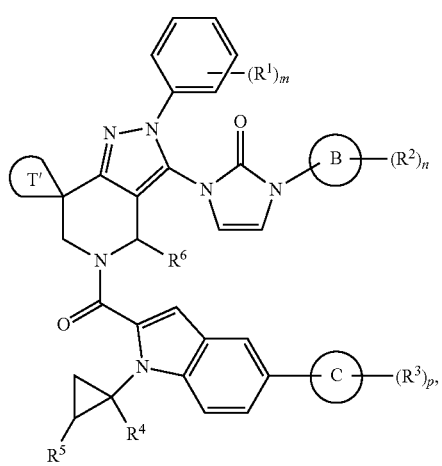

(II-1)

(II-2)
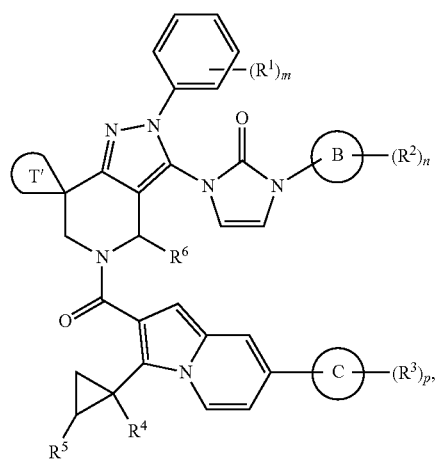
(III-2)
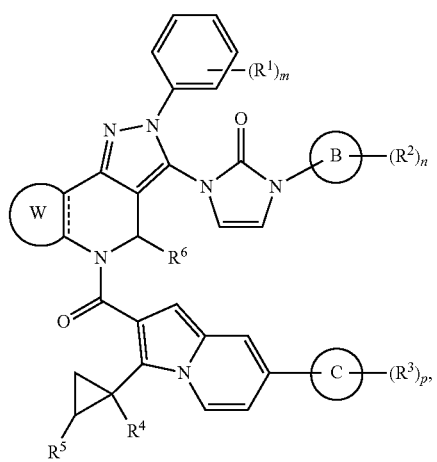
(II-3)
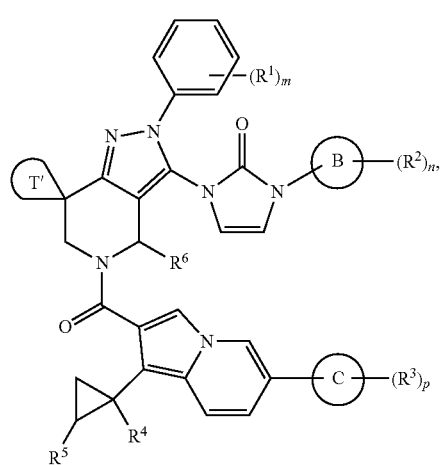
(III-3)
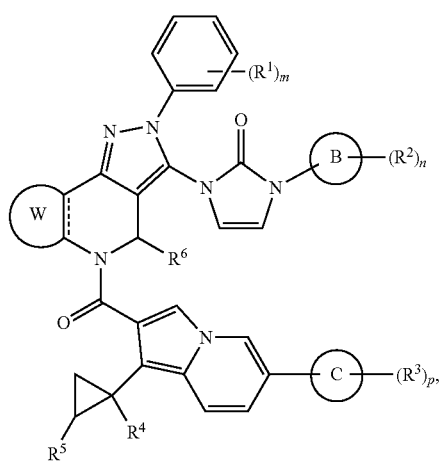
(III-1)
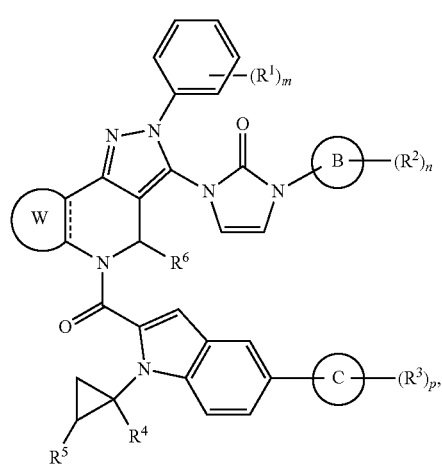
(IV-1)
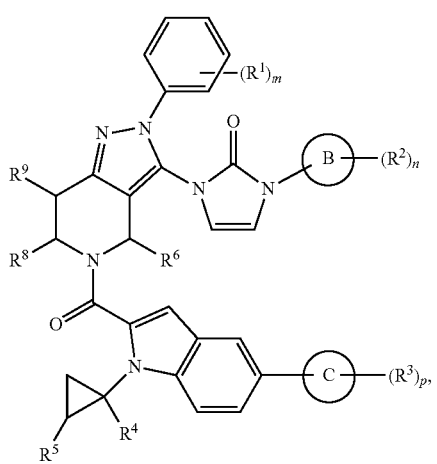

-continued
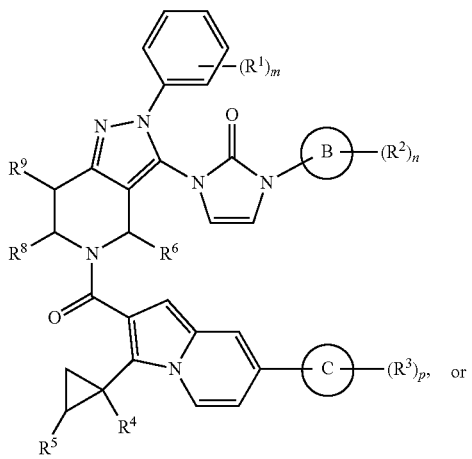
wherein
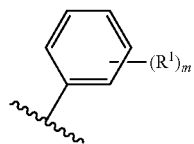
is selected from the group consisting of
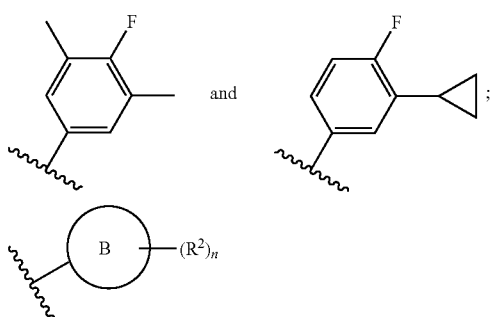
is selected from the group consisting of
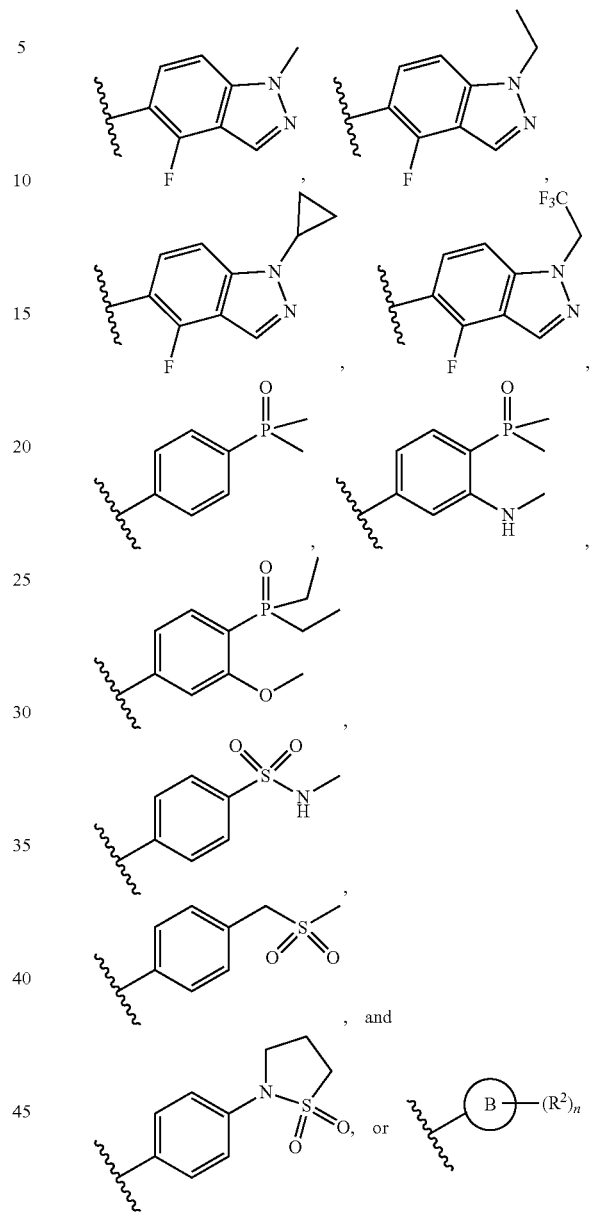
is selected from the group consisting of
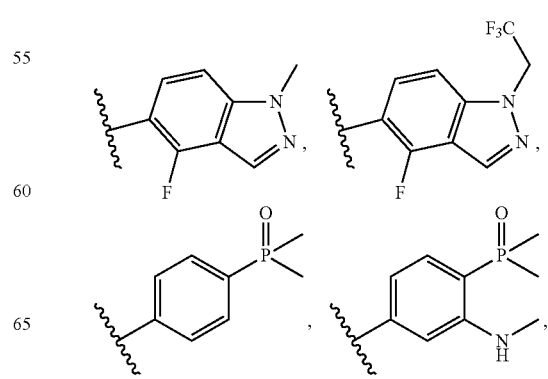

-continued

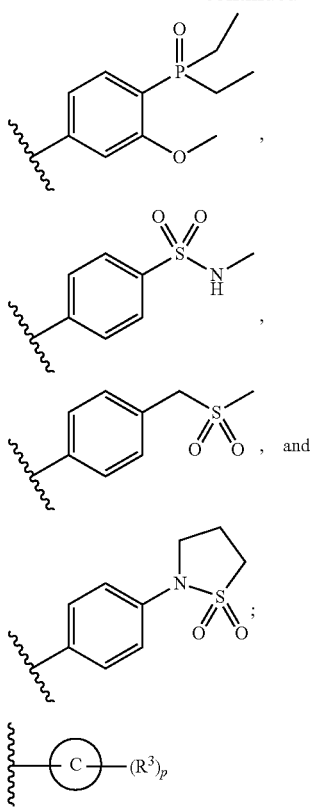

is selected from the group consisting of

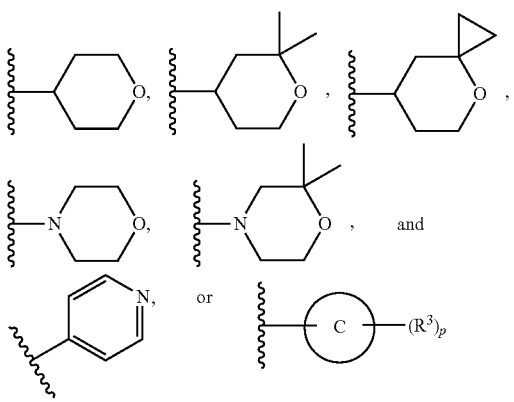

is selected from the group consisting of

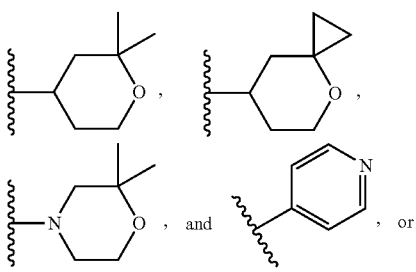

-continued

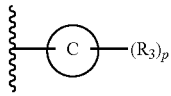

is selected from the group consisting of

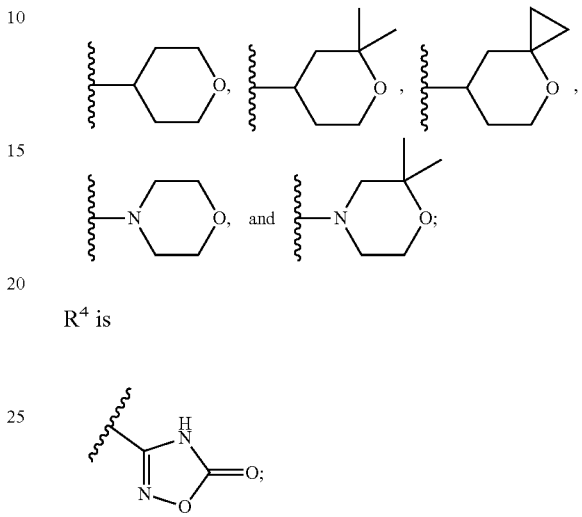

$R^4$ is

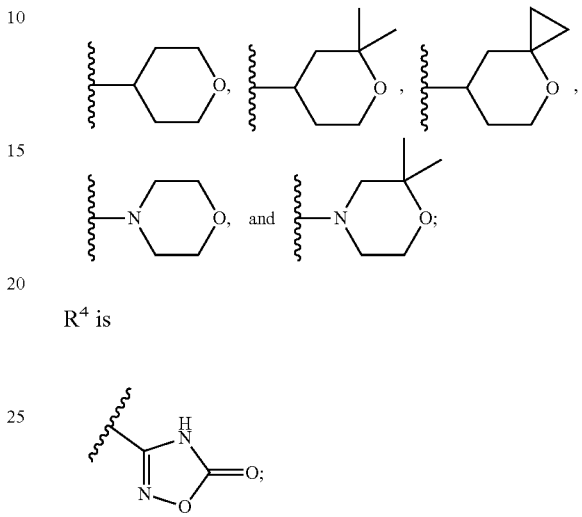

$R^5$ is hydrogen or methyl;
$R^6$ is methyl;
" ===== " is a single bond or a double bond;
rings T, T', and W are independently selected from the group consisting of $C_{3-10}$ cycloalkyl, $C_{3-8}$ cycloalkenyl, 3- to 12-membered heterocyclyl, and 5- to 6-membered heteroaryl, and the rings are unsubstituted or substituted independently with 1, 2, or 3 $R^X$; or
$R^1$ and $R^6$, together with the atoms to which they are attached, form a $C_{3-8}$ cycloalkyl or 4- to 8-membered heterocyclyl containing 1, 2, or 3 heteroatoms, wherein the heteroatoms are independently selected from the group consisting of oxygen, sulfur, nitrogen, and phosphorus, and the ring thereof is unsubstituted or substituted with 1, 2, or 3 $R^X$; and $R^9$ is hydrogen; or
$R^9$ and $R^6$, together with the atoms to which they are attached, form a $C_{3-8}$ cycloalkyl or 4- to 8-membered heterocyclyl containing 1, 2, or 3 heteroatoms, wherein the heteroatoms are independently selected from the group consisting of oxygen, sulfur, nitrogen, and phosphorus, and the ring thereof is unsubstituted or substituted with 1, 2, or 3 $R^X$; and $R^5$ is hydrogen;
each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen.

Furthermore, in the above-mentioned compound, the rings T and T' are independently selected from the group consisting of cyclopropyl, cyclobutyl, cyclopentyl, cyclohexyl, and oxocyclobutyl; or the rings T and T' are independently selected from the group consisting of oxiranyl, oxetanyl, oxolanyl, oxanyl, aziridinyl, azetidinyl, azinanyl, and thietanyl; and the cyclopropyl, cyclobutyl, cyclopentyl, cyclohexyl, oxocyclobutyl, oxiranyl, oxetanyl, oxolanyl, oxanyl, aziridinyl, azetidinyl, azinanyl, and thietanyl are unsubstituted or substituted independently with 1, 2, or 3 $R^X$, and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen.

Alternatively, in the above-mentioned compound, the rings T and T' are selected from the group consisting of

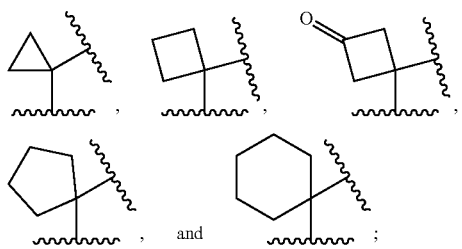

or the rings T and T' are selected from the group consisting of

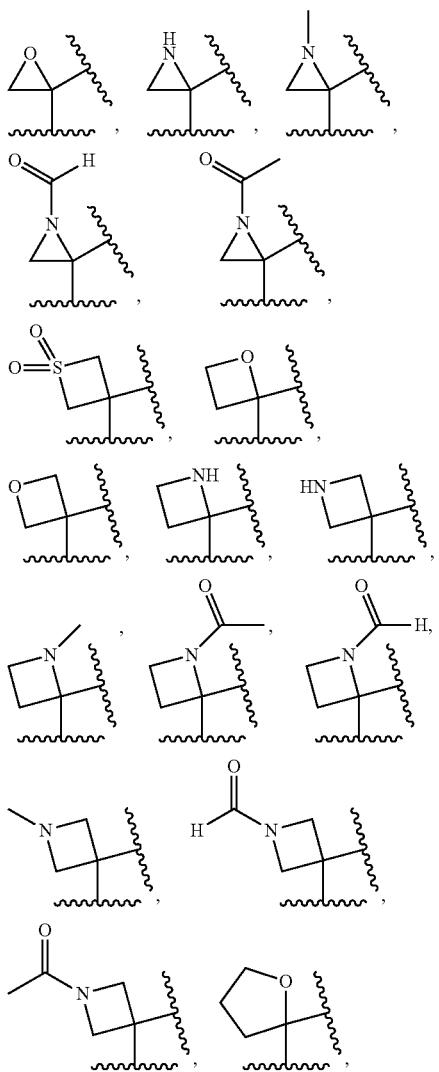

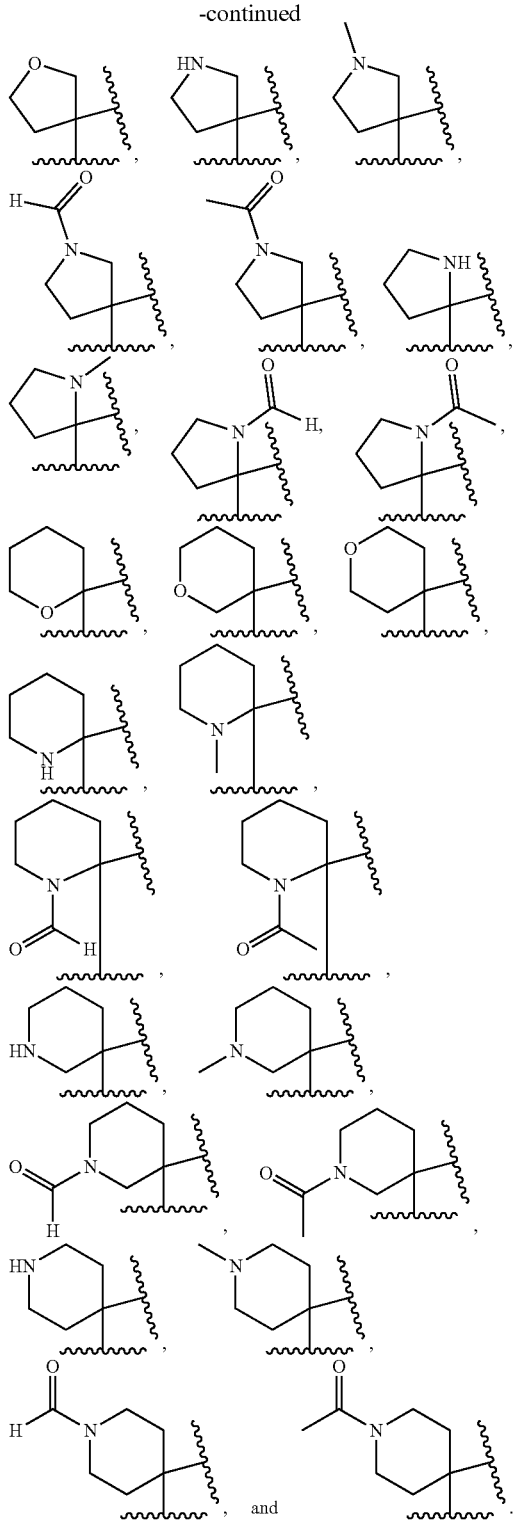

Or furthermore, in the above-mentioned compound, the ring W is selected from the group consisting of cyclopropyl, cyclobutyl, cyclopentyl, cyclohexyl, oxocyclohexyl, cyclohexenyl, and oxocyclohexenyl; or the ring W is selected from the group consisting of oxiranyl, oxetanyl, oxolanyl, oxanyl, aziridinyl, azetidinyl, and azinanyl; or the ring W is selected from the group consisting of furanyl, pyrrolyl, imidazolyl, pyrazolyl, triazolyl, oxazolyl, pyridinyl, pyridazinyl, pyrazinyl, and pyrimidinyl. The cyclopropyl, cyclobutyl, cyclopentyl, cyclohexyl, oxocyclohexyl, cyclohexenyl, oxocyclohexenyl, oxiranyl, oxetanyl, oxolanyl, oxanyl, aziridinyl, azetidinyl, azinanyl, furanyl, pyrrolyl, imidazolyl, pyrazolyl, triazolyl, oxazolyl, pyridinyl, pyridazinyl, pyrazinyl, and pyrimidinyl are unsubstituted or substituted independently with 1, 2, or 3 $R^X$, and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl)amino, haloalkyl, acyl, sulfonyl, sulfonamido, and halogen.

Preferably, in the above-mentioned compound, the ring W is selected from the group consisting of

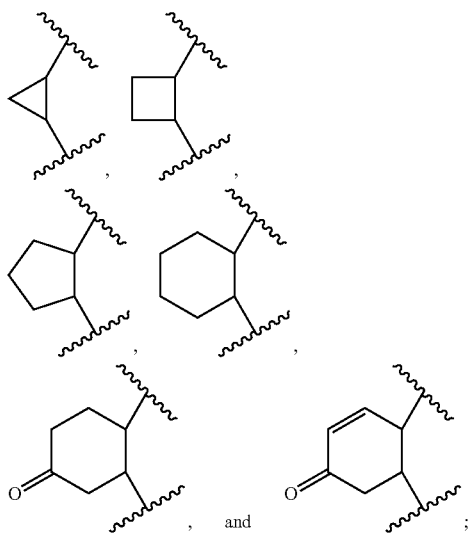

or the ring W is selected from the group consisting of

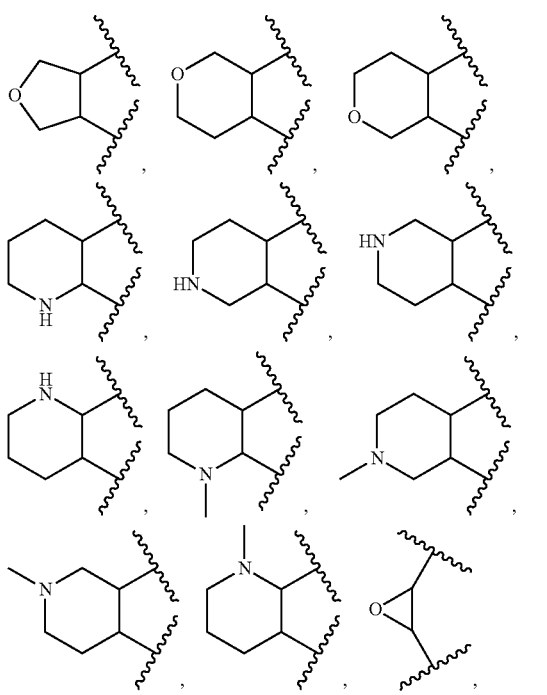

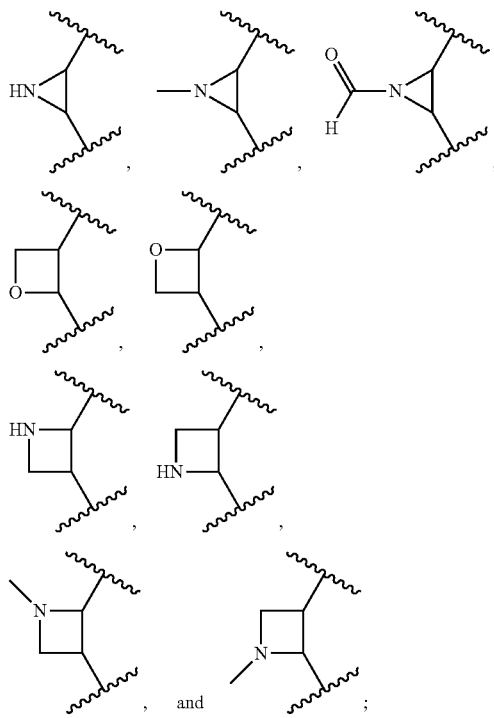

or the ring W is selected from the group consisting of

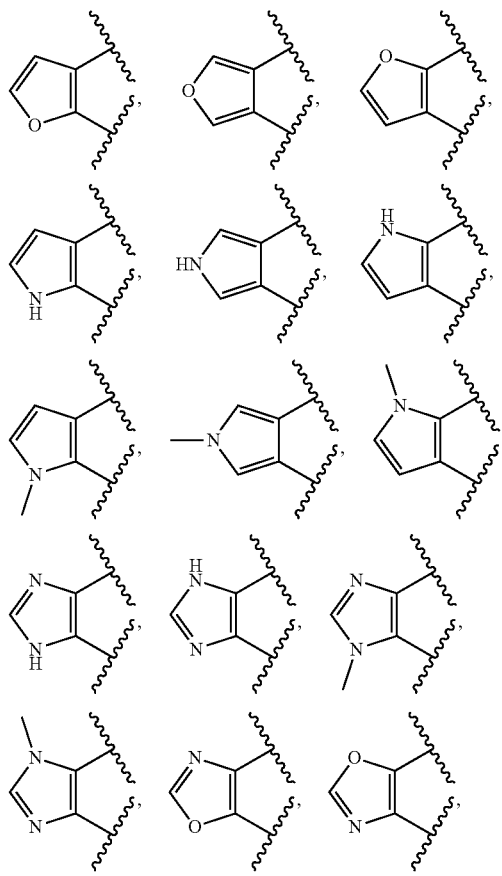

-continued
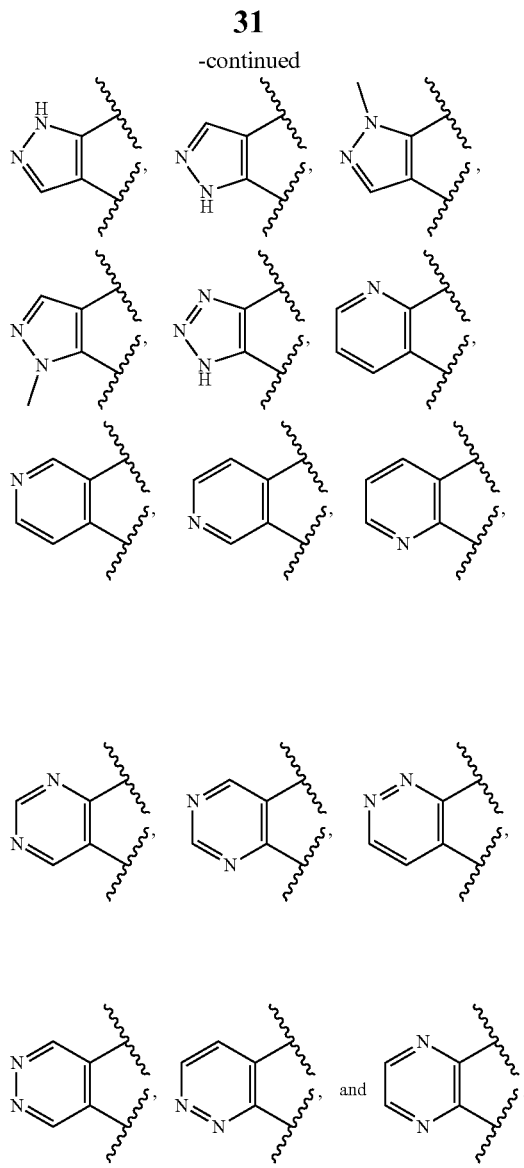
In some embodiments, the compound of Formula I provided above has any one of the following structures:
(II-1)
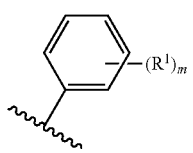
-continued
(II-2)
(II-3)
wherein
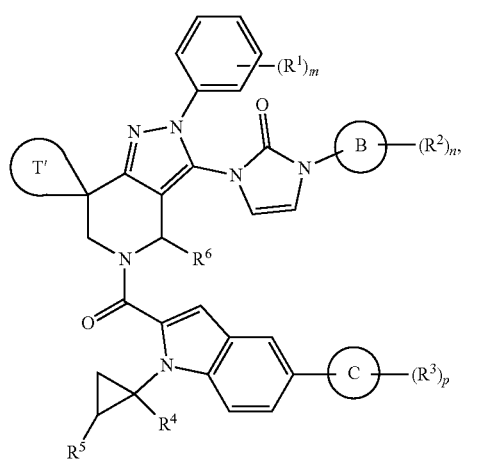
is selected from the group consisting of
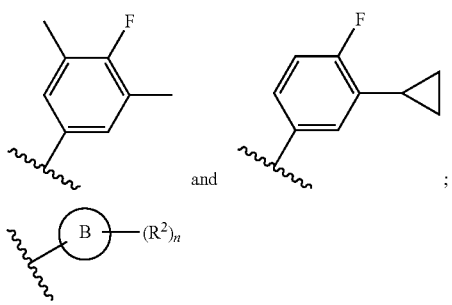

is selected from the group consisting of
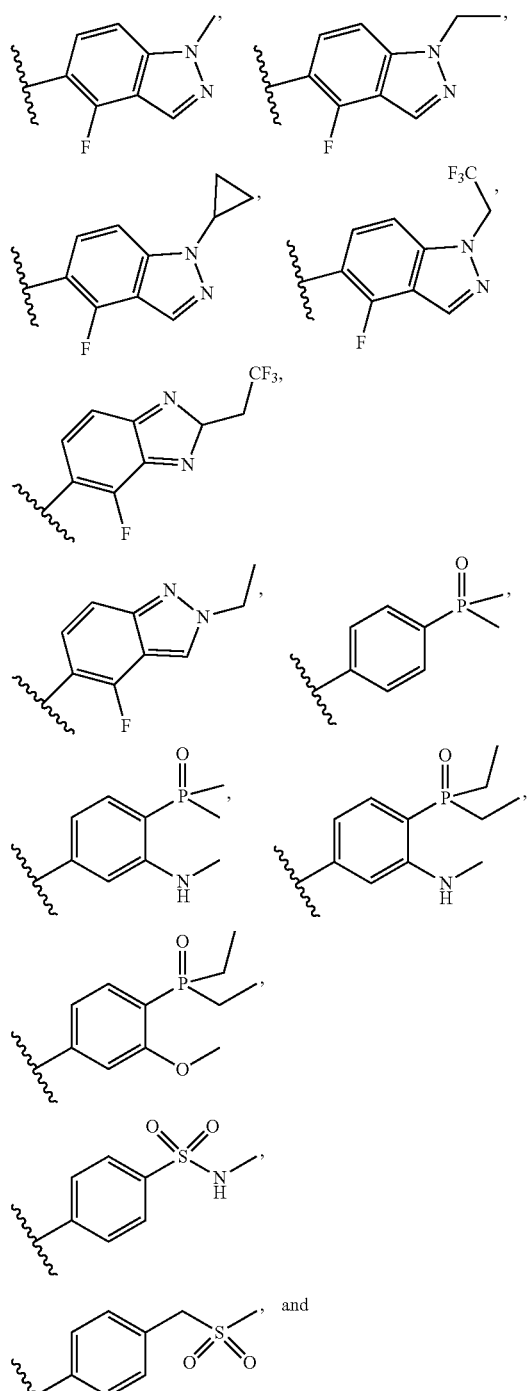
is selected from the group consisting of
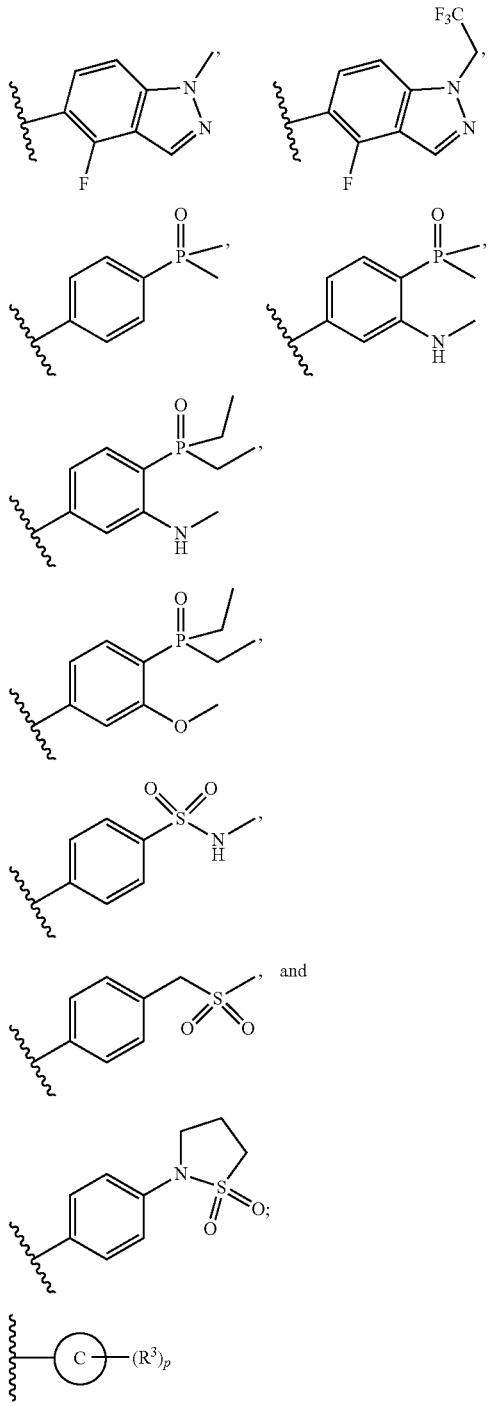
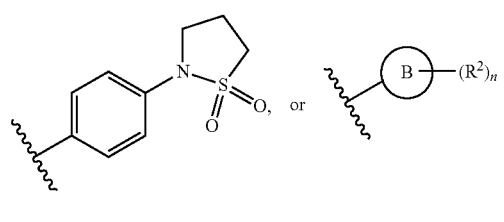
is selected from the group consisting of
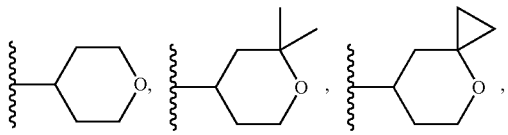

is selected from the group consisting of

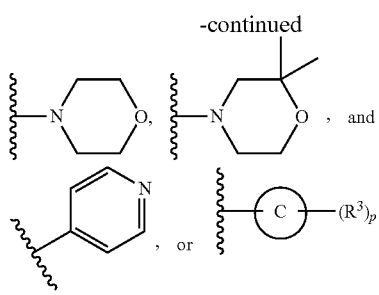

is selected from the group consisting of

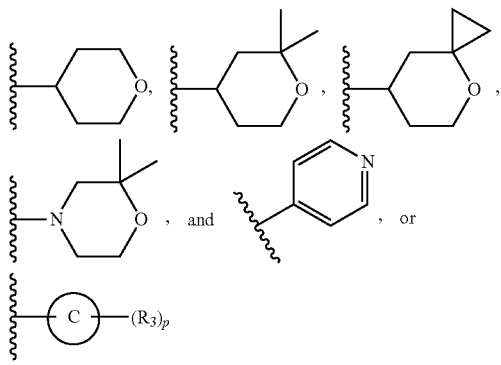

$R^4$ is

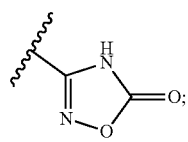

$R^5$ is hydrogen or methyl;
$R^6$ is methyl;
ring T' is independently selected from the group consisting of $C_{3-10}$ cycloalkyl, $C_{3-8}$ cycloalkenyl, 3- to 12-membered heterocyclyl, and 5- to 6-membered heteroaryl, and the ring is unsubstituted or substituted independently with 1, 2, or 3 $R^X$; and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl) amino, haloalkyl, acyl, sulfonyl, sulfonamido, and halogen.

Furthermore, in the above-mentioned compound, the ring T' is selected from the group consisting of cyclopropyl, cyclobutyl, cyclopentyl, cyclohexyl, and $C_{4-8}$ cycloalkenyl; the cyclopropyl, cyclobutyl, cyclopentyl, cyclohexyl, and $C_{4-8}$ cycloalkenyl are unsubstituted or substituted independently with 1, 2, or 3 $R^X$, and each $R^X$ is independently selected from the group consisting of hydroxyl, oxo, $C_{1-6}$ alkyl, $C_{2-6}$ alkenyl, alkylamino, —O—$C_{1-6}$ alkyl, —O—$C_{1-6}$ cycloalkyl, and halogen, or each $R^X$ is independently selected from the group consisting of hydroxyl, oxo, $C_{1-6}$ alkyl, —O—$C_{1-6}$ alkyl, —O—$C_{1-6}$ cycloalkyl, and halogen.

Alternatively, in the above-mentioned compound, the ring T' is selected from the group consisting of oxiranyl, oxetanyl, oxolanyl, oxanyl, aziridinyl, azetidinyl, azolidinyl, azinanyl, thietanyl, thiolanyl, and thianyl; the oxiranyl, oxetanyl, oxolanyl, oxanyl, aziridinyl, azetidinyl, azolidinyl, azinanyl, thietanyl, thiolanyl, and thianyl are unsubstituted or substituted independently with 1, 2, or 3 $R^X$, and each $R^X$ is independently selected from the group consisting of hydroxyl, oxo, $C_{1-6}$ alkyl, alkoxy, —C(O)H, —C(O)—$C_{1-6}$ alkyl, —C(O)—$C_{1-6}$ cycloalkyl, —C(O)—$C_{1-6}$ alkyl-$C_{1-6}$ alkoxy, —C(O)-haloalkyl, —C(O)—$C_{1-6}$ alkoxy, —C(O)—$C_{1-6}$ alkylamino, —C(O)-aminoalkyl, —C(O)NH$_2$, sulfonyl, and halogen.

Preferably, in the above-mentioned compound, the ring T' is selected from the group consisting of

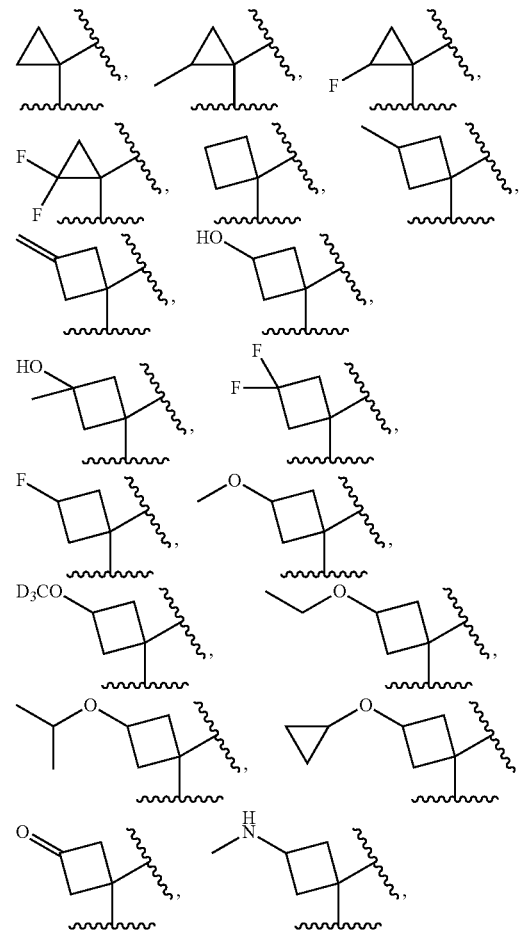

-continued
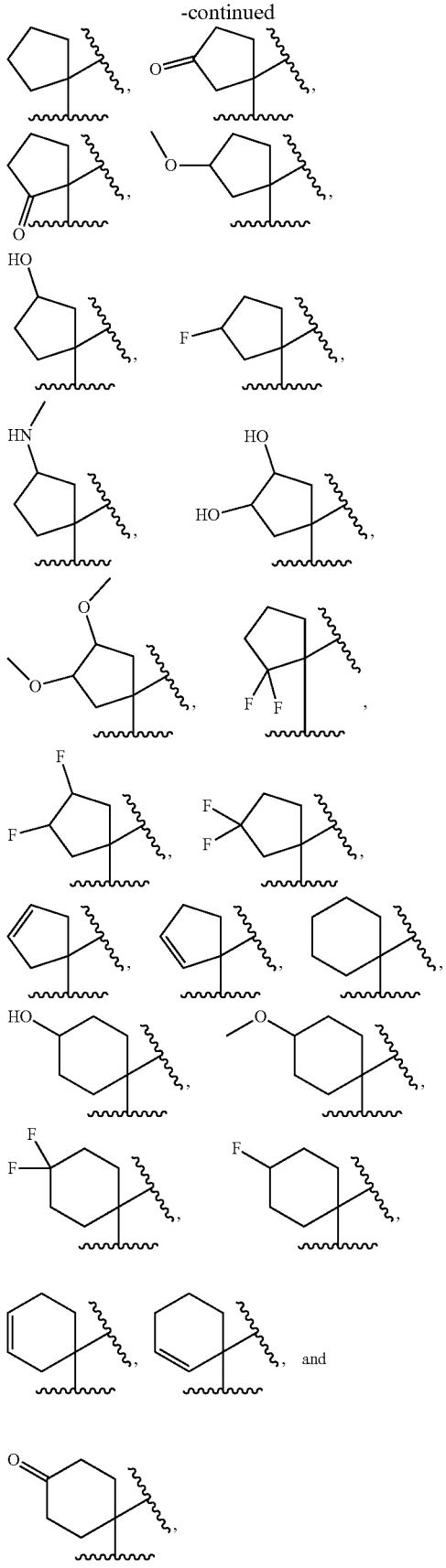
or the ring T' is selected from the group consisting of
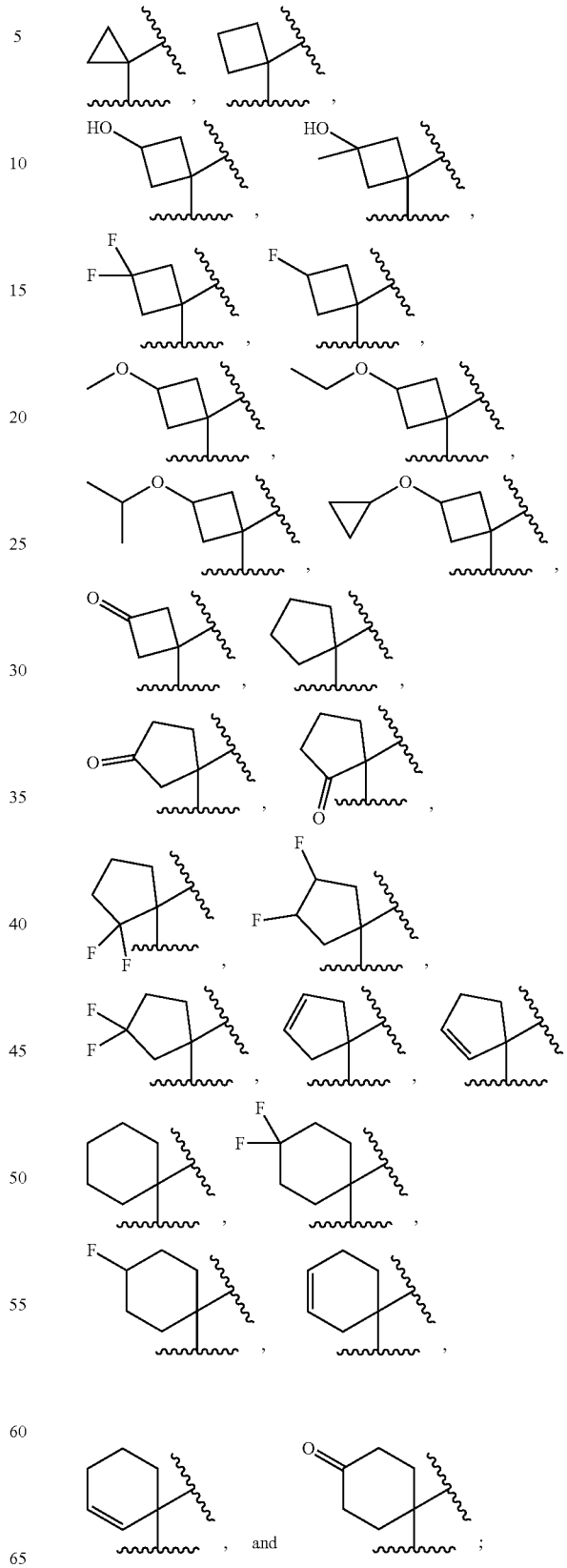

or the ring T' is selected from the group consisting of
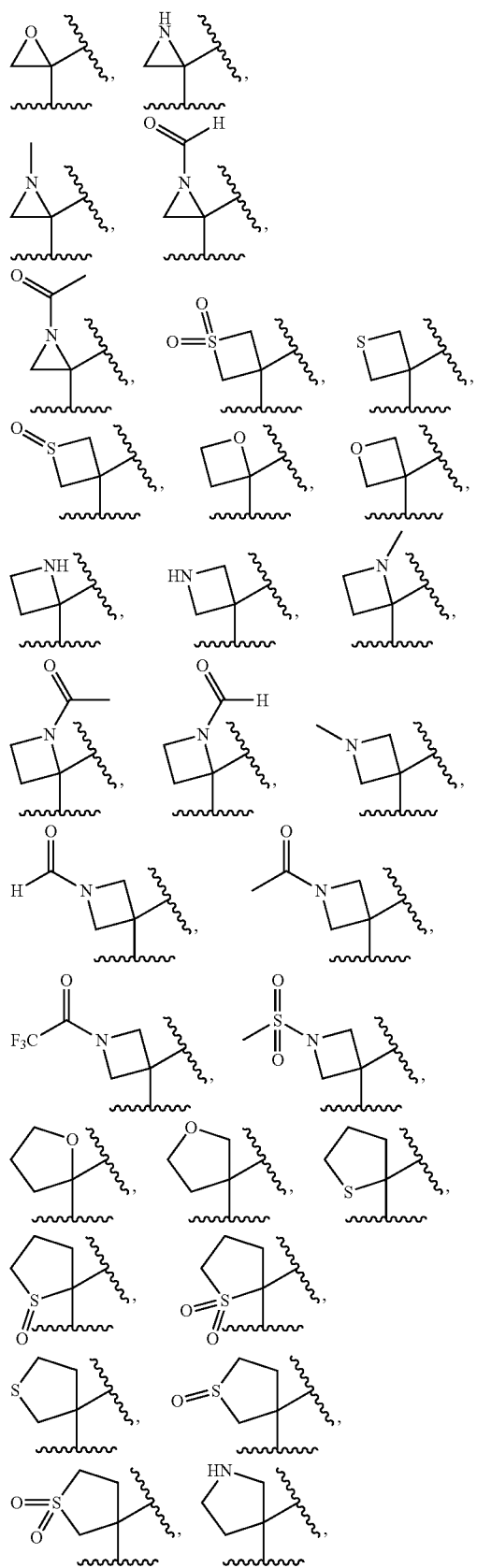
-continued
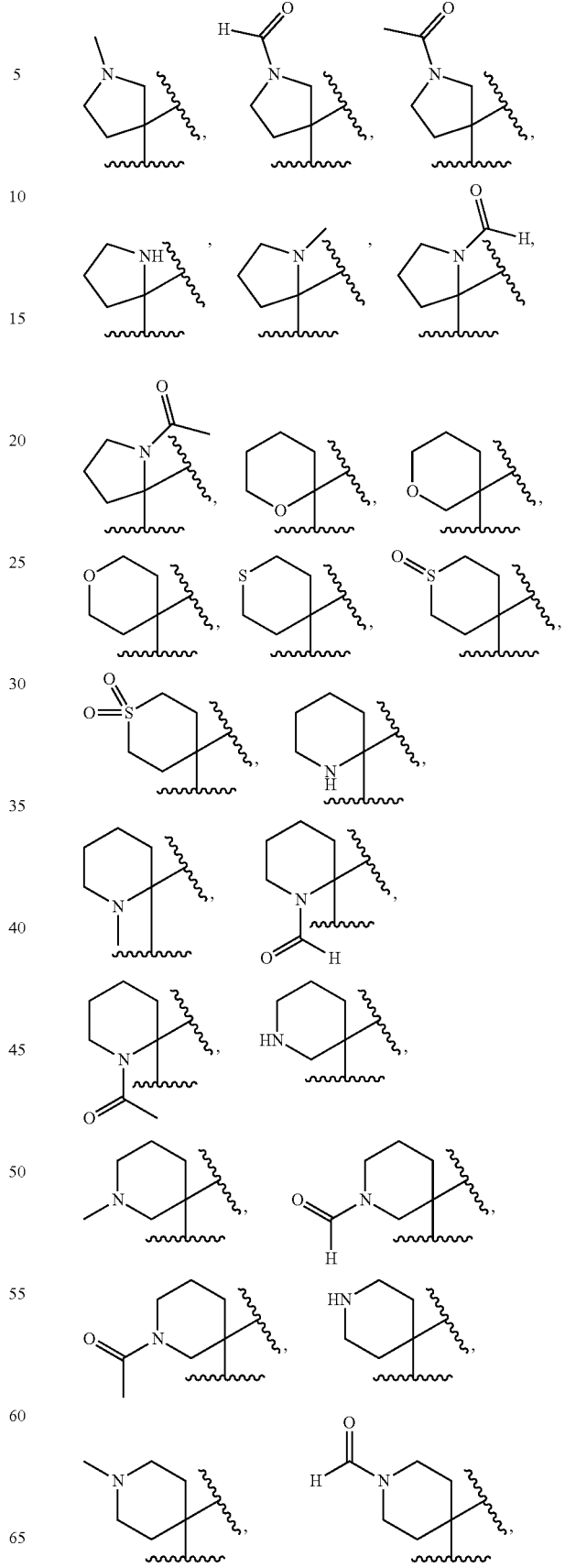

-continued

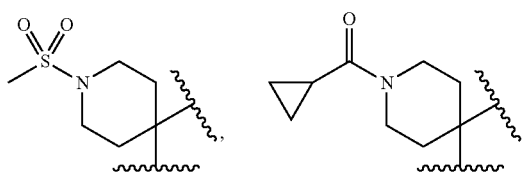
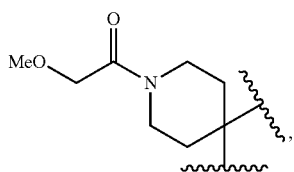
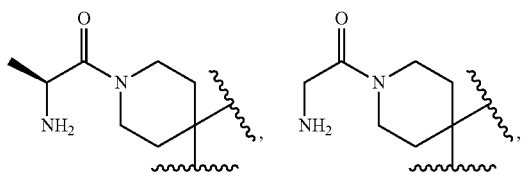
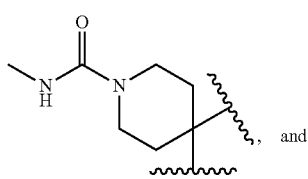, and
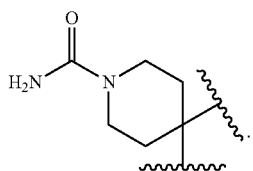.
In some embodiments, the compound of Formula I provided above has the following structure:
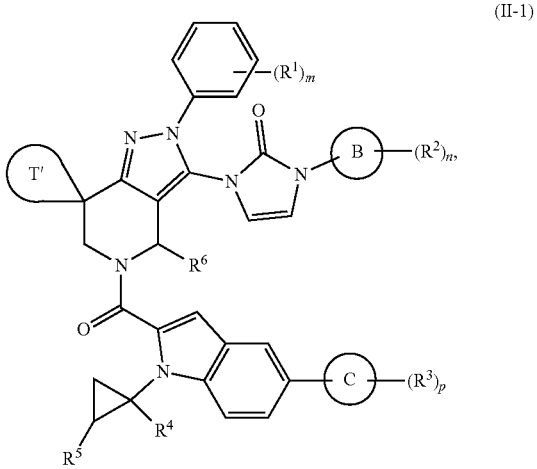
(II-1)
wherein
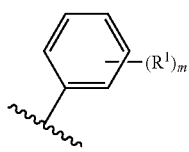
is selected from the group consisting of
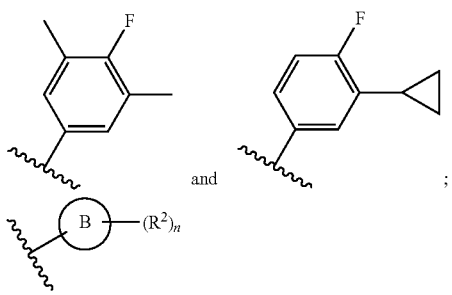
and ;
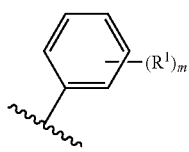
is selected from the group consisting of
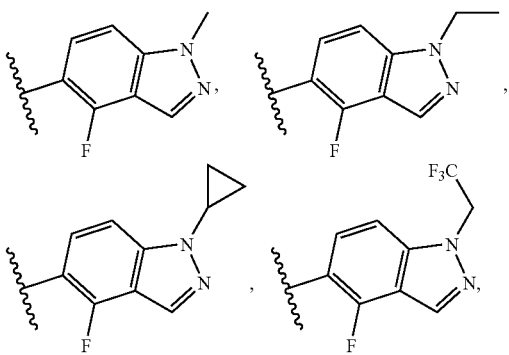

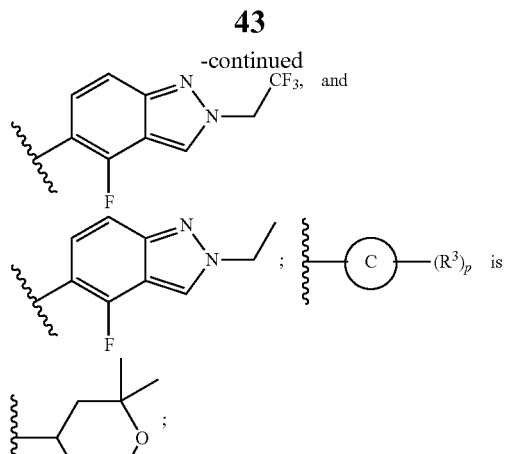

$R^4$ is

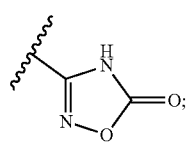

$R^5$ is methyl;

$R^6$ is methyl;

ring T' is independently selected from the group consisting of $C_{3-10}$ cycloalkyl, $C_{3-8}$ cycloalkenyl, 3- to 12-membered heterocyclyl, and 5- to 6-membered heteroaryl, and the ring is unsubstituted or substituted independently with 1, 2, or 3 $R^X$; and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl) amino, haloalkyl, acyl, sulfonyl, sulfonamido, and halogen.

Furthermore, in the above-mentioned compound, the ring T' is $C_{3-6}$ cycloalkyl, preferably $C_{3-4}$ cycloalkyl; the ring is unsubstituted or substituted independently with 1, 2, or 3 $R^X$, preferably 1 or 2 $R^X$; and each $R^X$ is independently selected from the group consisting of $C_{1-3}$ alkyl, vinyl, —O—$C_{1-6}$ alkyl, and halogen, preferably the group consisting of methyl, vinyl, methoxy, and fluorine.

Preferably, in the above-mentioned compound, the ring T' is selected from the group consisting of

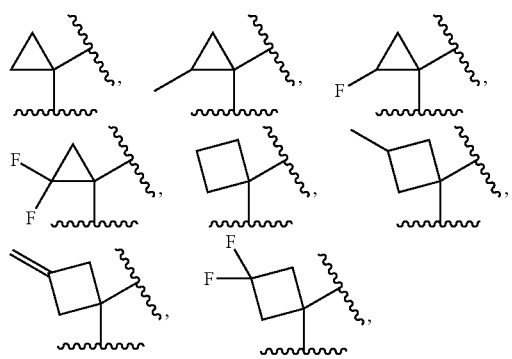

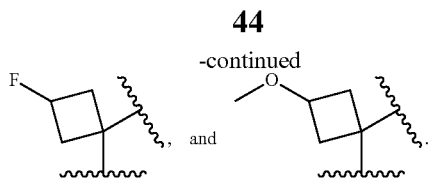

In some embodiments, the compound of Formula I provided above has the following structure:

(II-1-1)

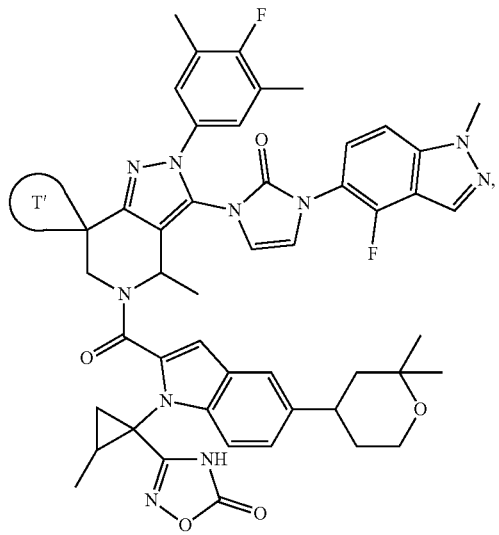

wherein ring T' is independently selected from the group consisting of $C_{3-10}$ cycloalkyl, $C_{3-8}$ cycloalkenyl, 3- to 12-membered heterocyclyl, and 5- to 6-membered heteroaryl, and the ring is unsubstituted or substituted independently with 1, 2, or 3 $R^X$; and each $R^X$ is independently selected from the group consisting of hydroxyl, oxo, $C_{1-6}$ alkyl, $C_{2-6}$ alkenyl, $C_{2-6}$ alkynyl, $C_{3-6}$ cycloalkyl, cyano, alkoxy, alkylamino, di(alkyl) amino, haloalkyl, acyl, sulfonyl, sulfonamido, and halogen.

Furthermore, in the above-mentioned compound, the ring T' is $C_{3-6}$ cycloalkyl, preferably $C_{3-4}$ cycloalkyl; the ring is unsubstituted or substituted independently with 1, 2, or 3 $R^X$, preferably 1 or 2 $R^X$; and each $R^X$ is independently selected from the group consisting of $C_{1-3}$ alkyl, vinyl, —O—$C_{1-6}$ alkyl, and halogen, preferably the group consisting of methyl, vinyl, methoxy, and fluorine.

Preferably, in the above-mentioned compound, the ring T' is selected from the group consisting of

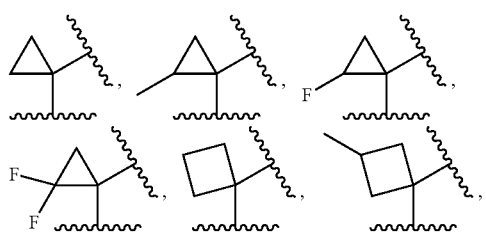

-continued
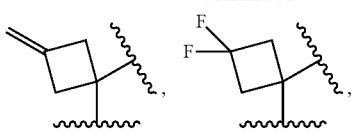
preferably the group consisting of
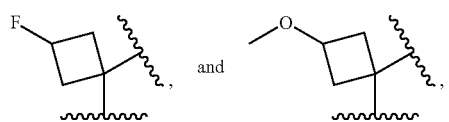
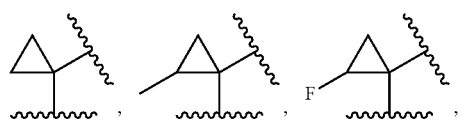
and
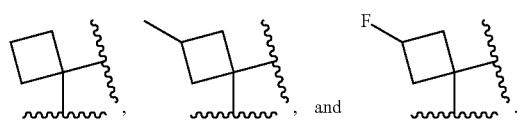
Non-limiting illustrative compounds of the present disclosure are as shown below:
1
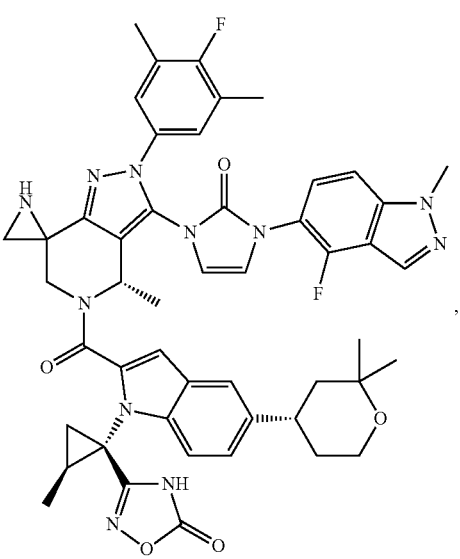
-continued
2
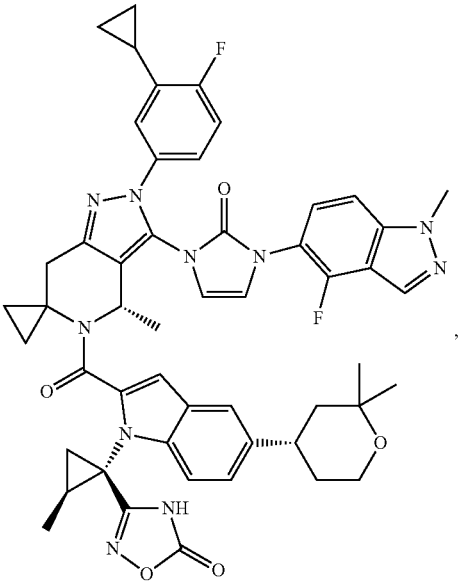
,
3

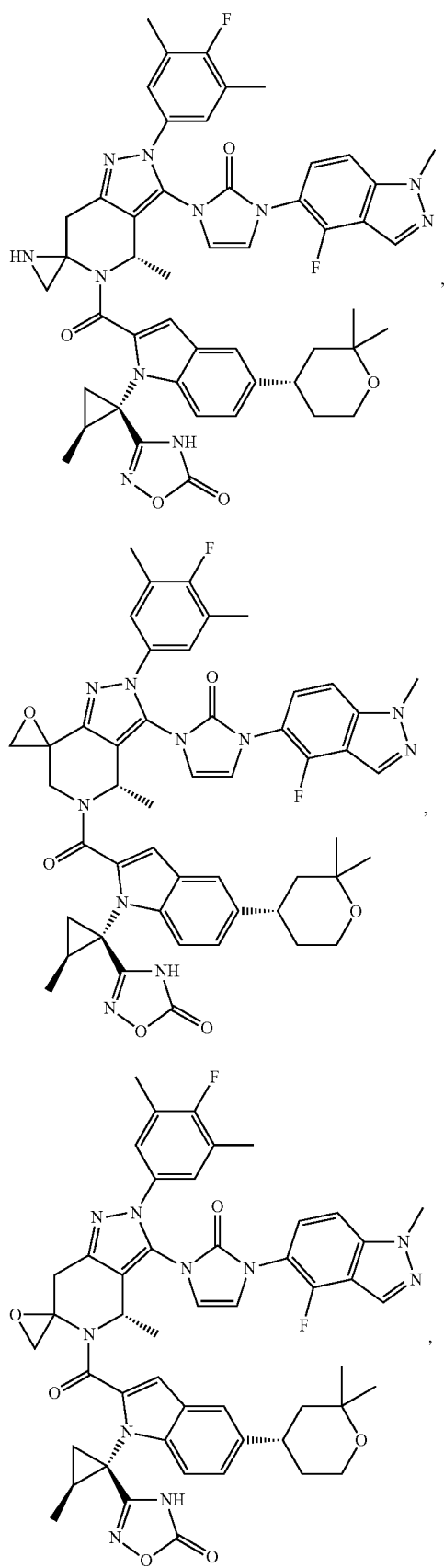
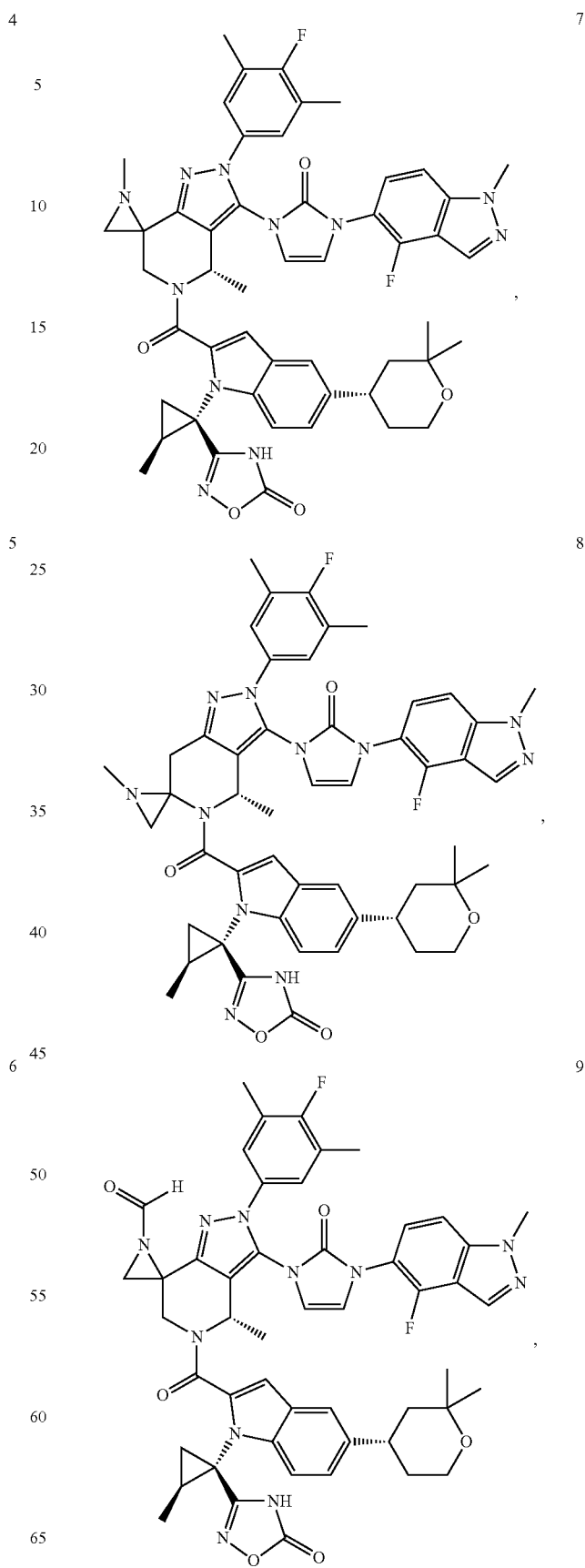

49
-continued
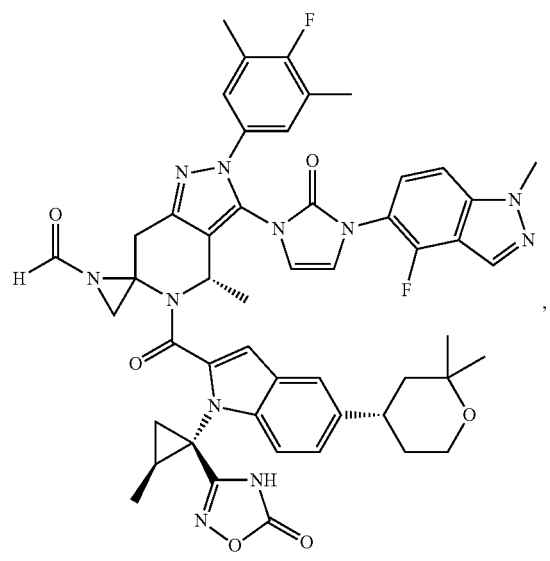
10
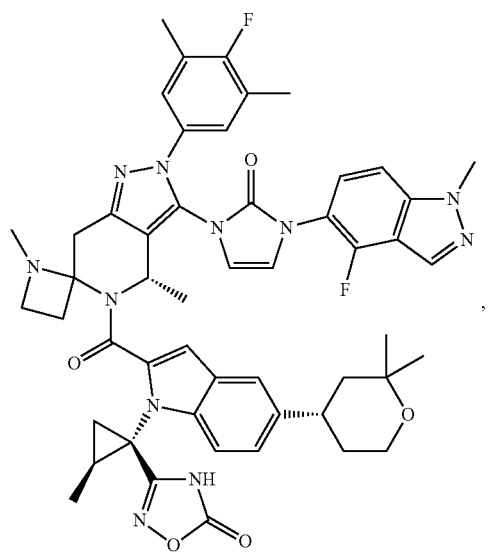
11
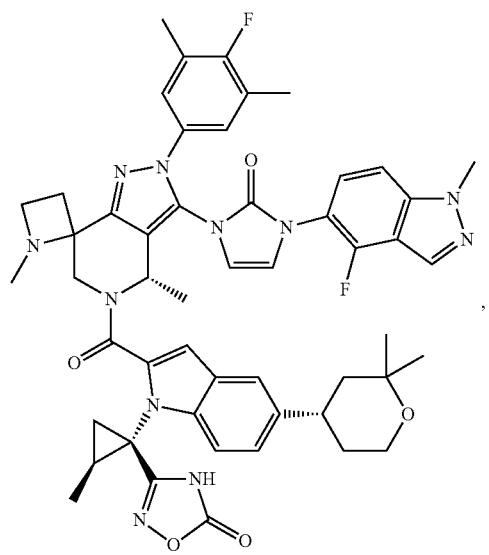
12
50
-continued
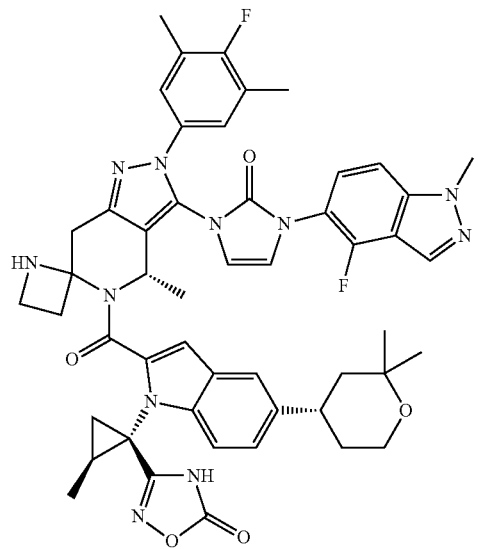
13
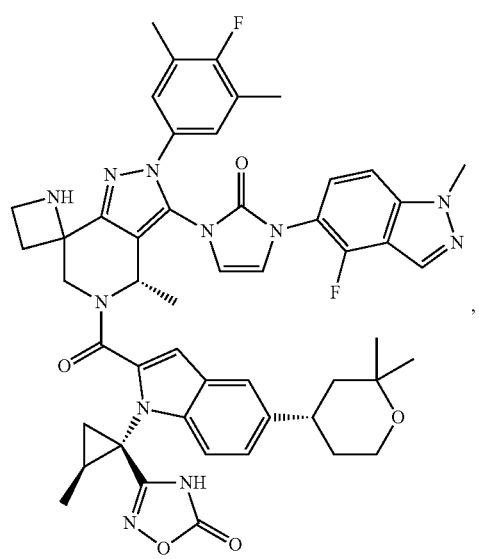
14
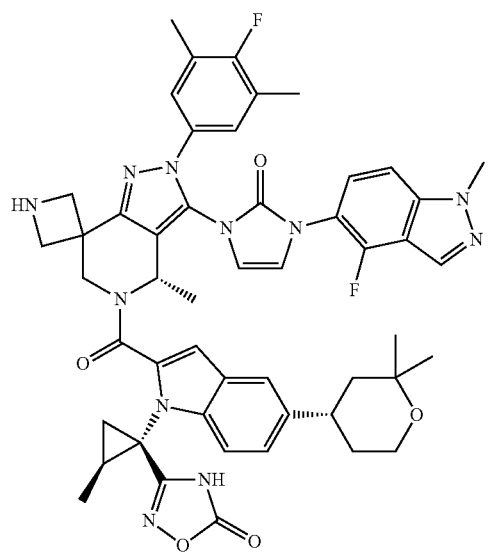
15

16
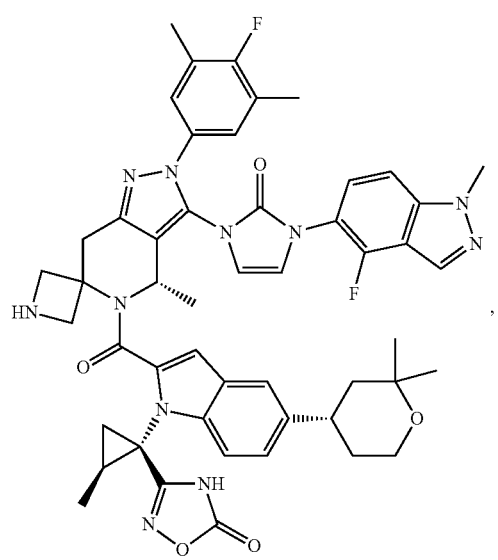
,
17
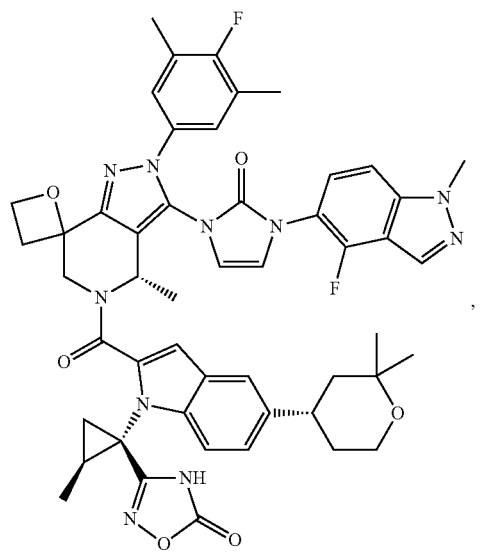
,
18
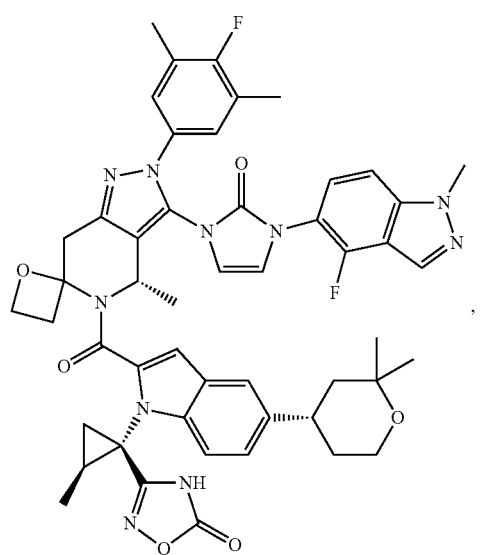
,
19
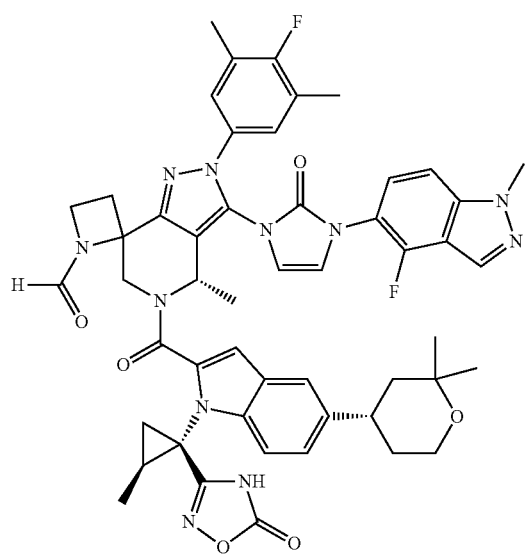
,
20
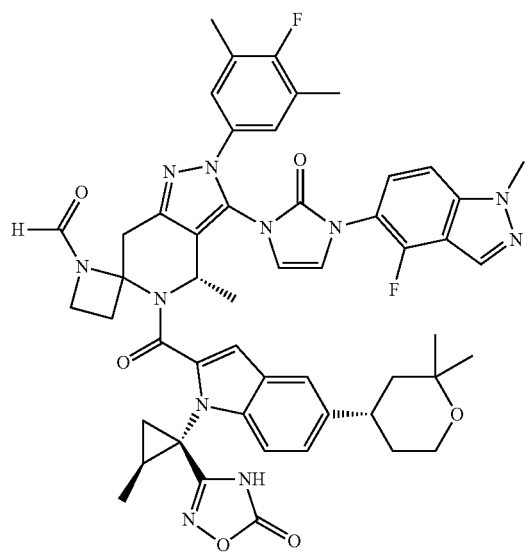
, 21
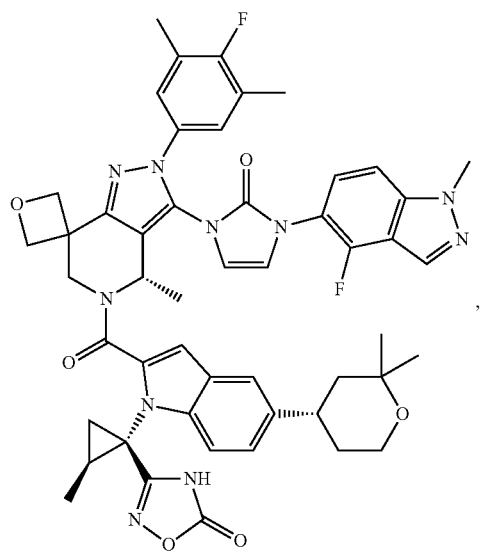
,
22
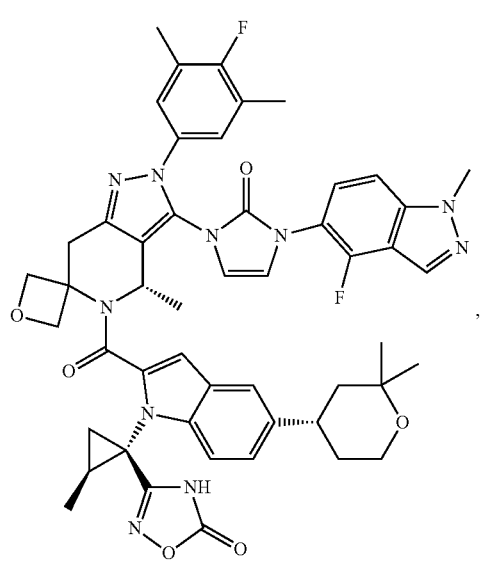
,
23
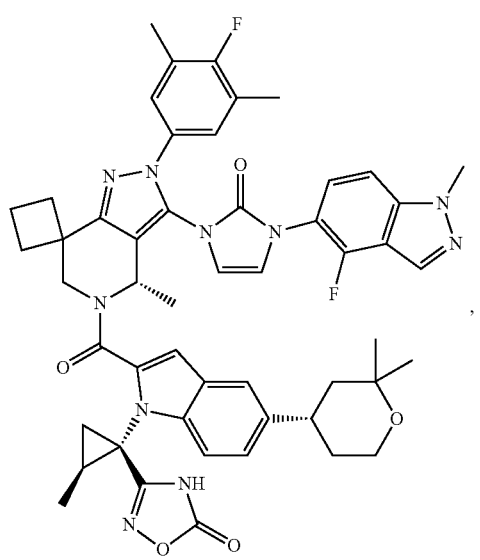
,
24
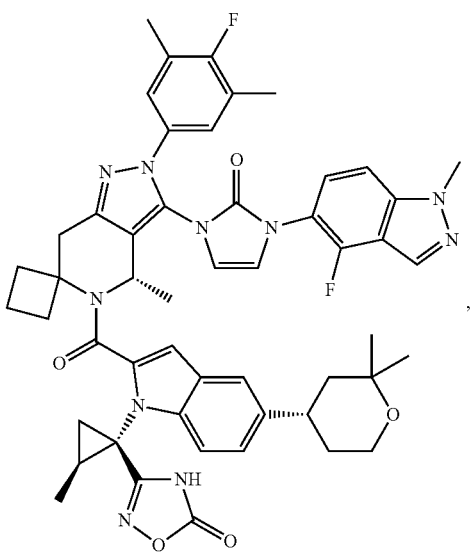
,
25
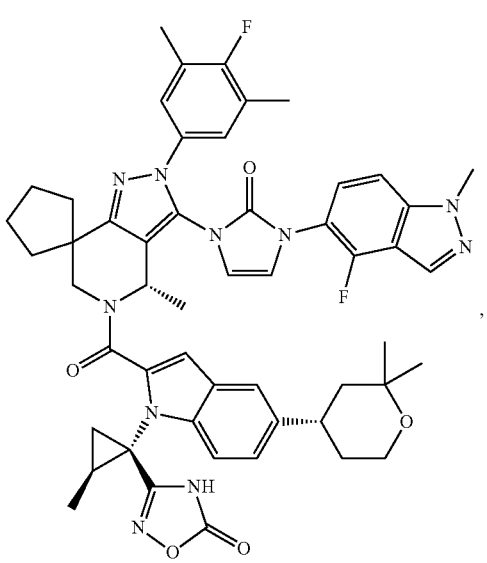
,
26
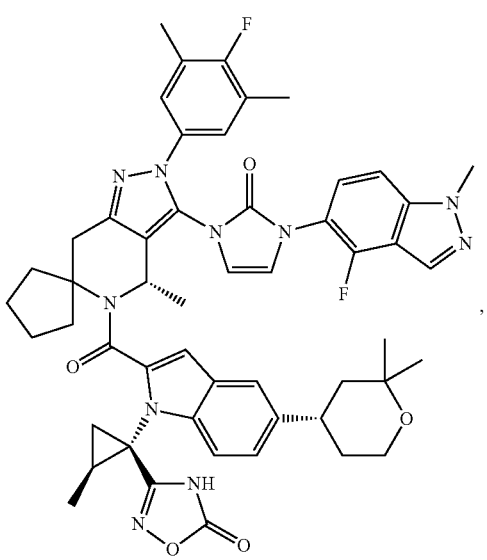
, 27
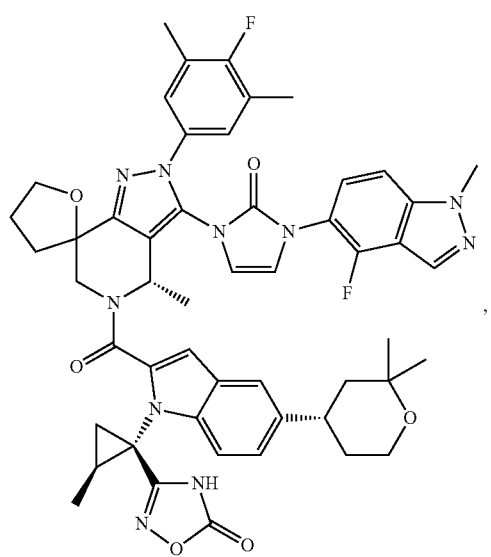
28
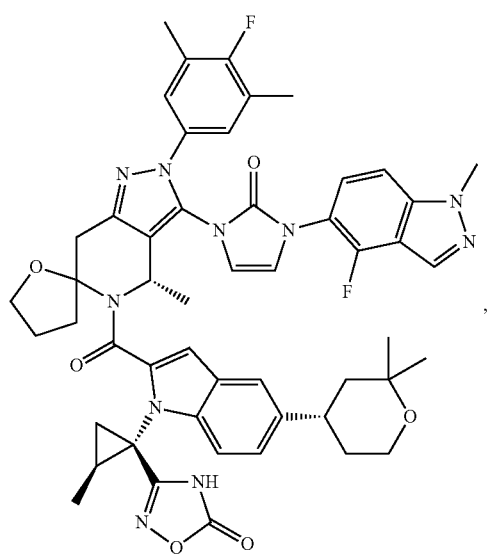
29
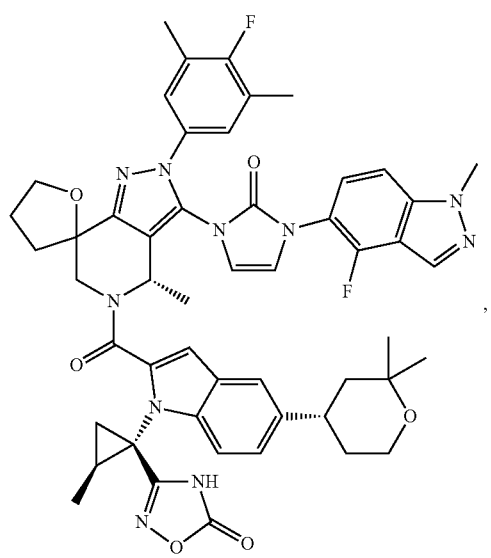
30
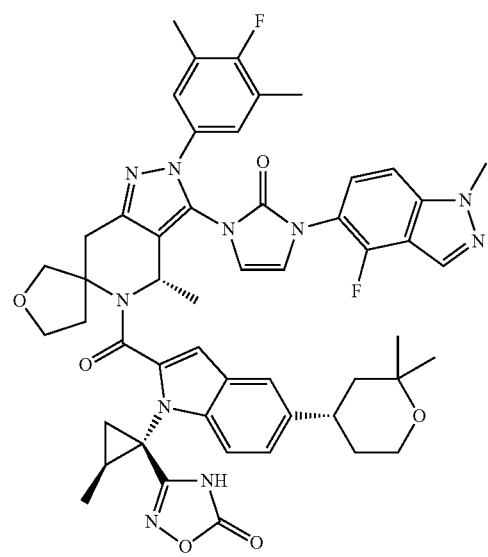
31
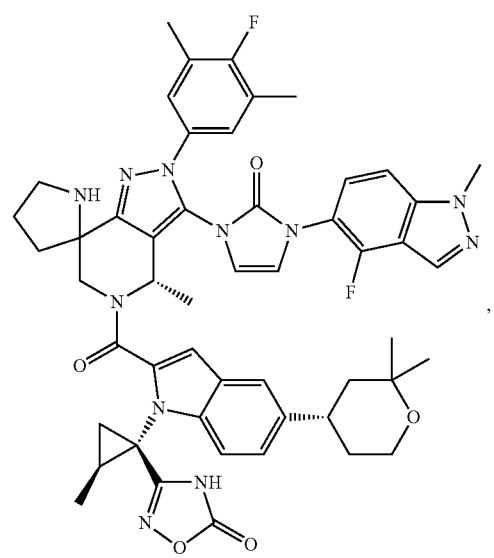
32
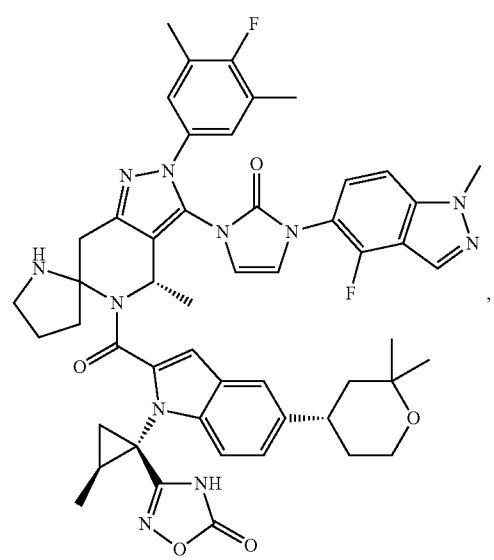

33
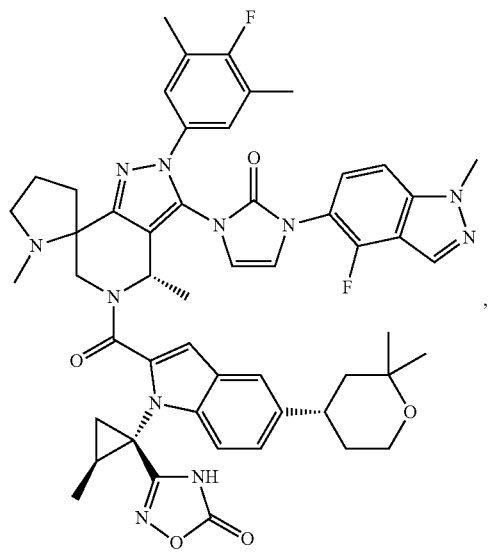
34
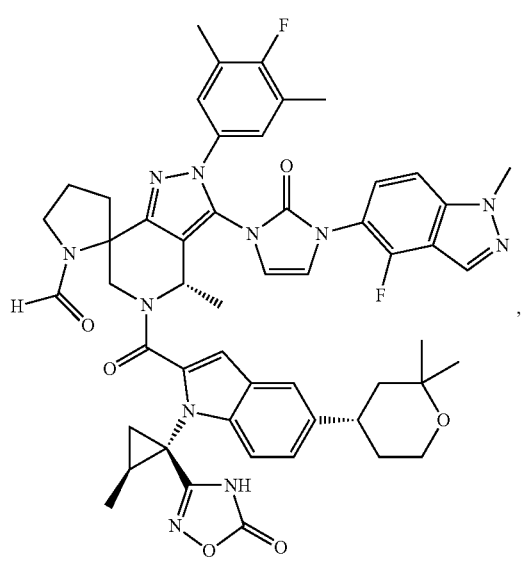
36
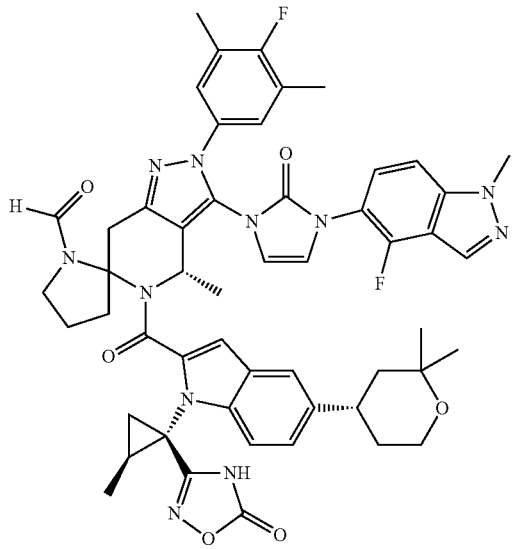
37
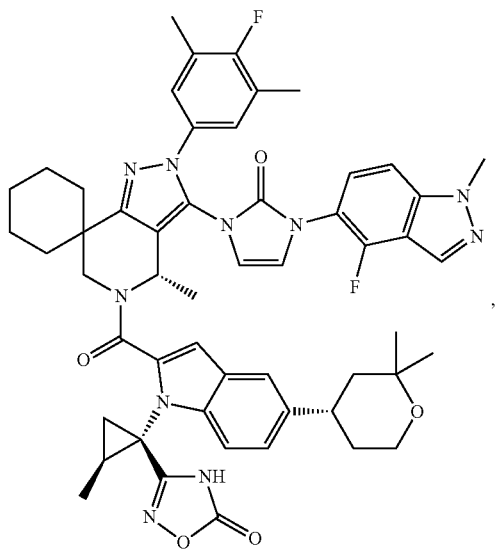
38
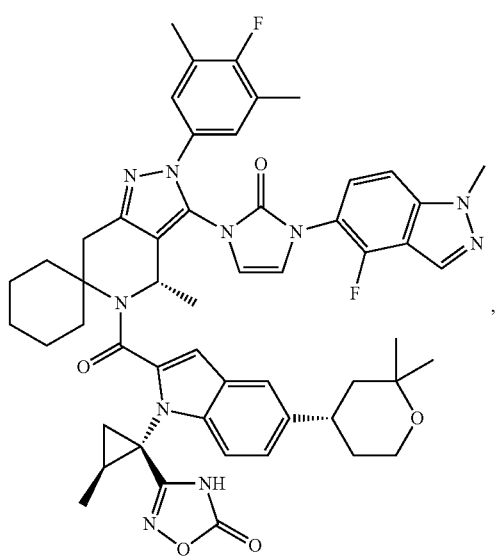

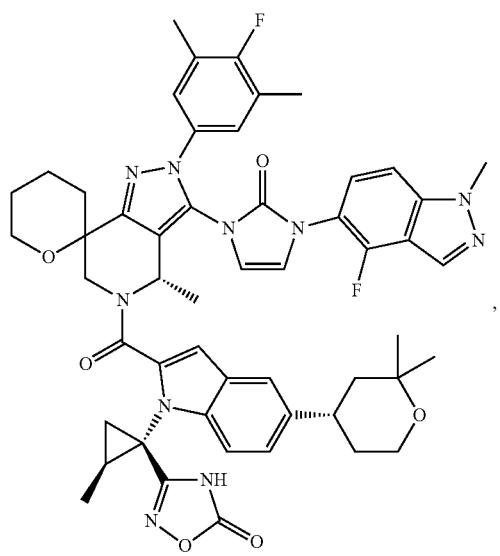
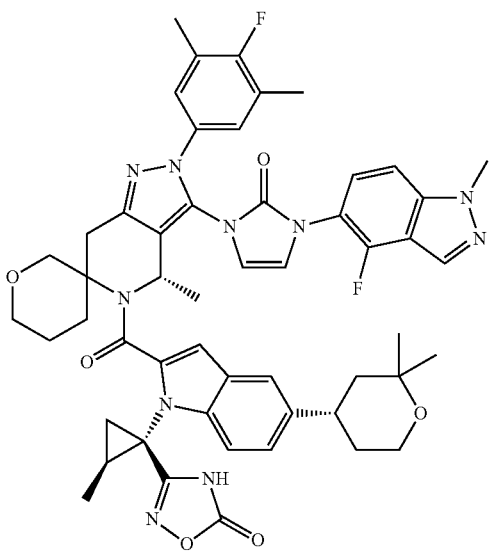
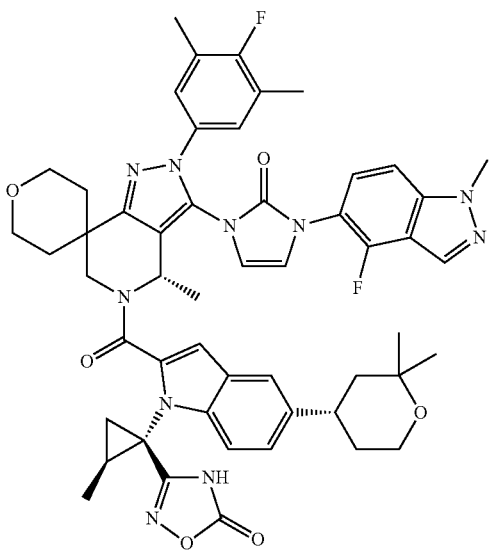

44
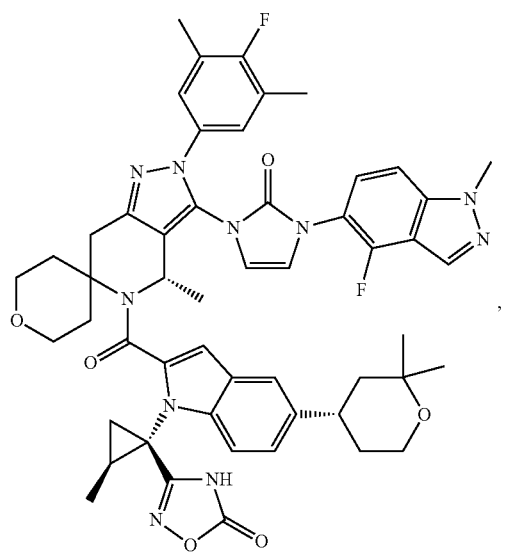
,
46
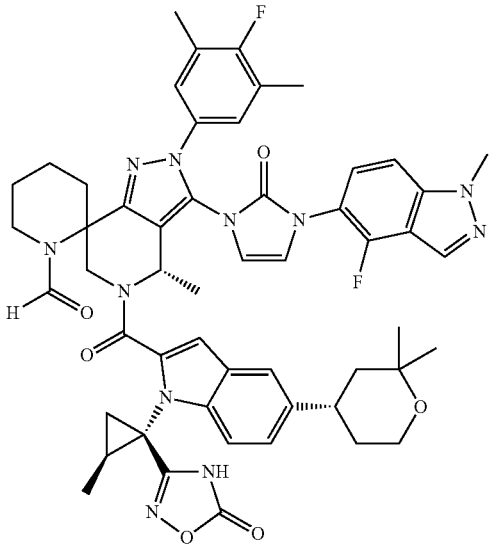
,
47
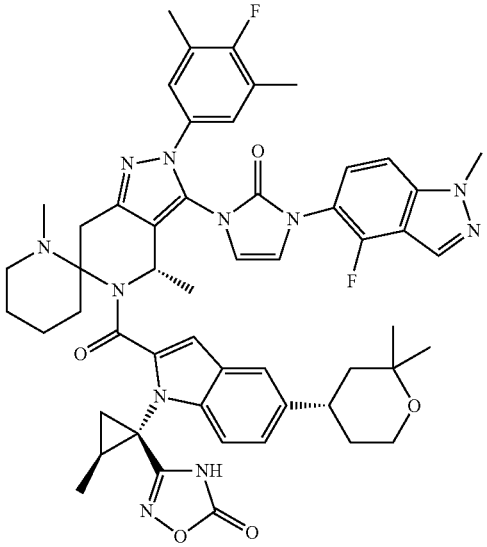
,
45
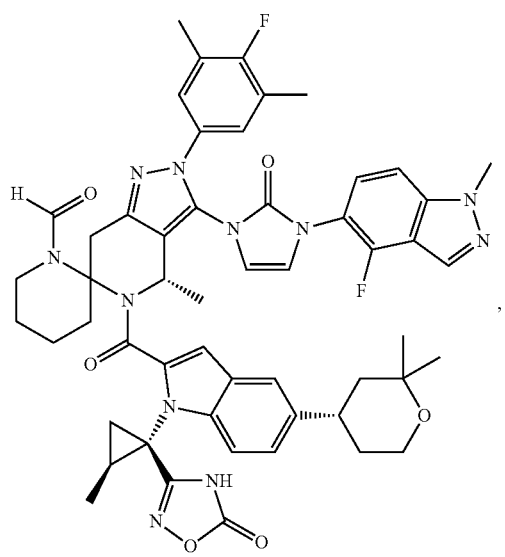
,
48
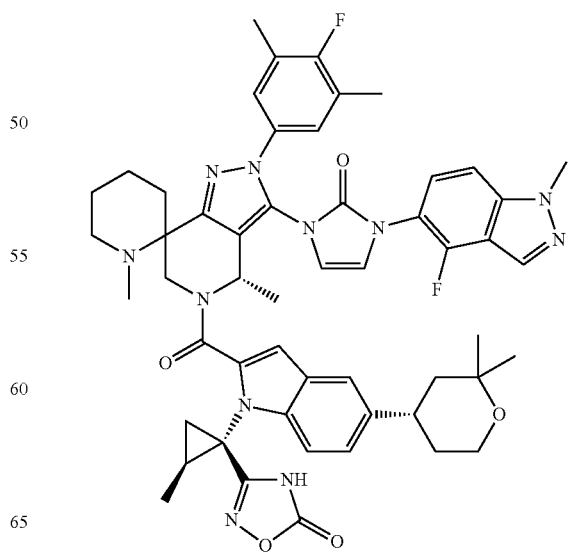
, -continued
49
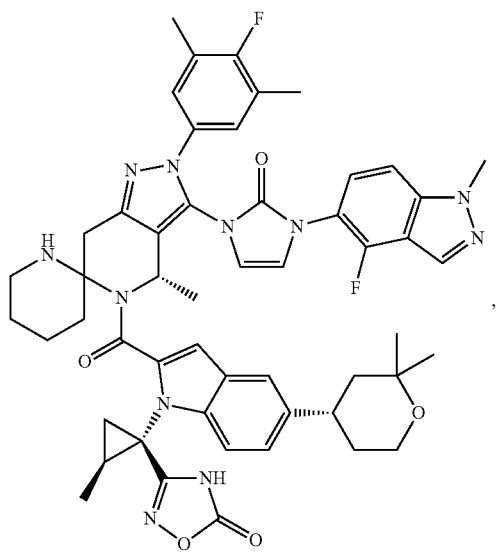
50
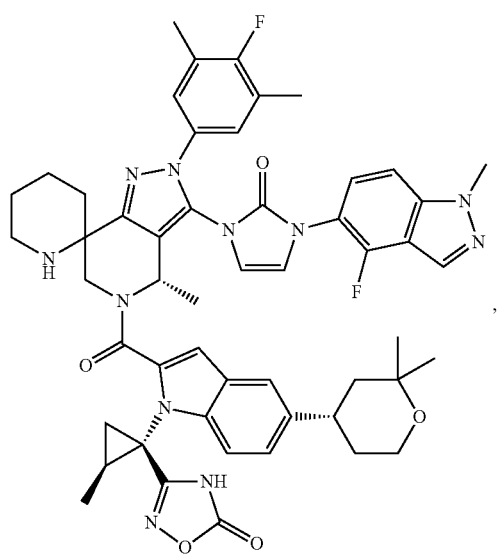
51
52
-continued
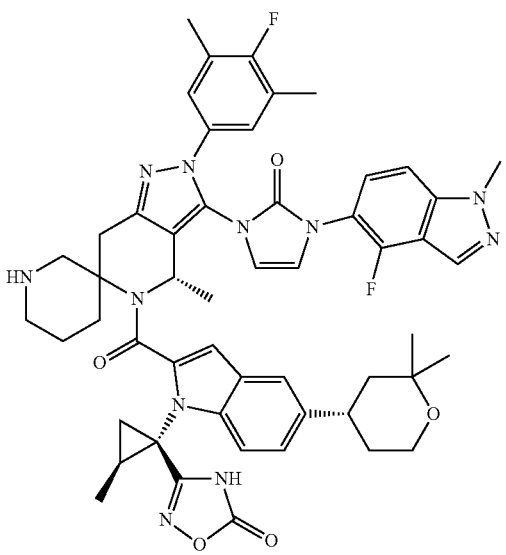
53
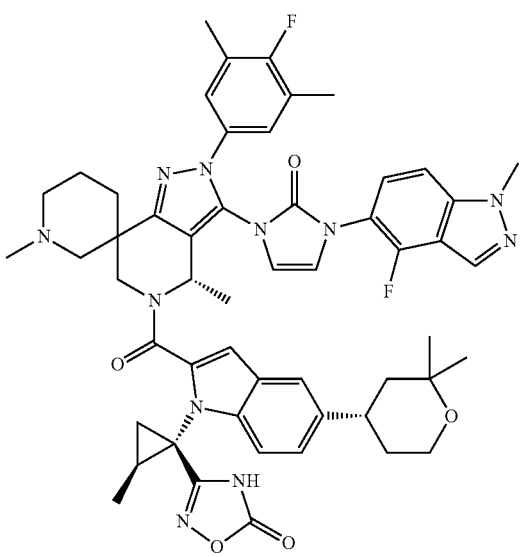

54
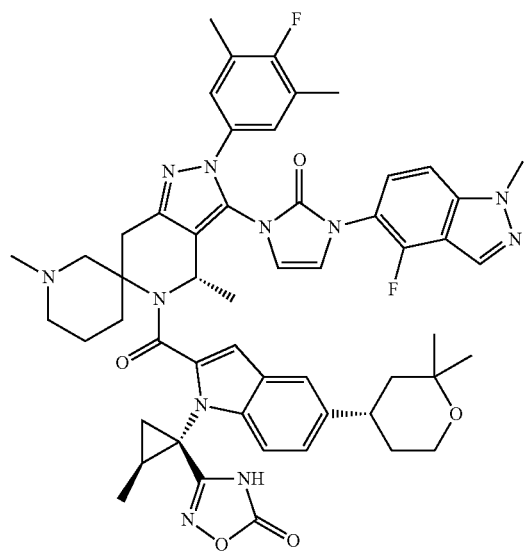
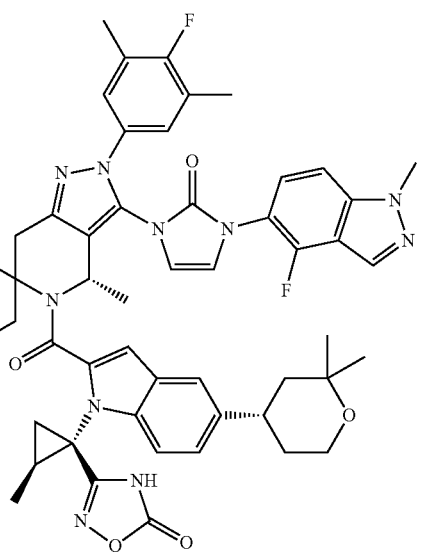
55
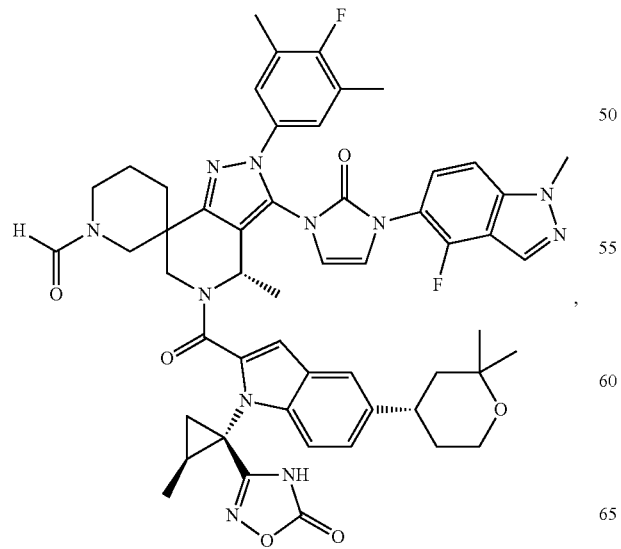
57
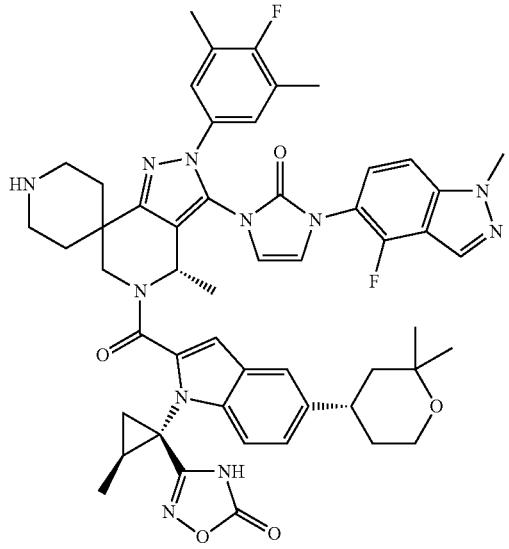

58
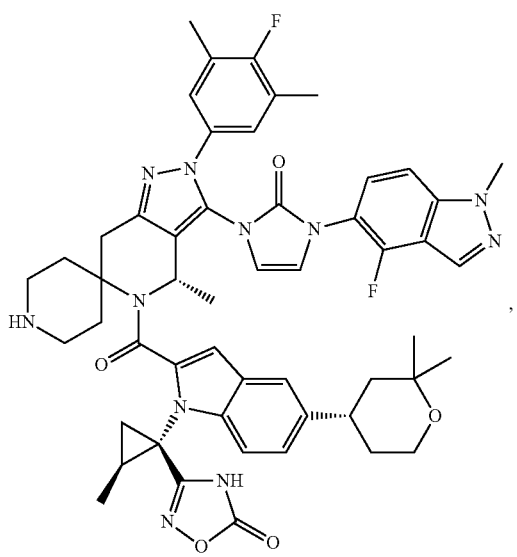
,
59
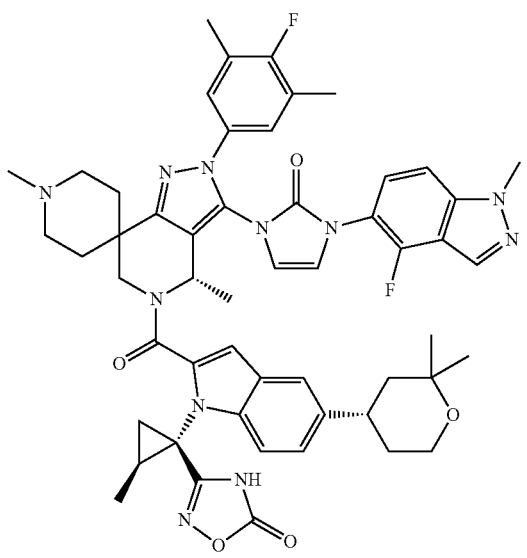
,
60
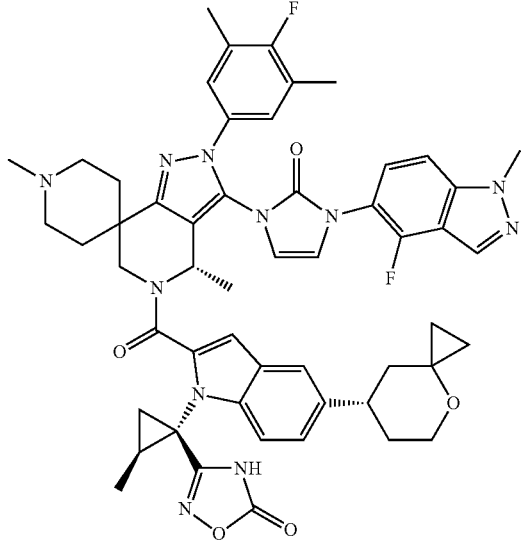
,
61
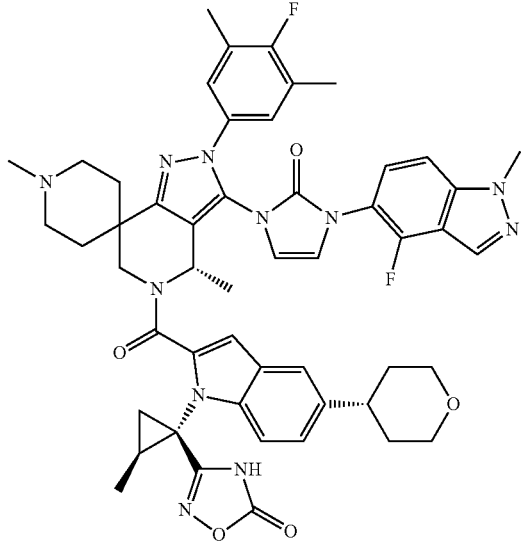
,

69
62
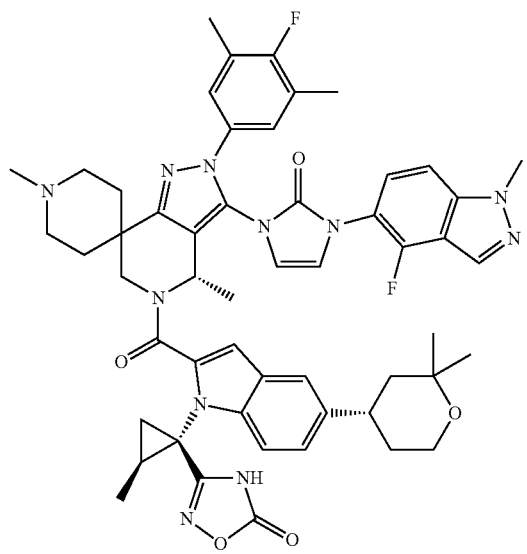
63
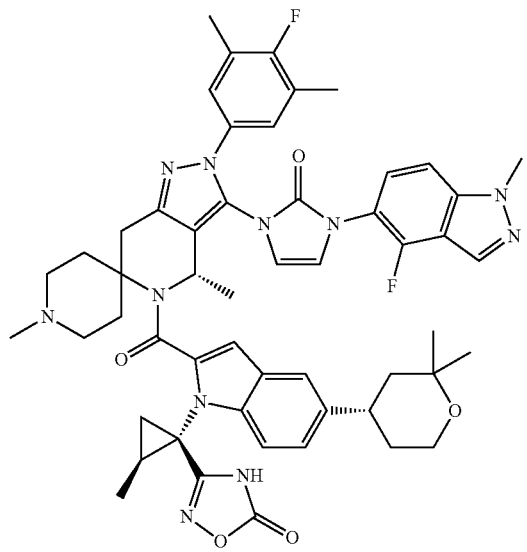
70
64
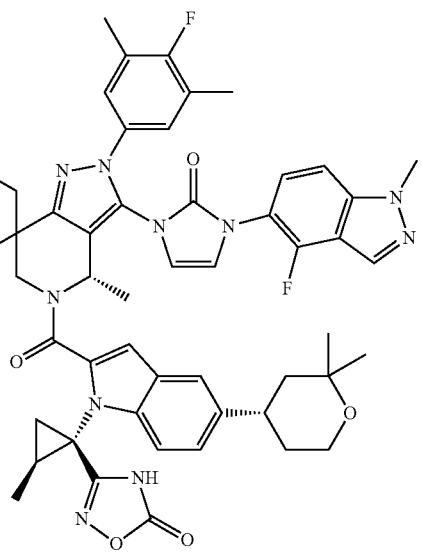
65
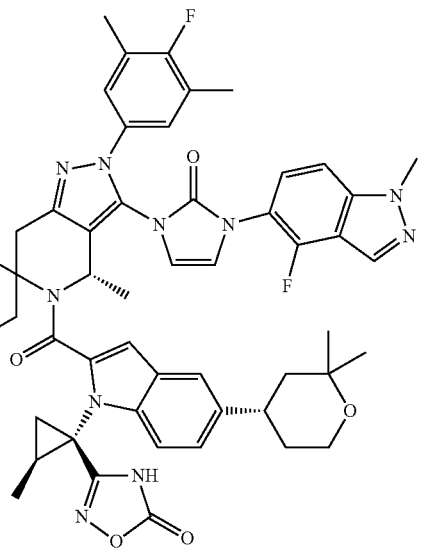

66
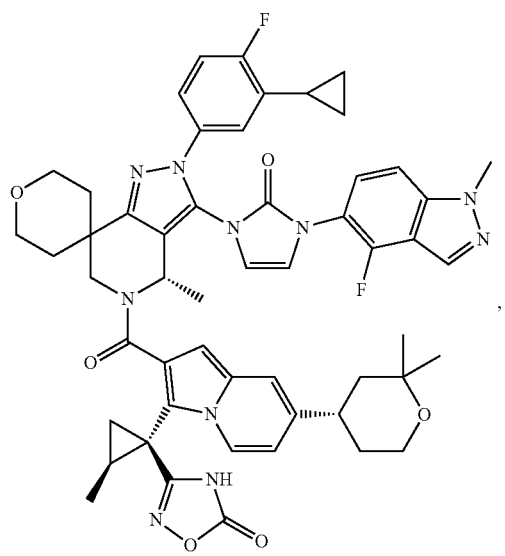
67
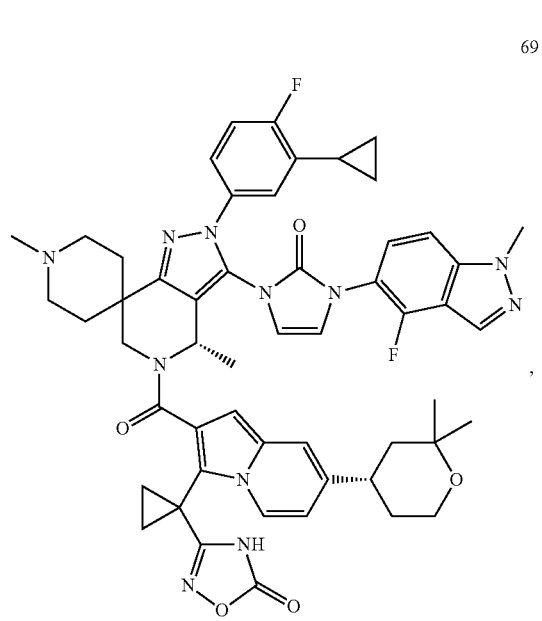
68
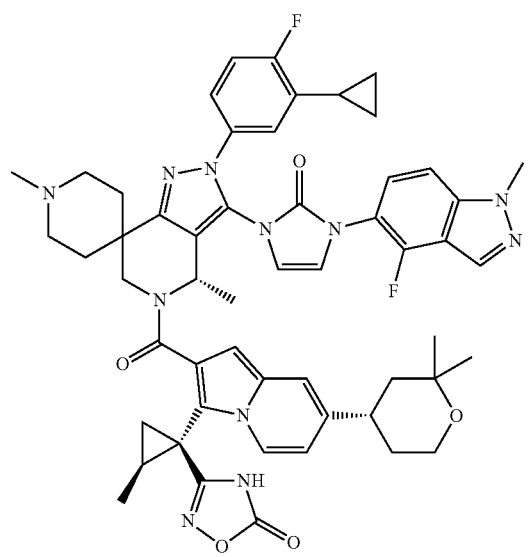
69

-continued
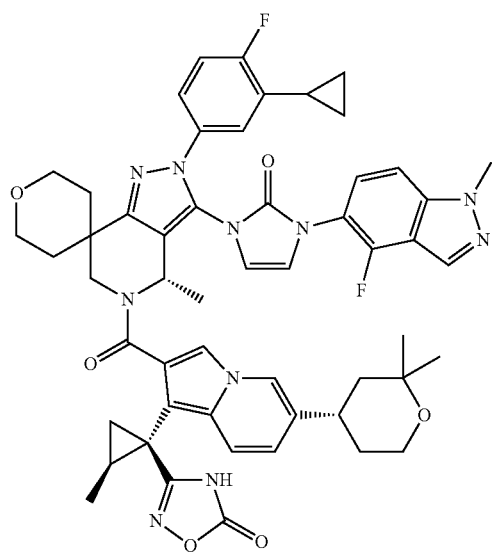
70
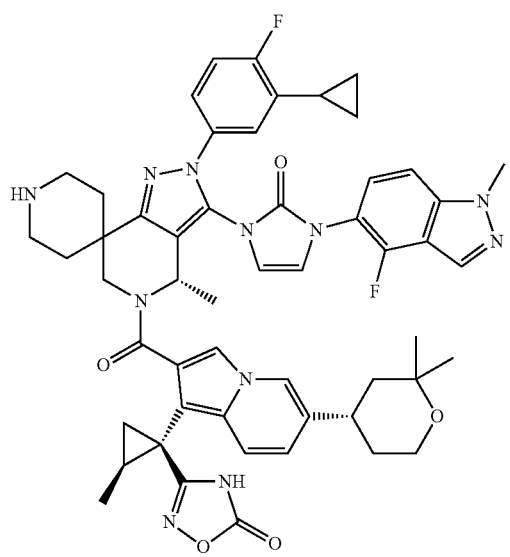
71
-continued
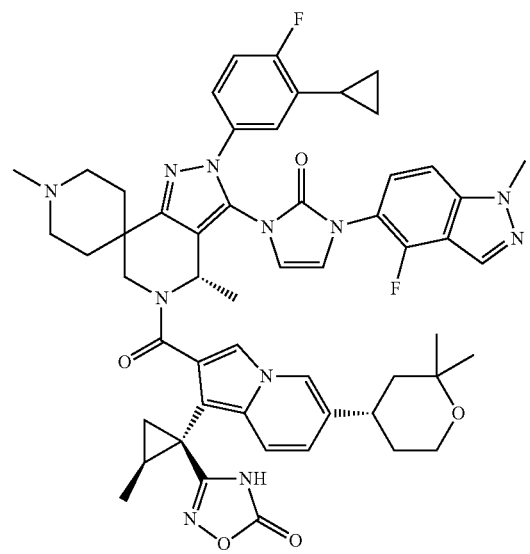
72
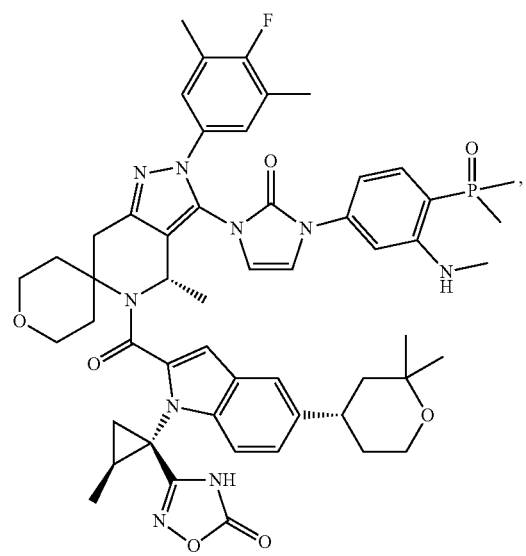
73

74
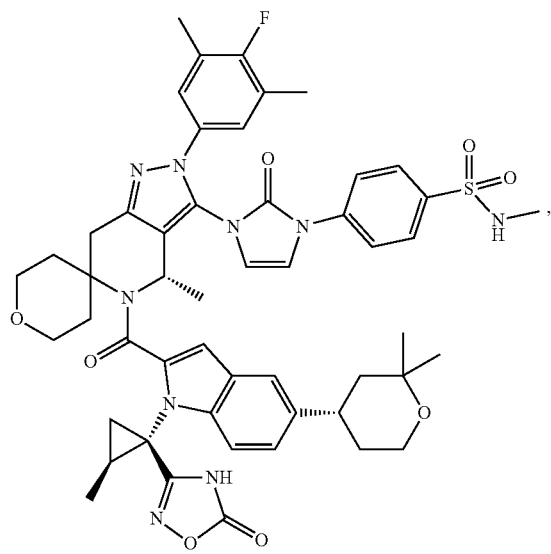
75
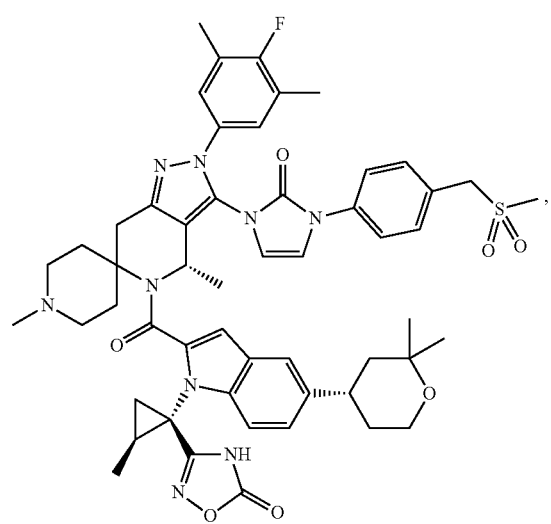
76
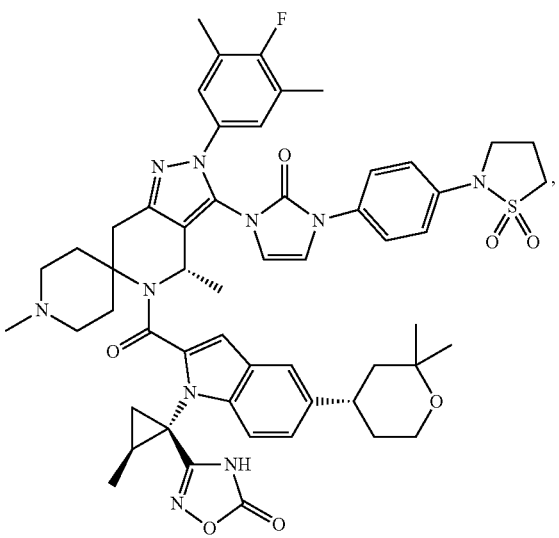
77
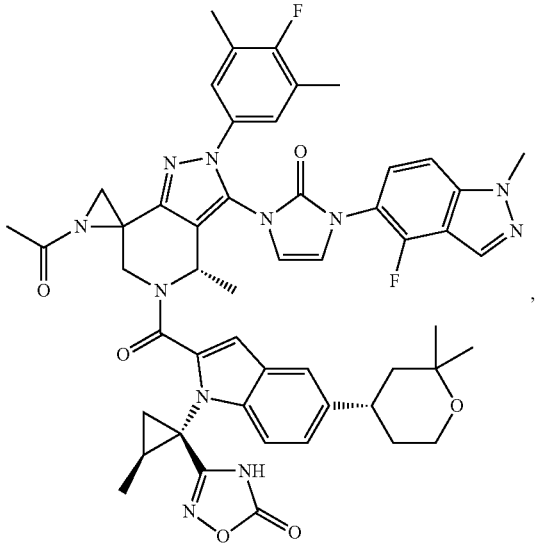
78
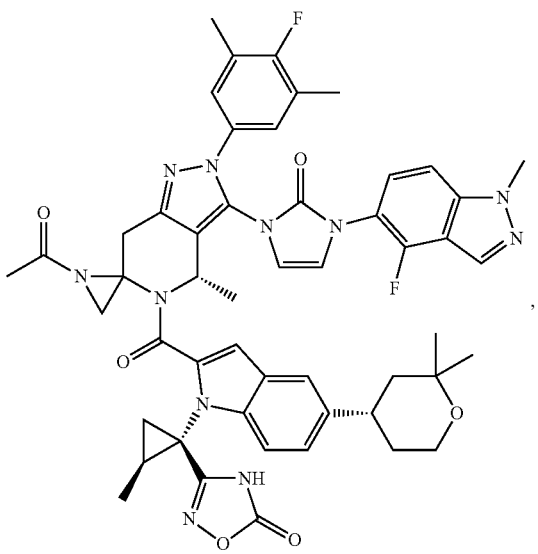

77
-continued
79
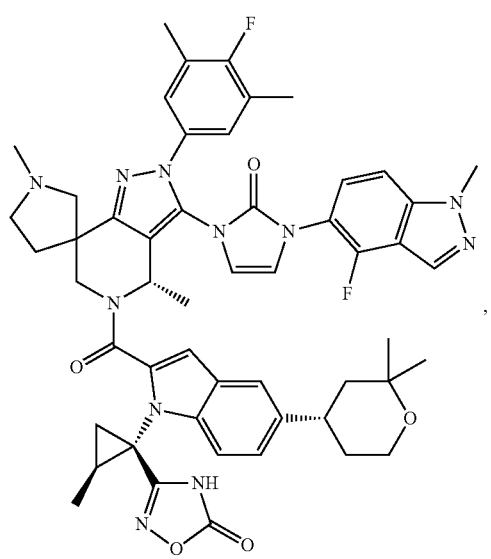
80
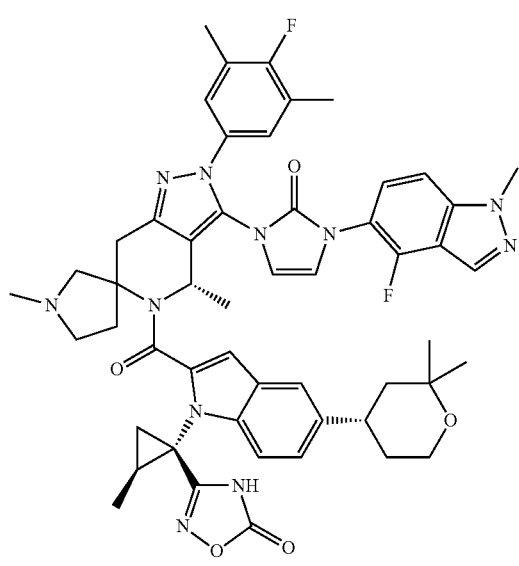
78
-continued
81
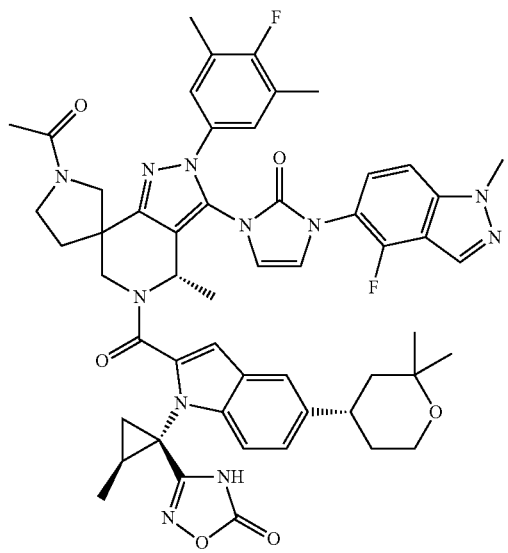
82
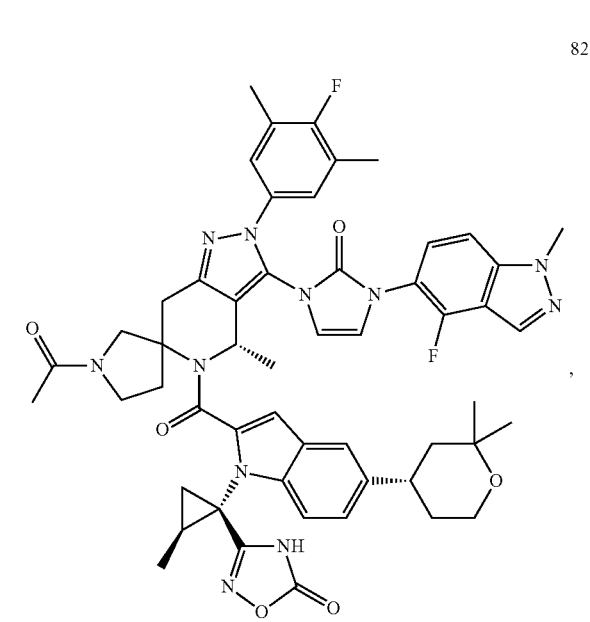

83
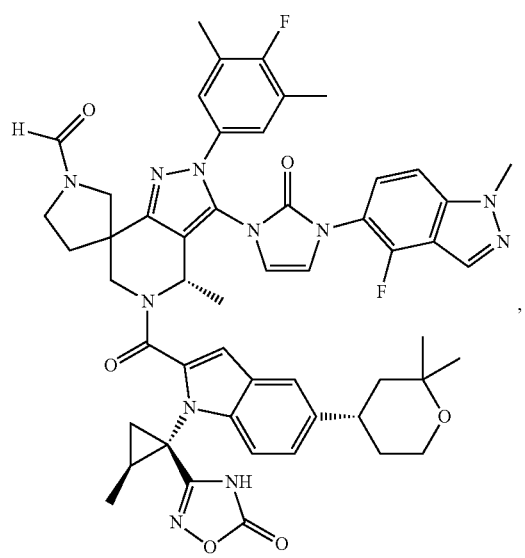
84
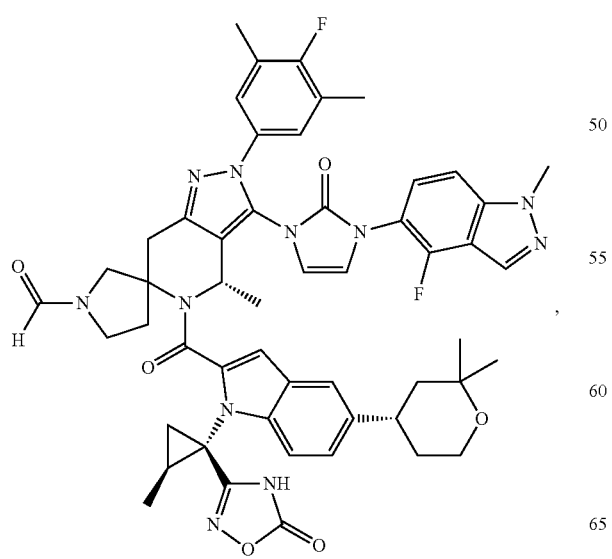
85
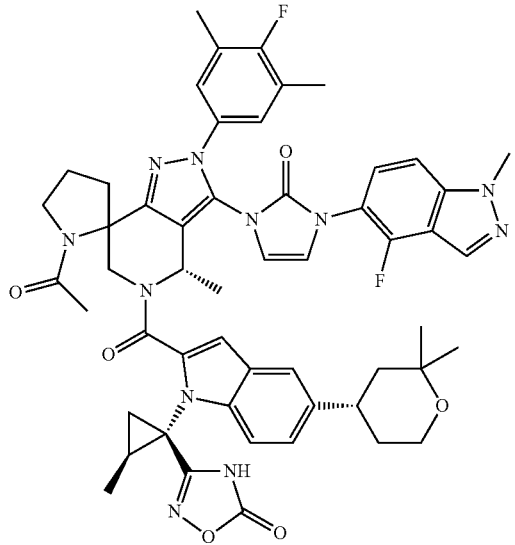
86
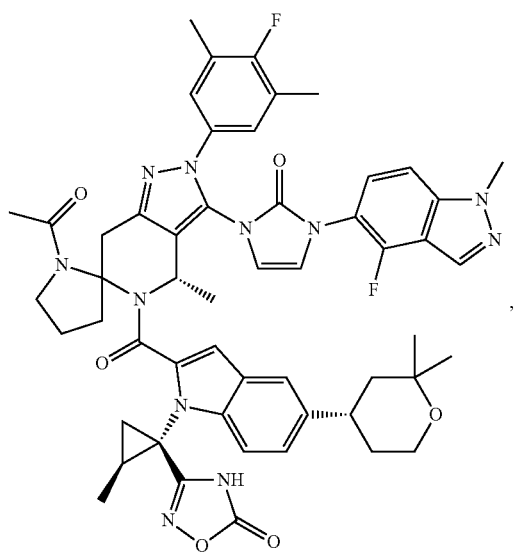

87
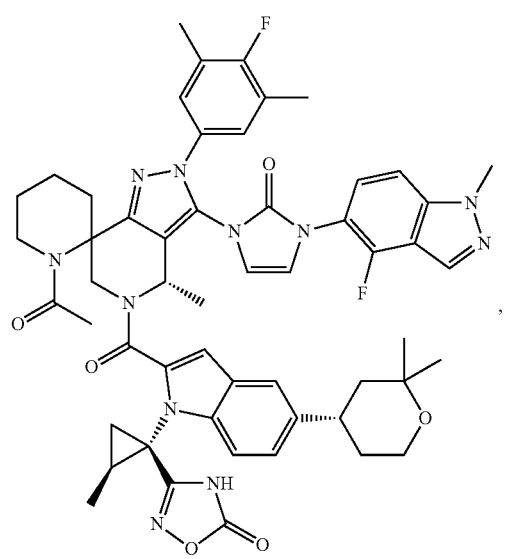
88
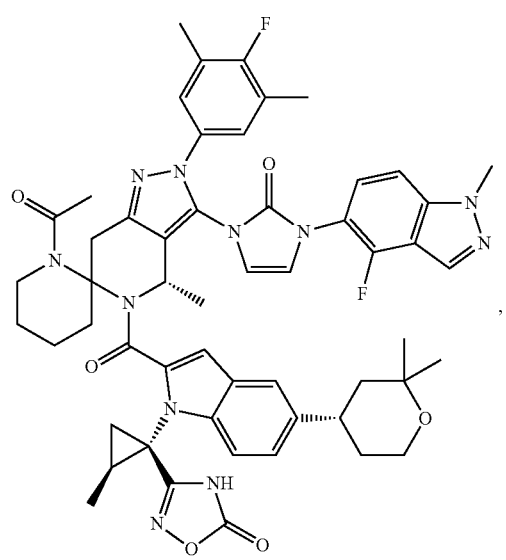
89
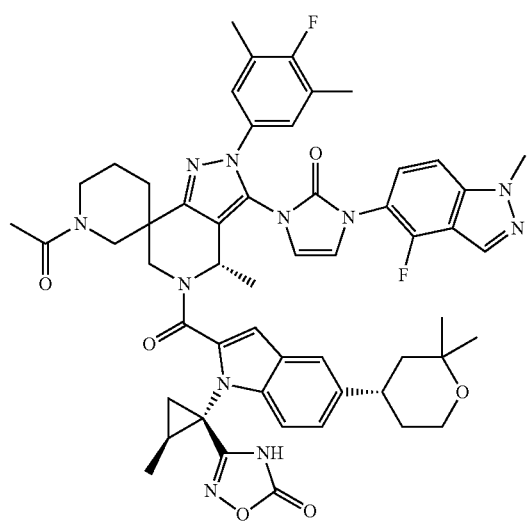
90
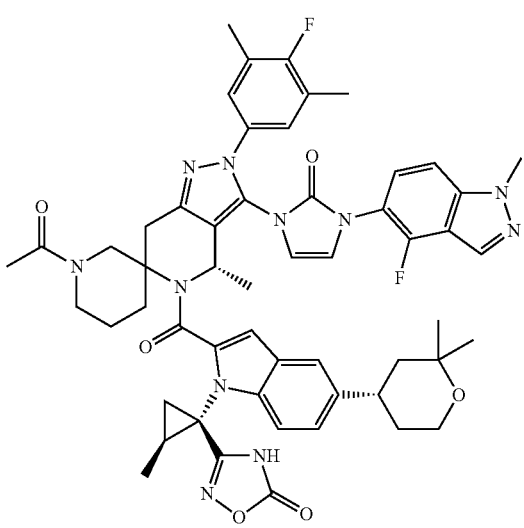
91
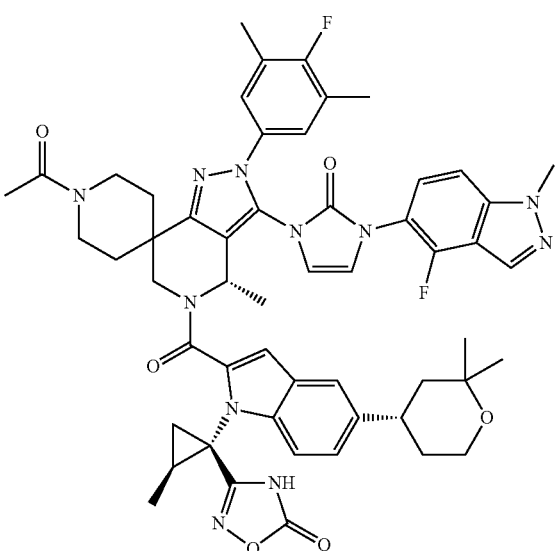
92
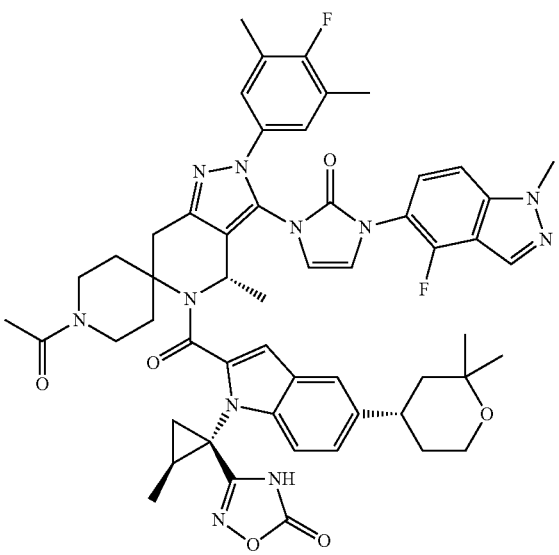

93
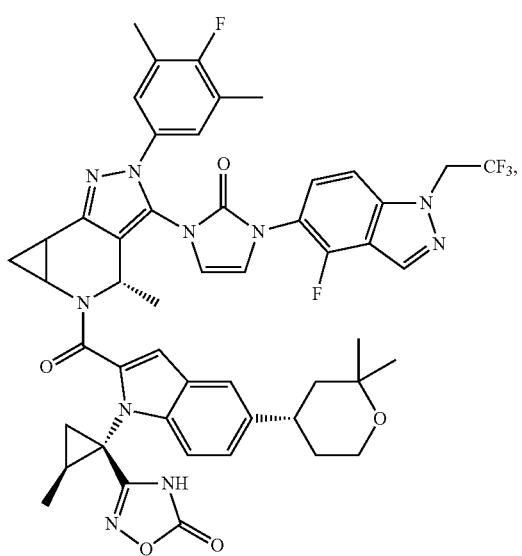
94
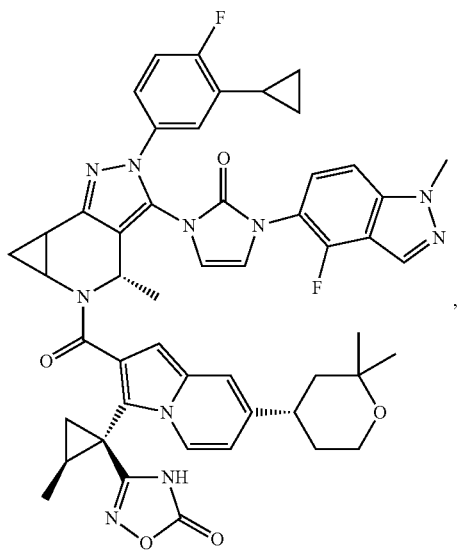
95
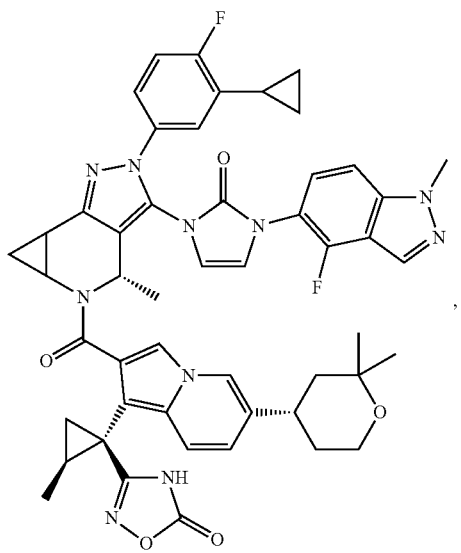
96
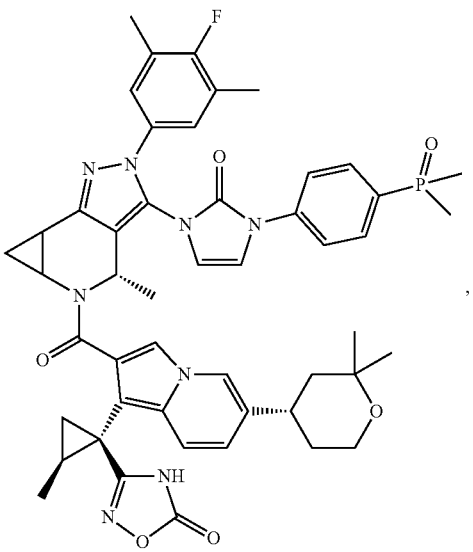
97
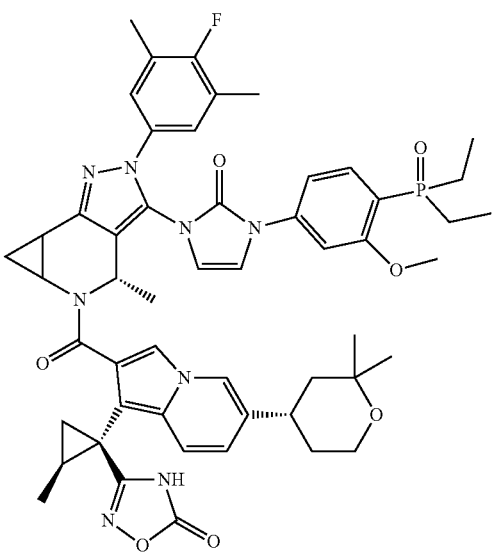

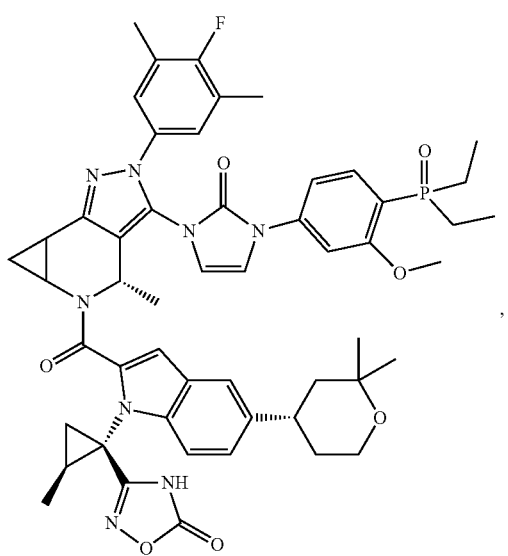
98
99
100
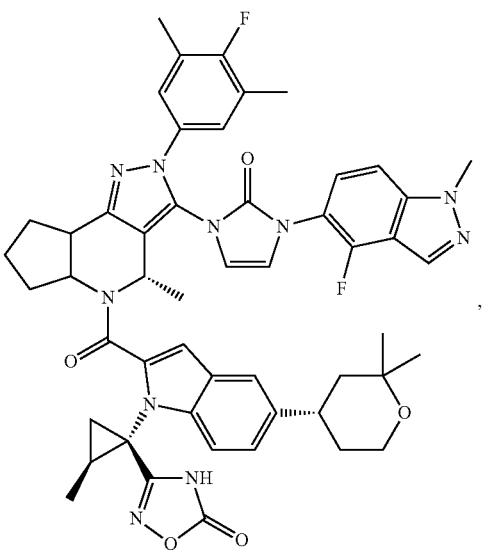
101
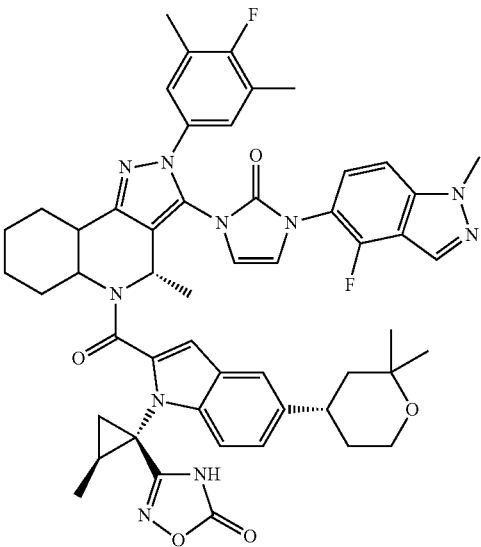
102

103
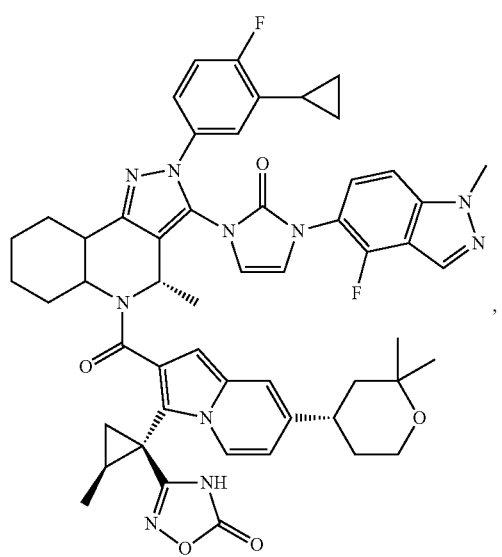
,
104
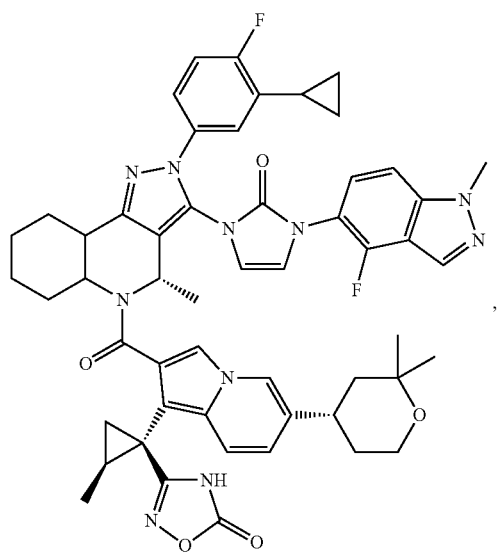
,
105
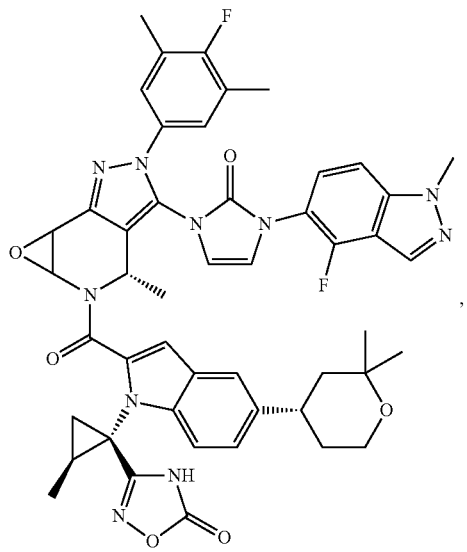
,
106
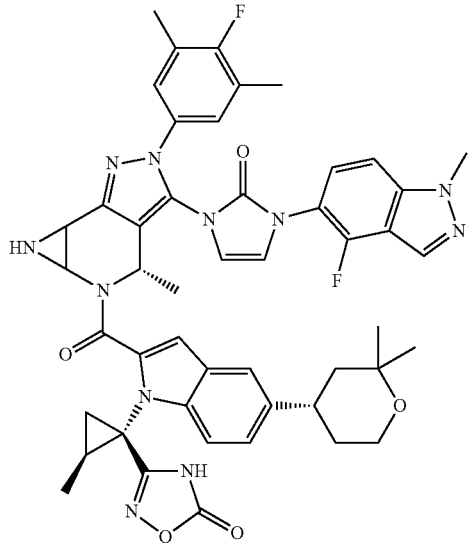
,
107
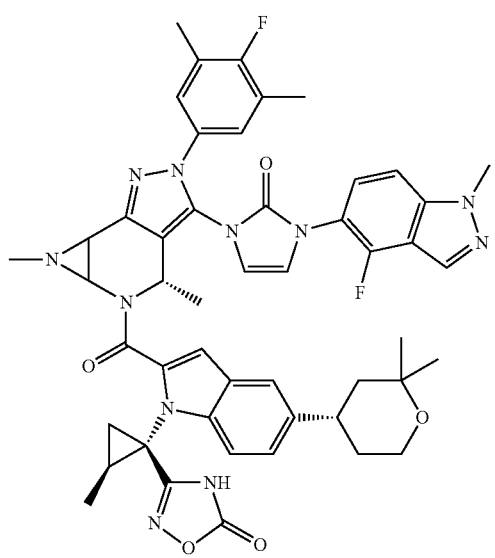
,

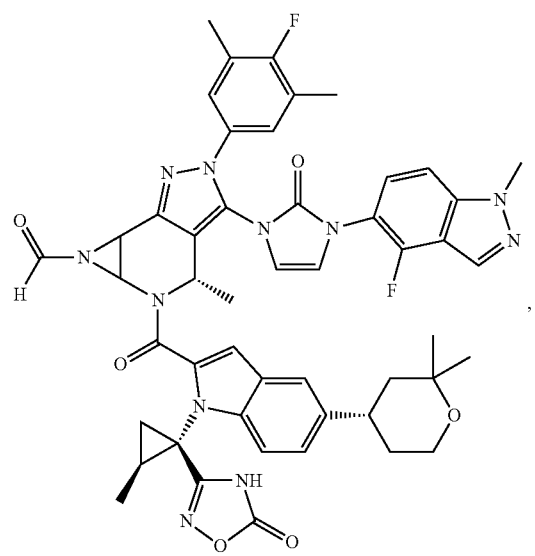
108
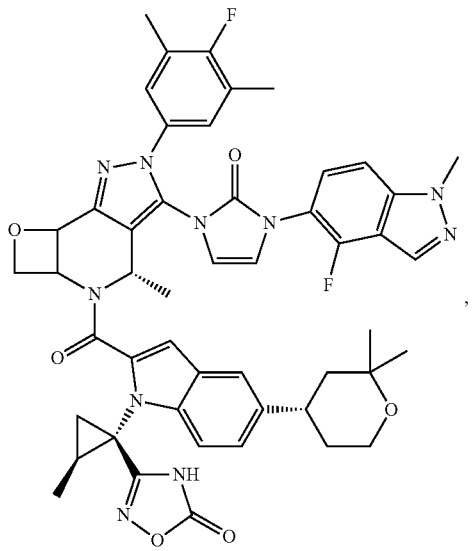
110
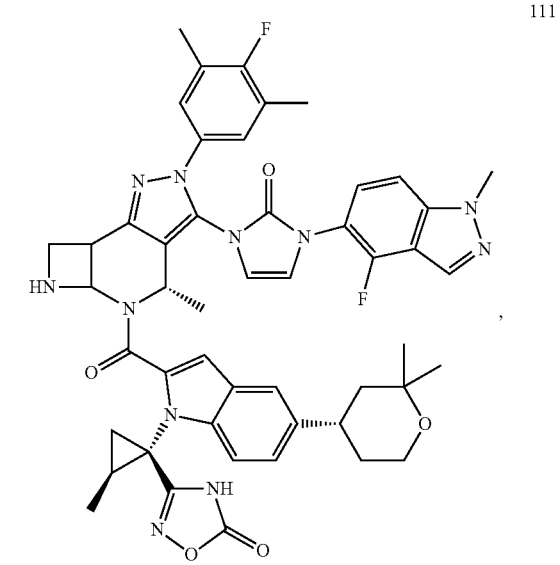
111
109

91
-continued
112
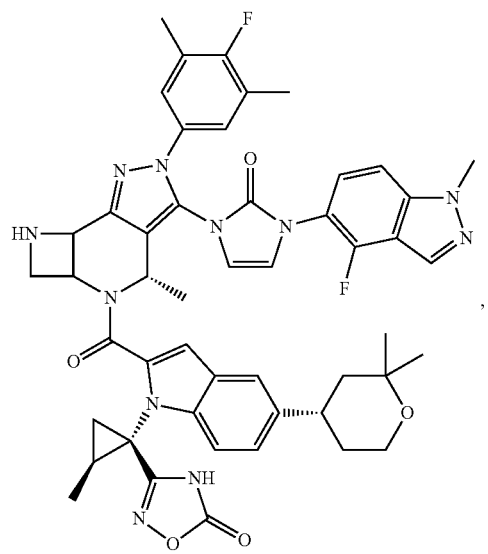
,
113
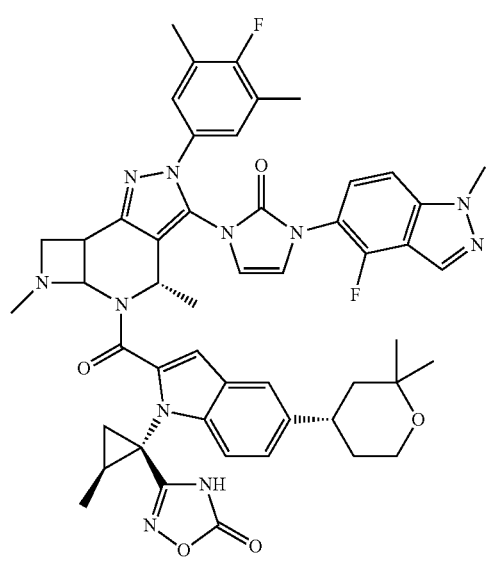
,
114
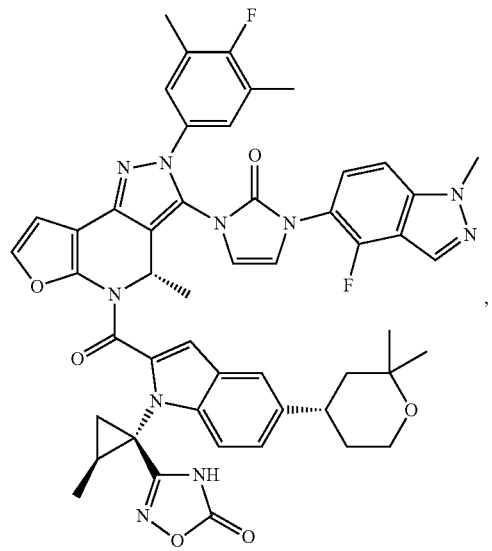
,
92
-continued
115
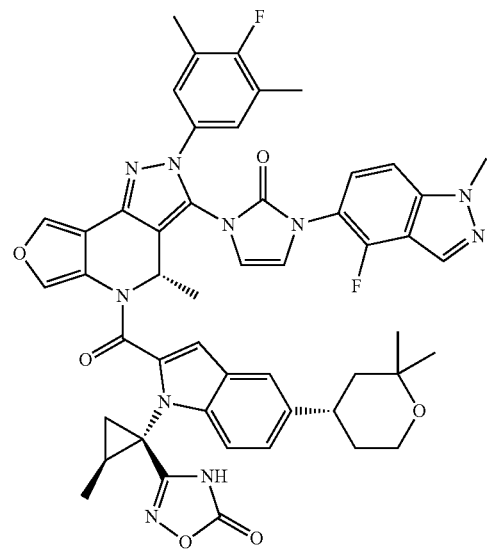
,
116
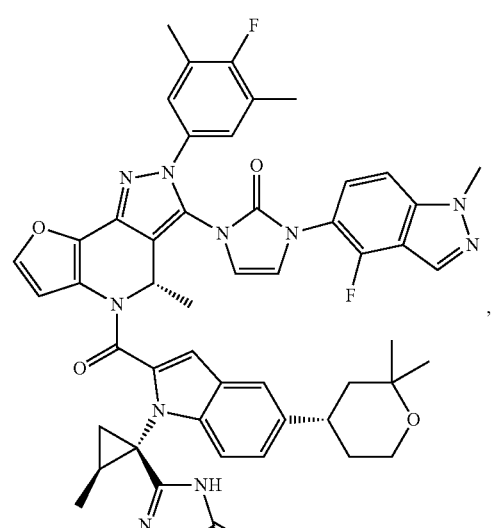
,
117
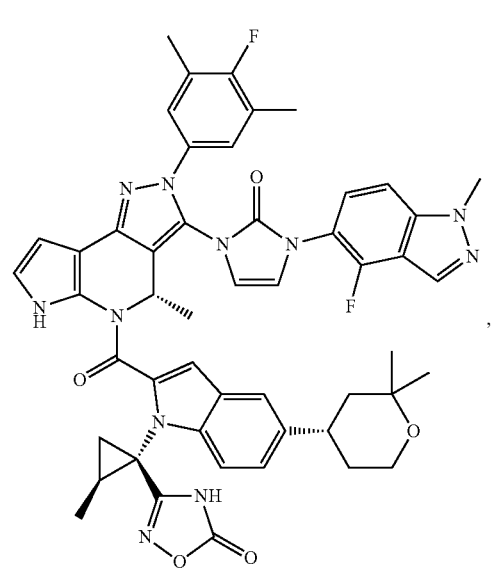
, 93
-continued
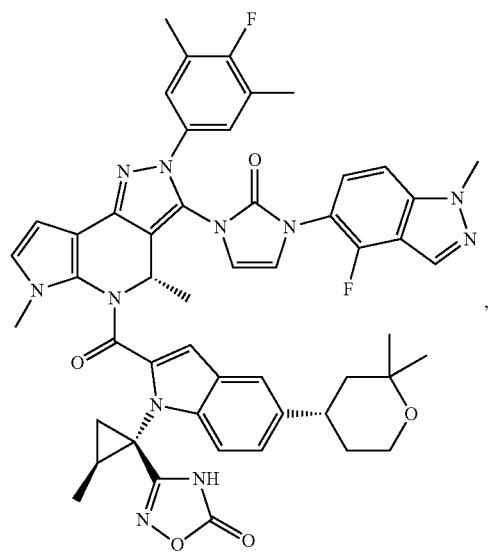
118
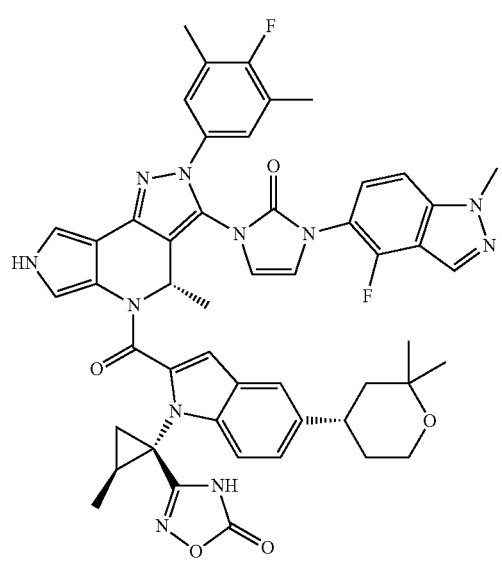
119
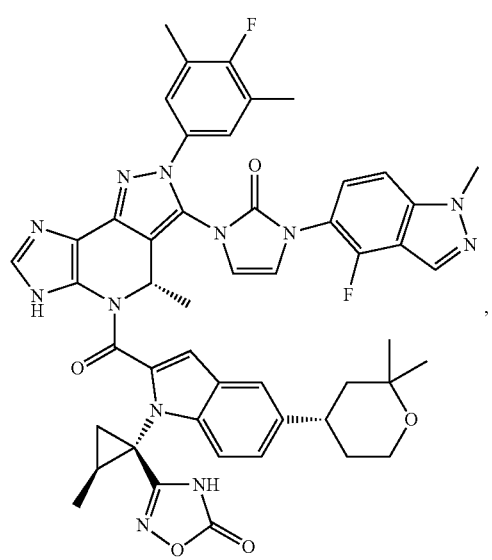
120
94
-continued
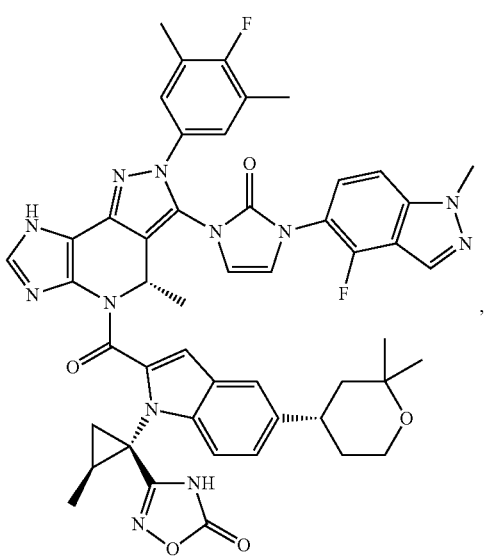
121
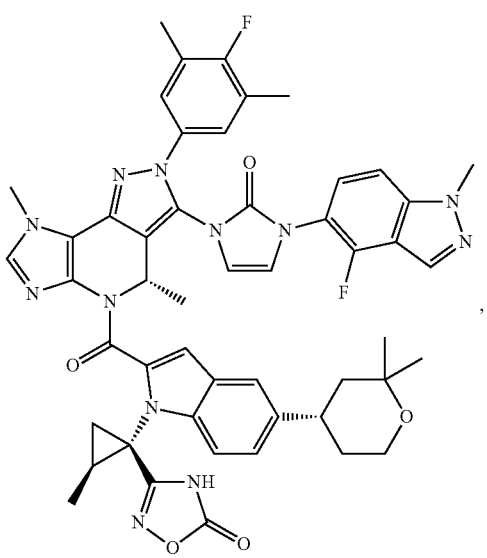
122
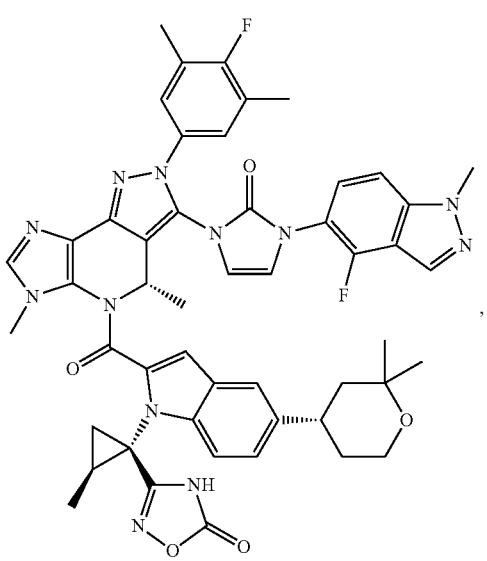
123

124
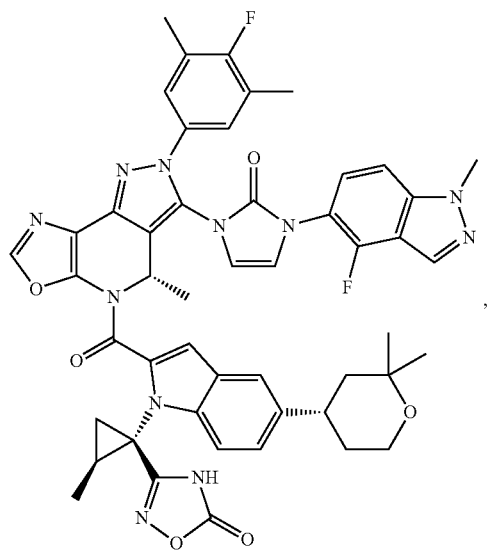
125
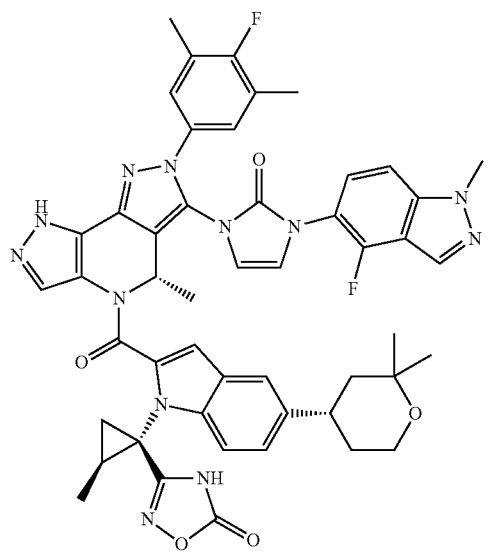
127
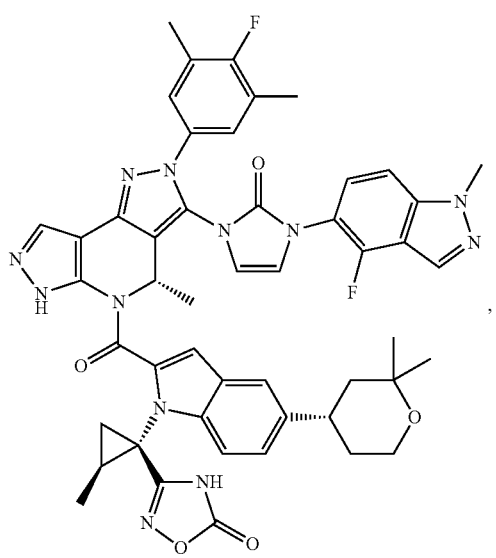
126
128
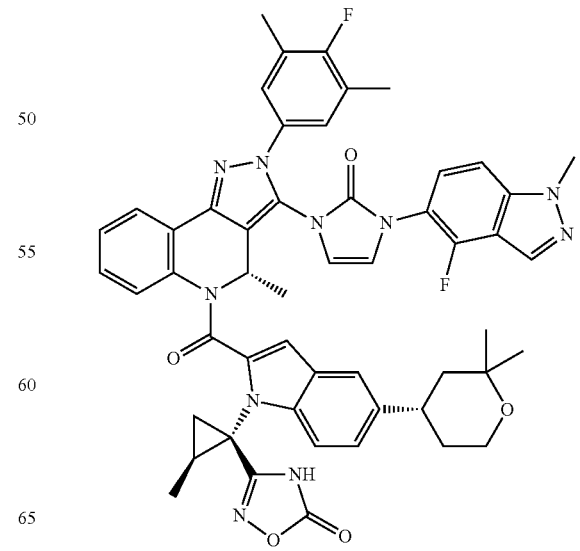

129
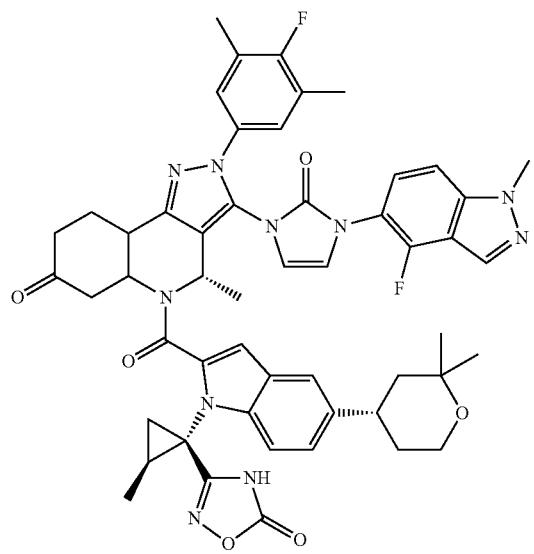
,
130
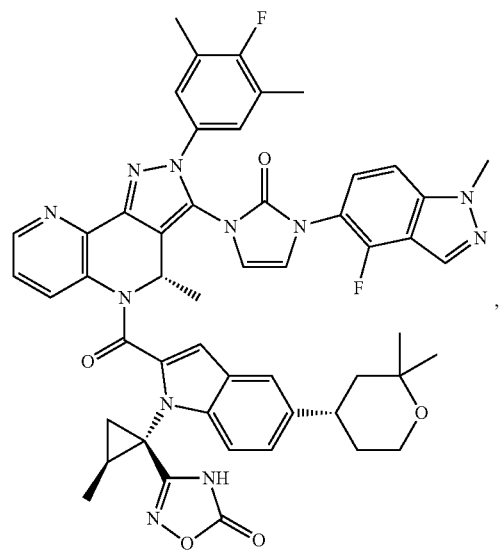
,
131
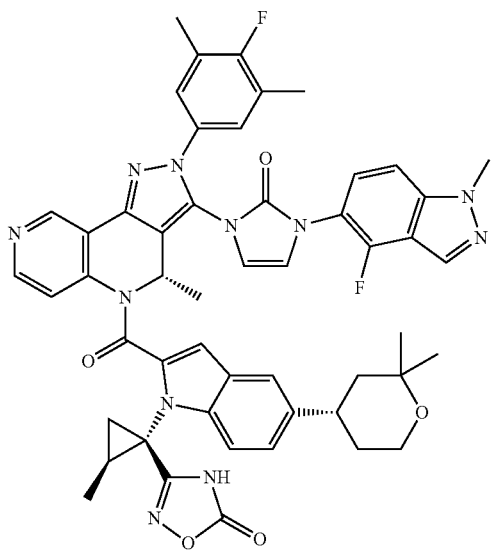
,
132
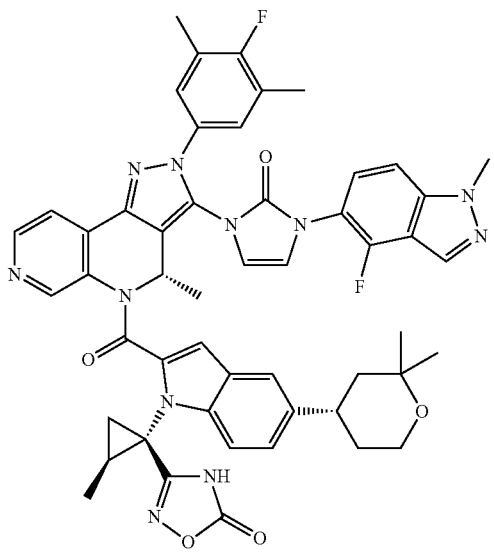
,

133
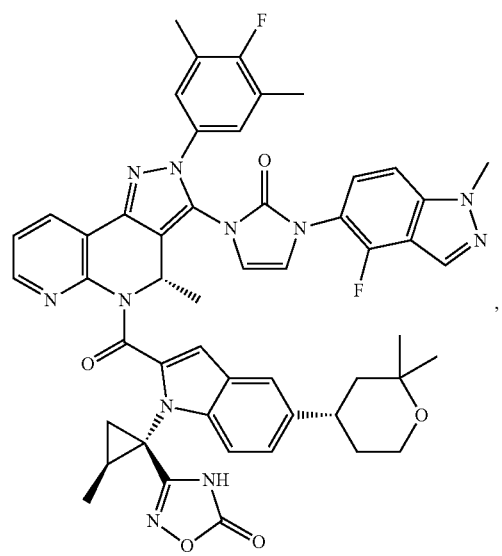
135
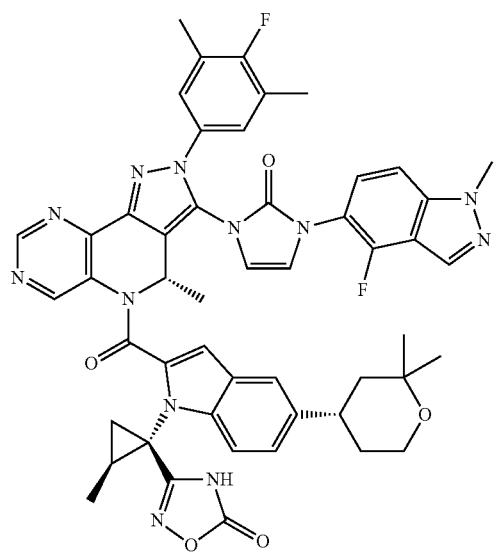
,
134
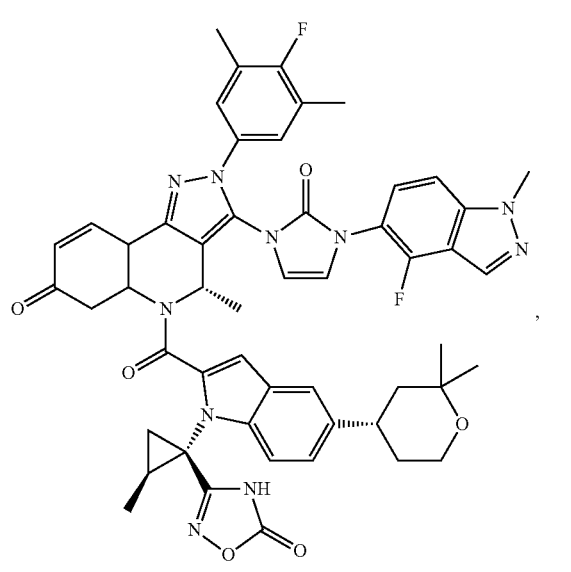
136
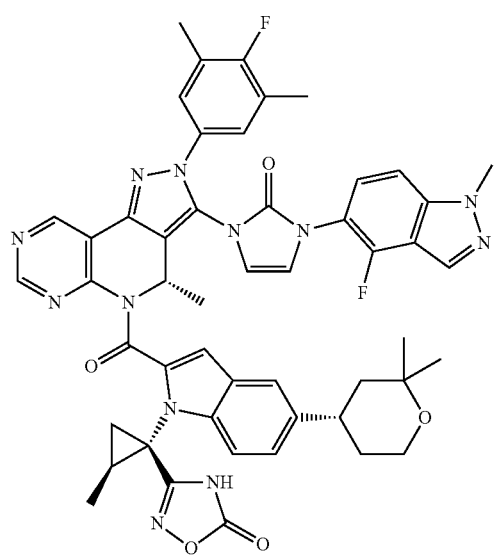
,

137
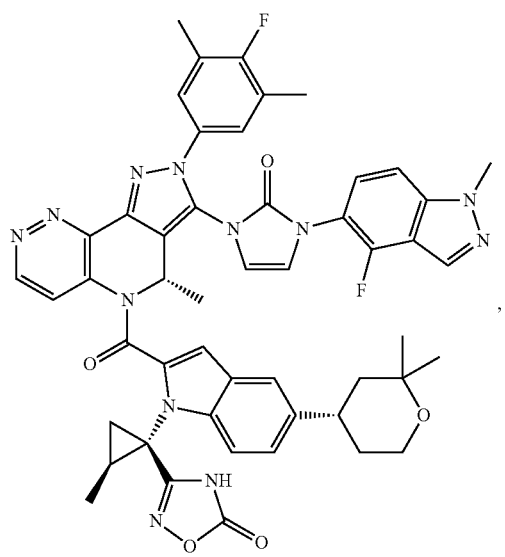
,
139
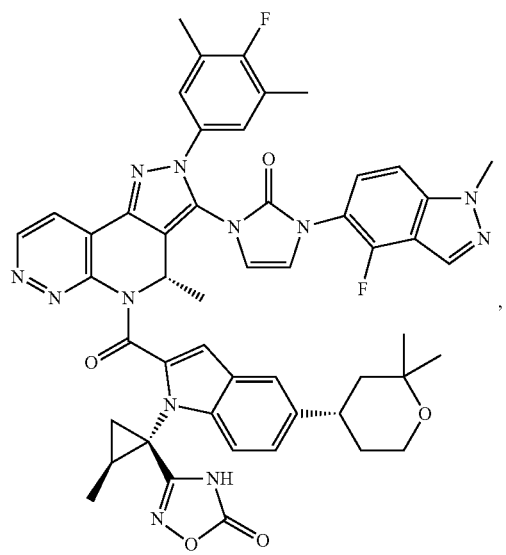
,
138
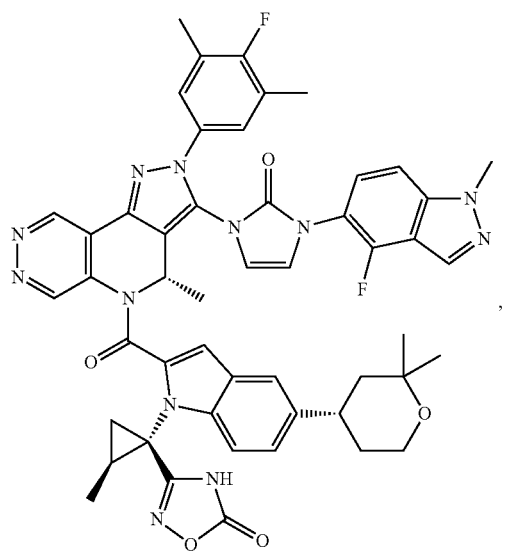
,
140
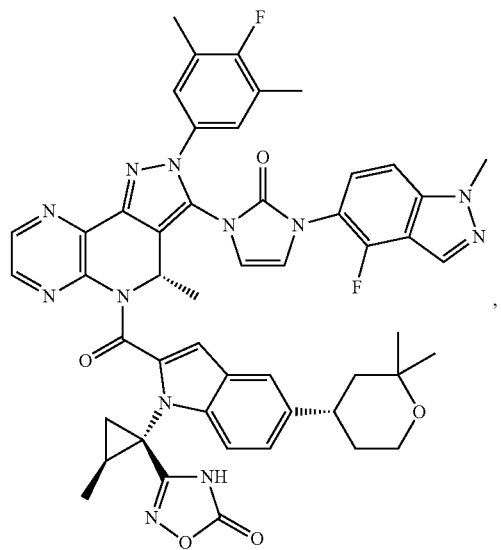
,

141
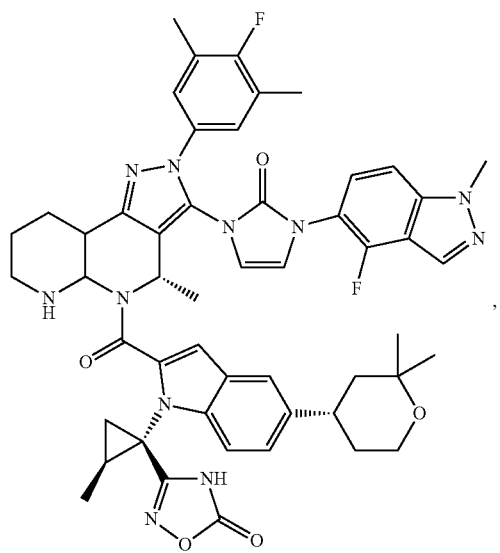
142
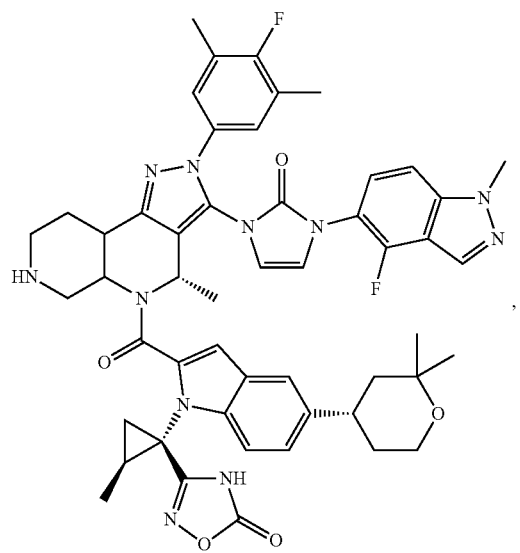
143
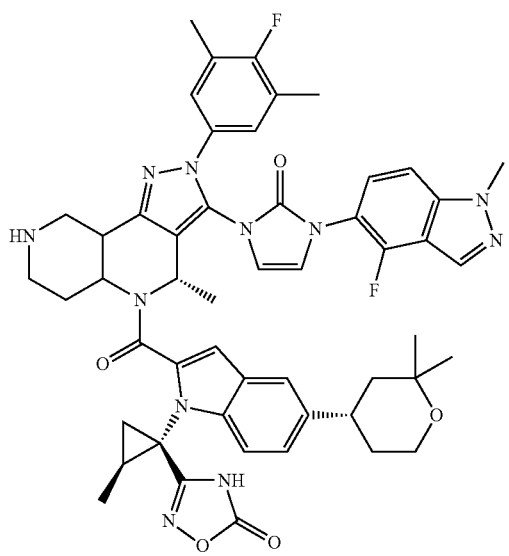
144
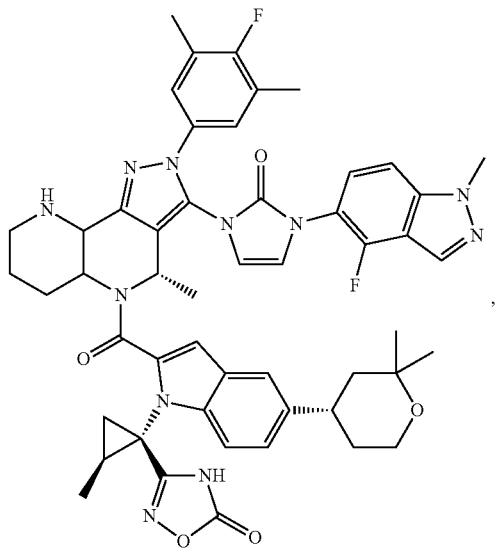

145
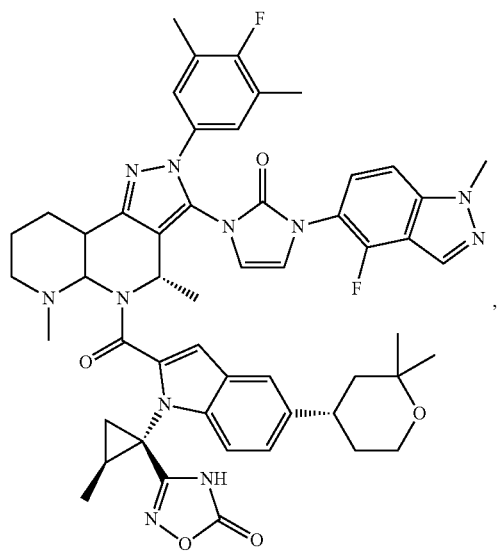
,
146
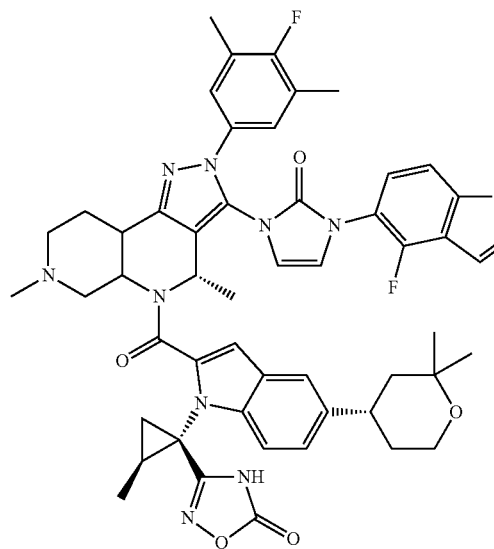
,
147
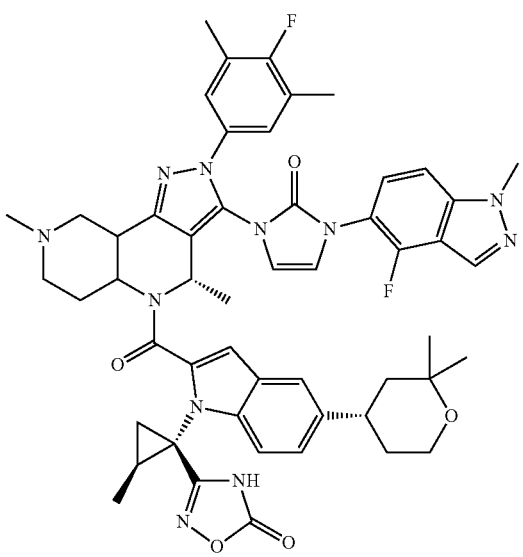
,
148
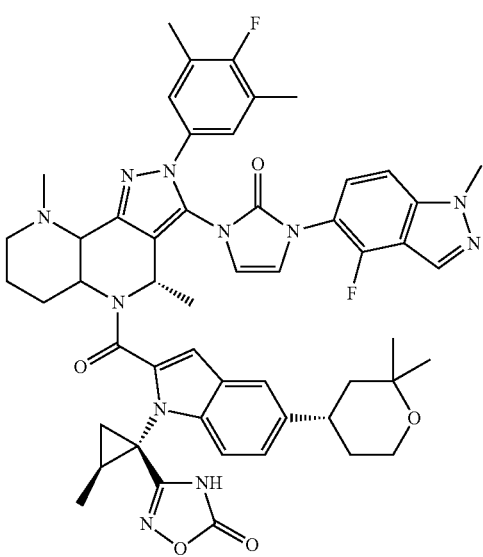
,

149
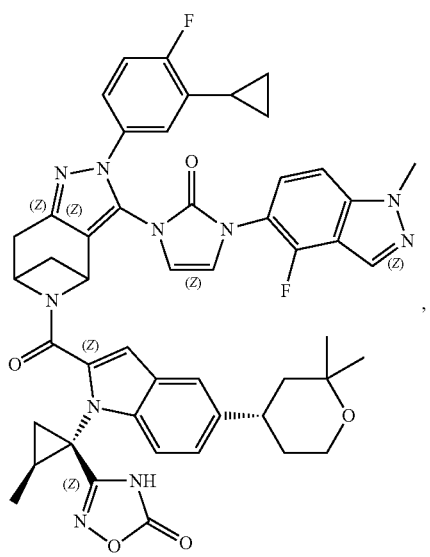
151
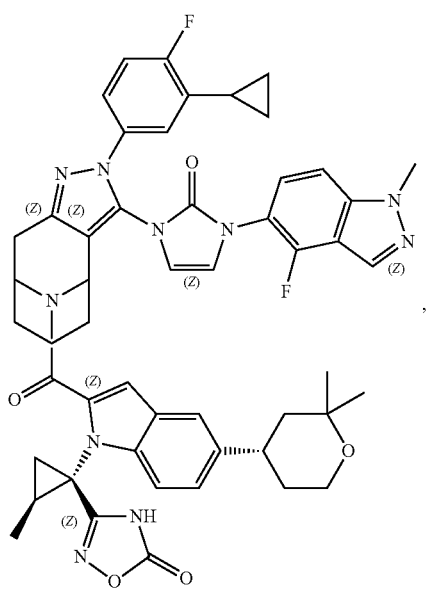
150
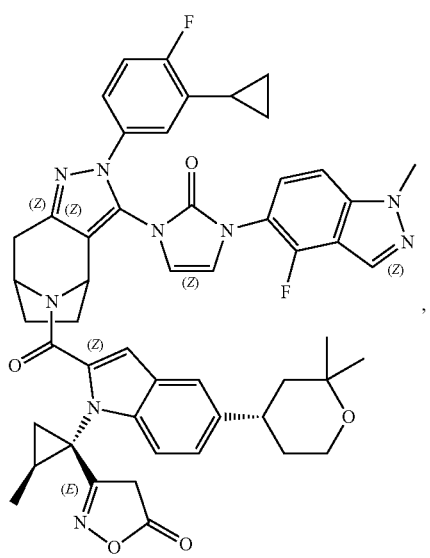
152
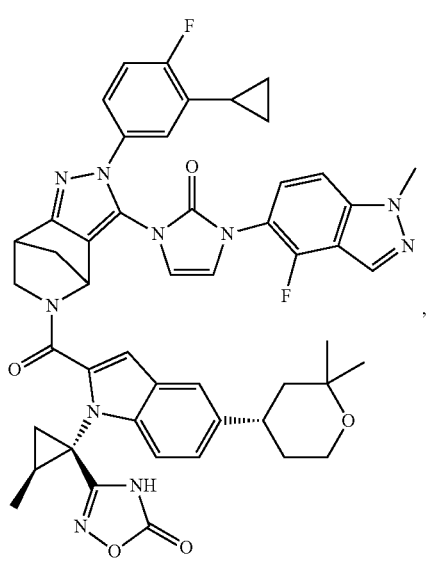

153
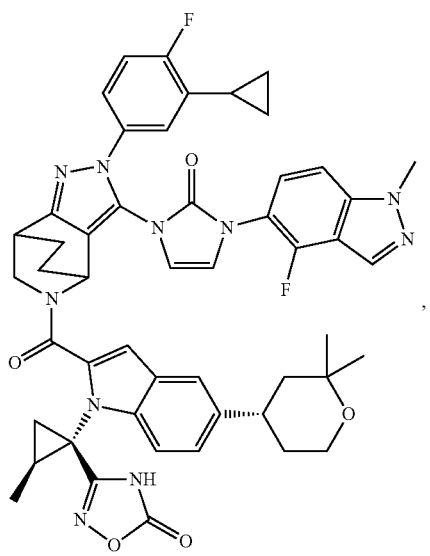
,
154
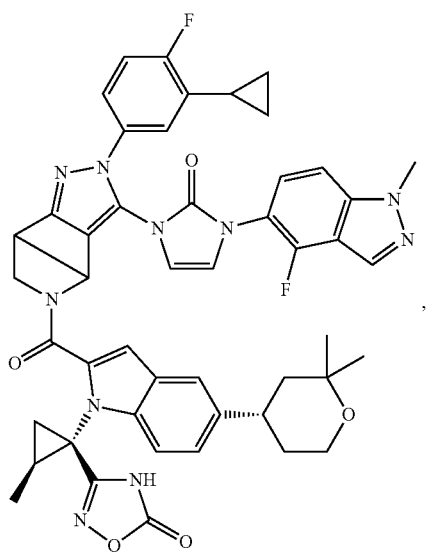
,
155
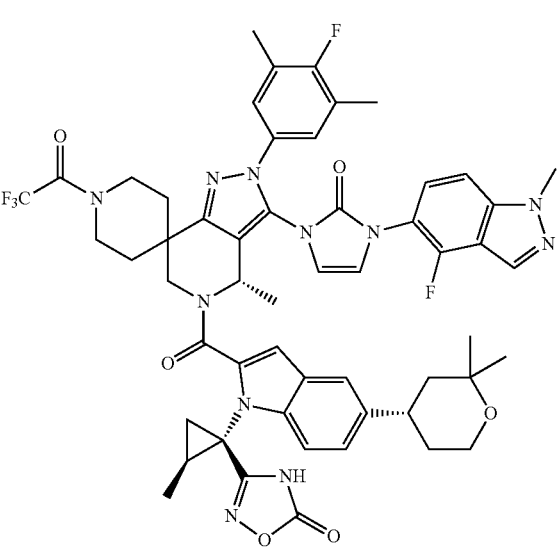
,
156
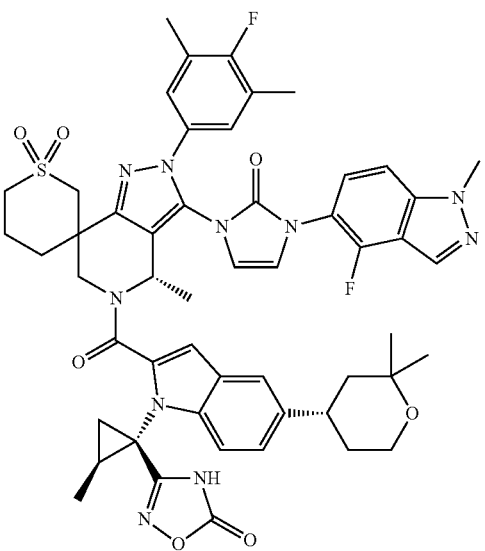
,
157
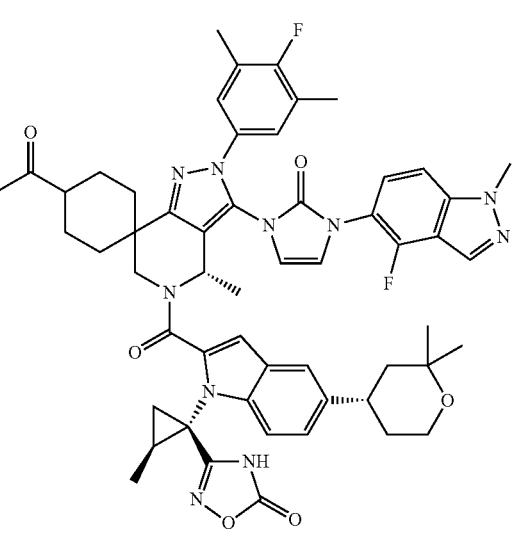
,
158
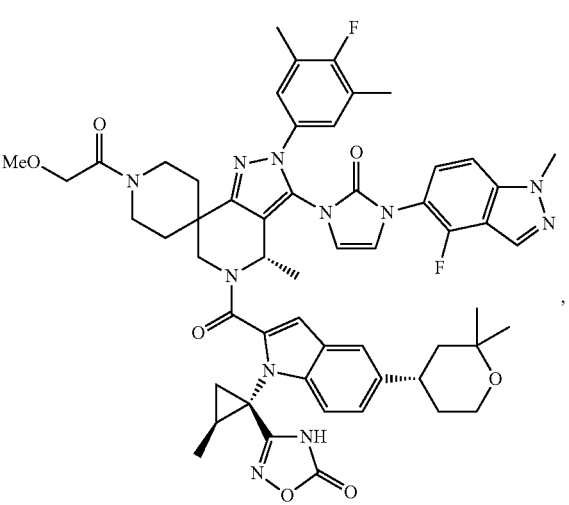
, 159
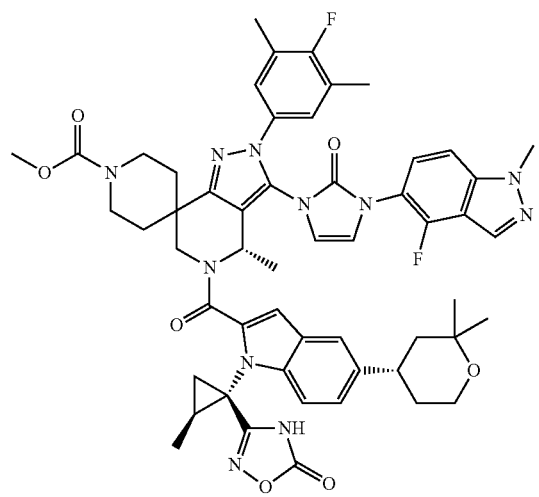
160
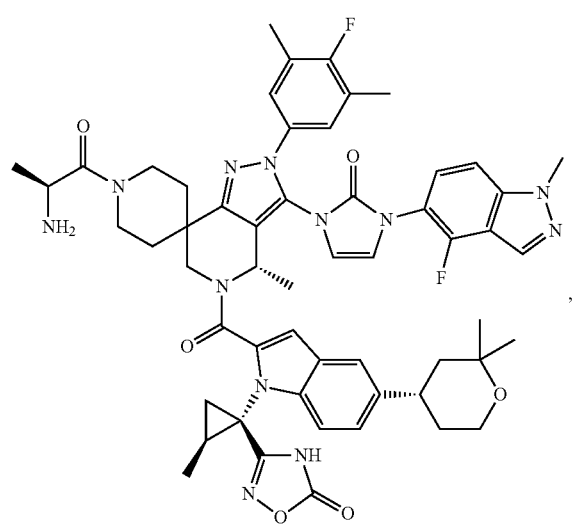
161
162
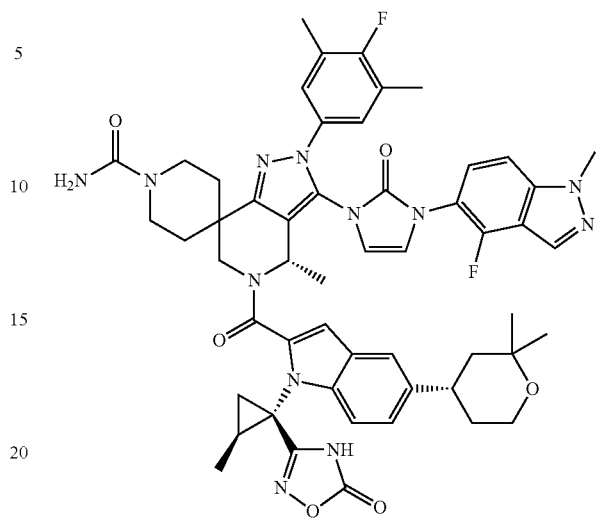
163
164
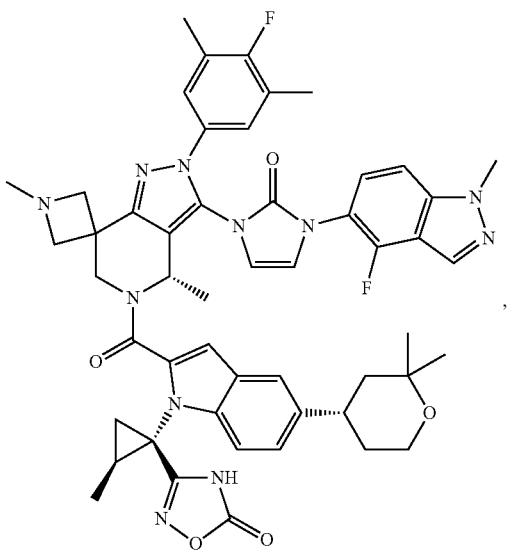

165
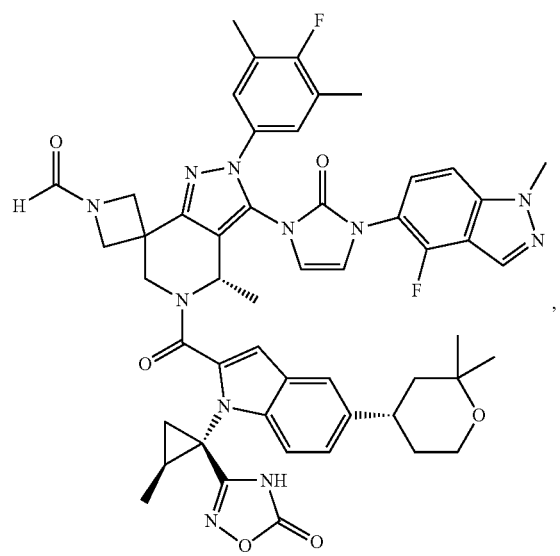
166
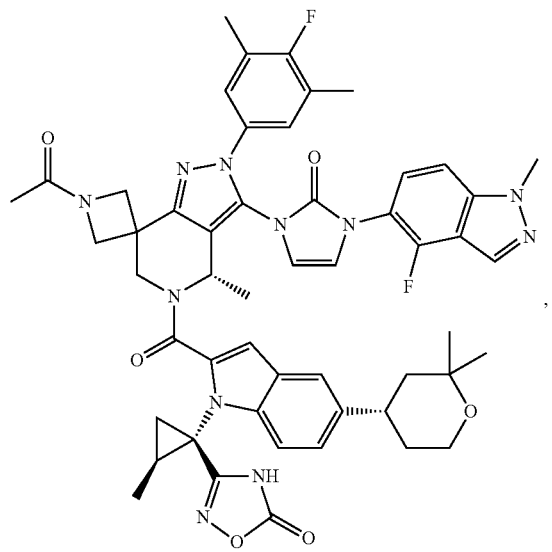
167
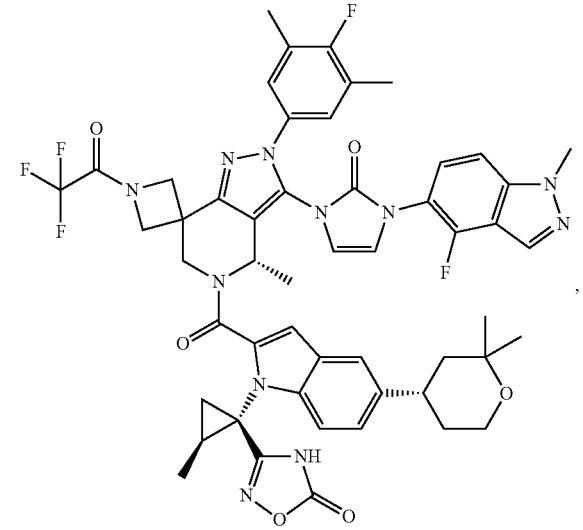
168
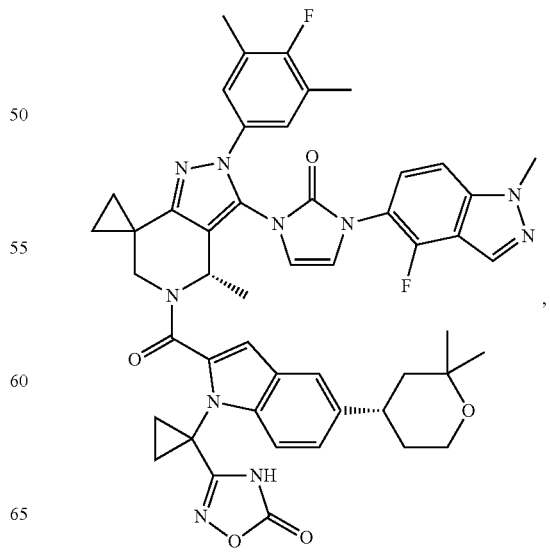
169

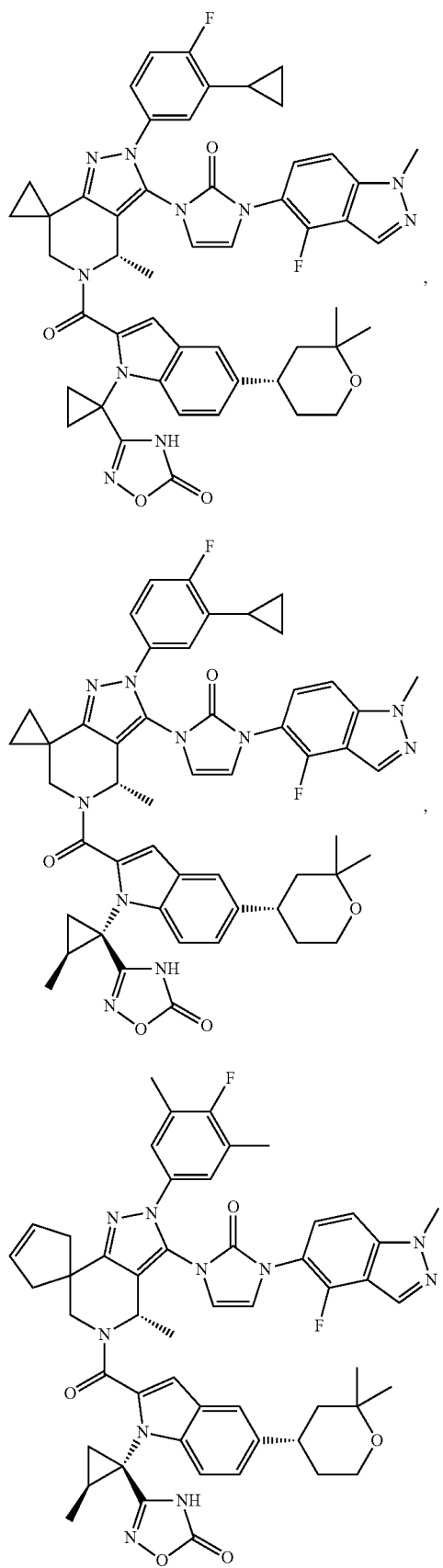
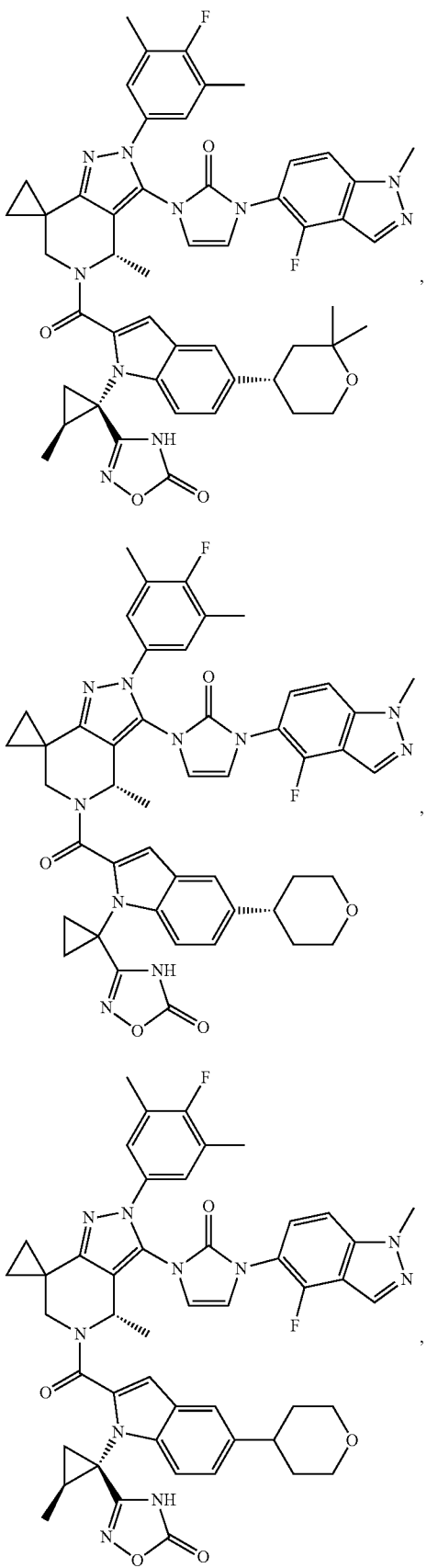

176
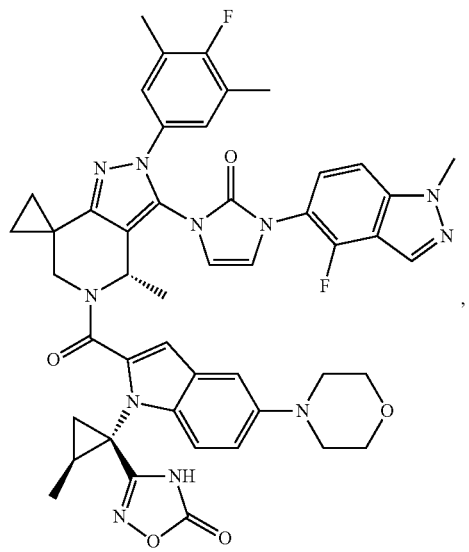,
177
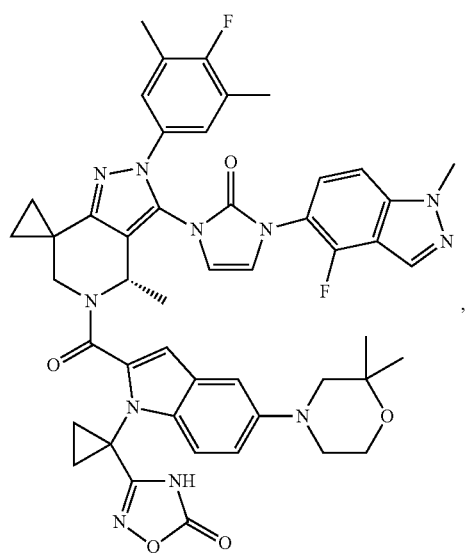,
178
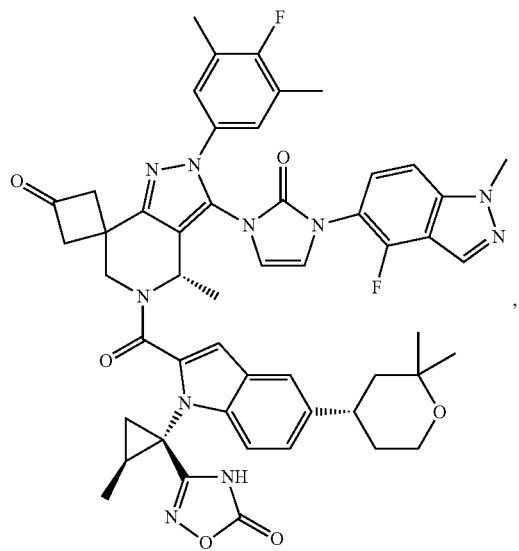,
179
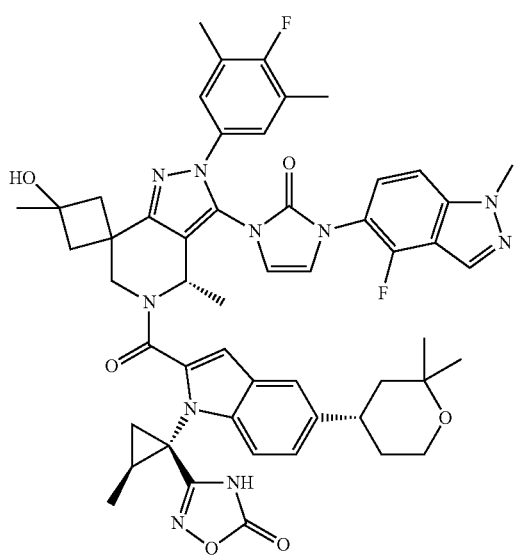,
180
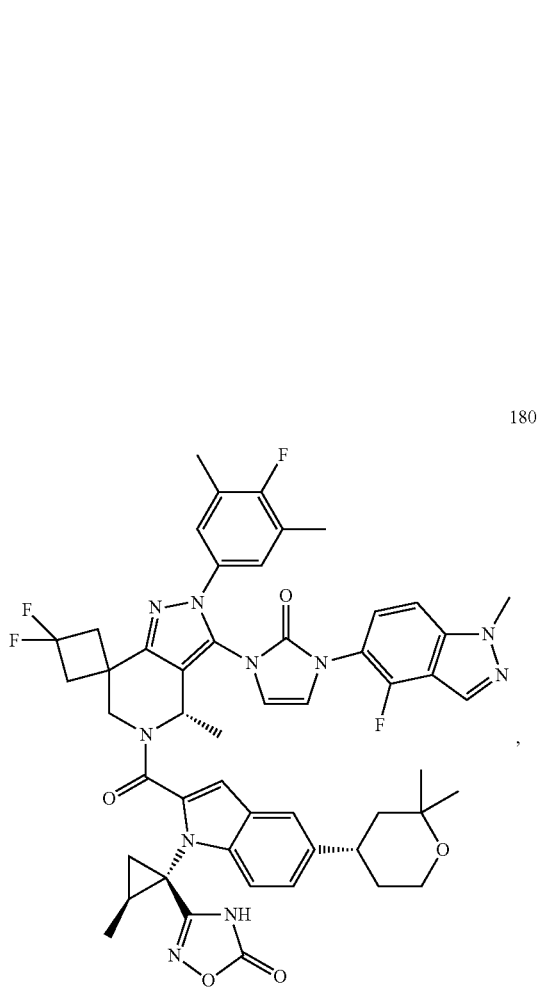, 181
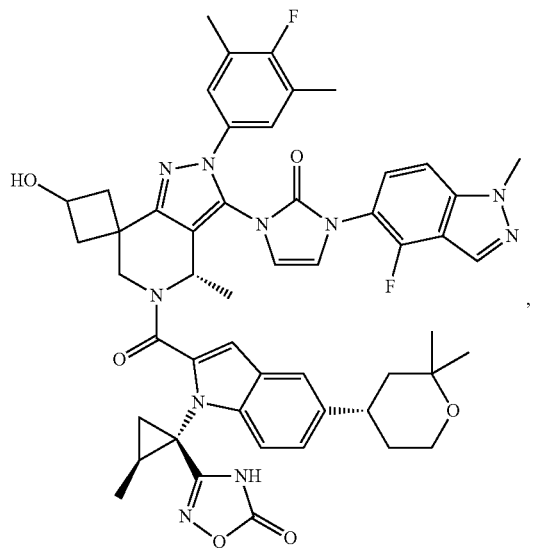
182
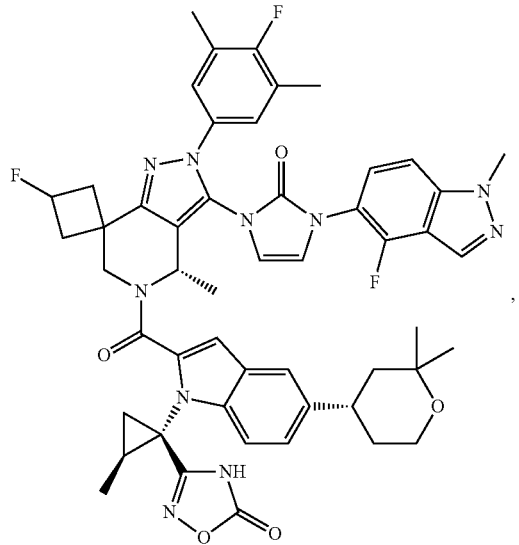
183
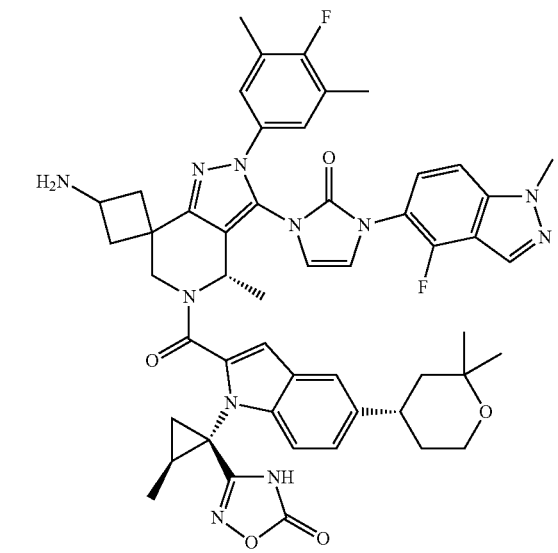
184
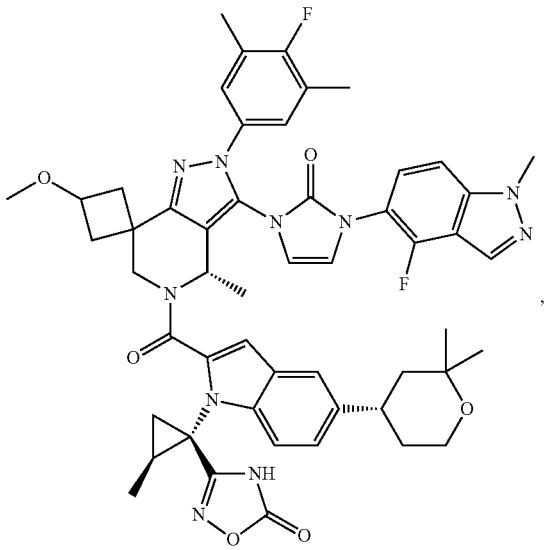

185
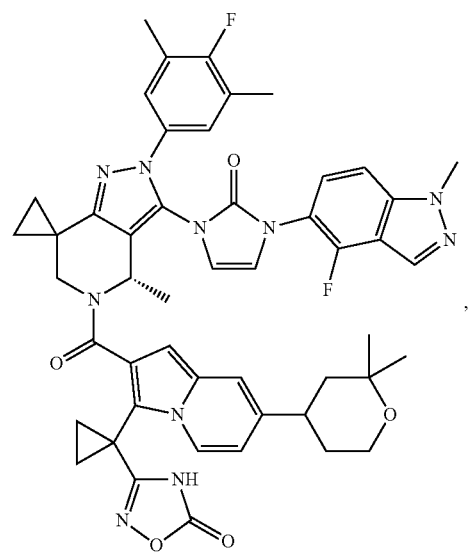
186
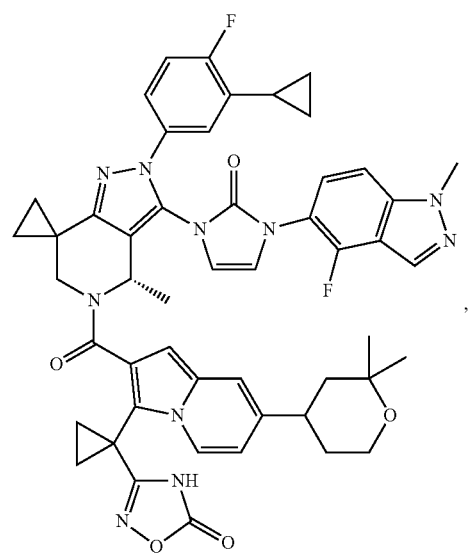
187
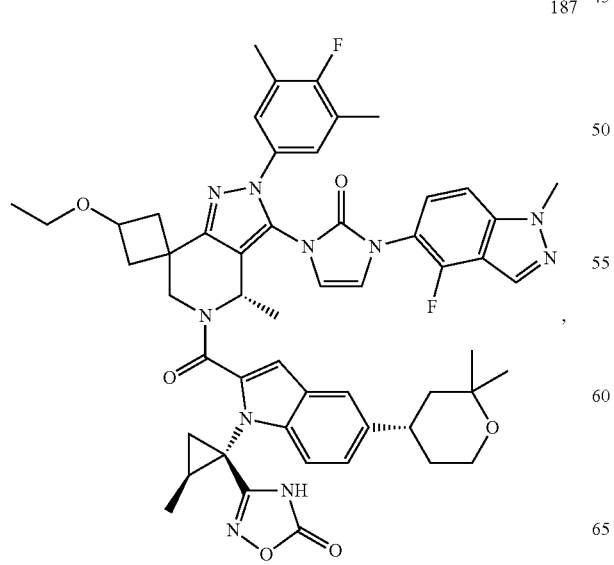
188
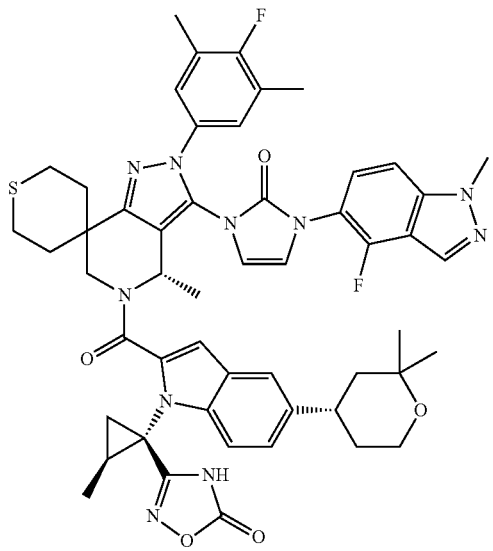
189
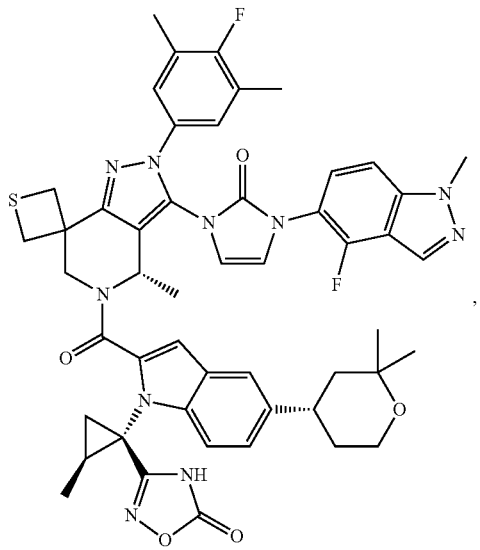

190
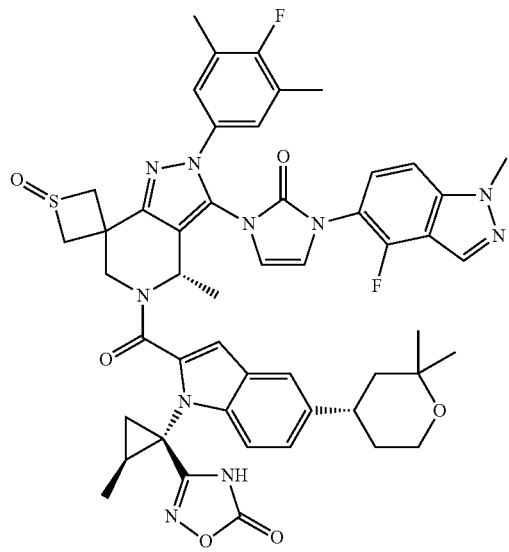
191
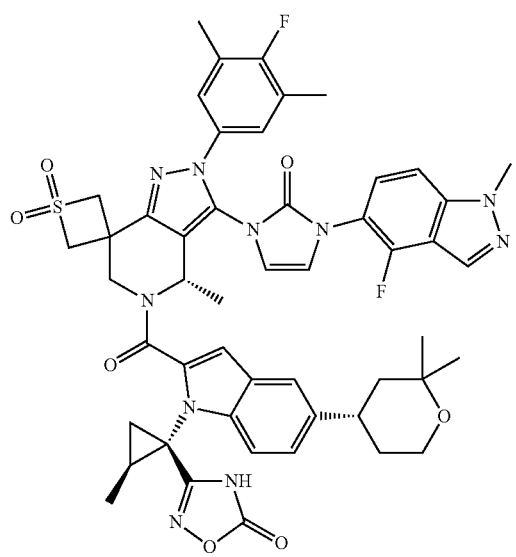
192
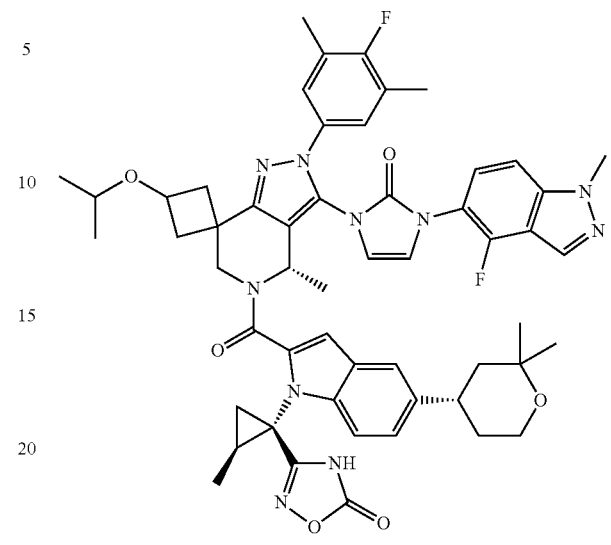
193
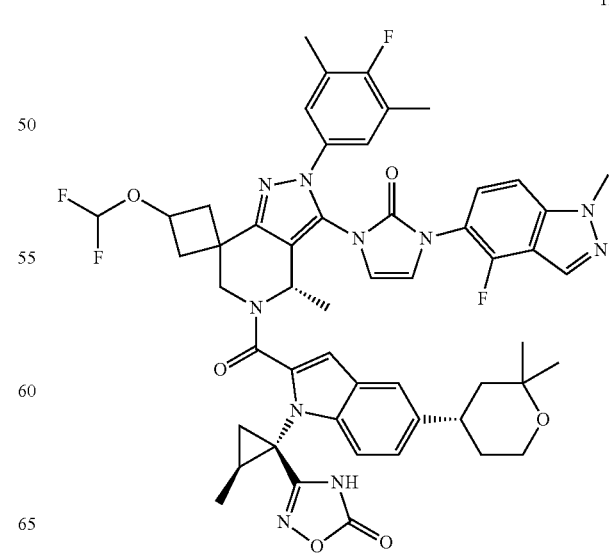
194

125
-continued
195
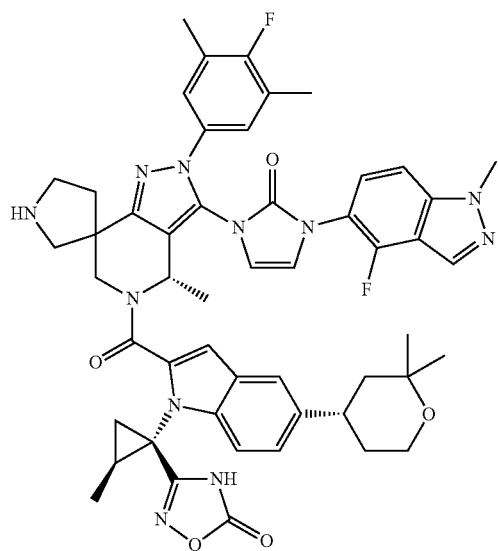
196
197
126
-continued
198
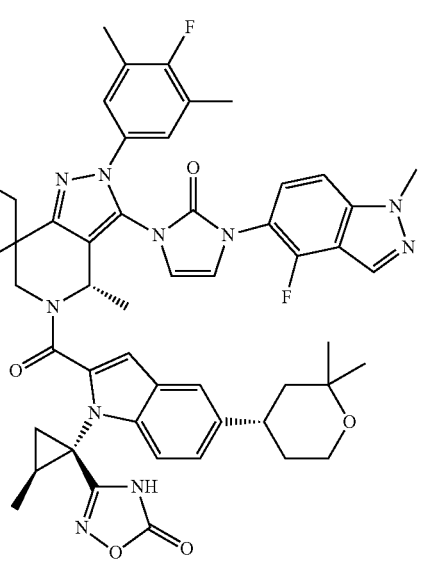
199
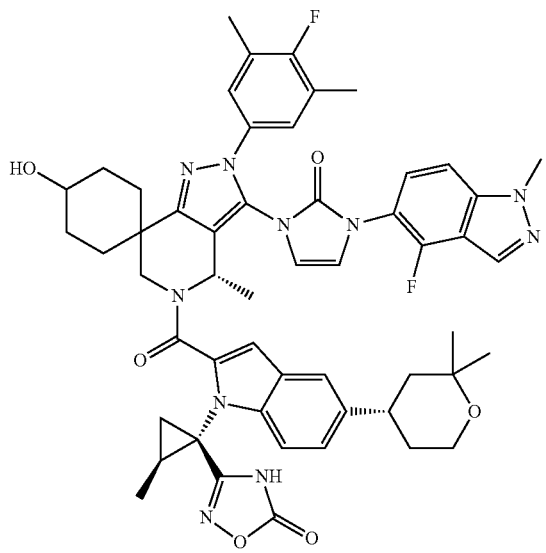

127
-continued
200
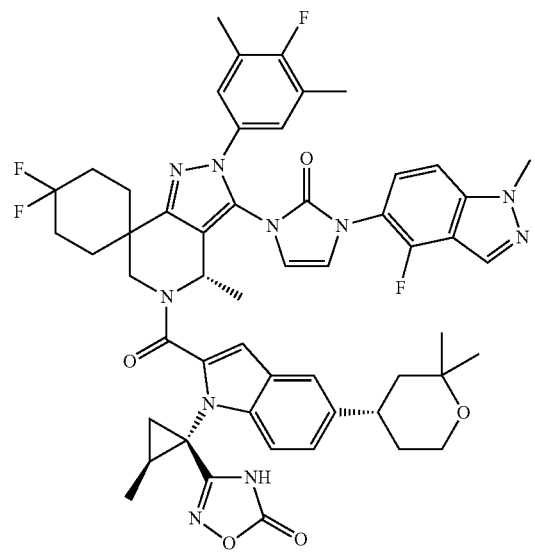
201
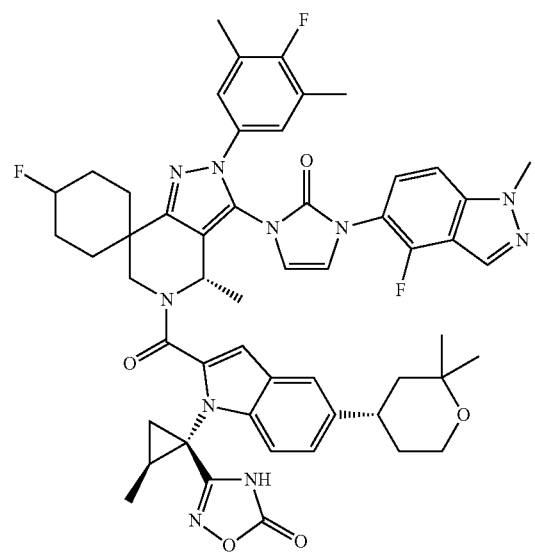
128
-continued
202
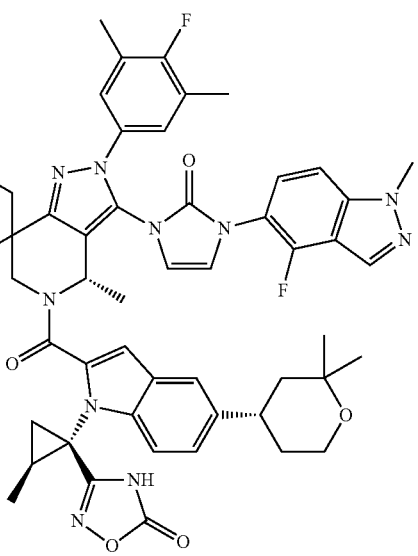
203
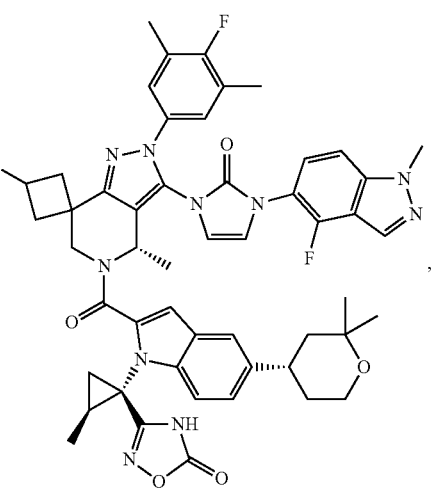
204

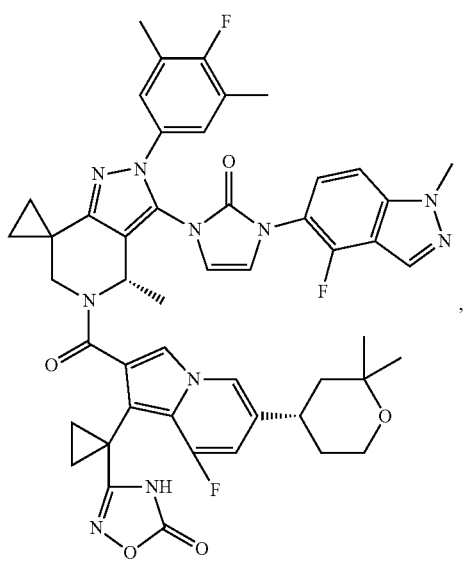
205
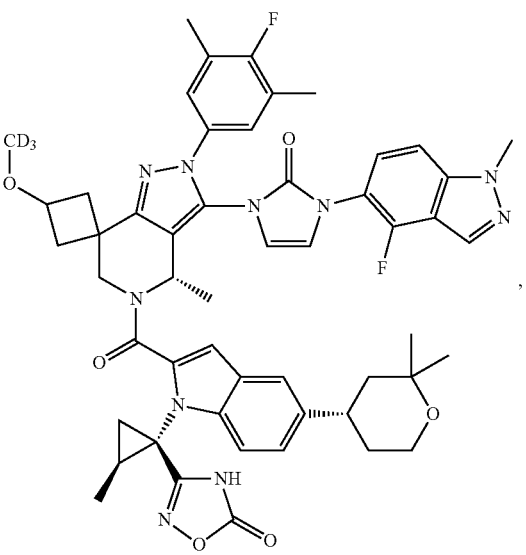
207
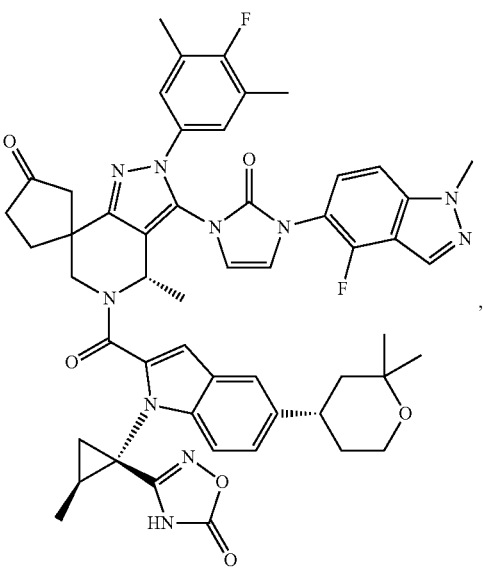
208

209
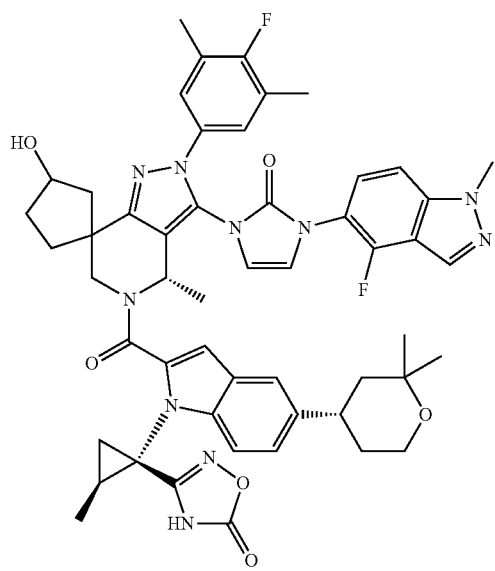
211
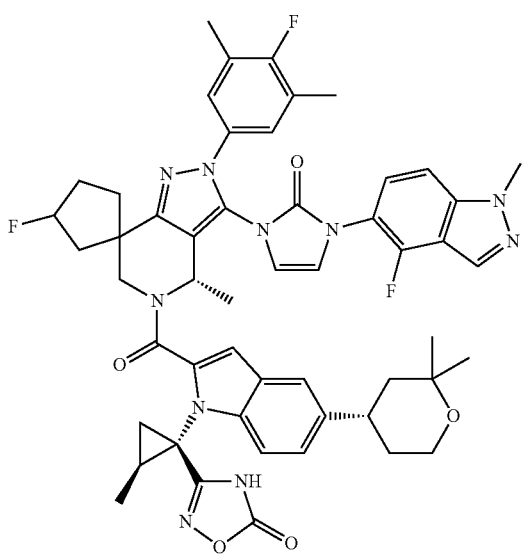
210
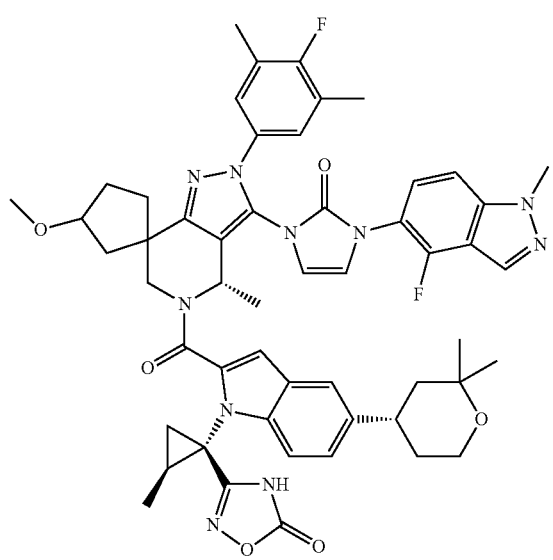
212
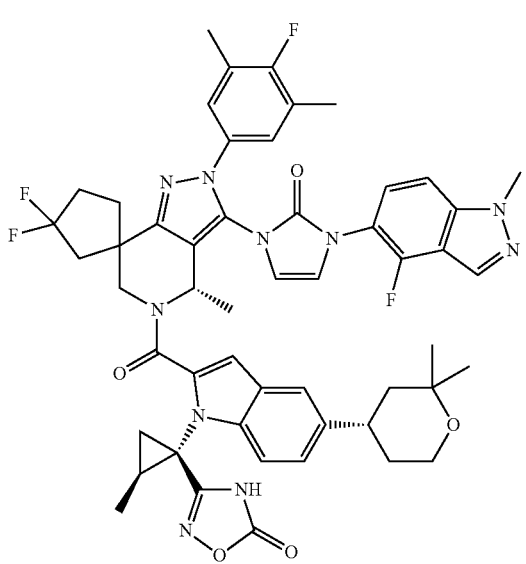

133
-continued
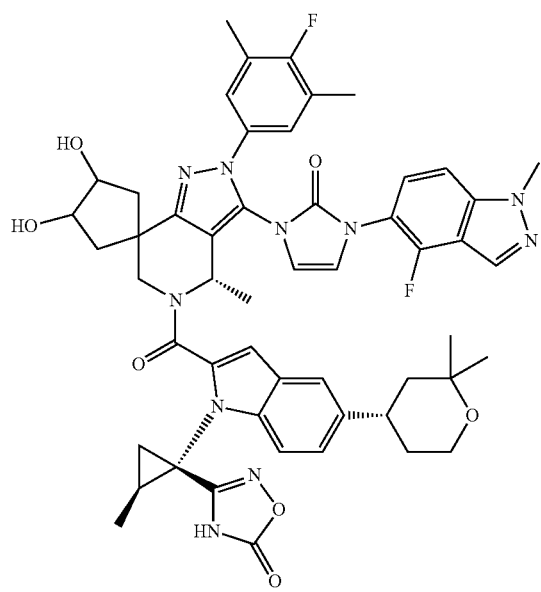
213
,
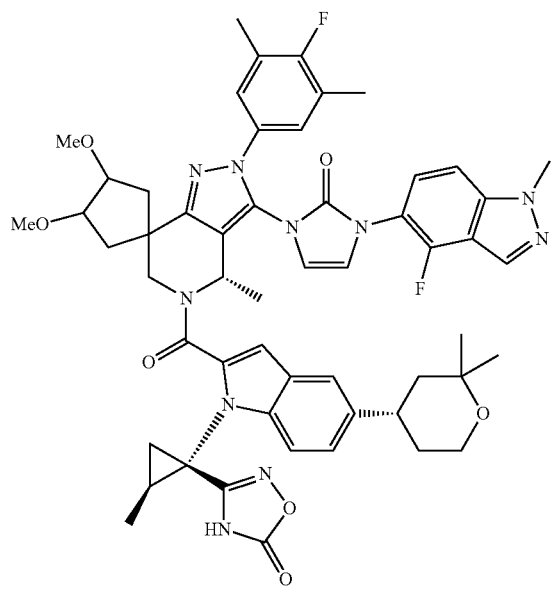
214
,
134
-continued
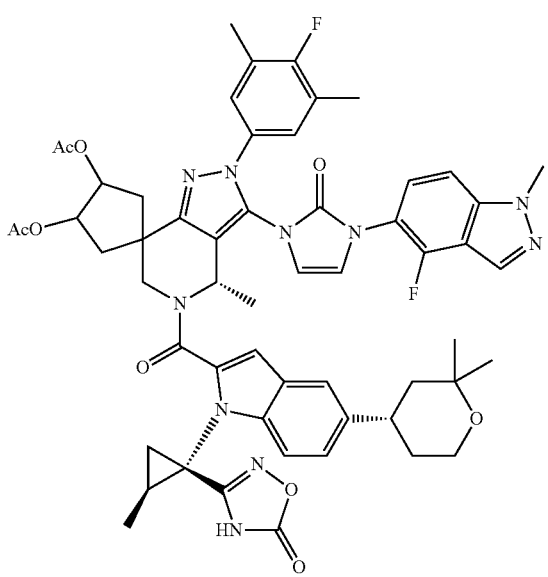
215
,
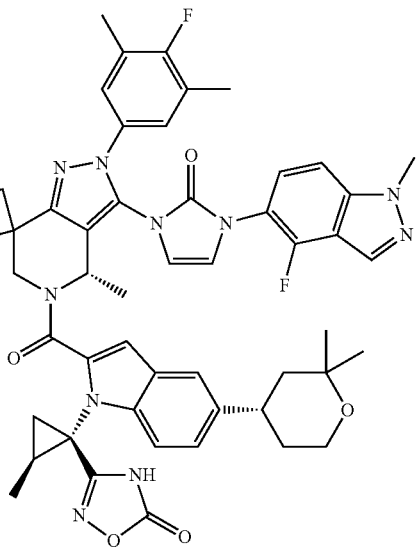
216
, 217
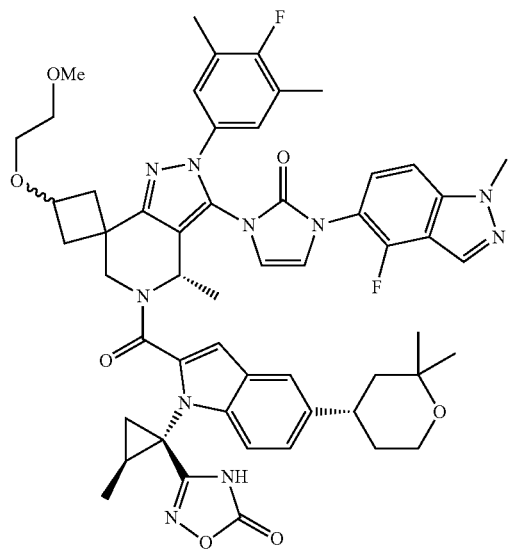
219
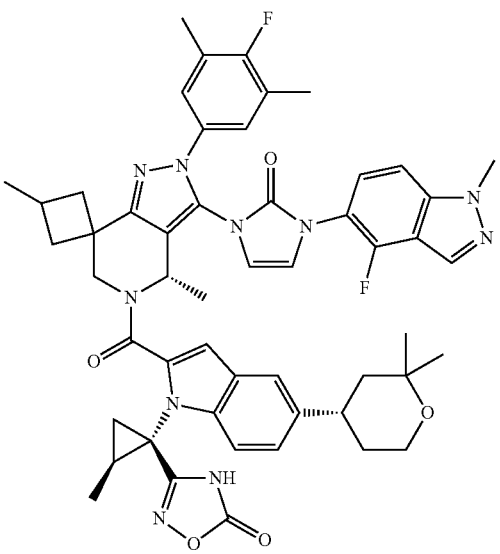
218
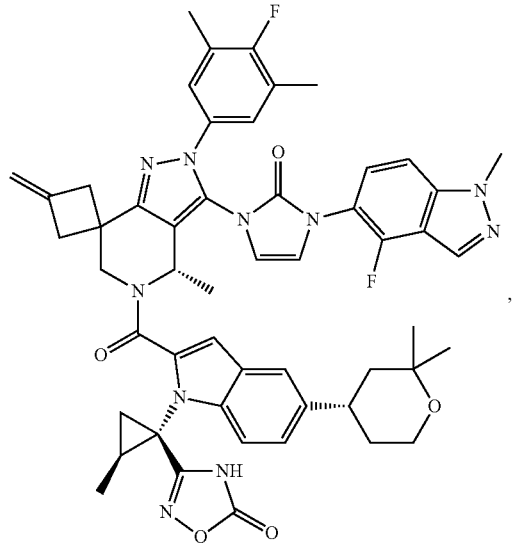
220

221
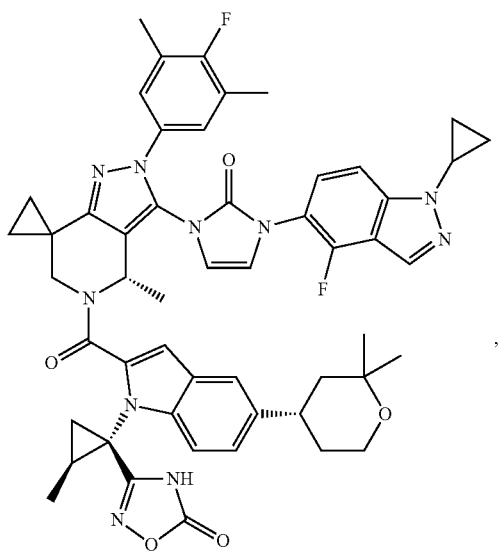
222
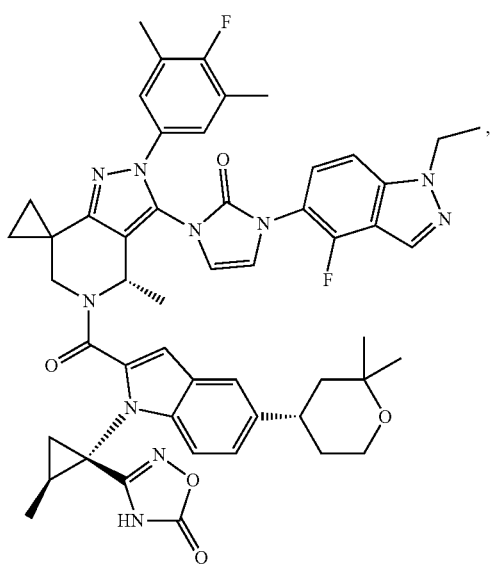
223
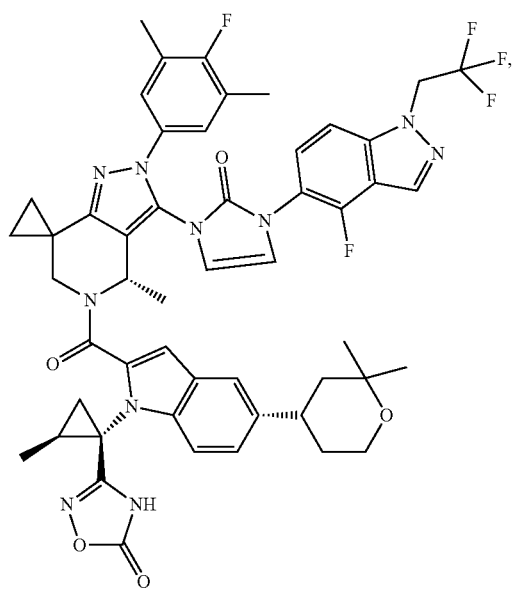
224
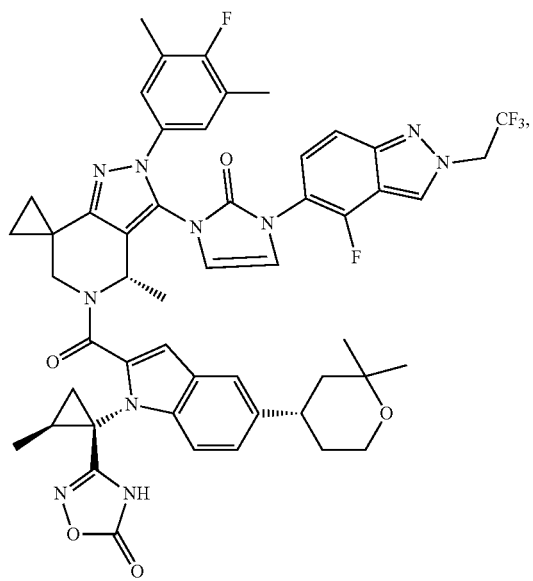

225
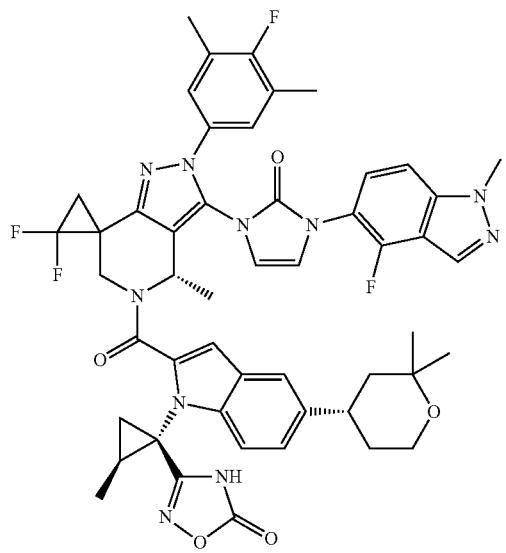
226
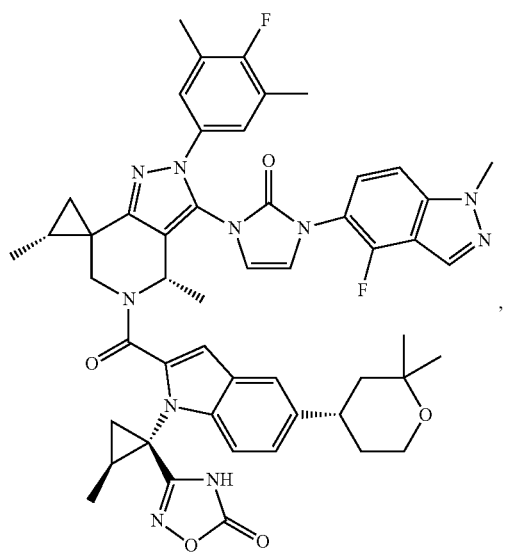
,
227
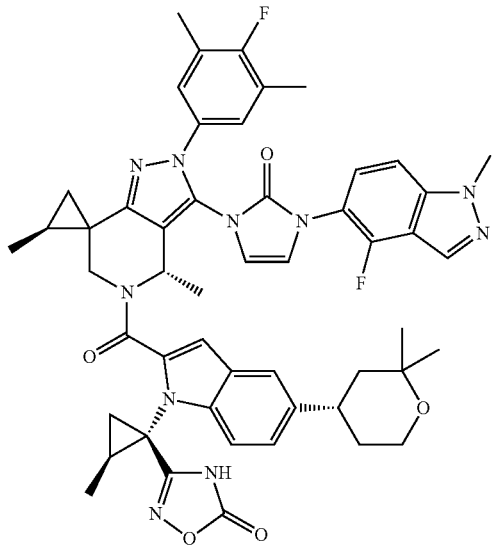
,
228
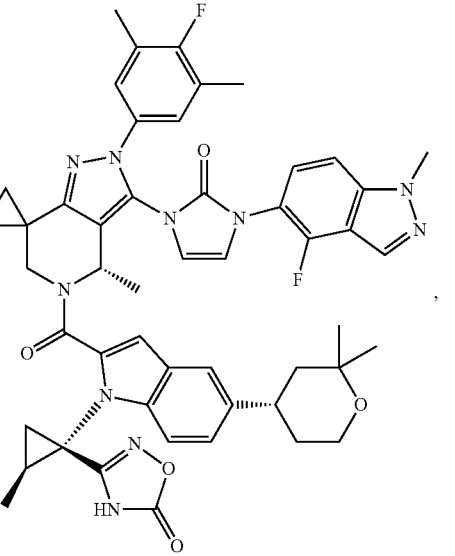
, and

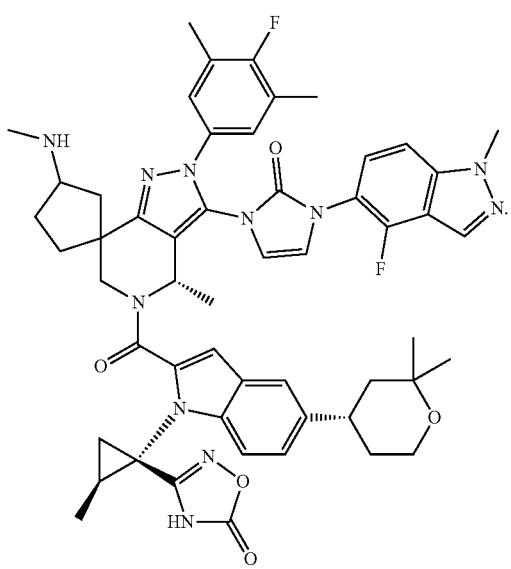

The present disclosure further provides methods for preparing the above-mentioned compound of Formula I, including, but not limited to, the following steps (see the Examples for details of the synthetic methods of some of the compounds):
Generic Preparation Method 1

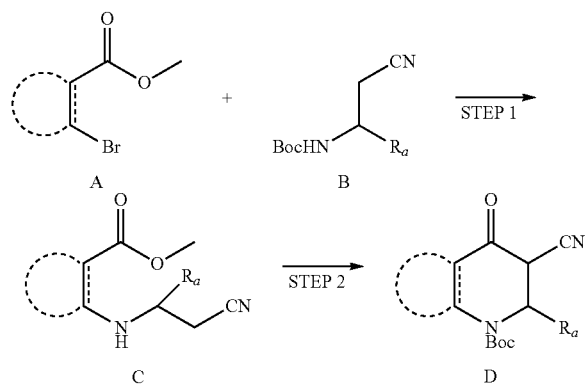

Cyanoketone intermediate D can be successfully prepared by the above synthetic route. Firstly, bromocarboxylate compound A is prepared from commercial raw materials, and then subjected to the Buchwald-Hartwig coupling reaction with aminonitrile compound B to afford intermediate C. Subsequently, the intermediate D is prepared by the cyclization reaction of intermediate C.
Generic Preparation Method 2

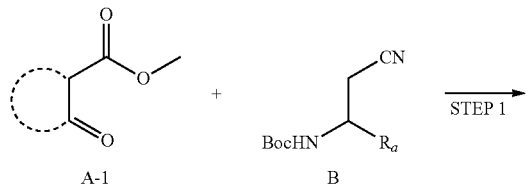

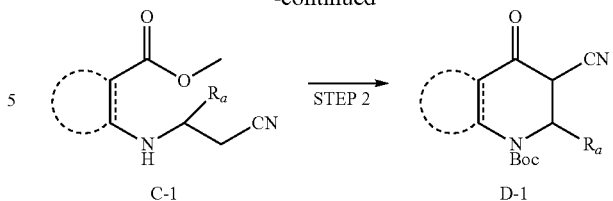

Another type of cyanoketone intermediate D-1 can be successfully prepared by the above synthetic route. Firstly, commercial raw material A-1 and aminonitrile compound B are subjected to the reductive amination reaction to afford a corresponding intermediate C-1. Subsequently, the intermediate D-1 is prepared by the cyclization reaction of intermediate C-1 under basic conditions.
Generic Preparation Method 3

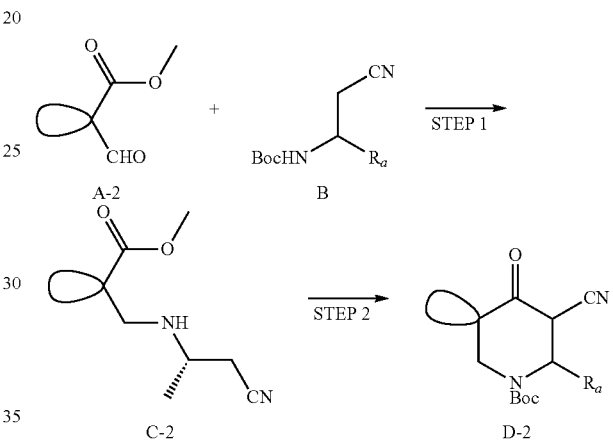

Cyanoketone intermediate D-2 can be successfully prepared by the above synthetic route. Firstly, commercial raw material (or prepared) A-2 and aminonitrile compound B are subjected to the reductive amination reaction to afford intermediate C-2. Subsequently, the intermediate D-2 is prepared by the Boc protection and cyclization reaction of intermediate C-2 under basic conditions.
Generic Preparation Method 4

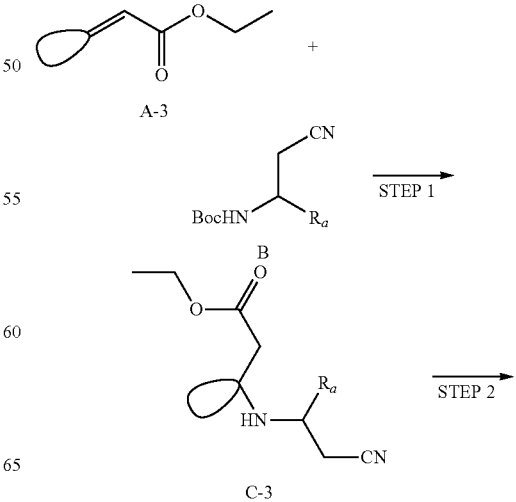

-continued

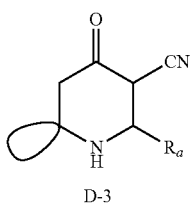

D-3

Cyanoketone intermediate D-3 can be successfully prepared by the above synthetic route. Firstly, commercial (or prepared) raw material A-3 and aminonitrile compound B are subjected to the Michael addition reaction to afford intermediate C-3. Subsequently, the intermediate D-3 is prepared by the Boc protection and cyclization reaction of intermediate C-3 under basic conditions.

Generic Preparation Method 5

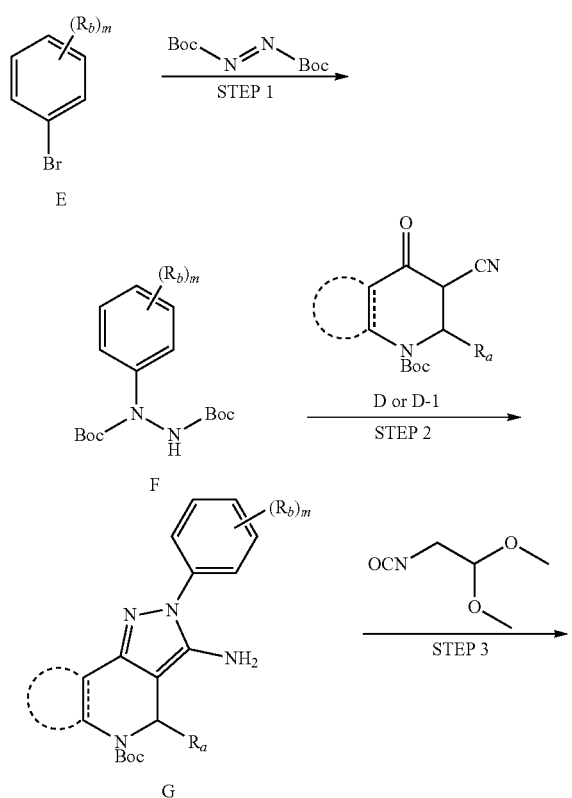

-continued

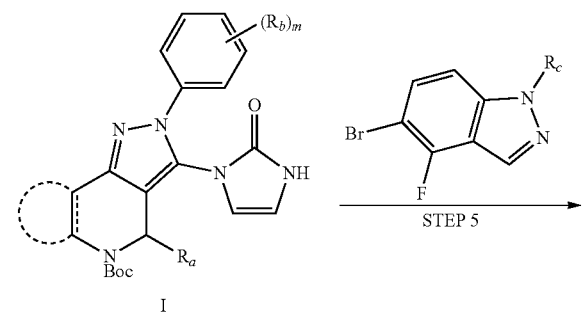

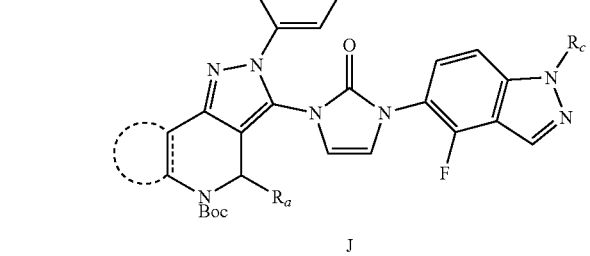

Key intermediate J can be successfully prepared by the above synthetic route. Firstly, bromoarene E undergoes the lithium-halogen exchange and the addition reaction with di-tert-butyl azodicarboxylate to afford intermediate F. Subsequently, the intermediate F is subjected to the cyclization reaction with the cyanoketone intermediate obtained by Generic Preparation Method 1 or 2 to afford compound G. Next, the compound G is subjected to the addition reaction with isocyanate and to the cyclization reaction under acidic conditions to afford urea compound I. Finally, the urea compound I undergoes the Buchwald-Hartwig coupling reaction or the Ullmann coupling reaction with a substituted indazole compound to afford key intermediate J.

Generic Preparation Method 6

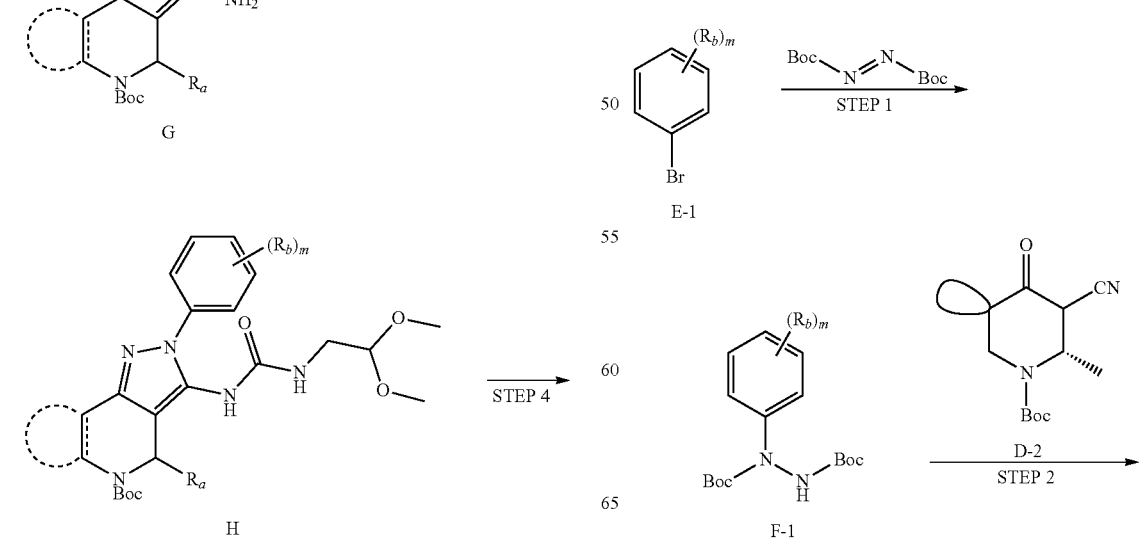

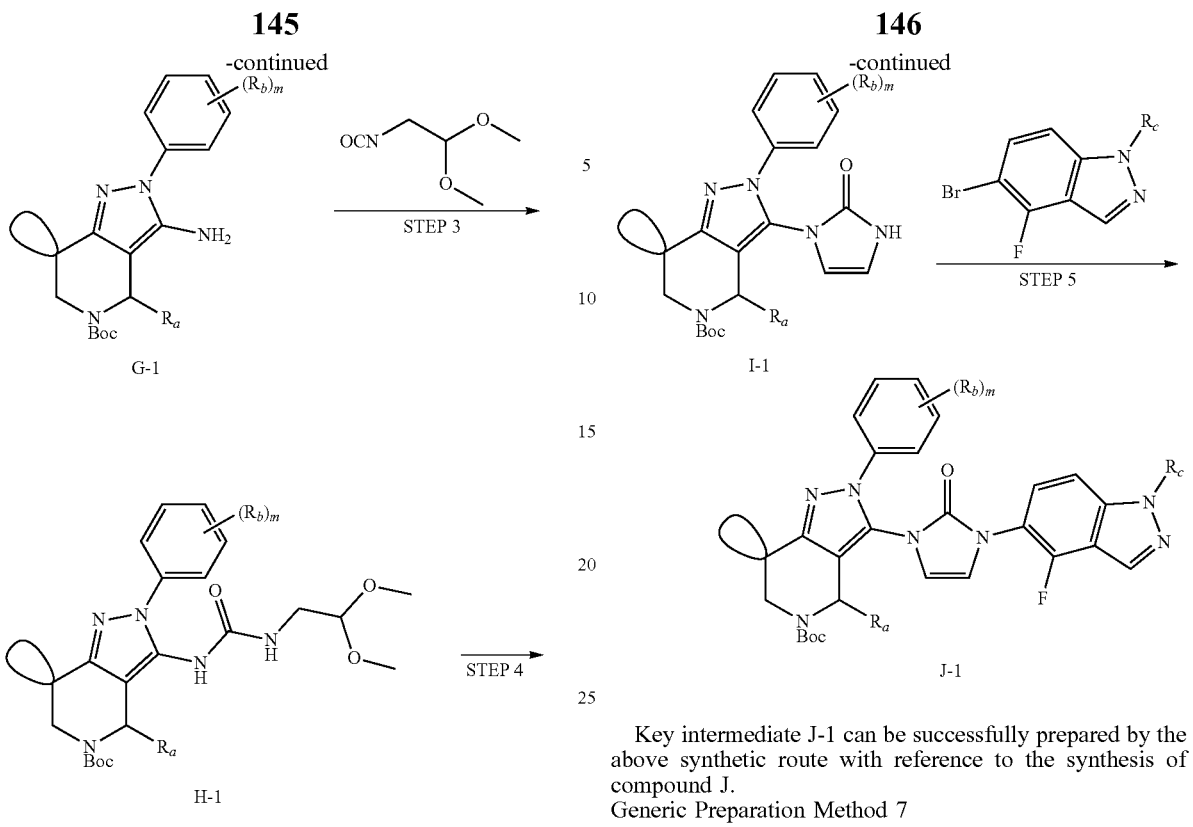
Key intermediate J-1 can be successfully prepared by the above synthetic route with reference to the synthesis of compound J.
Generic Preparation Method 7
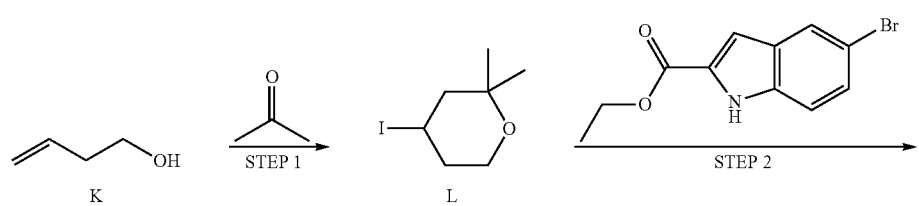
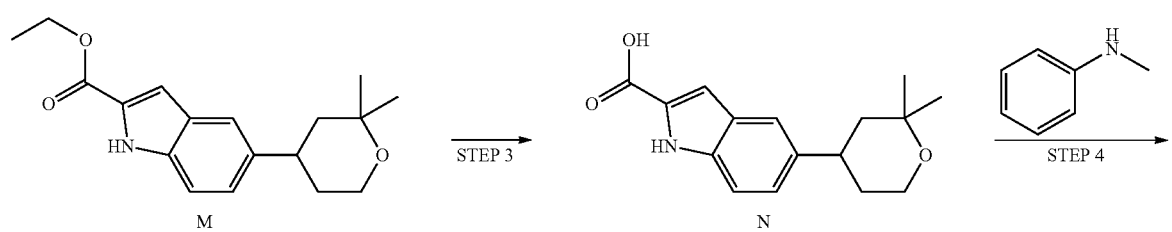
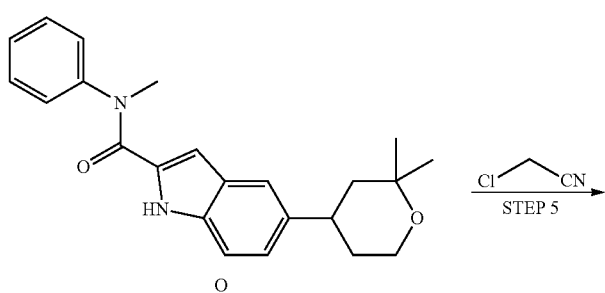

-continued
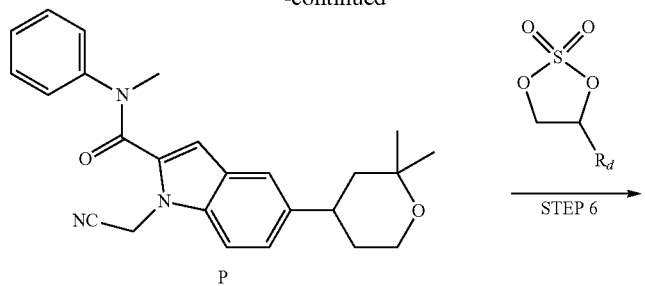
P
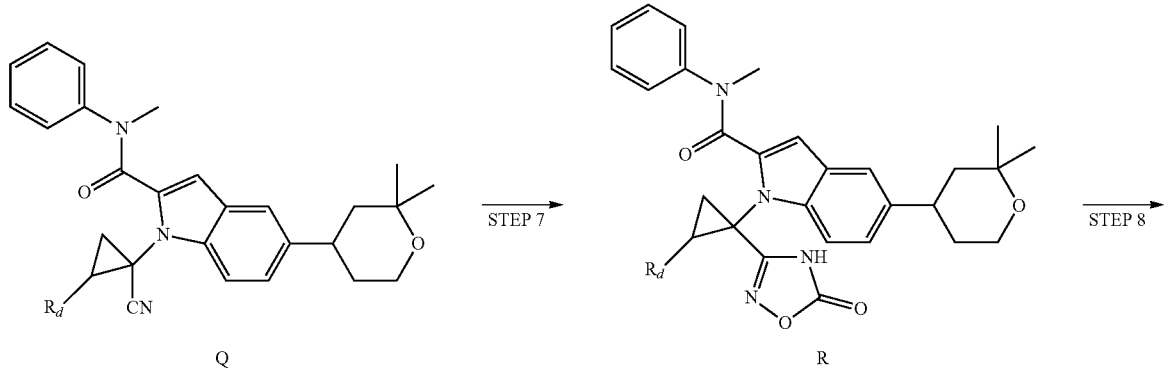
Q R
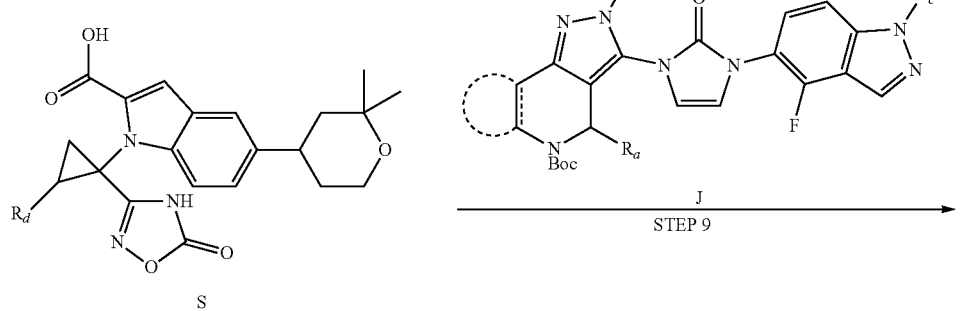
S
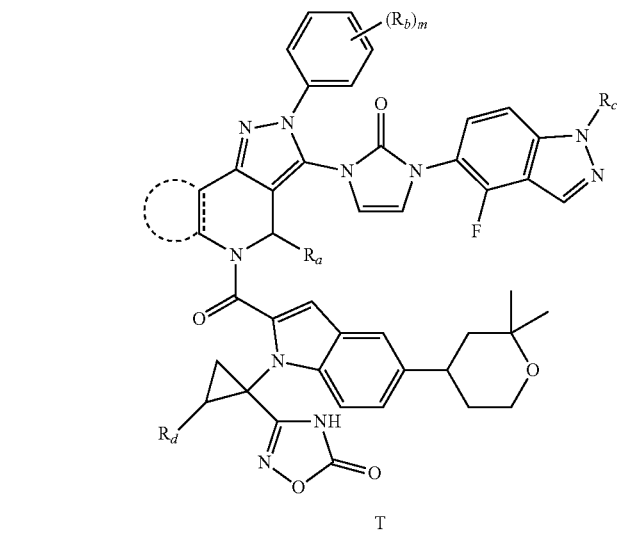
T

Target compound T can be successfully prepared by the above synthetic route. Firstly, commercial raw material K and acetone are used as starting materials to afford iodotetrahydropyran intermediate L in the presence of an iodine source. Followed by the Negishi reaction to afford intermediate M, and undergoes the hydrolysis and condensation reactions to afford compound O. Subsequently, a cyano group is introduced into the compound O through the nucleophilic substitution reaction and the giving compound reacted with a cyclic sulfate as raw material to construct the three-membered ring, while the cyano moiety is further reacted with hydroxylamine and carbonyldiimidazole to afford intermediate R. Acid S is synthesized through the hydrolysis reaction of R and then undergoes the condensation reaction with the product of compound J obtained after deprotection under acidic conditions to afford compound T.

Generic Preparation Method 8

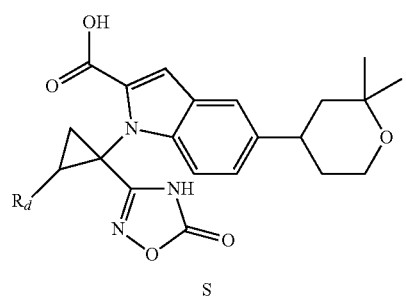

S

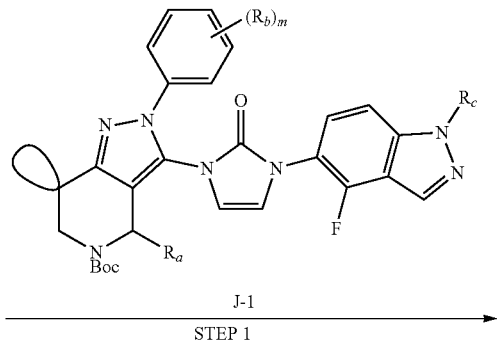

J-1
STEP 1

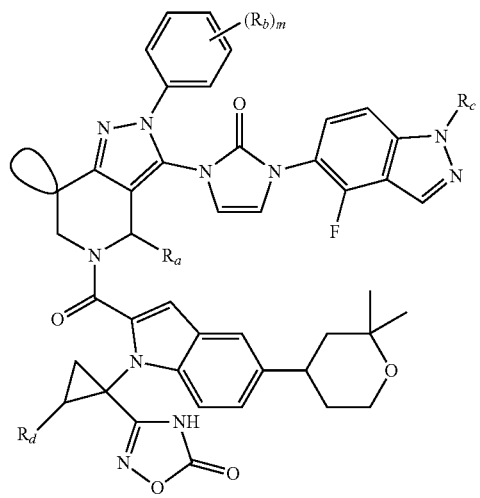

T-1

Target compound T-1 can be successfully prepared by the above synthetic route. Compounds S and J-1 can be transformed into compound T-1 under condensation reaction conditions.

Generic Preparation Method 9

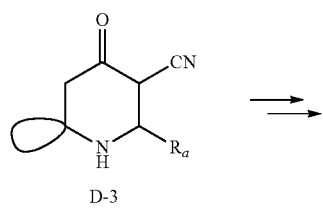

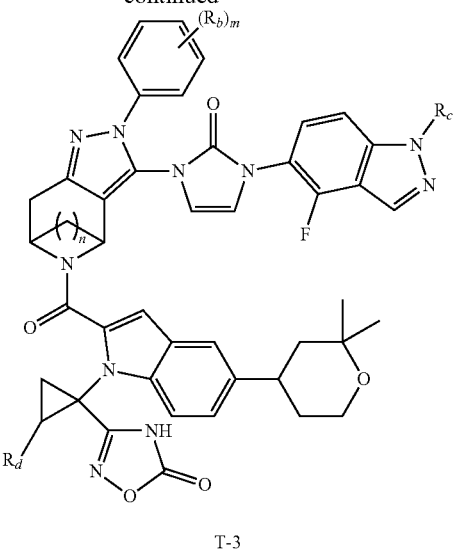

Target compound T-3 can be successfully prepared by the above synthetic route. Firstly, cyano is introduced into commercial raw material U-1 under basic conditions to afford intermediate U-2. Subsequently, compound T-3 can be prepared with reference to Generic Preparation Methods 6 and 8.

Generic Preparation Method 11

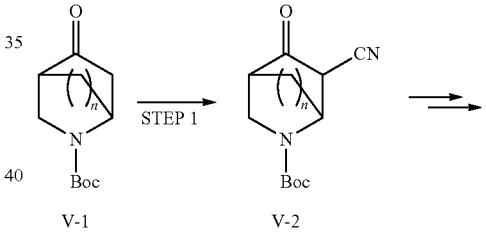

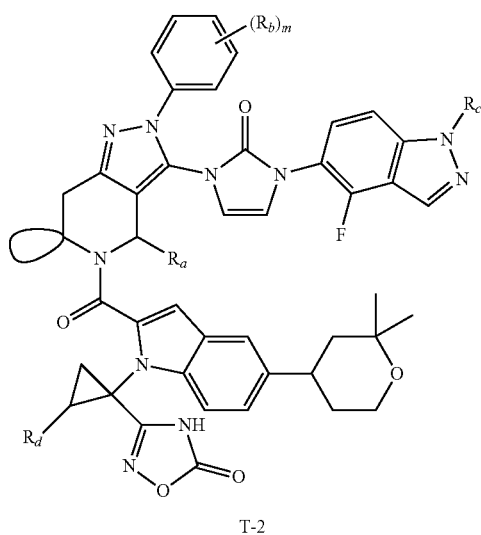

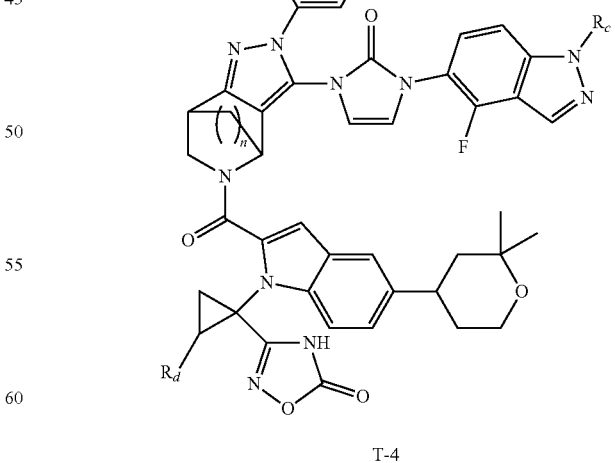

Compound T-2 can be prepared by replacing D-2 with D-3 with reference to Generic Preparation Methods 6 and 8.

Generic Preparation Method 10

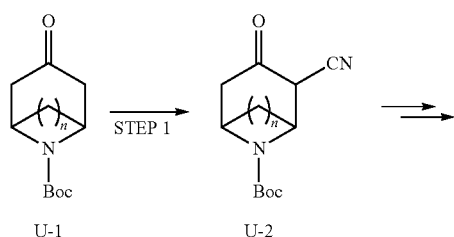

Target compound T-4 can be successfully prepared by the above synthetic route. Firstly, cyano is introduced into commercial (or prepared) raw material V-1 under basic conditions to afford intermediate V-2. Subsequently, compound T-4 can be prepared with reference to Generic Preparation Methods 6 and 8.

In another aspect, the present disclosure provides a pharmaceutical composition, comprising the above-mentioned compound, or the isotope-labelled compound, stereoisomer, or pharmaceutically acceptable salt thereof, and a pharmaceutically acceptable excipient and/or carrier (e.g. at least one pharmaceutically acceptable carrier).

In another aspect, the present disclosure provides a method for modulating GLP-1R, comprising administering, to a system or subject in need thereof, an effective amount (e.g. a therapeutically effective amount) of the above-mentioned compound (e.g. the compound of Formula I), or the isotope-labelled compound, stereoisomer, or pharmaceutically acceptable salt thereof, or the above-mentioned pharmaceutical composition, in order to modulate the GLP-1R.

In another aspect, the present disclosure provides a method for treating, ameliorating, or preventing a disease or condition responsive to inhibition of GLP-1R, comprising administering, to a system or subject in need thereof, an effective amount (e.g. a therapeutically effective amount) of the above-mentioned compound (e.g. the compound of Formula I), or the isotope-labelled compound, stereoisomer, or pharmaceutically acceptable salt thereof, or the above-mentioned pharmaceutical composition, and optionally combining with a second therapeutic agent, in order to treat, ameliorate, or prevent the disease or condition.

In another aspect, the present disclosure provides a method for treating, ameliorating, or preventing a disease or condition mediated by GLP-1R, comprising administering, to a system or subject in need thereof, an effective amount (e.g. a therapeutically effective amount) of the above-mentioned compound (e.g. the compound of Formula I), or the isotope-labelled compound, stereoisomer, or pharmaceutically acceptable salt thereof, or the above-mentioned pharmaceutical composition, and optionally combining with a second therapeutic agent, in order to treat, ameliorate, or prevent the disease or condition.

In another aspect, the present disclosure provides use of the above-mentioned compound (e.g. the compound of Formula I), or the isotope-labelled compound, stereoisomer, or pharmaceutically acceptable salt thereof, or the above-mentioned pharmaceutical composition in the manufacture of a medicament for the modulation of GLP-1R.

In another aspect, the present disclosure provides use of the above-mentioned compound (e.g. the compound of Formula I), or the isotope-labelled compound, stereoisomer, or pharmaceutically acceptable salt thereof, or the above-mentioned pharmaceutical composition in the manufacture of a medicament for the treatment, amelioration, or prevention of a disease or condition responsive to inhibition of GLP-1R. In a particular embodiment, the compound or pharmaceutical composition according to the present disclosure may be used alone or in combination with a second therapeutic agent to treat, ameliorate, or prevent the disease or condition responsive to inhibition of GLP-1R.

In another aspect, the present disclosure provides use of the above-mentioned compound (e.g. the compound of Formula I), or the isotope-labelled compound, stereoisomer, or pharmaceutically acceptable salt thereof, or the above-mentioned pharmaceutical composition in the manufacture of a medicament for the treatment, amelioration, or prevention of a disease or condition mediated by GLP-1R. In a particular embodiment, the compound or pharmaceutical composition according to the present disclosure may be used alone or in combination with a second therapeutic agent to treat, ameliorate, or prevent the disease or condition mediated by GLP-1R.

In another aspect, the present disclosure provides the above-mentioned compound (e.g. the compound of Formula I), or the isotope-labelled compound, stereoisomer, or pharmaceutically acceptable salt thereof, or the above-mentioned pharmaceutical composition for use in the modulation of GLP-1R.

In another aspect, the present disclosure provides the above-mentioned compound (e.g. the compound of Formula I), or the isotope-labelled compound, stereoisomer, or pharmaceutically acceptable salt thereof, or the above-mentioned pharmaceutical composition for use in the treatment, amelioration, or prevention of the disease or condition responsive to inhibition of GLP-1R.

In another aspect, the present disclosure provides the above-mentioned compound (e.g. the compound of Formula I), or the isotope-labelled compound, stereoisomer, or pharmaceutically acceptable salt thereof, or the above-mentioned pharmaceutical composition for use in the treatment, amelioration, or prevention of the disease or condition mediated by GLP-1R.

Specifically, the disease or condition according to the present disclosure includes, but is not limited to, autoimmune diseases, transplant-associated diseases, infectious diseases, or other diseases or conditions mediated by GLP-1R. The disease or condition includes, but is not limited to, diabetes, diabetic complications, obesity, impaired glucose tolerance, overweight, hyperlipidemia, hypercholesterolemia, atherosclerosis, hypertension, coronary heart disease, congestive heart failure, arrhythmia, cerebral infarction, stroke, liver disease, non-alcoholic fatty liver disease, non-alcoholic steatohepatitis, dementia, Parkinson's disease, and diabetic nephropathy.

The novel GLP-1R inhibitor provided herein has at least one advantageous property selected from the group consisting of ease of drug administration, solubility, drug-drug interactions, potency, stability, selectivity, toxicity, drug resistance, and pharmacokinetic and pharmacodynamic properties.

Definitions of Terms

Unless otherwise specified herein, the terms of the present disclosure have the following meanings:

Unless otherwise defined, all technical and scientific terms used herein have the same meanings as typically understood by those skilled in the art. Unless otherwise specified, all patents, patent applications, publications, etc. cited herein are incorporated by reference in their entirety. If there are multiple definitions of the same term in the present disclosure, the definition in this section shall prevail.

It should be appreciated that the preceding general descriptions and the following specific descriptions are merely illustrative and are not intended to limit any of the claims. The singular used herein includes the plural, unless otherwise specified. It should be noted that in the description and appended claims, the singular references such as "one", "a/an", and "this" include the plural references, unless otherwise indicated herein. In addition, "comprising", "including", and similar terms are not limiting.

Unless otherwise indicated, the mass spectrometry (MS), nuclear magnetic resonance (NMR), high performance liquid chromatography (HPLC), infrared (IR) and ultraviolet/visible (UV/Vis) spectroscopy, and conventional pharmacological techniques used herein are existing technologies.

Unless otherwise defined, the nomenclatures and experimental methods and techniques involved in the analytical chemistry, organic synthetic chemistry, medicinal chemistry, and pharmaceutical chemistry herein are all known. Standard techniques can be utilized for chemical synthesis, chemical analysis, drug preparation, formulation and administration, and patient treatment. Reaction and purification techniques can be implemented referring to the manufacturer's instructions, or to the known and commonly used techniques, or to the methods described herein. The techniques and operations described above can be implemented by the conventional known methods and the methods in the literatures cited in the present description. In the description, the groups and substituents can be selected by those skilled in the art to form stable structures and compounds that comply with the valence bond theory. When a substituent is indicated as a chemical formula, a group in the chemical formula written from left to right is the same as that written from right to left. For example, $CH_2O$ and $OCH_2$ are the same.

"Substitution" means that a hydrogen atom is substituted with a substituent. It should be noted that the substituent on a particular atom is restricted by its valence state.

The term "$C_{i-j}$" or "i- to j-membered" used herein means that this moiety has i to j carbon atoms or i to j atoms. For example, "$C_{1-6}$ alkyl" means that the alkyl has 1 to 6 carbon atoms. Similarly, $C_{3-10}$ cycloalkyl means that the cycloalkyl has 3 to 10 carbon atoms.

When any variable (such as R) occurs more than once in the structure of a compound, it is independently defined at each occurrence. Thus, for example, if a group is substituted with 0 to 2 R, this group can be optionally substituted with at most two R, and R is independently selected at each occurrence. In addition, only when substituent(s) and/or variant(s) thereof in combination with this group result in stable compounds can such combination(s) be allowed.

"One or more" or "at least one" refers to one, two, three, four, five, six, seven, eight, nine, or more.

Unless otherwise specified, the term "hetero" refers to a heteroatom or a heteroatom group (i.e., a group containing heteroatom(s)), namely, atoms other than carbon and hydrogen atoms or groups containing such atoms. Preferably, the heteroatom is independently selected from the group consisting of O, N, S, P, and the like. In the embodiments involving two or more heteroatoms, the two or more heteroatoms can be the same, or the two or more heteroatoms can be partially or fully different.

"Alkyl", whether used alone or in combination with other terms, refers to a branched or linear, saturated aliphatic hydrocarbyl group with the specific number of carbon atoms. Unless otherwise indicated, "alkyl" refers to $C_{1-10}$ alkyl. For example, "$C_{1-6}$" in "$C_{1-6}$ alkyl" refers to a linear or branched alkyl having 1, 2, 3, 4, 5, or 6 carbon atoms. For example, "$C_{1-8}$ alkyl" includes, but is not limited to, methyl, ethyl, n-propyl, isopropyl, n-butyl, tert-butyl, isobutyl, pentyl, hexyl, heptyl, and octyl.

"Cycloalkyl", whether used alone or in combination with other terms, refers to a monocyclic or polycyclic (e.g. bicyclic or tricyclic), saturated hydrocarbon ring system, typically having 3 to 16 ring atoms. All the ring atoms of cycloalkyl are carbon atoms and cycloalkyl contains neither heteroatom nor double bond. In polycyclic cycloalkyl, two or more rings can be arranged in a fused, bridged, or spiro form. Examples of monocyclic cycloalkyl system include, but are not limited to, cyclopropyl, cyclobutyl, cyclopentyl, cyclohexyl, cycloheptyl, and cyclooctyl. Bridged cycloalkyl is a polycyclic system containing 3 to 10 carbon atoms, and further contains one or two alkylene bridges each consisting of 1, 2, or 3 carbon atoms and connecting two non-adjacent carbon atoms in the ring system. Cycloalkyl can be fused with aryl or heteroaryl. In some embodiments, cycloalkyl is in a benzo-fused form. Examples of bridged cycloalkyl system include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0³,⁷]nonane, and tricyclo[3.3.1.1³,⁷]decane (adamantane). Monocyclic and bridged cycloalkyl can be attached to the parent molecular moiety through any substitutable atom in the ring system.

"Cycloalkenyl", whether used alone or in combination with other terms, refers to a partially unsaturated cyclic hydrocarbon group consisting of 3 to 8 carbon atoms and containing at least one carbon-carbon double bond. Cycloalkenyl includes monocyclic and bicyclic systems, wherein the bicyclic system includes spirocyclic, fused cyclic, and bridged cyclic systems, and any of the rings in these systems is non-aromatic. The $C_{3-8}$ cycloalkenyl includes cycloalkenyl having 3 to 8 carbon atoms, etc., which can be monovalent, divalent, or polyvalent. Examples of $C_{3-8}$ cycloalkenyl include, but are not limited to, cyclopropenyl, cyclobutenyl, cyclopentenyl, cyclopentadienyl, cyclohexenyl, cyclohexadienyl, etc.

"Alkenyl", whether used alone or in combination with other terms, refers to a linear, branched, or cyclic, non-aromatic hydrocarbyl group containing 2 to 10 carbon atoms and having at least one carbon-carbon double bond. In some embodiments, there is one carbon-carbon double bond, and up to four non-aromatic carbon-carbon double bonds may be present. Therefore, "$C_{2-6}$ alkenyl" refers to alkenyl containing 2 to 6 carbon atoms. The alkenyl group includes, but is not limited to, vinyl (including the case where only one carbon atom in a carbon-carbon double bond serves as a ring atom, for example,

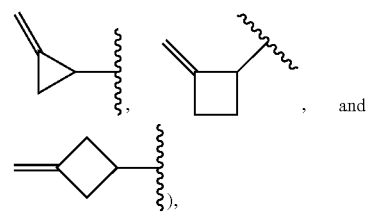

propenyl, butenyl, 2-methylbutenyl, and cyclohexenyl. The linear, branched, or cyclic moiety of alkenyl may contain a double bond, and if indicated as a substituted alkenyl, it means that the alkenyl may be substituted.

"Alkynyl", whether used alone or in combination with other terms, refers to a linear, branched, or cyclic hydrocarbyl group containing 2 to 10 carbon atoms and at least one carbon-carbon triple bond. In some embodiments, there may be as many as three carbon-carbon triple bonds. Therefore, "$C_{2-6}$ alkynyl" refers to alkynyl containing 2 to 6 carbon atoms. The alkynyl group includes, but is not limited to, ethynyl, propynyl, butynyl, 3-methylbutynyl, etc. The linear, branched, or cyclic moiety of alkynyl may contain a triple bond, and if indicated as a substituted alkynyl, it means that the alkynyl may be substituted.

"Halogen", whether used alone or in combination with other terms, refers to fluorine, chlorine, bromine, and iodine.

"Alkoxy", whether used alone or in combination with other terms, refers to a group formed by attaching the alkyl as defined above to an oxygen atom via a single bond. Alkoxy is attached to the remaining moiety of the molecule via the oxygen atom. Alkoxy can be denoted by —O-alkyl. "$C_{1-10}$ alkoxy" refers to alkoxy containing 1 to 10 carbon atoms, and can have a linear or branched structure. Alkoxy includes, but is not limited to, methoxy, ethoxy, n-propoxy, isopropoxy, butoxy, pentoxy, hexoxy, etc.

"Alkylamino", whether used alone or in combination with other terms, refers to a group formed by attaching the alkyl as defined above to a nitrogen atom via a single bond. Alkylamino is attached to the remaining moiety of the molecule via the nitrogen atom. Alkylamino can be denoted by —NH(alkyl). "$C_{1-10}$ alkylamino" refers to alkylamino containing 1 to 10 carbon atoms, and can have a linear or branched structure. Alkylamino includes, but is not limited to, methylamino, ethylamino, n-propylamino, isopropylamino, butylamino, hexylamino, etc.

"Di(alkyl)amino", whether used alone or in combination with other terms, refers to a group formed by attaching two alkyls as defined above to a nitrogen atom via single bonds. Di(alkyl)amino is attached to the remaining moiety of the molecule via the nitrogen atom. Di(alkyl)amino can be denoted by —N(alkyl)$_2$. "Di($C_{1-10}$ alkyl)amino" refers to di($C_{1-10}$ alkyl)amino having two alkyl moieties each containing 1 to 10 carbon atoms, and can have a linear or branched structure.

"Aryl", whether used alone or in combination with other terms, refers to a monocyclic, bicyclic, or tricyclic, monovalent aromatic hydrocarbon ring system having 6, 7, 8, 9, 10, 11, 12, 13, or 14 carbon atoms (a "$C_{6-14}$ aryl" group), in particular a ring having 6 carbon atoms (a "$C_6$ aryl" group), such as phenyl; or a ring having 10 carbon atoms (a "$C_{10}$ aryl" group), such as naphthyl; or a ring having 14 carbon atoms (a "$C_{1-4}$ aryl" group), such as anthryl. Aryl can be fused with cycloalkyl or heterocyclyl.

A divalent group formed from a substituted benzene derivative and having a free valence electron on a ring atom is designated as a substituted phenylene group. A divalent group, which is derived from a monovalent polycyclic hydrocarbyl group whose name ends with "-yl", is obtained by further removing a hydrogen atom attached to a carbon atom containing a free valence electron and is named by adding "-idene" to the name of the monovalent group. For example, naphthyl with two linking positions is referred to as naphthylidene.

"Heteroaryl", whether used alone or in combination with other terms, refers to a monocyclic, bicyclic, or tricyclic, monovalent aromatic ring system having 5, 6, 7, 8, 9, 10, 11, 12, 13, or 14 ring atoms (a "5- to 14-membered heteroaryl" group), in particular 5, 6, 9, or 10 atoms, and containing at least one heteroatom which can be identical or different, where the heteroatom is selected from the group consisting of N, O, and S. Heteroaryl can be fused with cycloalkyl or heterocyclyl.

In some embodiments, "heteroaryl" refers to:
a 5- to 8-membered monocyclic aromatic ring containing 1 to 4, or 1 to 3 in some embodiments, heteroatoms selected from the group consisting of N, O, and S, while all the remaining atoms are carbon atoms, and at least one of the heteroatoms is present in the aromatic ring; and a 8- to 12-membered bicyclic aromatic ring containing 1 to 6, or 1 to 4 in some embodiments, or 1 to 3 in some embodiments, heteroatoms selected from the group consisting of N, O, and S, while all the remaining atoms are carbon atoms, and at least one of the heteroatoms is present in the aromatic ring; and a 11- to 14-membered tricyclic aromatic ring containing 1 to 8, or 1 to 6 in some embodiments, or 1 to 4 in some embodiments, or 1 to 3 in some embodiments, heteroatoms selected from the group consisting of N, O, and S, while all the remaining atoms are carbon atoms, and at least one of the heteroatoms is present in the aromatic ring. When the total number of S and O in the heteroaryl is greater than 1, these heteroatoms are not adjacent to one another. In some embodiments, the total number of S and O in the heteroaryl is not greater than 2. In some embodiments, the total number of S and O in the heteroaryl is not greater than 1.

Examples of heteroaryl include, but are not limited to, pyridinyl, pyrazinyl, pyrimidinyl, pyrazolyl, imidazolyl, pyridazinyl, triazinyl, pyrrolyl, oxazolyl, isoxazolyl, thiazolyl, isothiazolyl, thiadiazolyl, triazolyl, tetrazolyl, thienyl, and furanyl. Further, the heteroaryl includes, but is not limited to, indazolyl, indolyl, benzothienyl, benzofuranyl, benzimidazolyl, benzotriazolyl, quinoxalinyl, quinolinyl, and isoquinolinyl. "Heteroaryl" includes all N-oxidized derivatives of a nitrogen-containing heteroaryl.

The name of a monovalent heteroaryl group ends with "-yl", and the divalent group derived therefrom is obtained by further removing a hydrogen atom attached to a carbon atom containing a free valence electron. The divalent group is named by adding "-idene" to the name of the monovalent group. For example, a pyridinyl with two linking positions is referred to as pyridinylidene.

"Heterocyclic ring" (and its derivatives such as "heterocyclic" or "heterocyclyl") refers generally to a saturated or unsaturated, monocyclic or polycyclic (e.g. bicyclic), cyclic aliphatic hydrocarbon system typically having 3 to 12 ring atoms and containing at least one (e.g. 1, 2, 3 or 4) heteroatom independently selected from the group consisting of oxygen, sulfur, nitrogen, and phosphorus (preferably, oxygen, sulfur, and nitrogen). In a polycyclic system, two or more rings can be linked in a fused, bridged, or spiro manner, and the heterocyclic ring can be fused with aryl or heteroaryl. In some embodiments, the heterocyclic ring is in a benzo-fused form. Heterocyclic ring also includes the ring systems substituted with one or more oxo (=O) or imino (=NH) moieties. In some embodiments, the C, N, S, and P atoms in the heterocyclic ring are optionally substituted with oxo groups. In some embodiments, the C, S, and P are optionally substituted with imino groups, and the imino groups can be unsubstituted or substituted. Either the carbon atom or the heteroatom in the heterocyclic ring may be the linking position, provided that a stable structure can be formed. When there is a substituent on the heterocyclic ring, this substituent may be attached to any heteroatom or carbon atom in the heterocyclic ring, provided that a stable chemical structure that complies with the valence bond theory can be formed.

Suitable heterocyclic ring includes, for example, pyrrolidinyl, imidazolidinyl, pyrazolidinyl, piperidinyl, piperazinyl, and hexahydropyridazinyl. Examples of heterocyclic ring having one or more oxo moieties include, but are not limited to, piperidinyl-N-oxide, morpholinyl-N-oxide, 1-oxo-thiomorpholinyl, and 1,1-dioxo-thiomorpholinyl. Bicyclic heterocyclic ring includes, but is not limited to:

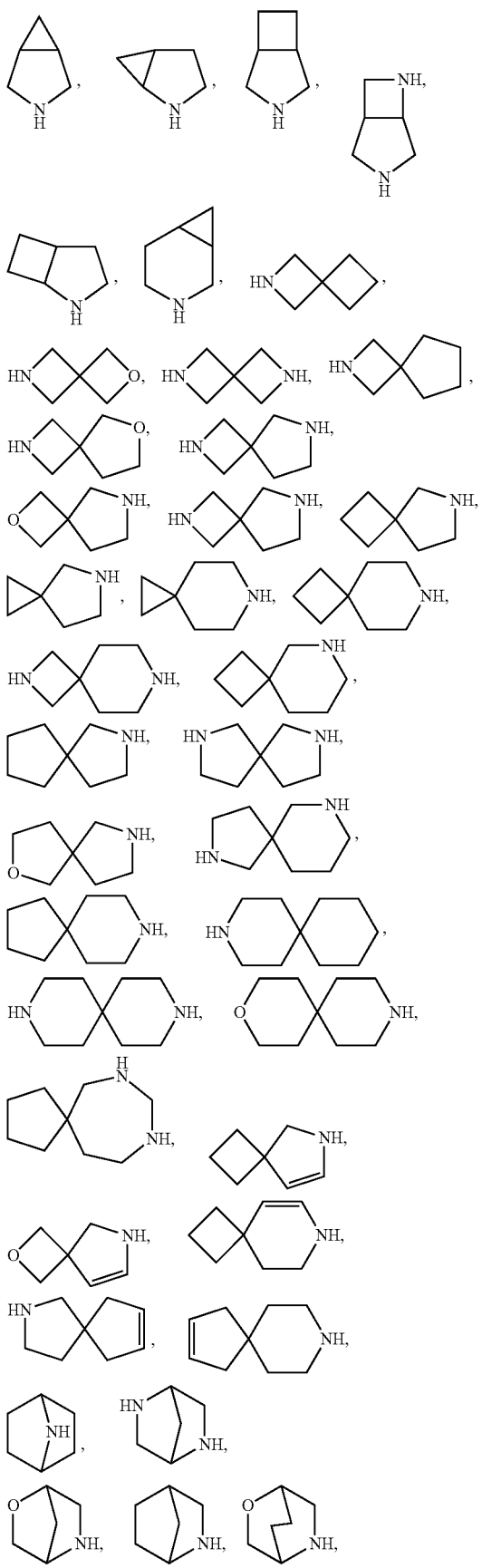
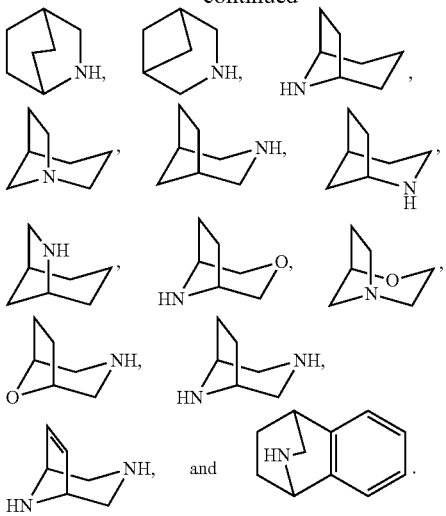

"Aryl-alkyl" (or "arylalkyl") refers to the alkyl as defined above that is substituted with the aryl as defined above. Exemplary arylalkyl includes, but is not limited to, benzyl, phenylethyl, naphthylmethyl, etc. In some embodiments, arylalkyl contains 7 to 20 or 7 to 11 carbon atoms. When "aryl-$C_{1-4}$ alkyl" is used, "$C_{1-4}$" refers to the number of carbon atoms of the alkyl moiety, rather than the aryl moiety.

"Heterocyclyl-alkyl" refers to the alkyl as defined above that is substituted with the heterocyclyl as defined above. When "heterocyclyl-$C_{1-4}$ alkyl" is used, "$C_{1-4}$" refers to the number of carbon atoms of the alkyl moiety, rather than the heterocyclyl moiety.

"Cycloalkyl-alkyl" refers to the alkyl as defined above that is substituted with the cycloalkyl as defined above. When "$C_{3-10}$ cycloalkyl-$C_{1-4}$ alkyl" is used, "$C_{3-10}$" refers to the number of carbon atoms of the cycloalkyl moiety, rather than the alkyl moiety, and "$C_{1-4}$" refers to the number of carbon atoms of the alkyl moiety, rather than the cycloalkyl moiety.

"Heteroaryl-alkyl" refers to the alkyl as defined above that is substituted with the heteroaryl as defined above. When "heteroaryl-$C_{1-4}$ alkyl" is used, "$C_{1-4}$" refers to the number of carbon atoms of the alkyl moiety, rather than the heteroaryl moiety.

To avoid ambiguity, for example, when referring to substitution of alkyl, cycloalkyl, heterocyclyl, aryl and/or heteroaryl, it means substitution of each of those groups individually or substitutions of combinations of those groups. That is, if R is aryl-$C_{1-4}$ alkyl and can be unsubstituted or substituted independently with at least one (e.g. 1, 2, 3 or 4) $R^X$, it should be understood that the aryl moiety can be unsubstituted or substituted independently with at least one (e.g. 1, 2, 3, or 4) $R^X$, and the alkyl moiety can also be unsubstituted or substituted independently with at least one (e.g. 1, 2, 3, or 4) $R^X$.

"Haloalkyl" refers to the alkyl as defined above that is substituted with the halogen as defined above. "$C_{1-4}$ haloalkyl" refers to haloalkyl containing 1 to 4 carbon atoms, which can have a linear or branched structure. Examples of haloalkyl include, but are not limited to, monofluoromethyl, difluoromethyl, trifluoromethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, and 2,2,2-trifluoroethyl.

"Hydroxyl", whether used alone or in combination with other terms, refers to an "—OH" group.

"Cyano", whether used alone or in combination with other terms, refers to a "—CN" group.

"Nitro", whether used alone or in combination with other terms, refers to a "—NO₂" group.

"Carboxyl", whether used alone or in combination with other terms, refers to a "—C(O)OH (or —CO₂H)" group.

"Carbonyl", whether used alone or in combination with other terms, refers to a "—C(O)—" group.

"Acyl", whether used alone or in combination with other terms, refers to a "—C(O)—R" group, wherein the group R includes, but is not limited to, hydrogen, alkyl, alkenyl, alkynyl, cycloalkyl, alkoxy, haloalkyl, heterocyclyl, aryl, heteroaryl, amino, alkylamino, or a monovalent group formed by a combination thereof, and is attached to the remaining moiety of the molecule via the carbonyl.

"Pharmaceutically acceptable salt" refers to a salt formed with a pharmaceutically acceptable non-toxic base or acid (including inorganic or organic bases and inorganic or organic acids). Salts of pharmaceutically acceptable inorganic bases can be selected from the group consisting of, for example, aluminum, ammonium, calcium, copper, iron, ferrous, lithium, magnesium, manganese, divalent manganese, potassium, sodium, and zinc salts. Further, the salts of pharmaceutically acceptable inorganic bases can be selected from the group consisting of ammonium, calcium, magnesium, potassium, and sodium salts. Salts of pharmaceutically acceptable organic bases can be selected from the group consisting of, for example, primary, secondary, and tertiary amine salts, and substituted amines include naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucosamine, Glucosamine, histidine, hydrabamine, isopropylamine, lysine, meglumine, morpholine, piperazine, piperidine, polyamine resins, procaine, purine, theobromine, triethylamine, trimethamine, tripropylamine, and tromethamine.

When the compound herein is a base, it is desirable to form a salt thereof with at least one pharmaceutically acceptable non-toxic acid selected from the group consisting of inorganic acids and organic acids, for example, acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, and p-toluenesulfonic acid. In some embodiments, the acid can be selected from the group consisting of, for example, citric acid, hydrobromic acid, hydrochloric acid, maleic acid, phosphoric acid, sulfuric acid, fumaric acid, and tartaric acid.

"Administration" (or "administering") or "dosing" refers to providing a subject in need of treatment with the compound or the pharmaceutically acceptable salt thereof or the pharmaceutical composition comprising the same herein.

"Effective amount" refers to a dose of a compound or a pharmaceutically acceptable salt thereof or a pharmaceutical composition comprising the same capable of eliciting a biological or medical response in a tissue, system, animal, or human being that is observable to a researcher, veterinarian, clinician, or other clinical personnel.

"Composition" includes a product comprising specific amounts of specific ingredients and any product directly or indirectly resulting from a combination of these specific amounts of specific ingredients. "Pharmaceutical composition" includes a product comprising an active ingredient (or active pharmaceutically ingredient) and an inert ingredient as a carrier, and any product made directly or indirectly (e.g. by combining, complexing, or aggregating) from two or more ingredients, or resulting from the decomposition of one or more ingredients, or resulting from other types of reactions or interactions of one or more ingredients.

"Pharmaceutically acceptable" is meant to be compatible with the other components in the formulation without unacceptable toxicity to a user.

A "subject" refers to a subject suffering from a disease, disorder, and the like, which includes mammals and non-mammals. Mammals include, but are not limited to, any member of the mammals: humans, non-human primates such as chimpanzees, and other apes and monkeys; farm animals such as cows, horses, sheep, goats, and pigs; domestic animals such as rabbits, dogs, and cats; experimental animals including rodents such as rats, mice, and guinea pigs. Non-mammalian animals include, but are not limited to, birds, fish, etc. In one embodiment of the present disclosure, the mammal is a human. When being subjected to such means as surgery and drug, the subject can also be referred to as a "testee".

"Treatment" includes relief, alleviation or amelioration of a disease or symptom, prevention of other symptoms, amelioration or prevention of metabolic factors underlying a symptom, for example, restraint of progression of a disease or symptom, alleviation of a disease or symptom, promotion of relief of a disease or symptom, or stopping signs of a disease or symptom, and extends to include prevention. "Treatment" further includes realization of therapeutic benefit and/or prophylactic benefit. The therapeutic benefit refers to eradication or amelioration of the condition under treatment. In addition, the therapeutic benefit is achieved by eradicating or ameliorating one or more physiologic signs associated with the underlying disease. While the patient may still suffer from the underlying disease, an amelioration of the patient's disease is observable. The prophylactic benefit means that a patient uses the composition to prevent the risk of suffering from a disease or uses it when one or more physiologic signs of the disease appear though the patient has not yet been diagnosed with this disease.

"Protective group" (Pg) refers to a series of substituents used to react with the other functional groups of a compound to block or protect a particular functional group. For example, "amino protective group" refers to a substituent attached to an amino group to block or protect an amino functional group on a compound. Suitable amino protective groups include, but are not limited to, acetyl, trifluoroacetyl, tert-butoxycarbonyl (BOC), benzyloxycarbonyl (CBZ), and 9-fluorenylmethoxycarbonyl (Fmoc) protective groups. Likewise, "hydroxyl protective group" refers to a series of substituents on hydroxyl effective in blocking or protecting hydroxyl functions. Suitable hydroxyl protective groups include, but are not limited to, acetyl and silyl. "Carboxyl protective group" refers to a series of substituents on carboxyl effective in blocking or protecting carboxyl functions. Common carboxyl protective groups include, but are not limited to, —CH₂CH₂SO₂Ph, cyanoethyl, 2-(trimethylsilyl)ethyl, 2-(trimethylsilyl)ethoxymethyl, 2-(p-toluenesulfonyl)ethyl, 2-(p-nitrobenzenesulfinyl)ethyl, 2-(diphenylphosphine)-ethyl, nitroethyl, etc. For the general descriptions and instructions of the protective groups, see the reference literature: Theodora W. Greene, Peter G. M. Wuts, Protective Groups in Organic Synthesis, 1999.

"NH" protective group includes, but is not limited to, trichloroethoxycarbonyl, tribromoethoxycarbonyl, benzyloxycarbonyl, p-nitrobenzylformyl, o-bromobenzyloxycarbonyl, chloroacetyl, dichloroacetyl, trichloroacetyl, trifluoroacetyl, phenylacetyl, formyl, acetyl, benzoyl, tert-pentyloxycarbonyl, tert-butyloxycarbonyl, p-methoxybenzyloxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropyloxycarbonyl, isopropyloxycarbonyl, phthaloyl, succinyl, alanyl, leucyl, 1-adamantyloxycarbonyl, 8-quinolyloxycarbonyl, benzyl, benzhydryl, trityl, 2-nitrophenylthio, methanesulfonyl, p-toluenesulfonyl, N,N-dimethylaminomethylene, benzylidene, 2-hydroxybenzylidene, 2-hydroxy-5-chlorobenzylidene, 2-hydroxy-1-naphthylidene, 3-hydroxy-4-pyridinylidene, cyclohexylidene, 2-ethoxycarbonylcyclohexylidene, 2-ethoxycarbonylcyclopentylidene, 2-acetylcyclohexylidene, 3,3-dimethyl-5-oxocyclohexylidene, diphenylphosphoryl, dibenzylphosphoryl, (5-methyl-2-oxo-2H-1,3-dioxolen-4-yl)methyl, trimethylsilyl, triethylsilyl, and triphenylsilyl.

"C(O)OH" protective group includes, but is not limited to, methyl, ethyl, n-propyl, isopropyl, 1,1-dimethylpropyl, n-butyl, tert-butyl, phenyl, naphthyl, benzyl, diphenylmethyl, triphenylmethyl, p-nitrobenzyl, p-methoxybenzyl, bis(p-methoxyphenyl)methyl, acetylmethyl, phenacyl, p-nitrophenacyl, p-bromophenacyl, p-methylsulfonylphenacyl, 2-tetrahydropyranyl, 2-tetrahydrofuranyl, 2,2,2-trichloroethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

"OH or SH" protective group includes, but is not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutoxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonium)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl(phenylmethyl), p-methoxybenzyl, 3,4-dimethoxybenzyl, diphenylmethyl, triphenylmethyl, tetrahydrofuranyl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, p-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may be present in the compounds of the present disclosure. For example, the compounds of the present disclosure may have a carbon-carbon double bond or a carbon-nitrogen double bond in the E or Z configuration. According to the Cahn-Ingold-Prelog priority rules, "E" represents a preferred substituent on the opposite side of the carbon-carbon double bond or carbon-nitrogen double bond, and "Z" represents a preferred substituent on the same side of the carbon-carbon double bond or carbon-nitrogen double bond. The compounds of the present disclosure may also be present as a mixture of "E" and "Z" isomers. The substituents around cycloalkyl or heterocyclyl can be defined as cis or trans configurations. In addition, the present disclosure includes different isomers formed as a result of different arrangements of the substituents around the adamantane ring system and mixtures thereof. Two substituents around a single ring in the adamantane ring system are defined as Z or E relative configurations. For example, see Cheryl D. Jones, Mira Kaselj, Ralph N. Salvatore, and William J. le Noble, J Org Chem 1998, 63, 8, 2758-2760.

The compounds of the present disclosure may contain asymmetrically substituted carbon atoms in the R or S configuration. For the definitions of "R" and "S", see Rules for the Nomenclature of Organic Chemistry Section E: Stereochemistry (Recommendations 1974), Pure & Appl. Chem, (1976) 45, 11-30. Compounds containing asymmetrically substituted carbon atoms are racemates if the amounts of R and S configurations are the same. If the amount of one of the configurations is greater than that of the other, the configuration of the chiral carbon atom is expressed as the configuration in the larger amount, preferably with an enantiomeric excess (ee) of about 85% to about 90%, more preferably about 95% to about 99%, and further about 99% or more. Therefore, the present disclosure includes racemic mixtures, relative and absolute stereoisomers, and mixtures of relative and absolute stereoisomers.

The compounds of the present disclosure may exist at an isotopic trace level or isotopically enriched level and contain one or more atoms whose atomic mass and mass number differs from that of the most abundant atom found in nature. The isotope may be radioactive or non-radioactive. Isotopes of atoms such as hydrogen, carbon, nitrogen, oxygen, phosphorus, sulfur, fluorine, chlorine and iodine include, but are not limited to, $^{2}H$ (D), $^{3}H$ (T), $^{13}C$, $^{14}C$, $^{15}N$, $^{18}O$, $^{32}P$, $^{35}S$, $^{18}F$, $^{36}Cl$, and $^{125}I$. Other isotopes containing these atoms and/or other atoms are also within the scope of the present disclosure.

In another embodiment, the isotope-labelled compound contains deuterium ($^{2}H$), tritium ($^{3}H$) or $^{14}C$ isotope. The isotope-labelled compounds of the present disclosure may be obtained by the methods well-known to those skilled in the art. These isotope-labelled compounds may be obtained by replacing the non-labeled reagents with the isotope-labelled reagents with reference to the examples and reaction schemes in the present disclosure. In some embodiments, the compound may be treated with an isotope-labelled reagent to replace an atom with an isotopic atom, for example, substitution of hydrogen with deuterium can be exchanged through the action of a deuterated acid such as $D_2SO_4/D_2O$.

The isotope-labelled compounds of the present disclosure may be used as the standard for the pharmacodynamic binding assay of the GLP-1R inhibitor. Isotope-containing compounds can be used in pharmaceutical studies to evaluate the mechanism of action and metabolic pathways of non-isotope-labeled parent compounds, and to study the in vivo metabolic outcomes of compounds (Blake et al., J.

Pharm. Sci. 1975, 64 (3): 367-391). Such metabolic studies are of great significance for designing safe and effective therapeutic drugs as this can determine whether the in vivo active compound or the metabolite of the parent compound used by the patient is toxic or carcinogenic (Foster et al., Advances in Drug Research, Academic press, London, 1985, Vol. 14: 2-36; Kato et al., J Labelled Comp Radiopharm. 1995, 36(10): 927-932; Kushner et al., Can J Physiol Pharmacol, 1999, 77: 79-88).

In addition, drugs containing non-radioactive active isotopes, such as deuterated drugs, referred to as "heavy drugs", can be used to treat, alleviate or prevent diseases and conditions associated with the GLP-1R activity. The proportion of a certain isotope in a compound that exceeds its natural abundance is called enrichment. The enrichment content includes, but is not limited to, for example, from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92 or 96/o to about 100%.

Stable isotope labeling of drugs can alter their physicochemical properties, such as pKa and liquid solubility. If isotope substitutions affect the regions associated with ligand-receptor interactions, these effects and alterations may influence the pharmacodynamic responses of the drug molecules. Some physical properties of stable isotope-labeled molecules differ from those of unlabeled molecules, while their chemical and biological properties are the same except for one important difference: any chemical bond containing a heavy isotope and an additional atom is stronger than a light isotope due to the increased mass of the heavy isotope. Accordingly, the presence of isotopes at the metabolic or enzymatic conversion sites will slow down this response, thereby potentially altering the pharmacokinetic profile or pharmacodynamics as compared to the non-isotopically labeled compounds.

DETAILED DESCRIPTION

In order to further illustrate the present disclosure, the compounds provided herein and the preparation methods and applications thereof will be described in detail below with reference to the examples.

Where the specific conditions are not specified in the examples, the experimental methods are carried out under conventional conditions. The examples are given to better explain the content of the present disclosure and shall not be interpreted as limiting the content of the present disclosure only to the examples listed herein. Non-essential improvements and modifications made by those skilled in the art to the examples on the basis of the above-mentioned content of the present disclosure still fall within the scope of protection of the present disclosure.

The full names of the abbreviations of the present disclosure are listed in Table 1.

TABLE 1

| Abbrev. | Full Name | Abbrev. | Full Name |
|---|---|---|---|
| MS | Mass spectrometry | NMR | Nuclear magnetic resonance |
| LCMS | Liquid chromatography mass spectrometry | DMF | N,N-Dimethylformamide |
| DCM | Dichloromethane | $CH_3CN$ | Acetonitrile |
| NMP | N-Methylpyrrolidone | CuI | Cuprous iodide |
| THF | Tetrahydrofuran | EA | Ethyl acetate |
| $K_2CO_3$ | Potassium carbonate | $NaBH_4$ | Sodium borohydride |
| Toluene | Toluene | NaHMDS | Sodium bis(trimethylsilyl)amide |
| DIPEA | N,N-Diisopropylethylamine | nBuLi | n-Butyllithium |
| HATU | O-(7-Azabenzotriazol-1-yl)-N,N,N',N'-tetramethyluronium hexafluorophosphate | $Yb(OTf)_3$ | Ytterbium(III) trifluoromethanesulfonate hydrate |
| DMAP | 4-Dimethylaminopyridine | LDA | Lithium diisopropylamide |
| $(CH_2O)_m$ | Polyoxymethylene | DMP | Dess-Martin periodinane |
| NaOAc | Sodium acetate | $NaBH(OAc)_3$ | Sodium triacetoxyborohydride |
| $(Boc)_2O$ | Di-tert-butyl dicarbonate | EtOH | Ethanol |
| Pyr | Pyridine | TFA | Trifluoroacetic acid |
| MsOH | Methanesulfonic acid | m-CPBA | 3-Chloroperbenzoic acid |
| LiHMDS | Lithium bis(trimethylsilyl)amide | CbzCl | Benzyl chloroformate |
| $Et_3SiH$ | Triethylsilyl hydride | $PdCl_2$ | Palladium chloride |
| TEA | Triethylamine | TBDPSCl | Tert-butyl diphenylchlorosilane |
| NaH | Sodium hydride | PCC | Pyridinium chlorochromate |
| $K_3PO_4$ | Potassium phosphate | ACN | Acetonitrile |
| TBAF | Tetrabutylammonium fluoride | NaClO | Sodium hypochlorite |
| TEMPO | 2,2,6,6-Tetramethylpiperidine oxide | $LiAlH(Ot-Bu)_3$ | Lithium tri-tert-butoxyaluminum hydride |
| $MeSO_3H$ | Methanesulfonic acid | IPA | Isopropanol |
| DBU | 1,8-Diazabicyclo[5.4.0]undec-7-ene | KHMDS | Potassium bis(trimethylsilyl)amide |
| CDI | Carbonyldiimidazole | BOMCl | Benzylchloromethyl ether |
| AcCl | Acetylchloride | TsCN | p-Toluenesulfonyl cyanide |
| TFAA | Trifluoroacetic anhydride | TMSNCO | Trimethylsilyl isocyanate |
| $PhI(OAc)_2$ | (Diacetoxyiodo)benzene | DAST | Diethylaminosulfur trifluoride |
| MeOH | Methanol | $Ti(Oi-Pr)_4$ | Titanium(IV) isopropoxide |
| MeI | Iodomethane | $Tf_2O$ | Trifluoromethanesulfonic anhydride |

TABLE 1-continued
| Abbrev. | Full Name | Abbrev. | Full Name |
|---|---|---|---|
| K₂OsO₄ | Potassium osmate | NaIO₄ | Sodium periodate |
| Ms₂O | Methanesulfonic anhydride | Na₂S | Sodium sulfide |
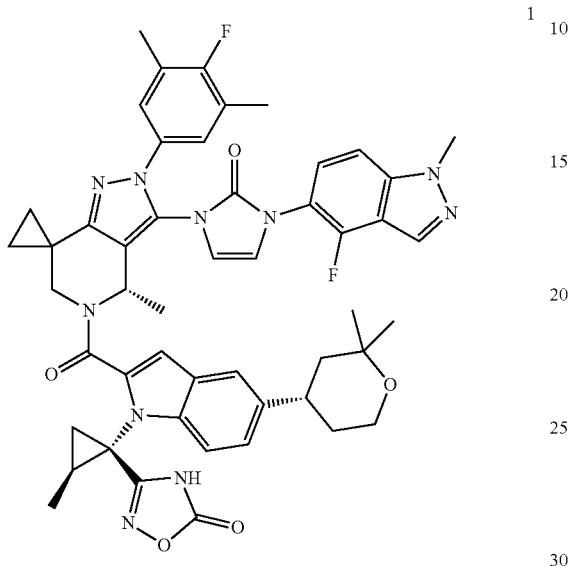
1
Synthetic Route
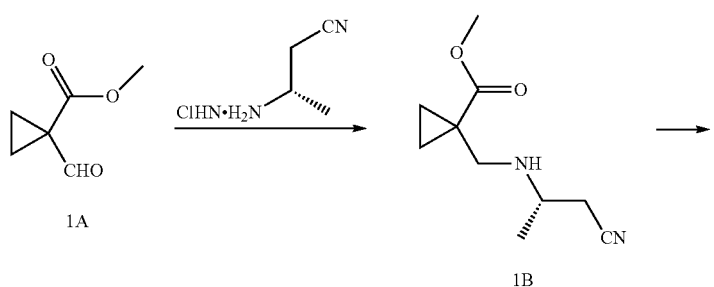
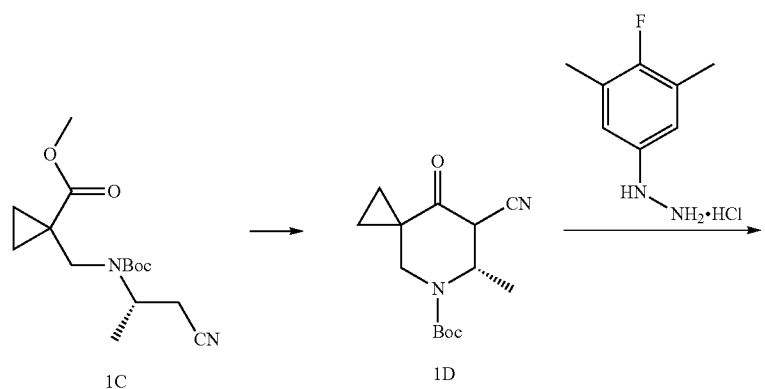

-continued
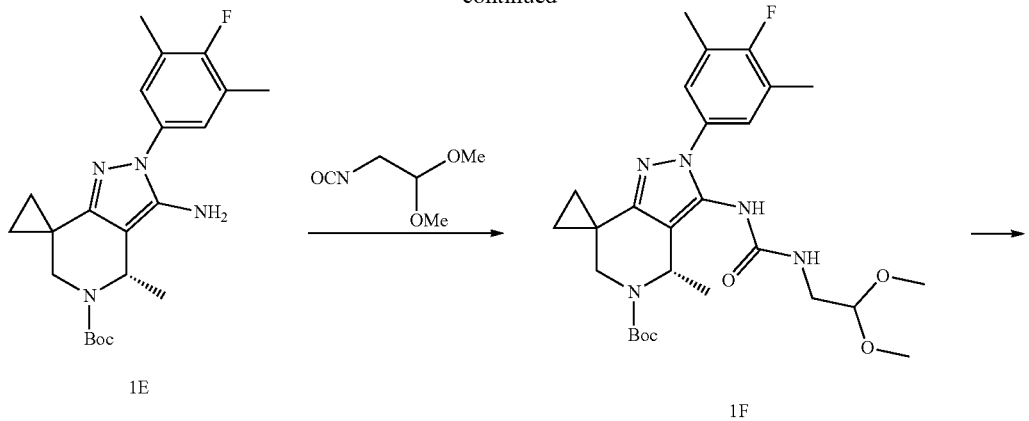
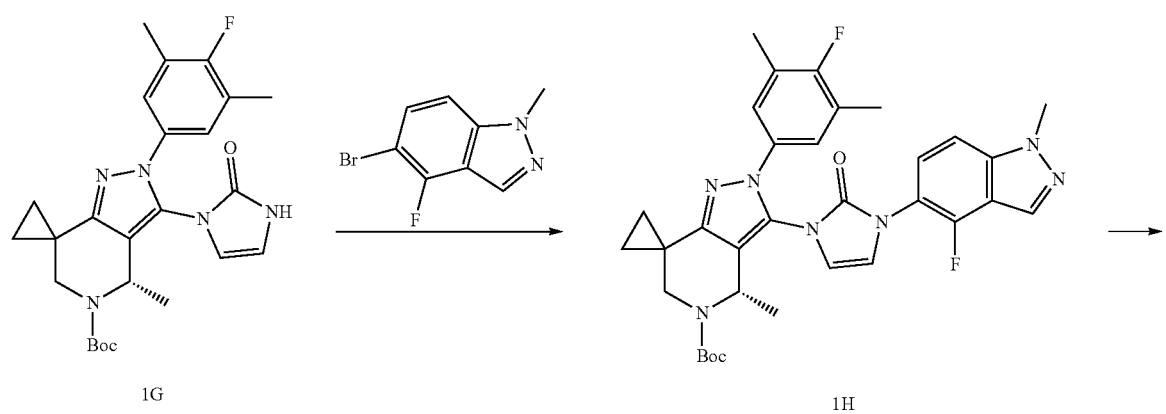
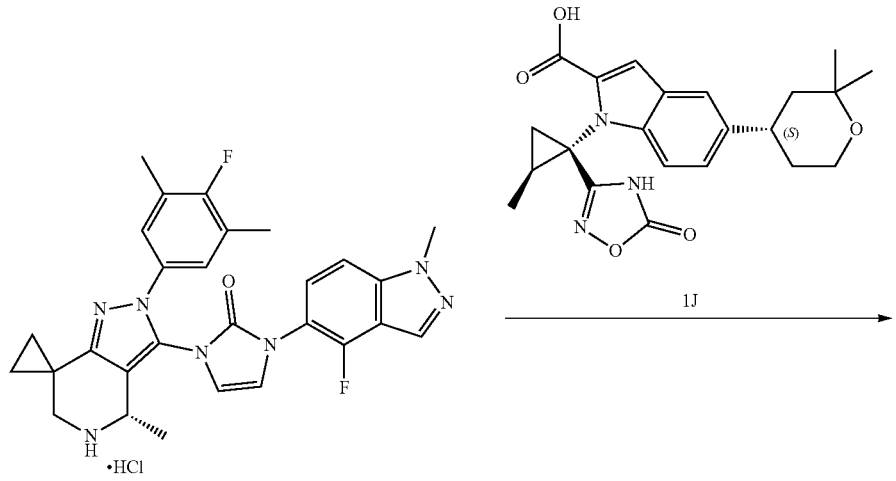

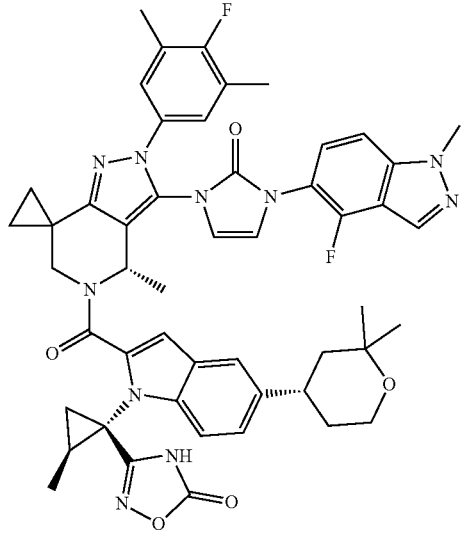

Synthesis of Compound 1B

Compound 1A (commercially available) (0.50 g, 3.92 mmol) and (S)-3-aminobutanenitrile hydrochloride (0.47 g, 3.92 mmol) were weighed and added into 20 mL of dichloromethane. Thereafter, anhydrous sodium acetate (0.33 g, 3.92 mmol) and sodium triacetoxyborohydride (0.83 g, 5.88 mmol) were added at 0° C., and reacted overnight at room temperature under nitrogen protection. The reaction was quenched with a saturated sodium bicarbonate solution. The reaction solution was adjusted to pH 8 to 9, extracted with dichloromethane, dried over anhydrous sodium sulfate, and filtered. The filtrate was concentrated to afford a crude product, and the crude product was used directly in the next reaction step without purification, [M+H]$^+$=197.

Synthesis of Compound 1C

Compound 1B (0.76 g, 3.92 mmol) was dissolved in 18 mL of dichloromethane. Thereafter, triethylamine (0.79 g, 7.84 mmol) and di-tert-butyl dicarbonate (1.28 g, 5.88 mmol) were added at room temperature, and stirred overnight at room temperature. After the reaction was complete, 20 mL of water was added to quench the reaction. The reaction solution was extracted with dichloromethane, dried over anhydrous sodium sulfate, and filtered. The filtrate was concentrated and then separated by column chromatography to afford Compound 1C (0.85 g, a colorless oily product), [M+H]$^+$=297.

Synthesis of Compound 1D

Compound 1C (0.85 g, 2.87 mmol) was dissolved in 20 mL of tetrahydrofuran. Under nitrogen protection, NaHMDS (2.0M THF solution, 2.9 mL, 5.74 mmol) was added dropwise at −20° C., during which the internal temperature was kept at no higher than −10° C. After the dropwise addition was finished, the reaction system was slowly returned to room temperature and stirred for 30 min. The reaction was quenched with a saturated aqueous ammonium chloride solution. The reaction solution was extracted with ethyl acetate, dried over anhydrous sodium sulfate, and filtered. The filtrate was concentrated and then separated by column chromatography to afford Compound 1D (0.57 g, a light yellow oily product), [M+H]$^+$=265.

Synthesis of Compound 1E

Compound 1D (0.13 g, 0.48 mmol), 4-fluoro-3,5-dimethylphenylhydrazine hydrochloride (0.14 g, 0.72 mmol), and pyridine hydrochloride (5.8 mg, 0.05 mmol) were weighed and dissolved in 2 mL of ethanol, and heated to 80° C. and reacted for 5 h under nitrogen protection. The solution was concentrated to remove the solvent. 20 mL of ethyl acetate was added, then washed with a saturated sodium bicarbonate solution. The organic phase was dried over anhydrous sodium sulfate and filtered. The filtrate was concentrated and then separated by column chromatography to afford Compound 1E (0.16 g, a light yellow oily product), [M+H]$^+$=401.

Synthesis of Compound 1F

Compound 1E (0.16 g, 0.40 mmol) was dissolved in 15 mL of pyridine, to which 2-isocyanato-1,1-dimethoxyethane (0.13 g, 1.00 mmol) was added in an ice-water bath, and reacted at room temperature for 5 h. The solution was directly concentrated to dryness via rotary evaporation and separated by silica gel column chromatography to afford Compound 1F (0.16 g, a light yellow solid), [M+H]$^+$=532.

Synthesis of Compound 1G

Compound 1F (160.1 mg, 0.30 mmol) was weighed and dissolved in 6 mL of tetrahydrofuran. Under nitrogen protection, methanesulfonic acid (28.9 mg, 0.30 mmol) was added and stirred at 60° C. for 4 h. After cooling to room temperature, the solution was adjusted to pH 8 to 9 with a saturated sodium bicarbonate solution, extracted with ethyl acetate, dried over anhydrous sodium sulfate, and filtered. The filtrate was concentrated and then separated by the silica gel column chromatography to afford Compound 1G (131.1 mg, a light yellow semisolid), [M+H]$^+$=468.

Synthesis of Compound 1H

Compound 1G (130.1 mg, 0.28 mmol) was dissolved in 12 mL of N-methylpyrrolidone. Thereafter, 5-bromo-4-fluoro-1-methylindazole (128.5 mg, 0.56 mmol), potassium carbonate (116.2 mg, 0.84 mmol), cuprous iodide (61.3 mg, 0.32 mmol), and (1S,2S)-(+)—N,N'-dimethyl-1,2-cyclohexanediamine (91.6 mg, 0.64 mmol) were added in sequence, and reacted at 130° C. for 3 h under nitrogen protection. The reaction system was added with 50 mL of purified water and extracted with ethyl acetate. The organic phases were combined, washed with purified water, washed with saturated saline, dried over anhydrous sodium sulfate, and filtered. The filtrate was concentrated and then separated by column chromatography to afford Compound 1H (170.3 mg, a light yellow oily product), [M+H]$^+$=616.

Synthesis of Compound 1I

Compound 1H (50.0 mg, 0.08 mmol) was weighed and dissolved in 1 mL of dichloromethane, and 2 mL of a solution (4 M) of hydrogen chloride in dioxane was added thereto in an ice bath and reacted at room temperature for 1 h. The solution was concentrated to afford a crude product, and the crude product was used directly in the next step without purification, [M+H]$^+$=516.

Synthesis of Compound 1

The crude product of Compound 1I (31.6 mg, 0.057 mmol) obtained in the previous step was weighed and dissolved in 2 mL of N,N-dimethylformamide. Thereafter, Compound 1J (23.5 mg, 0.057 mmol), HATU (28.2 mg, 0.074 mmol), DIPEA (29.4 mg, 0.23 mmol), and DMAP (2.1 mg, 0.017 mmol) were added in sequence and reacted at room temperature for 5 h. Purified water and ethyl acetate were added for extraction. The organic phase was concentrated and then separated by silica gel column chromatography to afford Compound 1 (30.1 mg, an off-white solid) with the HPLC purity of 99.8%. [M+H]$^+$=909; $^1$H NMR (400 MHz, DMSO-d$_6$) δ 11.56 (s, 1H), 8.19 (s, 1H), 7.53 (s, 2H), 7.38 (d, J=8.5 Hz, 2H), 7.24 (dd, J=8.6, 1.7 Hz, 1H), 7.11 (d, J=6.3 Hz, 2H), 6.91 (s, 1H), 6.78 (d, J=25.4 Hz, 2H), 5.65 (s, 1H), 4.08 (s, 3H), 3.94 (s, 1H), 3.77-3.65 (m, 3H), 3.03-2.97 (m, 1H), 2.23 (s, 6H), 1.74-1.66 (m, 4H), 1.65-1.45 (m, 7H), 1.39 (d, J=7.5 Hz, 2H), 1.27 (s, 5H), 1.18 (s, 5H).

Example 2

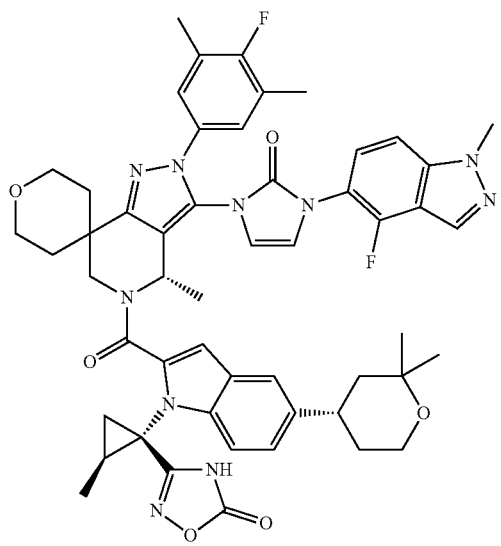

Synthetic Route

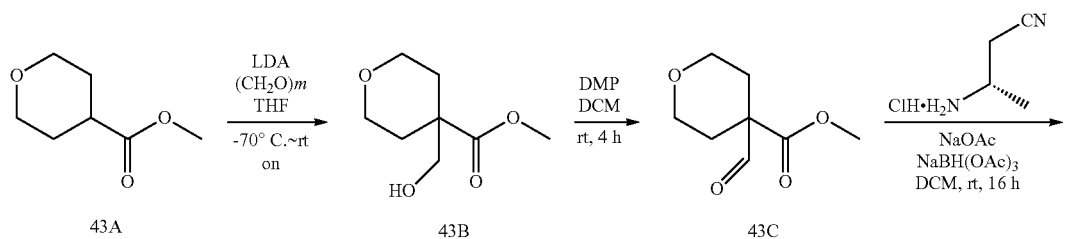

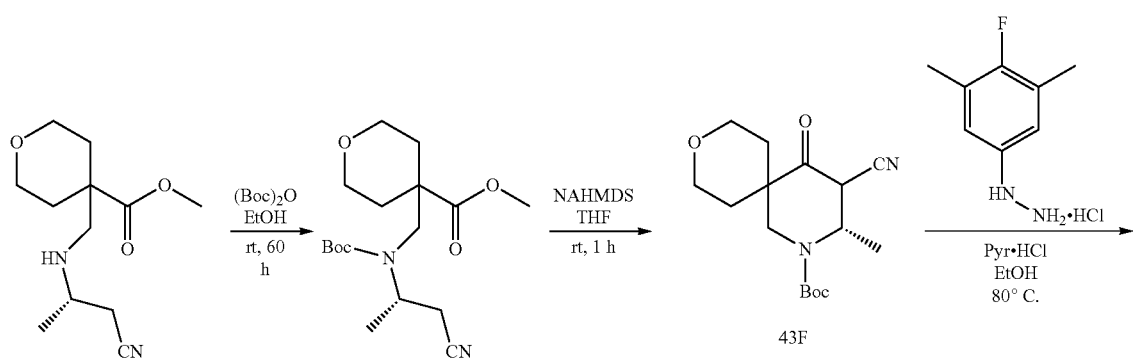

-continued
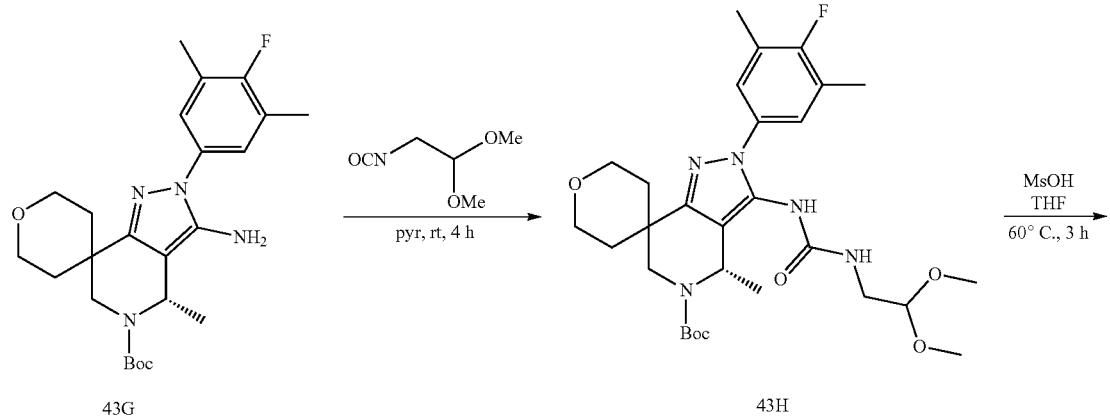
43G
43H
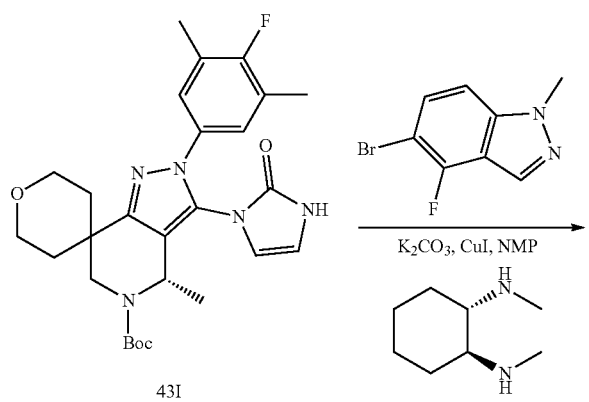
43I
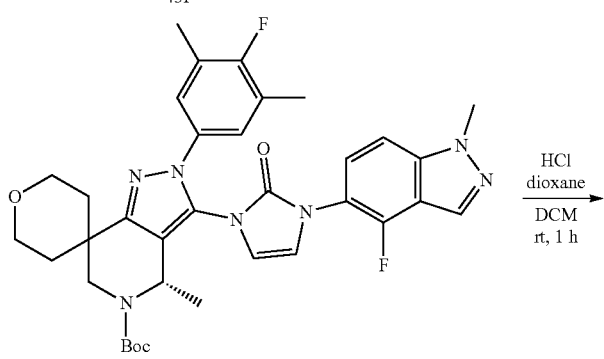
43J
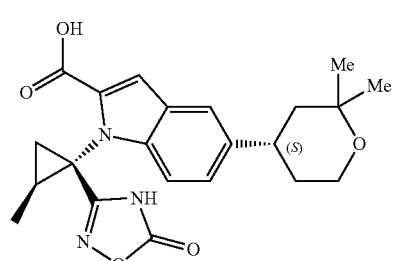
1G
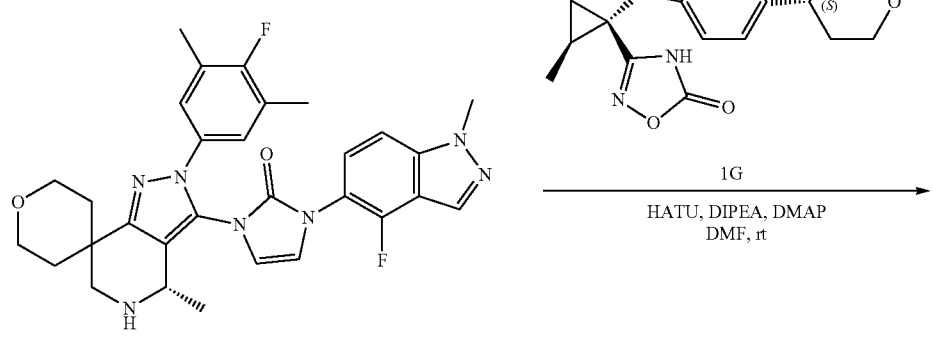
43K

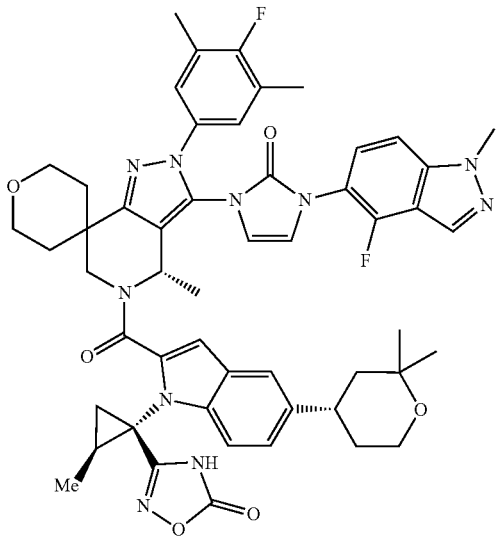

43

Synthesis of Compound 43B

Compound 43A (commercially available) (5.07 g, 35.14 mmol) was weighed and added into 80 mL of tetrahydrofuran, and cooled to −75° C. under nitrogen protection. Lithium diisopropylamide (2M, 21.1 mL) was slowly added dropwise, during which the internal temperature was kept at no higher than −70° C., when finished, stirred at −70° C. for 1.5 h, and polyoxymethylene (5.0 g, 166.50 mmol) was added at one time. The system was slowly warmed to room temperature and reacted overnight. The reaction system was slowly added into 2N HCl (30.0 mL), and extracted with ethyl acetate. The organic phases were combined, washed with a saturated sodium bicarbonate solution until pH is equal to 8 to 9, washed with saturated saline, dried over anhydrous sodium sulfate, and filtered. The filtrate was concentrated to afford a crude product. The crude product was separated by column chromatography to afford Compound 43B (0.89 g, a yellow oily product).

Synthesis of Compound 43C

Compound 43B (0.89 g, 5.11 mmol) was dissolved in 20 mL of dichloromethane. Thereafter, (1,1,1-triacetoxy)-1,1-dihydro-1,2-benzidoyl-3(1H)-one (3.25 g, 7.67 mmol) was added in an ice-water bath, and stirred at room temperature for 4 h. The reaction was quenched with a saturated sodium bicarbonate solution. The reaction solution was extracted with dichloromethane. The organic phases were combined, washed with a saturated aqueous sodium bicarbonate solution and a saturated sodium thiosulfate solution respectively, dried over anhydrous sodium sulfate, and filtered. The filtrate was concentrated to afford a crude product. The crude product was separated by column chromatography to afford Compound 43C (0.52 g, light yellow liquid).

Synthesis of Compound 43

With reference to Example 1, 1A was replaced with 43C to afford Compound 43 (20.1 mg, an off-white solid) with the HPLC purity of 98%. [M+H]$^+$=953; $^1$H NMR (600 MHz, CDCl$_3$) δ 11.20 (s, 1H), 8.13 (s, 1H), 7.60 (dd, J=13.2, 8.5 Hz, 1H), 7.53 (d, J=3.8 Hz, 2H), 7.28 (d, J=10.7 Hz, 2H), 7.16 (d, J=6.8 Hz, 2H), 6.86 (s, 1H), 6.62 (d, J=3.0 Hz, 1H), 6.31 (d, J=3.2 Hz, 1H), 5.70 (q, J=6.6 Hz, 1H), 4.12 (s, 3H), 4.04-3.94 (m, 2H), 3.94-3.79 (m, 3H), 3.35 (d, J=13.5 Hz, 1H), 3.18 (d, J=13.4 Hz, 1H), 3.08-3.00 (m, 2H), 2.30 (s, 6H), 1.80-1.73 (m, 8H), 1.68-1.59 (m, 2H), 1.57 (d, J=6.5 Hz, 3H), 1.35 (d, J=4.6 Hz, 10H).

Example 3

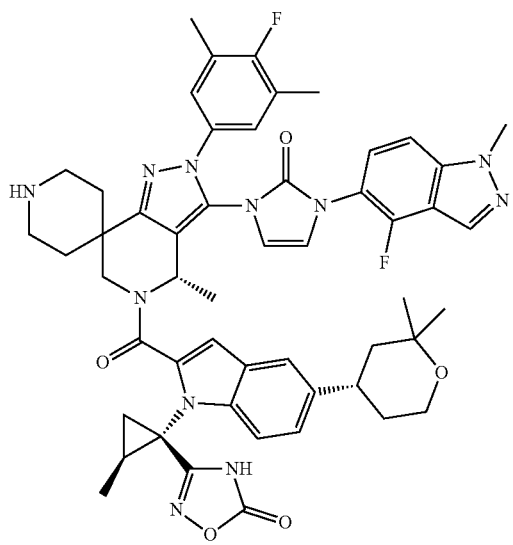

57

Synthetic Route
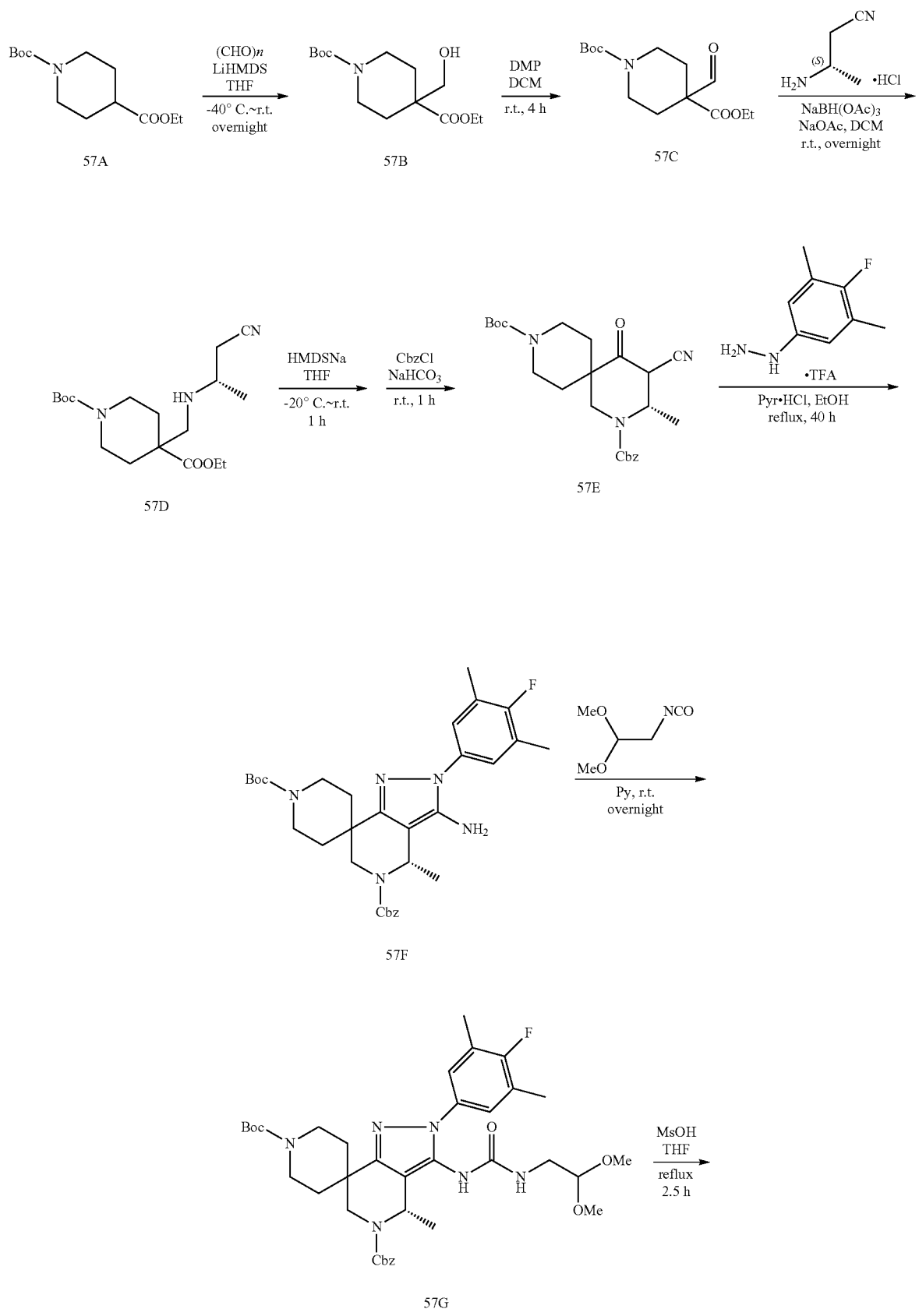

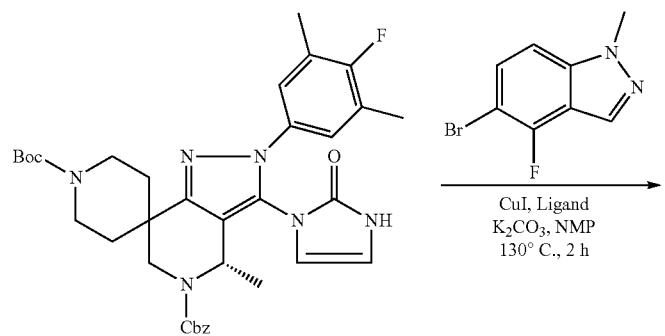
57H
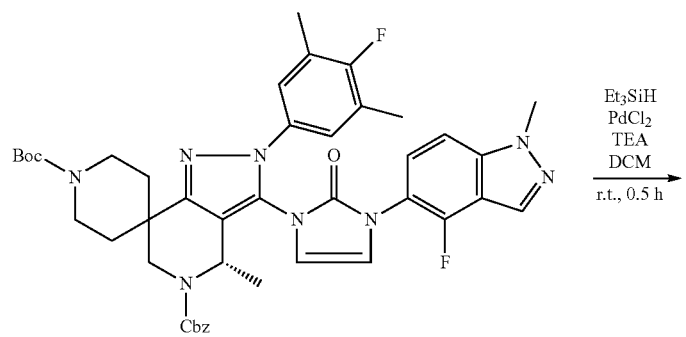
57I
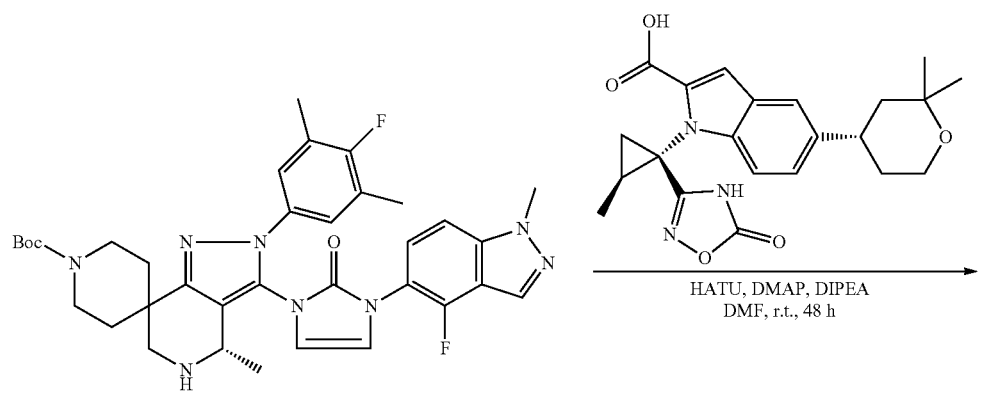
57J

-continued

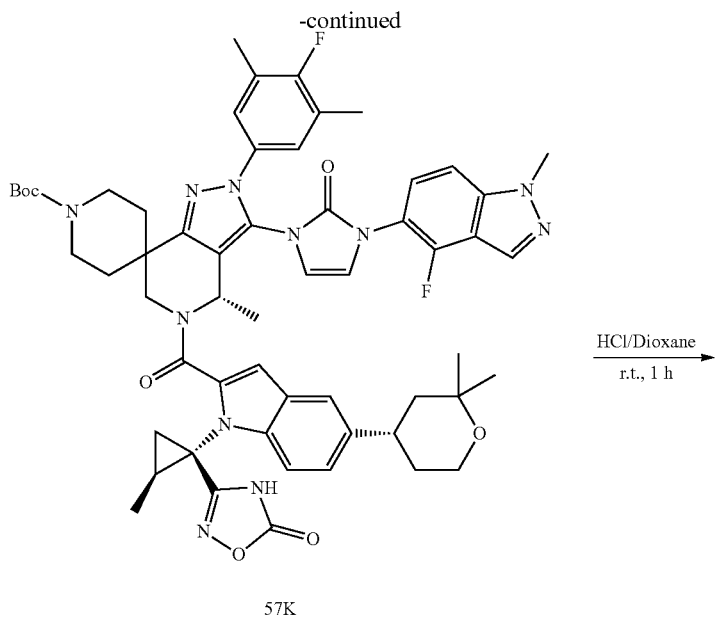

57K

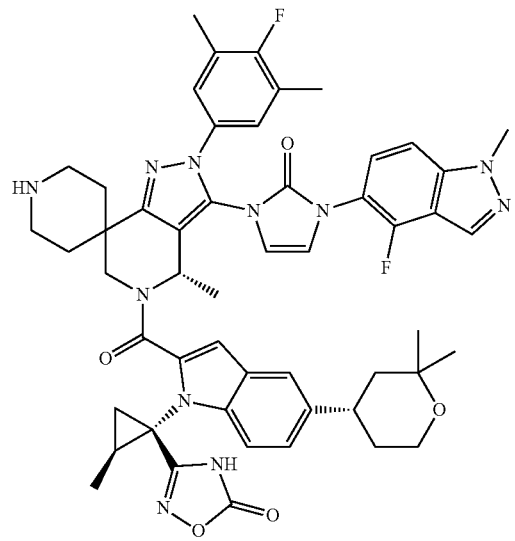

57

Synthesis of Compound 57B 57B was synthesized with reference to the preparation method for the intermediate R42 in the patent application WO2018071454 A1. [M+H]⁺=288.

Synthesis of Compound 57C

The crude product of Compound 57B (7.16 g, 24.91 mmol) obtained in the previous step was weighed and dissolved in dichloromethane (120 mL). Dess-Martin periodinane (15.84 g, 37.36 mmol) was added in batches in an ice bath. The ice bath was removed upon completion of the addition. The reaction system was stirred at room temperature for 5 h. A saturated NaHCO₃ solution (200 mL) was added to quench the reaction. The reaction solution was extracted with dichloromethane (200 mL) and subjected to liquid separation. The organic phase was washed with a solution of NaHCO₃ (200 mL) and saturated saline (200 mL) respectively, dried over anhydrous sodium sulfate, and followed by suction filtration. The filtrate was concentrated and then purified by silica gel column chromatography to afford Compound 57C (1.20 g). [M+H]⁺=286.

Synthesis of Compound 57D

With reference to the preparation method for Compound 1B in Example 1, 57D was synthesized by replacing 1A with 57C. [M+H]$^+$=354.

Synthesis of Compound 57E 57D (0.81 g, 2.28 mmol) was weighed and added into a 100-mL single-necked flask, dissolved by tetrahydrofuran (8 mL), and cooled by dry ice/ethanol until the external temperature was −25° C. HMDSNa (2.30 mL, 4.56 mmol) was measured using a syringe and slowly added into the reaction solution, and naturally warmed to room temperature. After 1 h, the reaction was quenched with saturated ammonium chloride in an ice bath. A saturated NaHCO$_3$ solution was added to adjust the reaction solution to pH 8 to 9. Benzyl chloroformate (0.58 g, 3.42 mmol) was added and stirred at room temperature for 2 h. The reaction was terminated, then adjusted with 10% citric acid to pH 6 to 7 in an ice bath. The reaction solution was extracted with ethyl acetate (50 mL) and subjected to liquid separation. The organic phase was washed with saturated saline (20 mL), dried over anhydrous sodium sulfate, and followed by suction filtration. The filtrate was concentrated and then purified by silica gel column chromatography to afford Compound 57E (0.86 g). [M+H]$^+$=442.

Synthesis of Compound 57F

With reference to the preparation method for Compound 1E in Example 1, 57F was synthesized by replacing 1D with 57E. [M+H]$^+$=578.

Synthesis of Compound 57G

With reference to the preparation method for Compound 57F, 57G was synthesized by replacing 1E with 57F. [M+H]$^+$=709.

Synthesis of Compound 57H

With reference to the preparation method for Compound 1G in Example 1, 57H was synthesized by replacing 1F with 57G. [M+H]$^+$=645.

Synthesis of Compound 57I

With reference to the preparation method for Compound 1H in Example 1, 57I was synthesized by replacing 1G with 57H. [M+H]$^+$=793.

Synthesis of Compound 57J 57I (0.21 g, 0.27 mmol), PdCl$_2$ (0.05 g, 0.27 mmol), and TEA (0.11 g, 1.08 mmol) were weighed and put into a 50-mL single-necked flask. Dichloromethane (5 mL) was used as a solvent. Et$_3$SiH (0.09 g, 0.81 mmol) was added under nitrogen protection. After stirring at room temperature for 1 h, methanol (5 mL) was added. The reaction system was further stirred for 20 min. The solution was filtrated through diatomite. The filtrate was concentrated to afford Compound 57J (0.29 g), which was used directly in the next reaction step. [M+H]$^+$=659.

Synthesis of Compound 57K

With reference to the preparation method for Compound 1 in Example 1, 57K was synthesized by replacing 1I with 57J. [M+H]$^+$=1052.

Synthesis of Compound 57

57K (0.20 g, 0.19 mmol) was weighed and put into a 50-mL single-necked flask, and a solution (5 mL) of hydrochloric acid in dioxane was added at room temperature and stirred at room temperature for 1 h. The reaction was terminated and concentrated, added with dichloromethane (20 mL) and a saturated NaHCO$_3$ solution (20 mL), and subjected to liquid separation. The organic phase was washed with saturated saline (20 mL), dried over anhydrous sodium sulfate, and followed by suction filtration. The filtrate was concentrated and then purified by silica gel column chromatography to afford Compound 57 (0.17 g). [M+H]$^+$=952.

Example 4

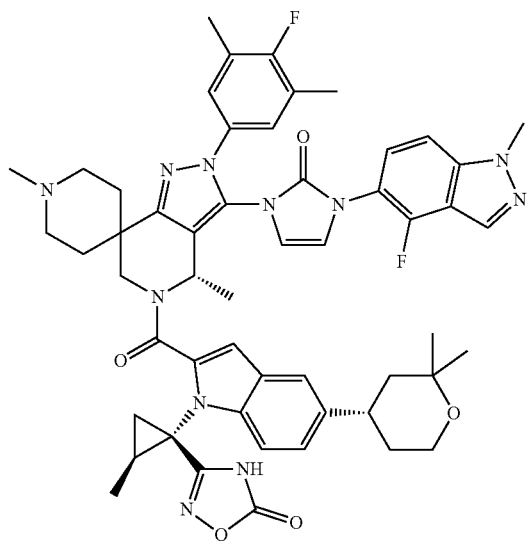

59

Synthetic Route

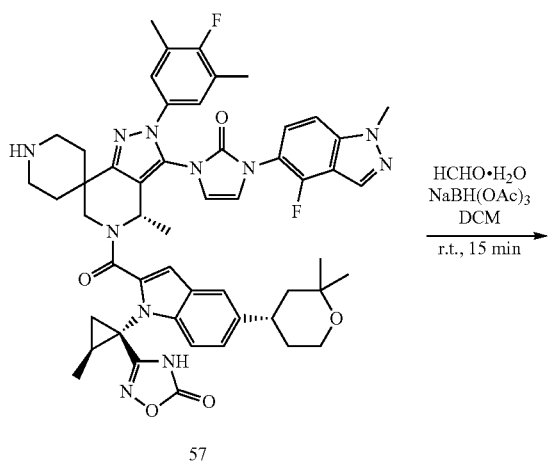

57

187

-continued

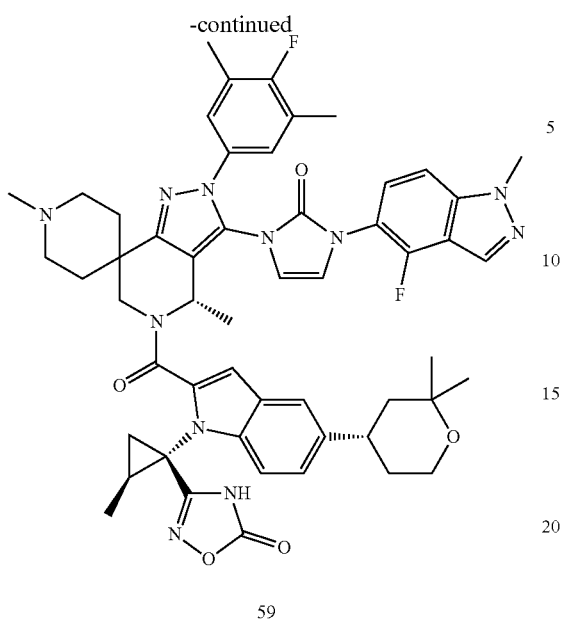

59

Synthesis of Compound 59

57 (19 mg, 0.02 mmol) and formaldehyde hydrate (10 mg, 0.12 mmol) were weighed and put into a 50-mL single-necked flask. Dichloromethane (2 mL) was used as a solvent. The reaction system was stirred at room temperature for 20 min. NaBH(OAc)₃ (6.5 mg, 0.03 mmol) was added in an ice bath. The reaction system was further stirred for 20 min. The reaction was quenched with a saturated NaHCO₃ solution (2 mL). The reaction system was extracted with dichloromethane, dried over anhydrous sodium sulfate, and followed by suction filtration. The filtrate was concentrated and then purified by silica gel preparative plate to afford Compound 59 (15 mg). [M+H]⁺=966.

Example 5

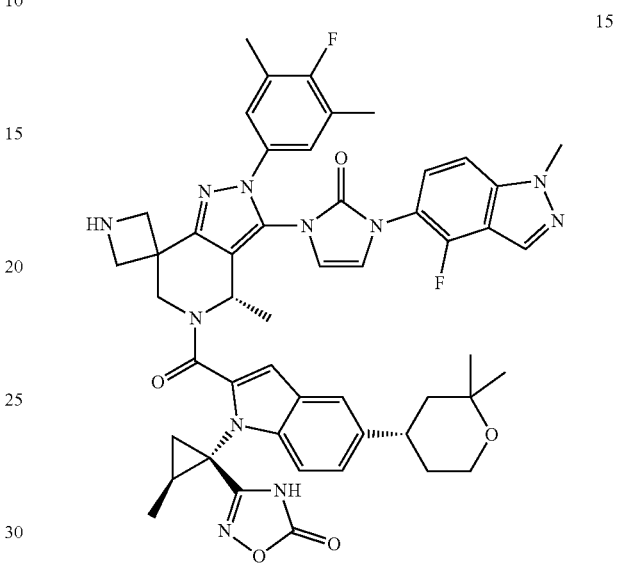

Synthetic Route

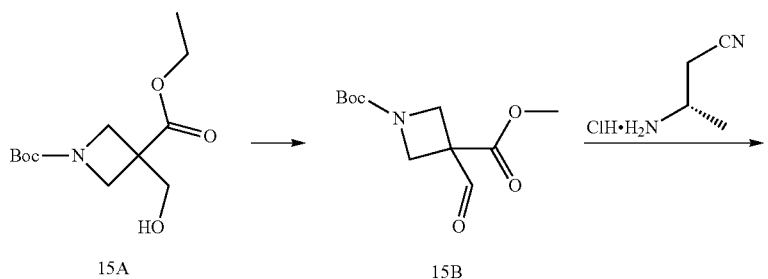

15A    15B

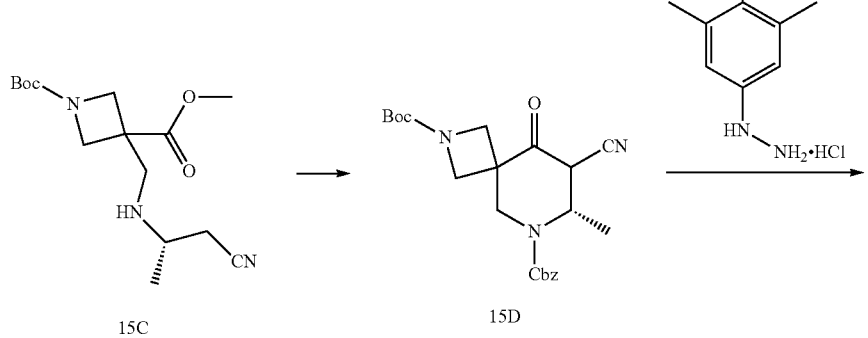

15C    15D 189 190
-continued
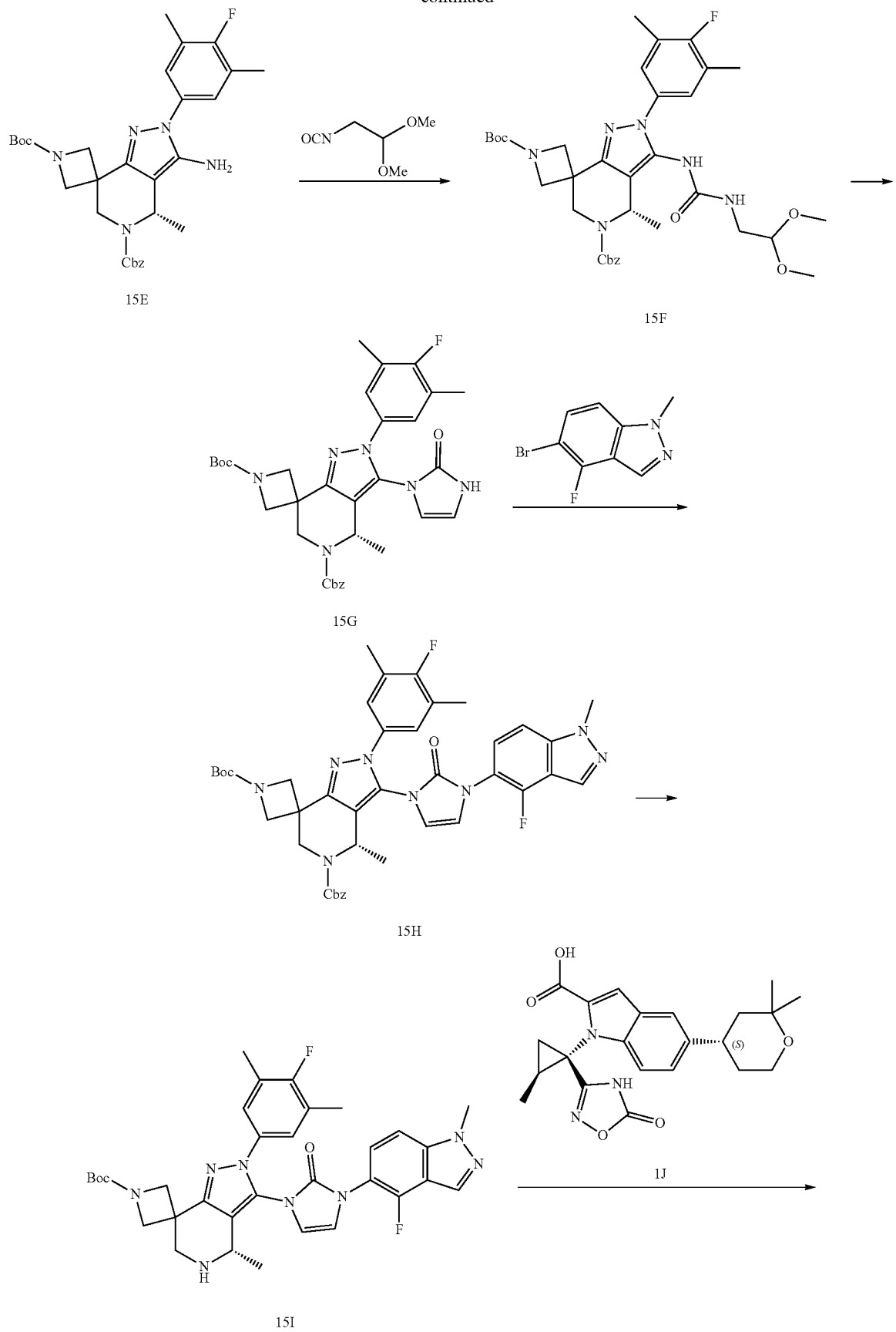

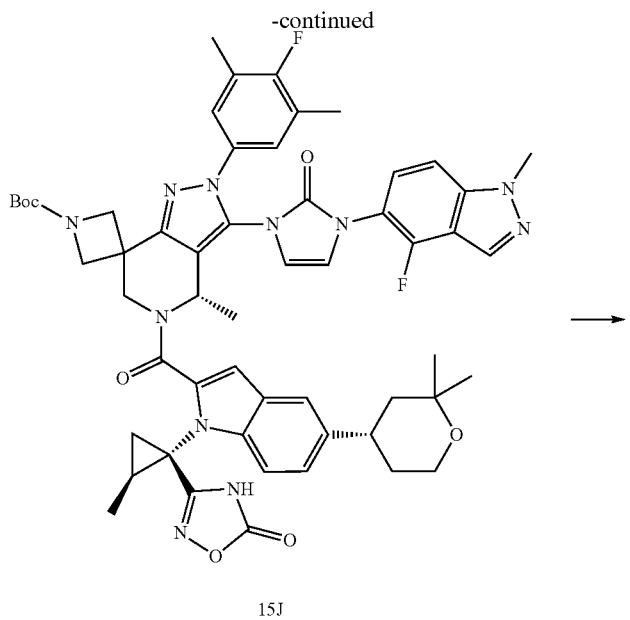

15J

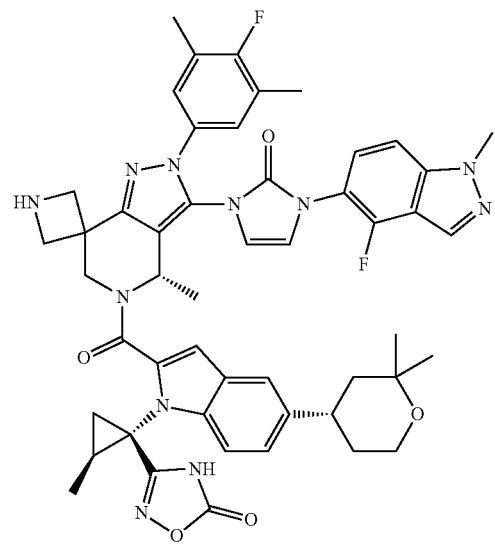

15

Synthesis of Compound 15A 15A was synthesized with reference to the patent application WO2021102314A1. [M+H]$^+$=260.

Synthesis of Compound 15B

Compound 15A (0.28 g, 1.07 mmol) was dissolved in 10 mL of dichloromethane. Thereafter, (1,1,1-triacetoxy)-1,1-dihydro-1,2-benzidoyl-3(1H)-one (0.68 g, 1.62 mmol) was added in an ice-water bath, and stirred at room temperature for 4 h. The reaction was quenched with a saturated sodium bicarbonate solution. The reaction solution was extracted with dichloromethane. The organic phases were combined, washed with a saturated aqueous sodium bicarbonate solution and a saturated sodium thiosulfate solution respectively, dried over anhydrous sodium sulfate, and filtered. The filtrate was concentrated to afford a crude product. The crude product was separated by column chromatography to afford Compound 15B (0.2 g, colorless liquid).

Synthesis of Compound 15

With reference to the preparation method for Compound 1 in Example 1, 15 was synthesized by replacing 1A with 15B. [M+H]$^+$=924.

Example 6
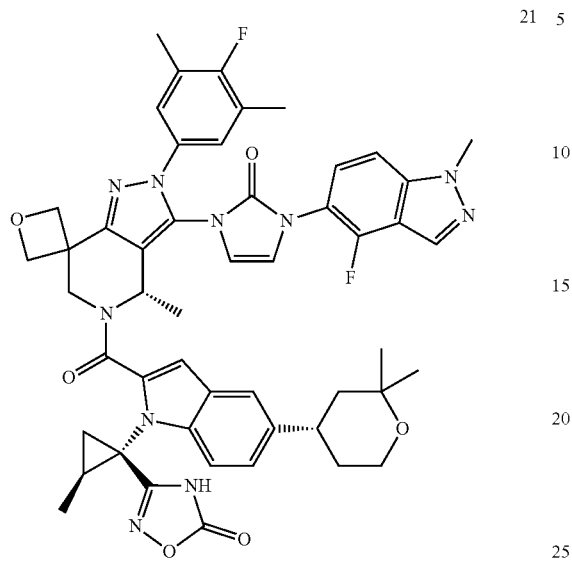
Synthetic Route
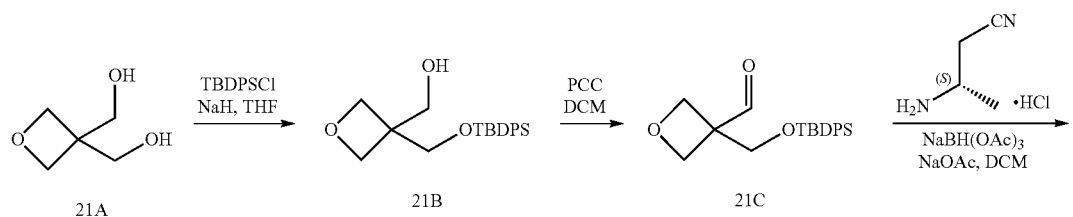
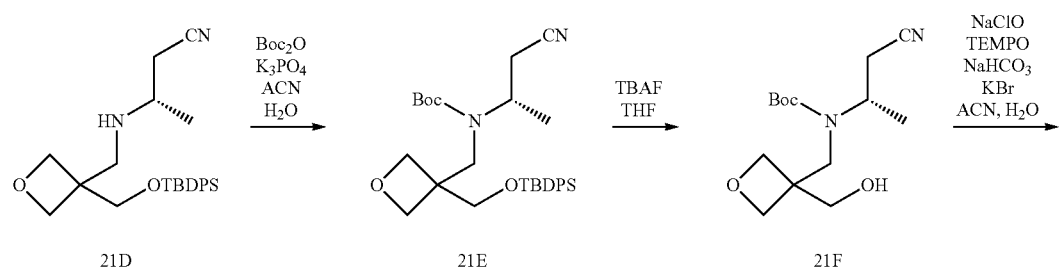
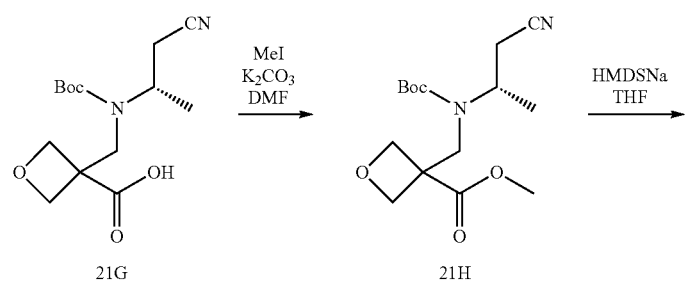

-continued
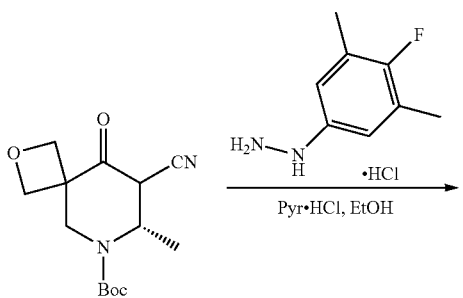
21I
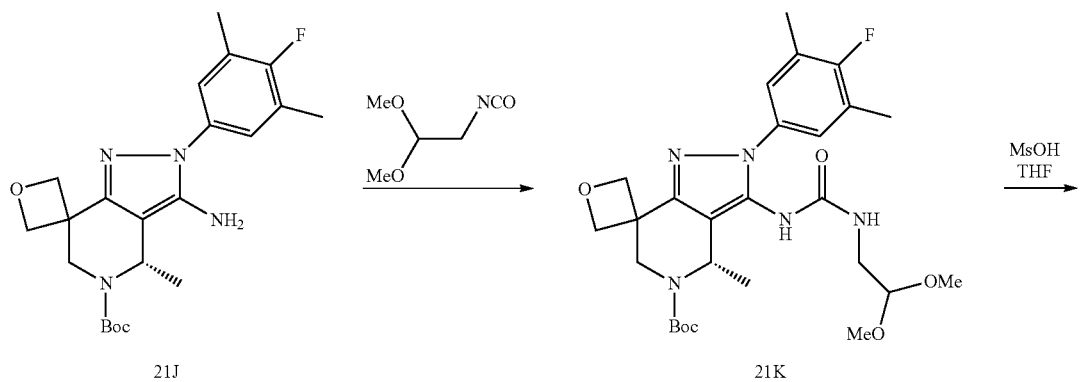
21J 21K
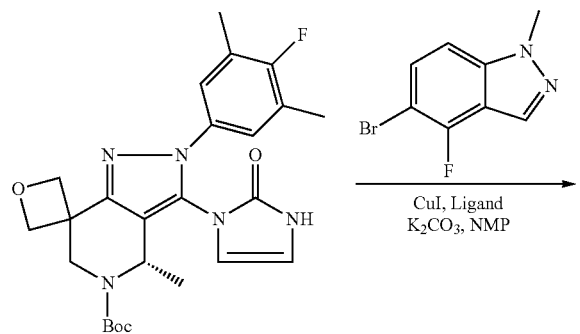
21L
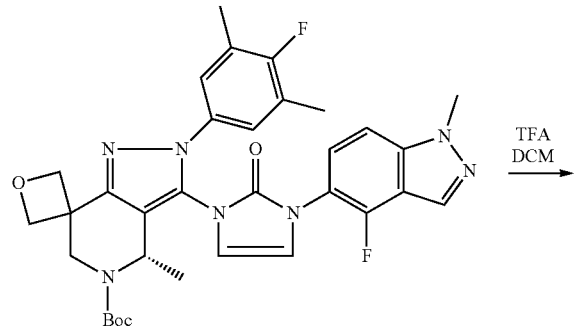
21M

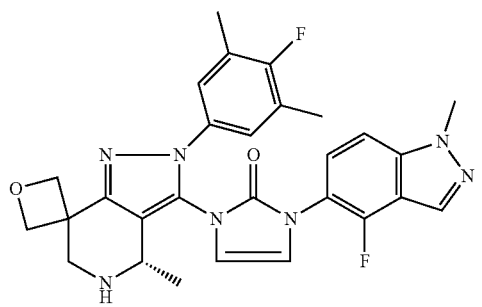

21N

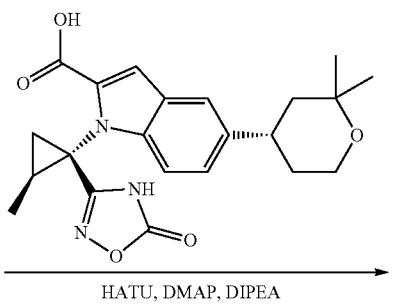

HATU, DMAP, DIPEA

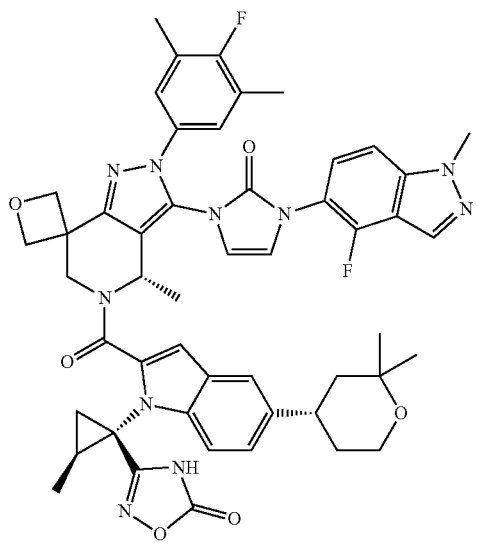

21

Synthesis of Compound 21C 21C was synthesized with reference to the method in Example 22 of the patent application CN115353512 A. [M+H]$^+$=355.

Synthesis of Compound 21D

With reference to the preparation method for Compound 1B in Example 1, 21D was synthesized by replacing 1A with 21C. [M+H]$^+$=423.

Synthesis of Compound 21E 21D (0.46 g, 1.08 mmol) was weighed and put into a 100-mL round-bottom flask. Acetonitrile (5 mL) and water (5 mL) were used as solvents. Potassium phosphate (0.69 g, 3.26 mmol) and Boc$_2$O (0.71 g, 3.26 mmol) were added in sequence at room temperature, and stirred overnight in an oil bath at 36° C. After the reaction was complete, the reaction solution was extracted with ethyl acetate (50 mL). The organic phase was washed with saturated saline (50 mL), dried over anhydrous sodium sulfate, and followed by suction filtration. The filtrate was concentrated and then purified by silica gel column chromatography to afford Compound 21E (0.37 g). [M+H]$^+$=523.

Synthesis of Compound 21F 21E (1.90 g, 3.64 mmol) was weighed and put into a 100-mL round-bottom flask, THF (20 mL) was added as a solvent, and TBAF (7.3 mL, 7.30 mmol) was added at room temperature, and stirred overnight at room temperature. After the reaction was complete, the reaction solution was extracted with DCM (50 mL*3). The organic phase was washed with saturated saline (50 mL), dried over anhydrous sodium sulfate, and followed by suction filtration. The filtrate was concentrated to afford a crude product of Compound 21F (1.80 g), which was used directly for the next reaction step. [M+H]$^+$=285.

Synthesis of Compound 21G

The crude product of 21F (0.57 g, 2.0 mmol), NaHCO$_3$ (0.34 g, 4.0 mmol), and KBr (0.48 g, 4.0 mmol) were weighed and put into a 100-mL round-bottom flask, acetonitrile (10 mL) and water (5 mL) were used as solvents, and TEMPO (0.03 g, 0.2 mmol) and 7% sodium hypochlorite solution (0.75 g, 10.0 mmol) were added in sequence at room temperature, and stirred at room temperature for 0.5 h. After the reaction was complete, the reaction solution was adjusted with 10% NaOH solution to pH 10 to 11 in an ice bath, and extracted with methyl tert-butyl ether (30 mL*2). The organic phase was discarded. The aqueous phase was adjusted with 50% H$_2$SO$_4$ to pH 4 to 5 in an ice bath, and extracted with dichloromethane (50 mL*3). The organic phase was dried over anhydrous sodium sulfate and followed by suction filtration. The filtrate was concentrated to afford a crude product of Compound 21G (0.46 g), which was used directly for the next reaction step. [M+H]$^+$=299.

Synthesis of Compound 21H

The crude product of 21G (0.46 g, 1.54 mmol) and K$_2$CO$_3$ (0.43 g, 3.08 mmol) were weighed and put into a 100-mL round-bottom flask. DMF (5 mL) was added as a solvent. Iodomethane (0.55 g, 3.85 mmol) was added at room temperature and stirred overnight at room temperature. After the reaction was complete, water was added to quench the reaction. The reaction solution was extracted with methyl tert-butyl ether (25 mL*4). The organic phase was washed with saturated saline (50 mL), dried over anhydrous sodium sulfate, and followed by suction filtration. The filtrate was concentrated and then purified by silica gel column chromatography to afford Compound 21H (0.18 g). [M+H]$^+$=312.

Synthesis of Compound 21

With reference to the preparation method for Compound 1 in Example 1, 21 was synthesized by replacing 1C with 21H. [M+H]$^+$=925.

Synthesis of Compound 23

With reference to the preparation method for Compound 15 in Example 5, Compound 23 was synthesized by replacing 15A with ethyl 1-(hydroxymethyl)cyclobutane-1-carboxylate (commercially available). [M+H]$^+$=923.

Example 7

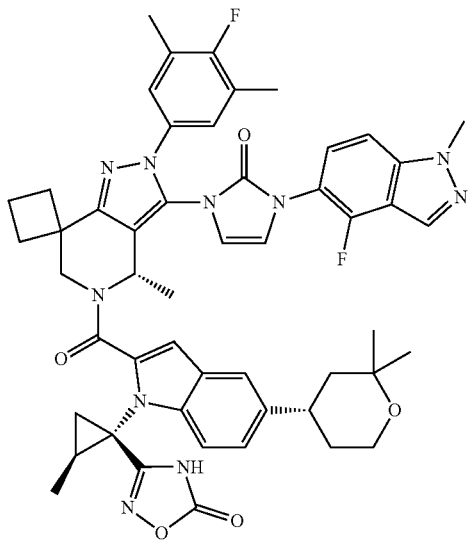

23

Example 8

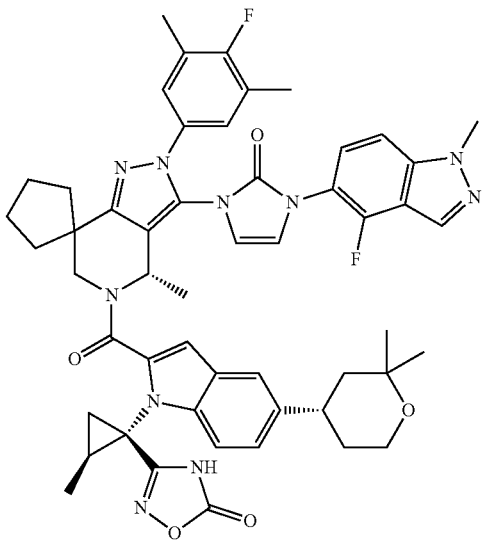

25

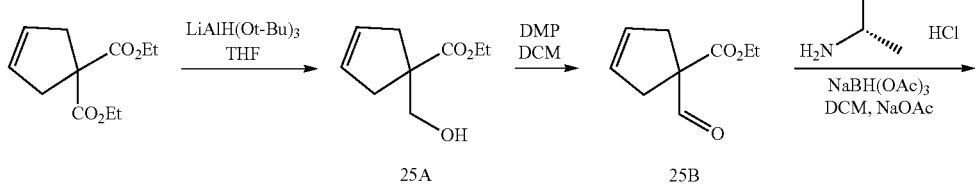

-continued
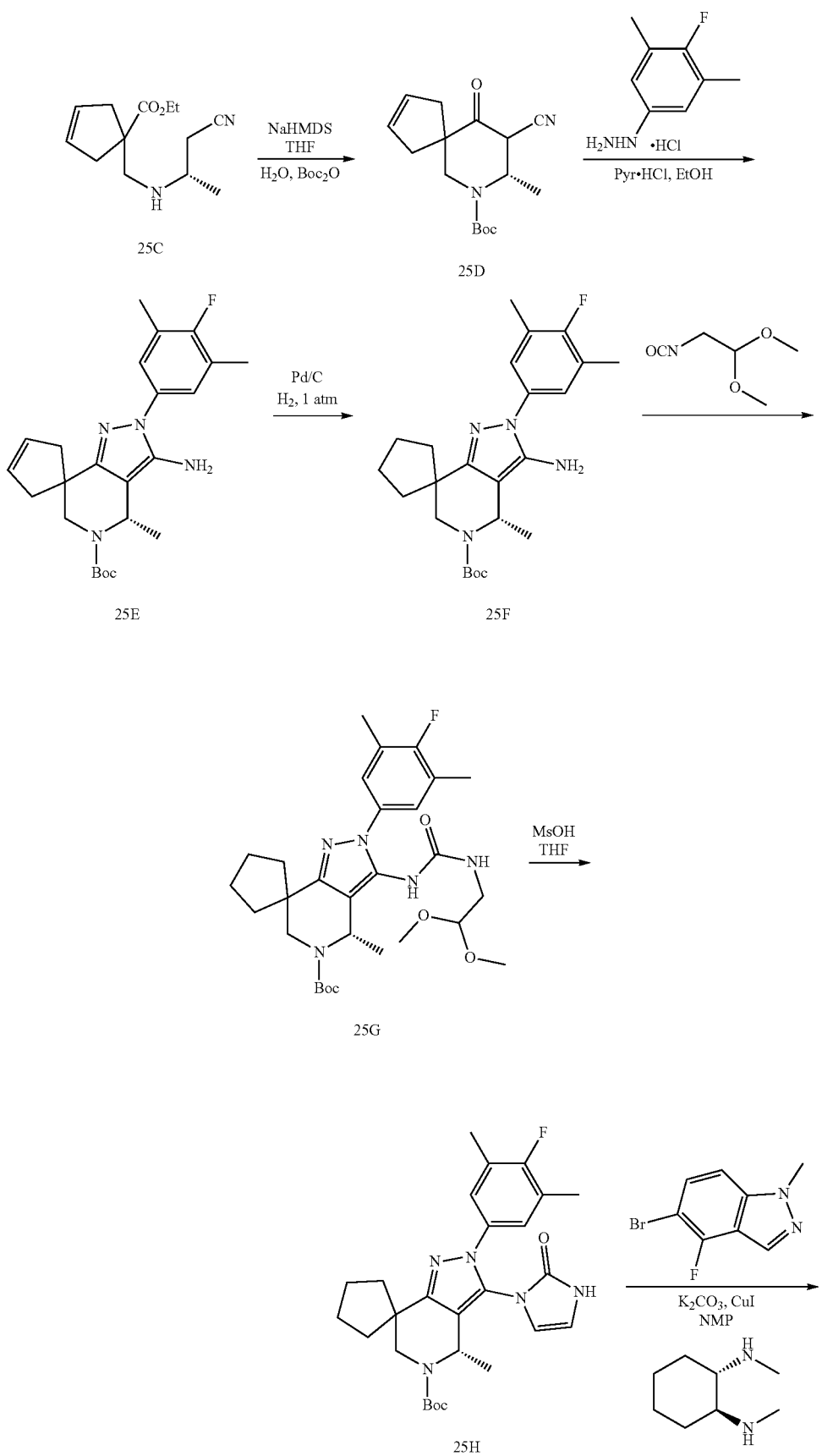

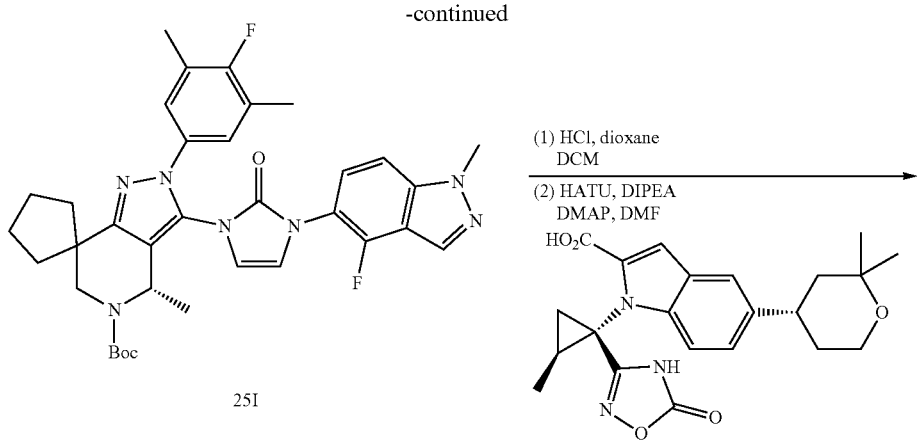

251

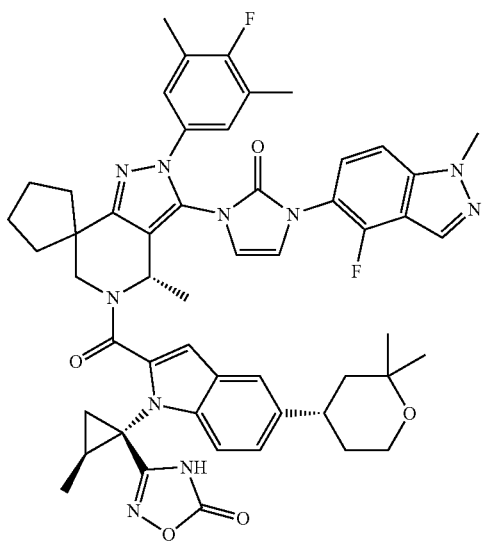

25

Synthesis of Compound 25A

The compound diethyl 3-cyclopentene-1,1-dicarboxylate (commercially available) (1.65 g, 8.95 mmol) was dissolved in 16.5 mL of tetrahydrofuran, and cooled to 0° C. to 5° C. in an ice-water bath. A solution of lithium tri-tert-butoxyaluminum hydride in tetrahydrofuran (22.7 mL, 1.0 mol/L, 22.7 mmol) was added dropwise, when finished, heated to 65° C. and reacted for 5 h. The reaction system was cooled to room temperature, and diluted with methyl tert-butyl ether. The reaction was quenched with a saturated sodium bisulfate solution. The reaction solution was extracted with methyl tert-butyl ether, dried over anhydrous sodium sulfate, and filtered. The filtrate was concentrated to afford Compound 25A (1.81 g, a colorless oily product), [M+H]$^+$=157.

Synthesis of Compound 25B

With reference to the preparation method for Compound 15B in Example 5, 25B was synthesized by replacing 15A with 25A. [M+H]$^+$=169.

Synthesis of Compound 25E

With reference to the preparation method for Compound 1E in Example 1, 25E was synthesized by replacing 1A with 25B. [M+H]$^+$=427.

Synthesis of Compound 25F

Compound 25E (200.0 mg, 0.47 mmol) was dissolved in 20 mL of ethyl acetate, added with 10% palladium on carbon (0.14 g, 50% water wet), and underwent hydrogenation with an atmospheric hydrogen balloon at room temperature for 2 h. The solution was filtered. The filtrate was concentrated to afford Compound 25F (0.18 g, a white solid), [M+H]$^+$=429.

Synthesis of Compound 25

With reference to the preparation method for the compound in Example 1, Compound 25 was synthesized by replacing 1E with 25F, with the HPLC purity of 99.4%. [M+H]$^+$=937; $^1$H NMR (600 MHz, CDCl$_3$) δ 11.27 (s, 1H), 8.13 (s, 1H), 7.60 (dd, J=12.4, 8.5 Hz, 1H), 7.50 (t, J=12.4 Hz, 2H), 7.29 (s, 1H), 7.25 (s, 1H), 7.14 (d, J=6.7 Hz, 2H), 6.81 (s, 1H), 6.60 (d, J=3.1 Hz, 1H), 6.32 (d, J=3.0 Hz, 1H), 5.72 (q, J=6.5 Hz, 1H), 4.11 (s, 3H), 3.84 (dd, J=10.0, 4.4 Hz, 2H), 3.33 (d, J=13.5 Hz, 1H), 2.57-2.44 (m, 2H), 2.28 (s, 6H), 1.81-1.71 (m, 8H), 1.70-1.62 (m, 6H), 1.57 (t, J=5.7 Hz, 3H), 1.34 (s, 5H), 1.26 (s, 5H).

Example 9

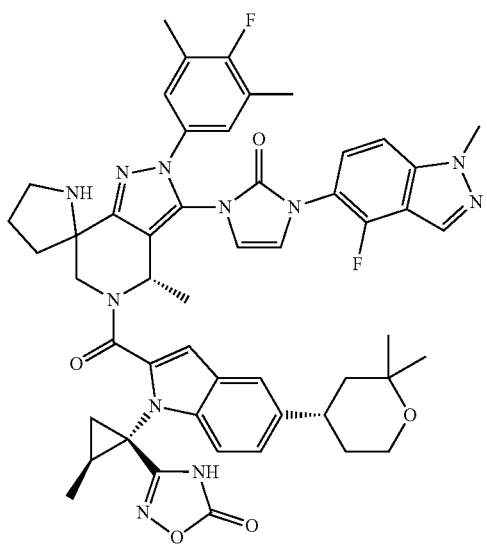

31

Synthetic Route

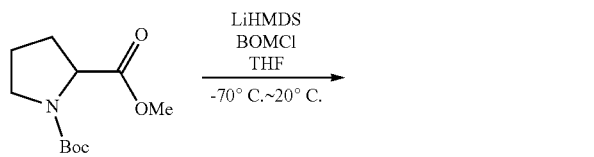

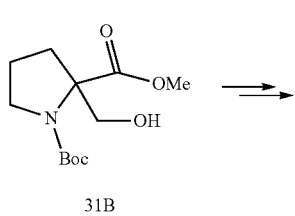

31A

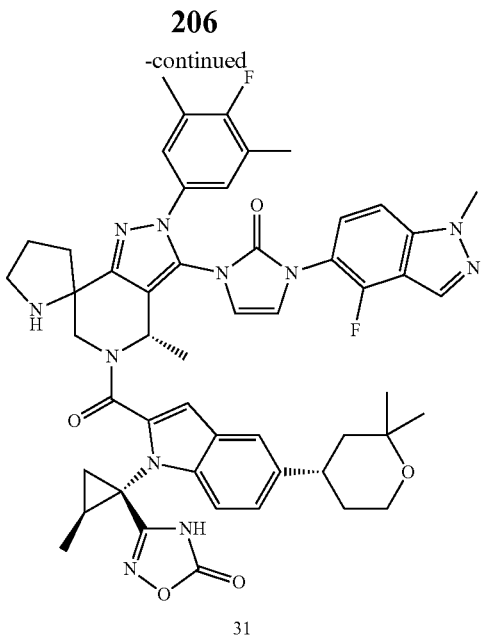

31

Synthesis of Compound 31A

The compound Boc-L-proline-methyl ester (commercially available) (5.0 g, 21.8 mmol) was dissolved in 40 mL of tetrahydrofuran, and cooled to −70° C. (under N₂ protection). LiHMDS (43.6 mL, 43.6 mmol) was added dropwise, when finished, stirred at −70° C. for 1 h. Benzyl(chloromethyl)ether (5.12 g, 32.7 mmol) was then added dropwise, when finished, slowly warmed to −20° C. and stirred for 2 h. The reaction system was warmed to 0° C., and the reaction was quenched with a saturated ammonium chloride solution. The reaction solution was extracted with ethyl acetate, dried over anhydrous sodium sulfate, and filtered. The filtrate was concentrated and then separated by column chromatography to afford Compound 31A (6.9 g, a colorless oily product), [M+H]⁺=350.

Synthesis of Compound 31B

Compound 31A (2.5 g, 7.2 mmol) was dissolved in 25 mL of methanol, added with 10% palladium on carbon (0.51 g, 50% water wet), and underwent hydrogenation with an atmospheric hydrogen balloon at room temperature for 2 h. The solution was filtered. The filtrate was concentrated to afford Compound 31B (1.9 g, a colorless oily product), [M+H]⁺=260.

Synthesis of Compound 31

With reference to the preparation method for Compound 25 in Example 8, Compound 31 was synthesized by replacing 25A with 31B. [M+H]⁺=938.

Example 10
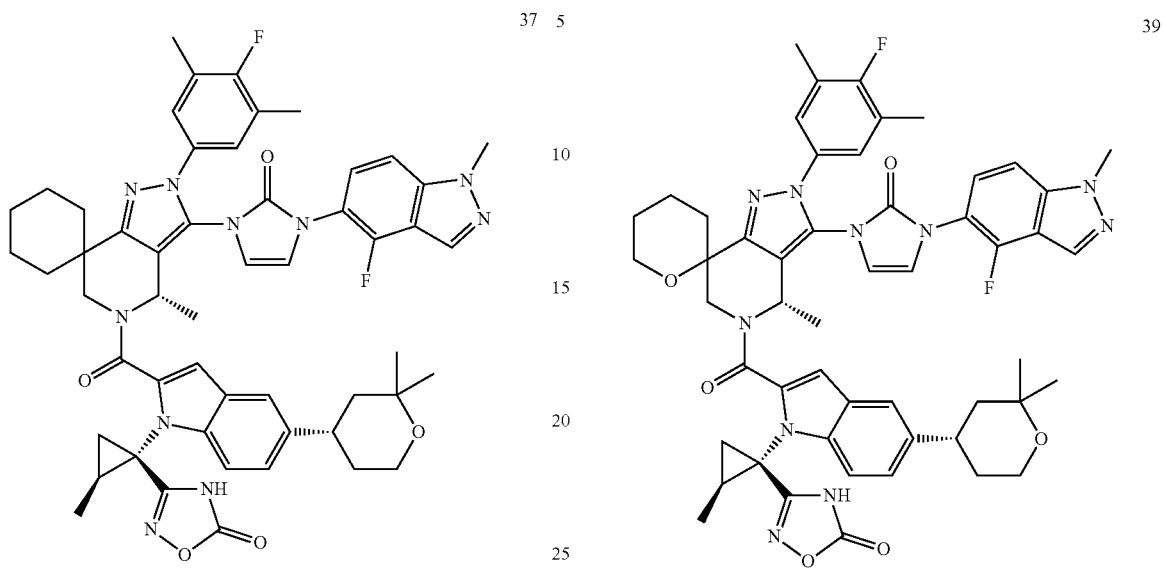
37
With reference to the preparation method for Compound 15 in Example 5, Compound 37 was synthesized by replacing 15A with ethyl 1-(hydroxymethyl)cyclohexane-1-carboxylate (commercially available). [M+H]$^+$=951.
Example 11
39
Synthetic Route
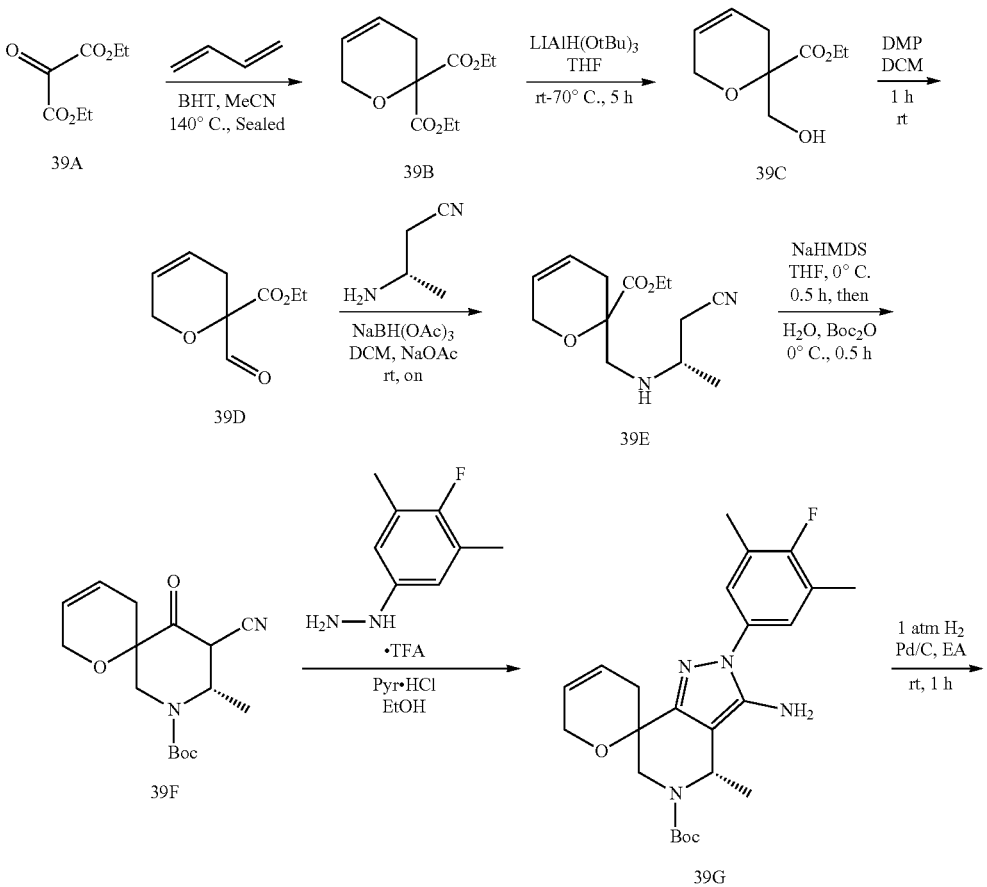

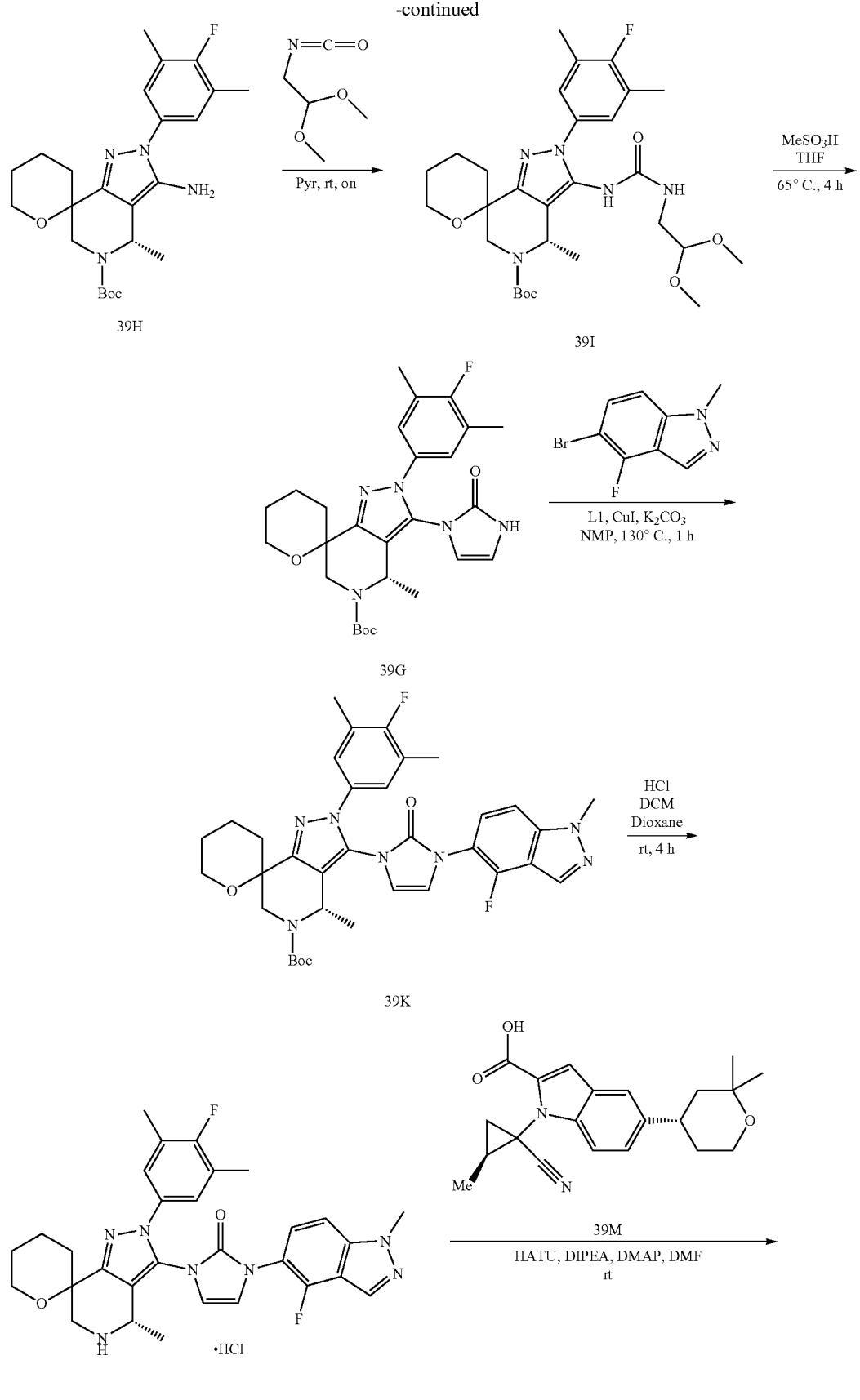

-continued
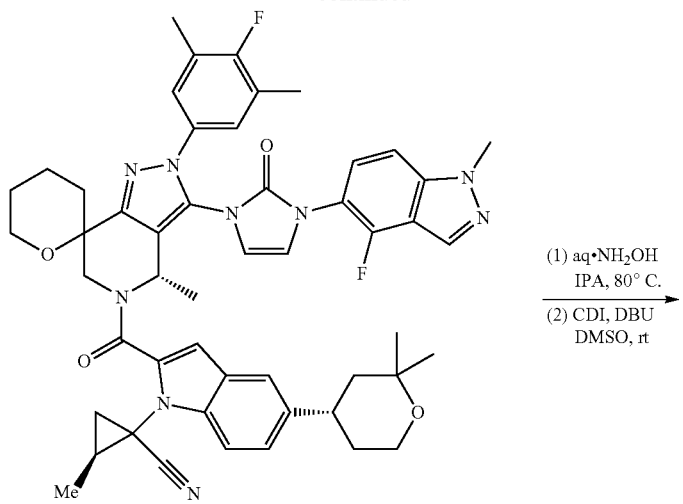
39N
(1) aq·NH$_2$OH
IPA, 80° C.
(2) CDI, DBU
DMSO, rt
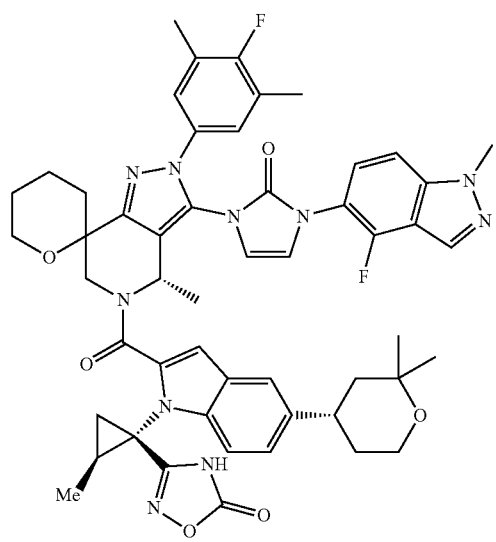
39
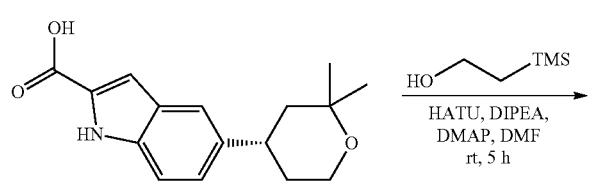
39O
HATU, DIPEA,
DMAP, DMF
rt, 5 h
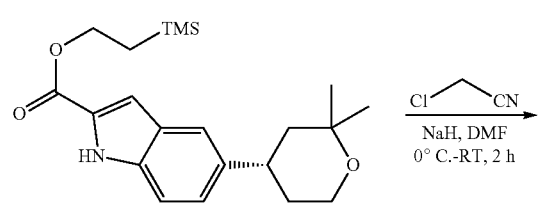
39P
NaH, DMF
0° C.-RT, 2 h

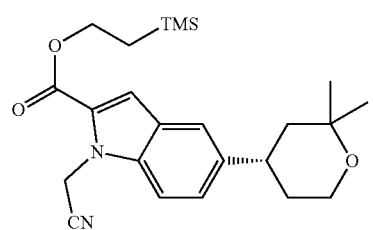

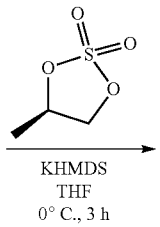

39Q

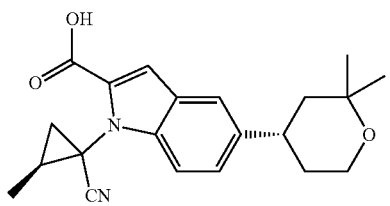

39M

Synthesis of Compound 39B 39A (commercially available) was used as a starting material to afford Compound 39B with reference to the method in the reference literature US20130183269A1, $[M+H]^+=229$.

Synthesis of Compound 39C

Compound 39B (0.61 g, 2.67 mmol) was dissolved in 16 mL of tetrahydrofuran, and cooled to 0° C. to 5° C. in an ice-water bath. A solution of lithium tri-tert-butoxyaluminum hydride in tetrahydrofuran (6.8 mL, 1.0 mol/L, 6.80 mmol) was added dropwise, when finished, heated to 65° C. and reacted for 5 h. The reaction system was cooled to room temperature and diluted with methyl tert-butyl ether. The reaction was quenched with 20% sodium bisulfate solution. The reaction solution was extracted with methyl tert-butyl ether, dried over anhydrous sodium sulfate, and filtered. The filtrate was concentrated and then separated by column chromatography to afford Compound 39C (0.40 g, a colorless oily product), $[M+H]^+=187$.

Synthesis of Compound 39D

With reference to the preparation method for Compound 15B in Example 5, 39D was synthesized by replacing 15A with 39C. $[M+H]^+=185$.

Synthesis of Compound 39G

With reference to the preparation method for Compound 1E in Example 1, 39G was synthesized by replacing 1A with 39D. $[M+H]^+=443$.

Synthesis of Compound 39H

Compound 39G (50.0 mg, 0.11 mmol) was dissolved in 5 mL of ethyl acetate, added with 10% palladium on carbon (0.15 g, 50% water wet), and underwent hydrogenation with an atmospheric hydrogen balloon at room temperature for 2 h. The solution was filtered. The filtrate was concentrated to afford Compound 39H (51.2 mg, a light yellow oily product), $[M+H]^+=445$.

Synthesis of Compound 39L

With reference to the preparation method for Compound 1I in Example 1, 39L was synthesized by replacing 1G with 39H. $[M+H]^+=560$.

Synthesis of Compound 39P

Compound 39O (203.4 mg, 0.74 mmol) was weighed and dissolved in 5 mL of N,N-dimethylformamide. Thereafter, 2-trimethylsilyl ethanol (109.2 mg, 0.92 mmol), HATU (359.0 mg, 0.94 mmol), DIPEA (159.0 mg, 1.23 mmol), and DMAP (209.2 mg, 1.71 mmol) were added in sequence, and reacted at 50° C. for 2 h. Purified water was added to precipitate. The solid was collected by filtration and vacuum dried to afford Compound 39P (216.6 mg, a yellow solid), $[M+H]^+=374$.

Synthesis of Compound 39Q

Compound 39P (216.6 mg, 0.58 mmol) was weighed and dissolved in 5 mL of N,N-dimethylformamide, and cooled to 0° C. to 5° C. in an ice-water bath. 60% Sodium hydride (31.6 mg, 0.79 mmol) was added in batches. Upon addition, the reaction was stirred at room temperature for 1 h, and chloroacetonitrile (57.0 mg, 0.75 mmol) was added dropwise and reacted at room temperature for 1 h. Purified water was added dropwise to quench the reaction. The reaction system was extracted with ethyl acetate, and the organic phase was washed with a saturated sodium chloride solution, dried over anhydrous sodium sulfate, and filtered. The filtrate was concentrated and then separated by column chromatography to afford Compound 39Q (199.8 mg, a white solid), $[M+H]^+=413$.

Synthesis of Compound 39M

Compound 39Q (199.8 mg, 0.48 mmol) and (4R)-4-methyl-1,3,2-dioxathiolane 2,2-dioxide (133.0 mg, 0.96 mmol) were dissolved in 5 mL of tetrahydrofuran, and cooled to 0° C. to 5° C. in an ice-water bath. A solution of potassium bis(trimethylsilyl)amide in tetrahydrofuran (2.4 mL, 1.0 mol/L, 2.40 mmol) was added dropwise, when finished, reacted at 0° C. to 5° C. for 3 h. A 5% citric acid solution was added dropwise to quench the reaction. The reaction solution was extracted with ethyl acetate, and the organic phase was washed with a saturated sodium chloride solution, dried over anhydrous sodium sulfate, and filtered. The filtrate was concentrated and then separated by column chromatography to afford Compound 39M (63.0 mg, a light yellow solid), $[M+H]^+=353$.

Synthesis of Compound 39N

Compounds 39L (20.0 mg, 0.033 mmol) and 39M (20.0 mg, 0.056 mmol) as well as N-methylimidazole (25.0 mg, 0.305 mmol) were weighed respectively and dissolved in 1 mL of acetonitrile, and N,N,N',N'-tetramethylchloroformamidinium hexafluorophosphate (33.0 mg, 0.117 mmol) was added under nitrogen protection and reacted overnight at room temperature. Purified water was added to quench the reaction. The reaction solution was extracted with ethyl acetate, and the organic phase was washed with a saturated sodium chloride solution, dried over anhydrous sodium sulfate, and filtered. The filtrate was concentrated and then separated by silica gel preparative plate to afford Compound 39N (19.1 mg, a light yellow solid), [M+H]$^+$=894.

Synthesis of Compound 39

Compound 39N (19.1 mg, 0.021 mmol) was weighed and dissolved in 1.5 mL of isopropanol, and 50% aqueous hydroxylamine solution (55.6 mg, 0.84 mmol) was added and reacted at 80° C. for 1 h. Purified water was added, and the reaction solution was extracted with ethyl acetate, and the organic phase was washed with a saturated sodium chloride solution, dried over anhydrous sodium sulfate, and filtered. The product obtained by concentrating the filtrate was dissolved in 1 mL of dimethyl sulfoxide, and CDI (10.1 mg, 0.062 mmol) and DBU (11.2 mg, 0.073 mmol) were added and reacted at room temperature for 1 h. Purified water was added to quench the reaction. The reaction solution was extracted with ethyl acetate, and the organic phase was washed with a saturated sodium chloride solution, dried over anhydrous sodium sulfate, and filtered. The filtrate was concentrated and then separated by silica gel preparative plate to afford Compound 39 (6.0 mg), [M+H]$^+$=953.

Example 12

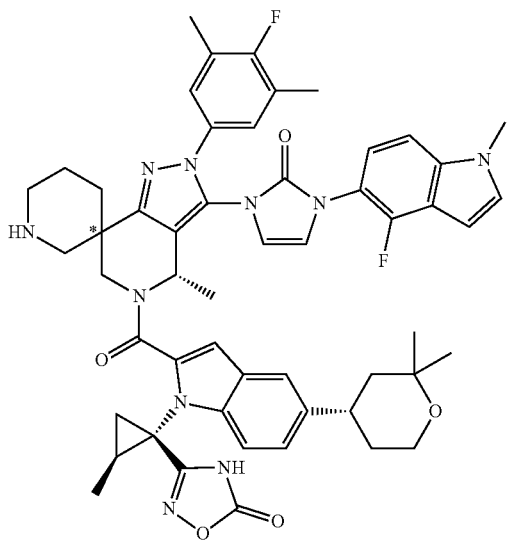

51

"*" indicated the chiral center with the R or S configuration, and 51-A and 51-B were two single stereoisomeric compounds and were collectively represented by Compound 51.

Synthetic Route

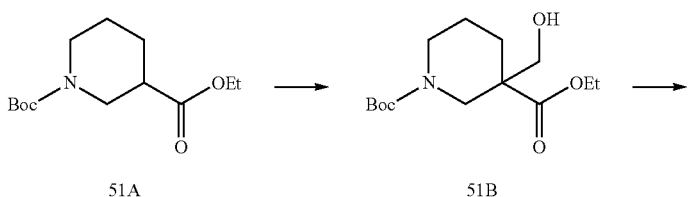

51A     51B

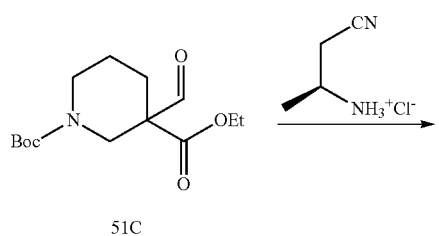

51C

-continued
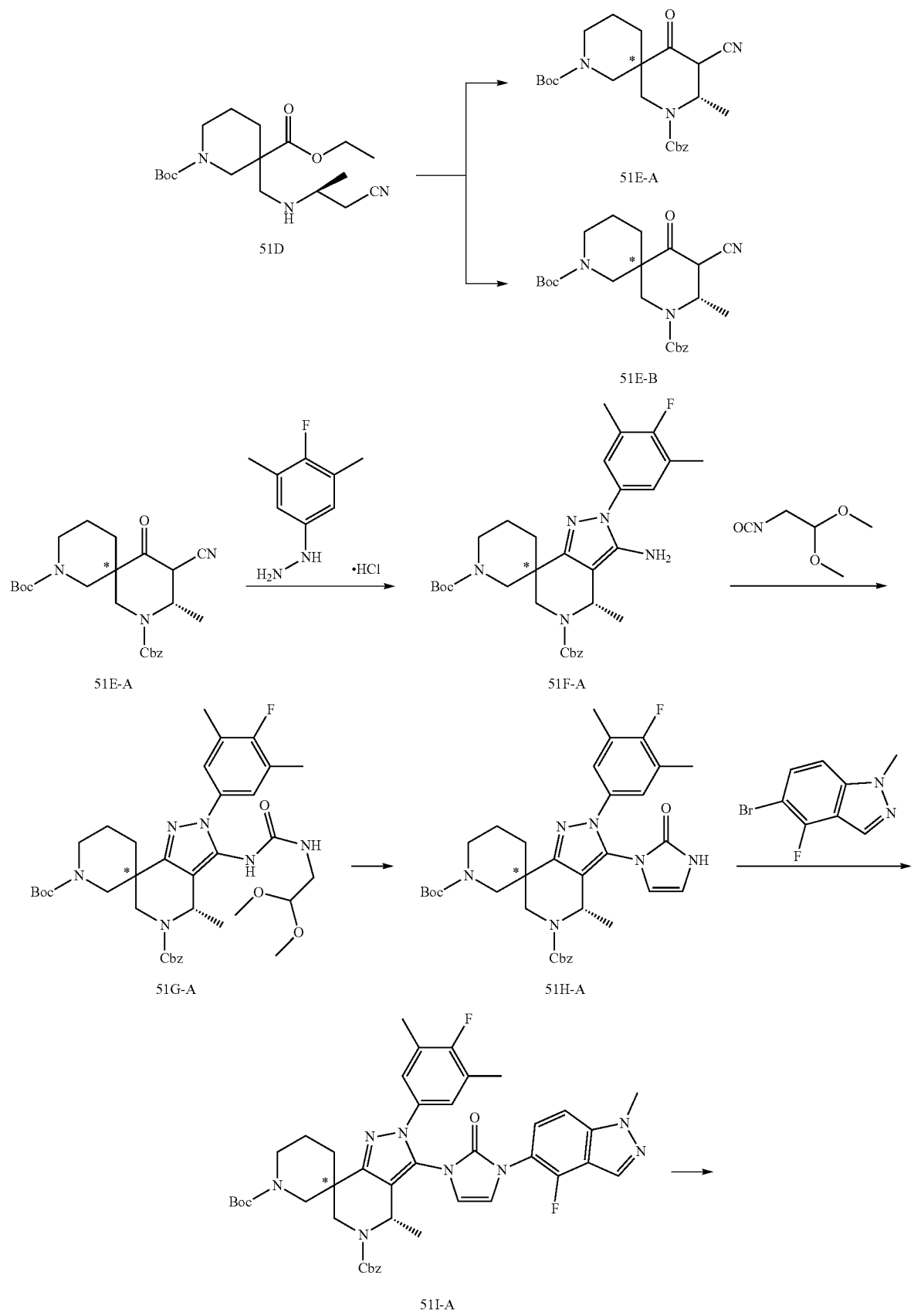

-continued
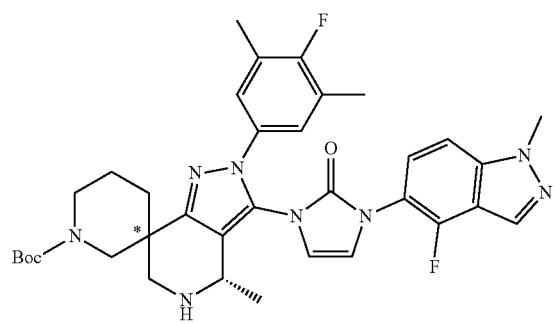
51J-A
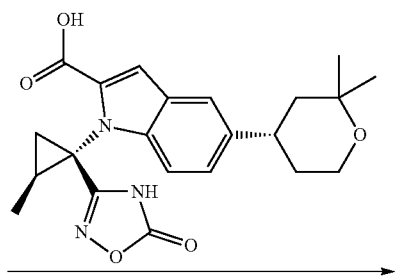
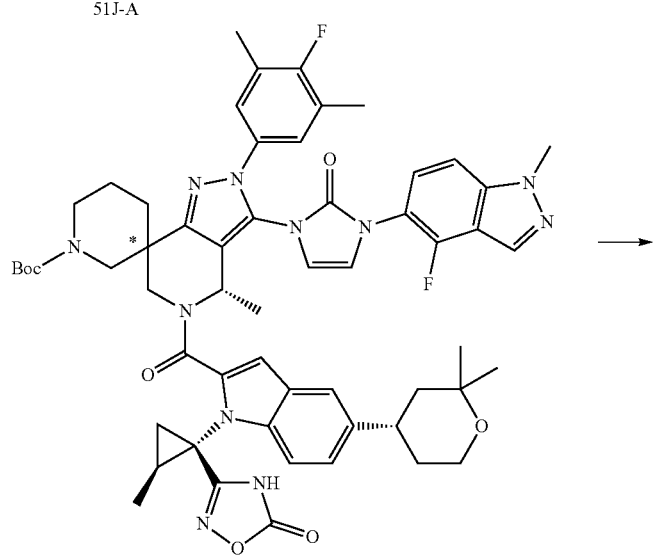
51K-A
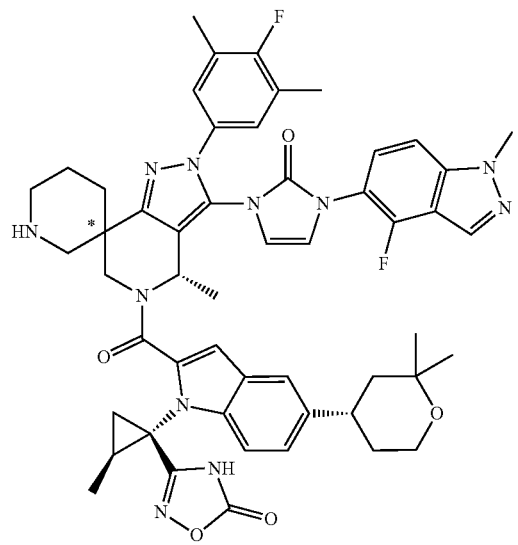
51-A

Synthesis of Compound 51B

Compound 51A (commercially available) (6.00 g, 23.32 mol) was weighed and added into 90 mL of tetrahydrofuran, and cooled to −78° C. Thereafter, LiHMDS (1M THF solution) was added dropwise. The temperature was controlled at no higher than −60° C., and the reaction was stirred for 30 min. Polyoxymethylene (2.10 g, 69.95 mol) was weighed and added to the solution. When the temperature was warmed to −10° C. to 0° C., the reaction was stirred for another 2 h. A saturated ammonium chloride solution was added to quench the reaction. The solution was extracted with ethyl acetate, and the organic phase was washed with water, washed with saturated saline, then dried over anhydrous $Na_2SO_4$, concentrated under reduced pressure, and then purified by column chromatography to afford 3.96 g of 51B as colorless oily liquid. $[M+H]^+=288$.

Synthesis of Compound 51C

Compound 51B (1.5 g, 5.22 mmol) was dissolved in 15 mL of dichloromethane. Thereafter, DMP (5.53 g, 13.05 mmol) was added in an ice bath. The reaction system was naturally returned to room temperature and stirred at room temperature for 2 h. 50 mL of a saturated aqueous $NaHCO_3$ solution was added to quench the reaction. The reaction solution was extracted with dichloromethane, and the organic phase was washed with a saturated aqueous $NaHCO_3$ solution, washed with water, washed with saturated saline, then dried over anhydrous $Na_2SO_4$, filtered, concentrated, and then separated by column chromatography to afford Compound 51C (0.91 g, colorless oily liquid), $[M+H]^+=286$.

Synthesis of Compound 51D

Compound 51C (0.91 g, 3.19 mmol) was dissolved in 20 mL of dichloromethane, and (S)-3-aminobutanenitrile hydrochloride (0.42 g, 3.51 mmol) and anhydrous sodium acetate (0.29 g, 3.51 mmol) were added and stirred at room temperature for 30 min. Sodium triacetoxyborohydride (1.35 g, 6.37 mmol) was then added and stirred overnight at room temperature. The reaction was quenched with a saturated aqueous $NaHCO_3$ solution. The solution was extracted with dichloromethane, dried over anhydrous sodium sulfate, filtered, concentrated, and then separated by column chromatography to afford Compound 51D (0.51 g, a light yellow oily product), $[M+H]^+=354$.

Synthesis of Compound 51E

Compound 51D (0.51 g, 1.45 mmol) was dissolved in 10 mL of tetrahydrofuran. Under nitrogen protection, NaHMDS (2.0M THF solution, 1.44 mL, 2.89 mmol) was added dropwise at 0° C., when finished, slowly returned to room temperature and stirred for 1 h. The reaction was adjusted with 5% citric acid until pH is approximately equal to 8. Benzyl chloroformate (0.37 g, 2.17 mmol) was added and reacted at room temperature for 1 h. The solution was extracted with ethyl acetate, and the organic phase was washed with saturated saline, dried over anhydrous sodium sulfate, filtered, concentrated, and then separated by column chromatography. Among the separated products, the compound with lower polarity was 51E-A (0.17 g, a light yellow oily product), $[M+H]^+=442$, and the compound with higher polarity was 51E-B (0.35 g, a light yellow oily product), $[M+H]^+=442$.

Synthesis of Compound 51F-A

Compound 51E-A (132.3 mg, 0.30 mmol), 4-fluoro-3,5-dimethylphenylhydrazine hydrochloride (171.4 mg, 0.90 mmol), and pyridine hydrochloride (3.5 mg, 0.03 mmol) were weighed and dissolved in 2.6 mL of ethanol, and heated to 80° C. and reacted for two days under nitrogen protection. Water was added to quench the reaction. The reaction solution was extracted with ethyl acetate. The organic phase was washed with a saturated sodium bicarbonate solution and dried over anhydrous sodium sulfate, filtered, and concentrated to afford a crude product. The crude product was dissolved in ACN, and TEA (90.9 mg, 0.90 mmol) and $(Boc)_2O$ (97.2 mg, 0.45 mmol) were added, stirred at room temperature for 1 h, concentrated under reduced pressure, and then separated by column chromatography to afford Compound 51F-A (71.3 mg, a brown-yellow solid), $[M+H]^+=578$.

Synthesis of Compound 51I-A

With reference to the synthetic method for Compound 1H in Example 1, 51I-A was synthesized by replacing 1G with 51F-A. $[M+H]^+=793$.

Synthesis of Compound 51J-A

Compound 51H-A (68.5 mg, 0.086 mmol) was weighed and dissolved in 1 mL of dichloromethane, and TEA (34.9 mg, 0.346 mmol) was added. After purging with nitrogen, triethylsilane (30.1 mg, 0.259 mmol) was added dropwise and reacted at room temperature for 3 h. After 0.5 mL of methanol was added to quench the reaction, the solution was subjected to suction filtration. The filter cake was washed three times with DCM/MeOH=5/1, and the eluate was concentrated under reduced pressure, and then purified by column chromatography to afford 60.8 mg of brown solid, $[M+H]^+=659$.

Synthesis of Compound 51K-A

Compound 51K-A was synthesized referring to the synthetic method for Compound 1, $[M+H]^+=1051$.

Synthesis of Compound 51-A

After Compound 51K-A (50.4 mg, 0.048 mmol) was weighed and dissolved in 1 mL of dichloromethane, 1 mL of a solution (4M) of hydrogen chloride in dioxane was added and stirred at room temperature for 1 h. The reaction was quenched by adding a saturated sodium bicarbonate solution. The solution was extracted with dichloromethane, dried over anhydrous sodium sulfate, filtered, concentrated, and then separated by a TLC plate to afford Compound 51-A (42.0 mg), $[M+H]^+=951$.

Synthesis of Compound 51-B

With reference to the preparation method for Compound 51-A, 51-B was synthesized by replacing 51E-A with 51E-B. $[M+H]^+=951$.

Example 13

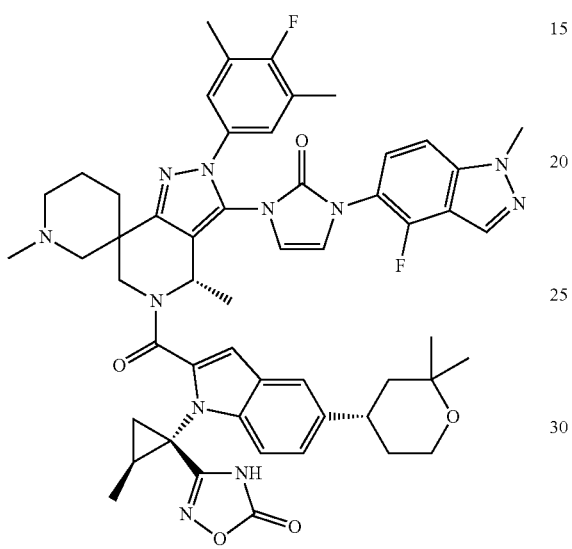

53

The compound in this example had four stereoisomers and the four single stereoisomeric compounds were 53-A, 53-B, 53-C, and 53-D respectively, which were collectively represented by Compound 53.

Synthesis of Compounds 53-A and 53-B

Compound 51-A (8.5 mg, 0.0089 mmol) was weighed and dissolved in dichloromethane, and 37% aqueous formaldehyde solution (4.3 mg, 0.1071 mmol) and sodium triacetoxyborohydride (2.9 mg, 0.0268 mmol) were added and stirred overnight at room temperature. A saturated sodium bicarbonate solution was added to quench the reaction. The reaction solution was extracted with dichloromethane and dried over anhydrous sodium sulfate. After filtration and concentration, the residue was purified by a TLC plate. Among the purified products, the compound with a large value of Rf was Compound 53-A (5.0 mg), $[M+H]^+=965$, and the compound with a small value of Rf was Compound 53-B (5.7 mg), $[M+H]^+=965$.

Synthesis of Compounds 53-C and 53-D

Compound 51-B (8.5 mg, 0.0089 mmol) was weighed and dissolved in dichloromethane, and 37% aqueous formaldehyde solution (4.3 mg, 0.1071 mmol) and sodium triacetoxyborohydride (2.9 mg, 0.0268 mmol) were added and stirred overnight at room temperature. A saturated sodium bicarbonate solution was added to quench the reaction. The reaction solution was extracted with dichloromethane and dried over anhydrous sodium sulfate. After filtration and concentration, the residue was purified by a TLC plate. Among the purified products, the compound with a large value of Rf was Compound 53—C (5.0 mg), $[M+H]^+=965$, and the compound with a small value of Rf was Compound 53-D (5.7 mg), $[M+H]^+=965$.

Example 14

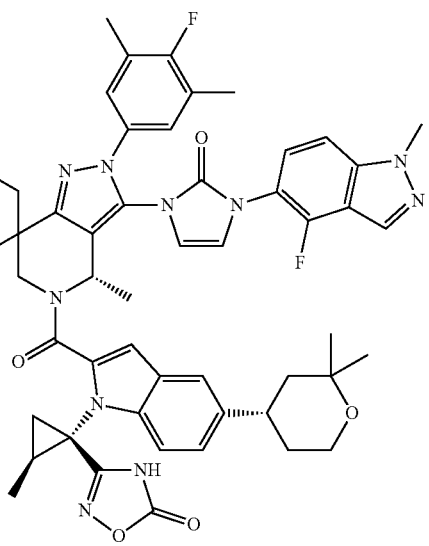

55

The compound in this example had two single stereoisomeric compounds: 55-A and 55-B, which were collectively represented by Compound 55.

Synthesis of Compound 55-A

Compound 51-A (8.7 mg, 0.0091 mmol) was weighed and dissolved in isopropyl formate, and heated in a sealed tube at 90° C. and stirred for 40 h. When concentrated under reduced pressure, the residue was purified by a TLC plate to afford Compound 55-A (6.4 mg), $[M+H]^+=979$.

Synthesis of Compound 55-B

With reference to the synthetic method for Compound 55-A, 55-B was synthesized by replacing 51-A with 51-B. $[M+H]^+=979$.

Example 15
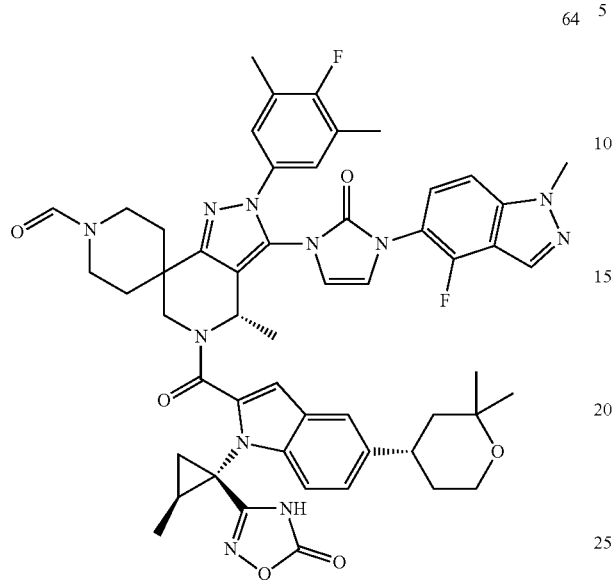
64
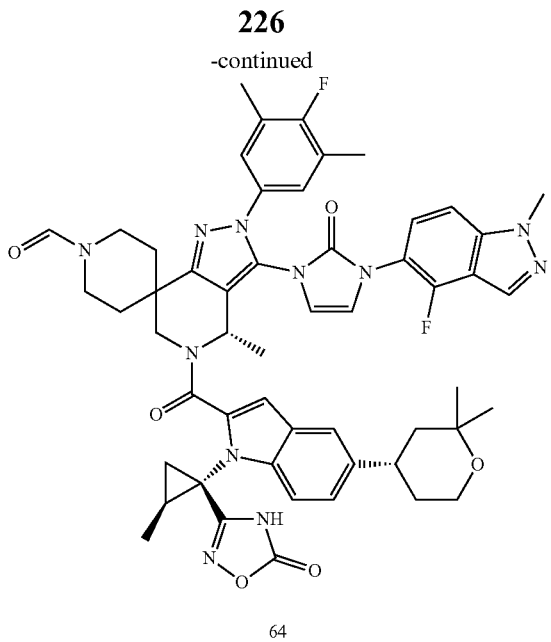
64
Synthesis of Compound 64
57 (9.5 mg, 0.01 mmol) was weighed and added into a 10-mL sealed tube. Isopropyl formate (1 mL) was used as a solvent. The solution was reacted overnight at 75° C. with the tube sealed. The reaction solution was cooled to room temperature, concentrated and then purified by silica gel preparative plate to afford Compound 64 (7.5 mg). $[M+H]^+=980$.
Example 16
Synthetic Route
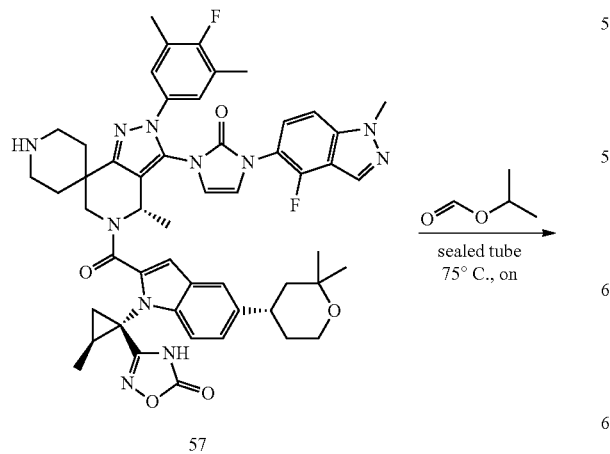
57
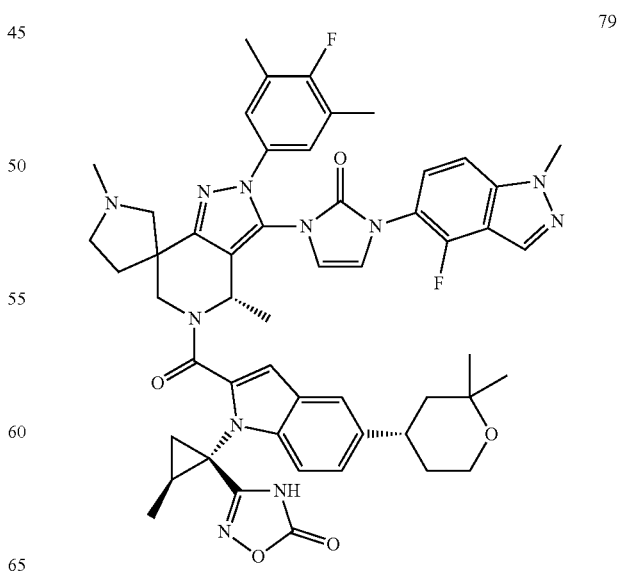
79

Synthetic Route

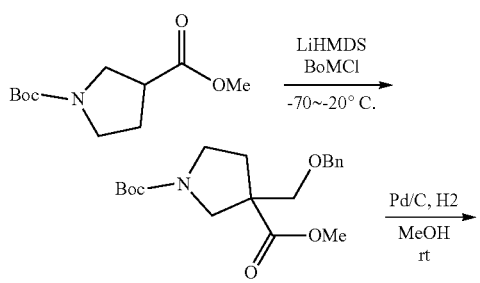

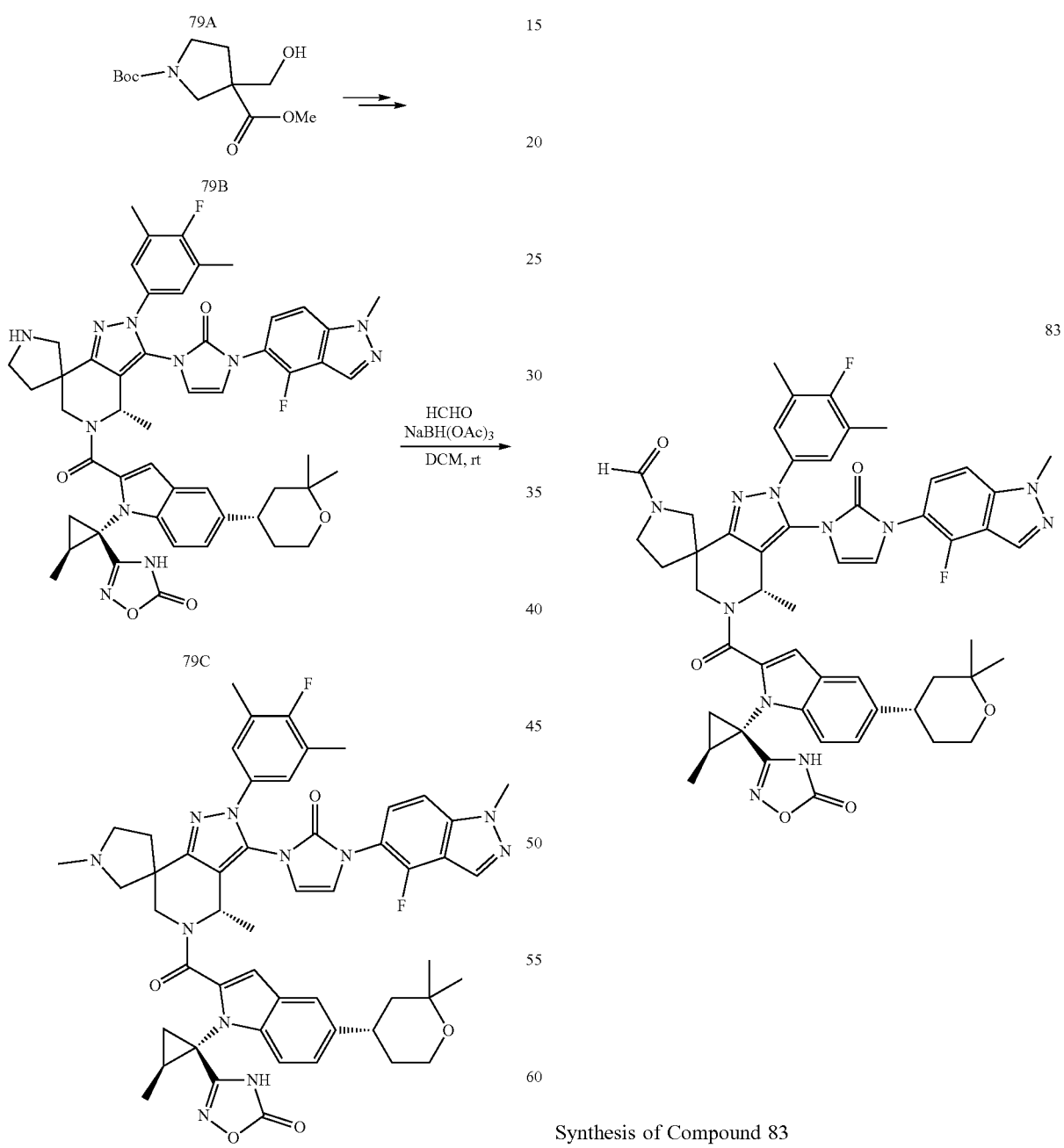

Synthesis of Compound 79C

With reference to the preparation method for Compound 31 in Example 9, Compound 79C was synthesized by replacing Boc-L-proline-methyl ester with methyl 1-Boc-pyrrolidine-3-carboxylate. $[M+H]^+=938$.

Synthesis of Compound 79

With reference to the preparation method for Compound 59 in Example 4, Compound 79 was synthesized by replacing Compound 57 with Compound 79C. $[M+H]^+=952$.

Example 17

Synthesis of Compound 83

With reference to the preparation method for Compound 64 in Example 15, Compound 83 was synthesized by replacing Compound 57 with Compound 79C. $[M+H]^+=966$.

Example 18

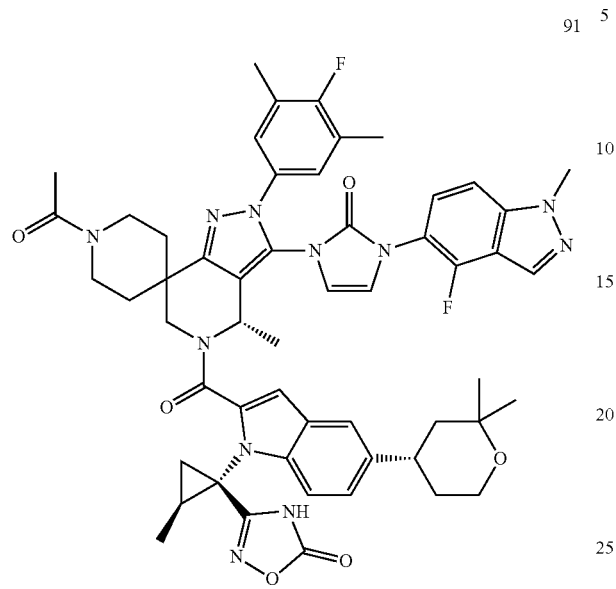

91

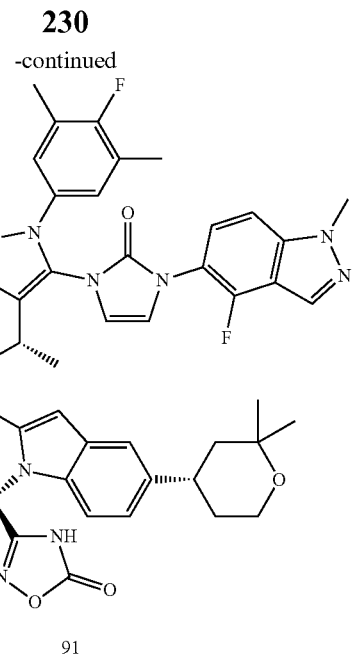

91

Synthesis of Compound 91

57 (10.1 mg, 0.01 mmol) was weighed and added into a 10-mL reaction tube. Dichloromethane (1 mL) was used as a solvent. Pyridine (4.1 mg, 0.05 mmol) and acetylchloride (1.8 mg, 0.02 mmol) were added in sequence in an ice bath. The reaction was naturally warmed and stirred for 2 h. In an ice bath, methanol (0.5 mL) was added to quench the reaction. The system was concentrated and then purified by silica gel preparative plate to afford Compound 91 (8.1 mg). [M+H]$^+$=994.

Example 19

Synthetic Route

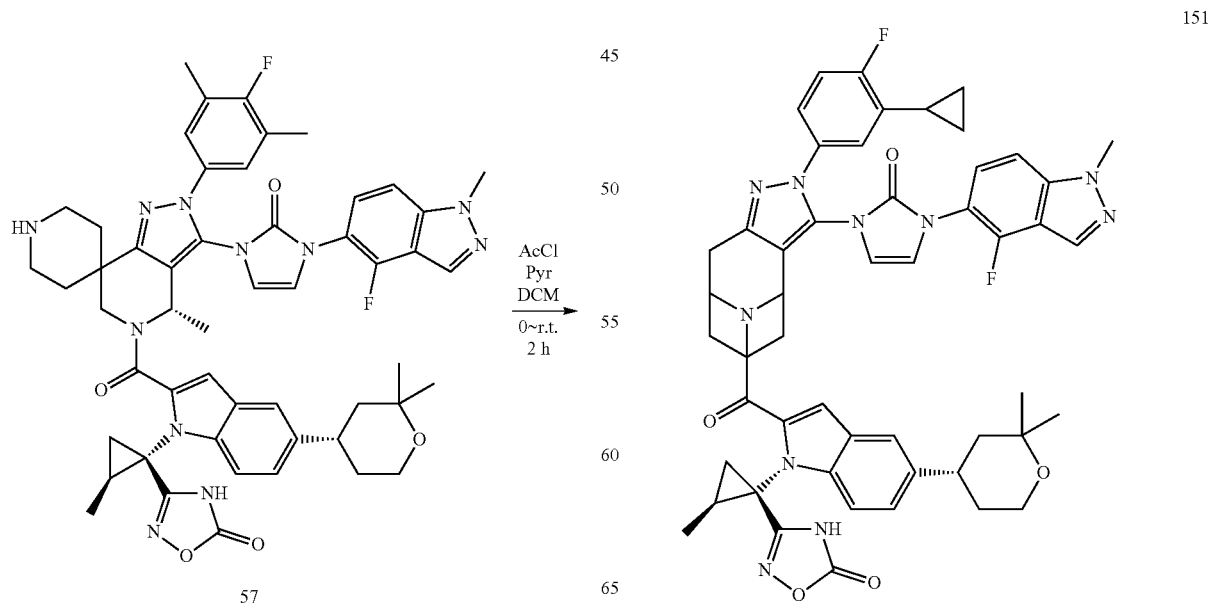

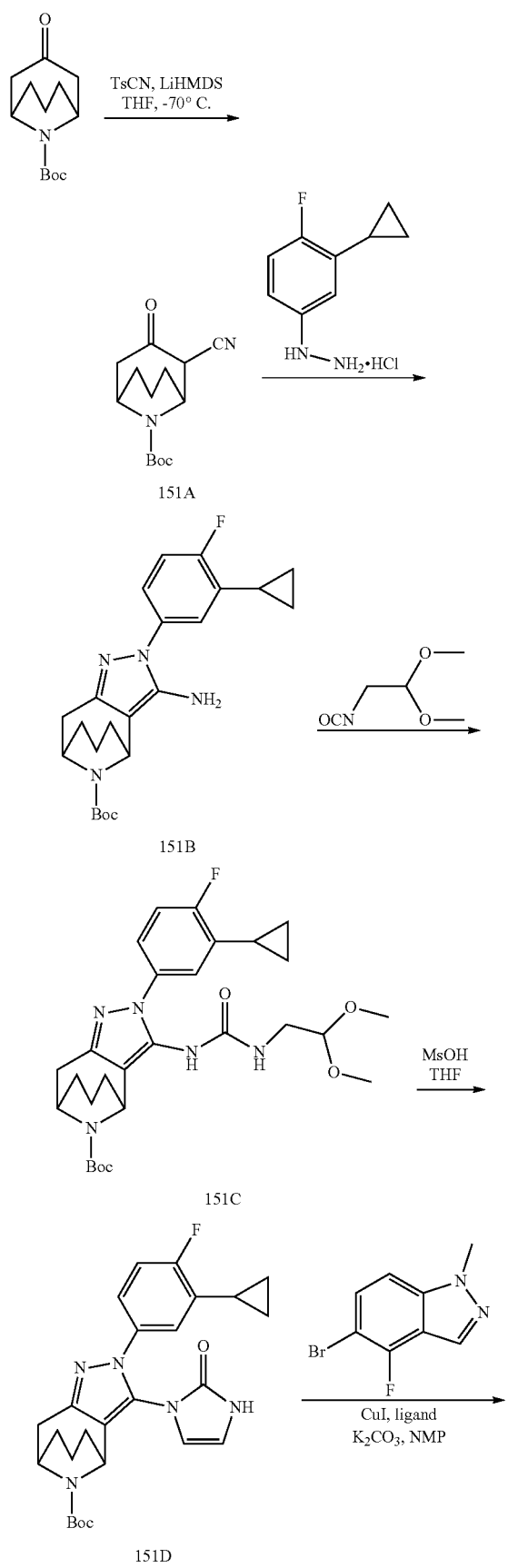
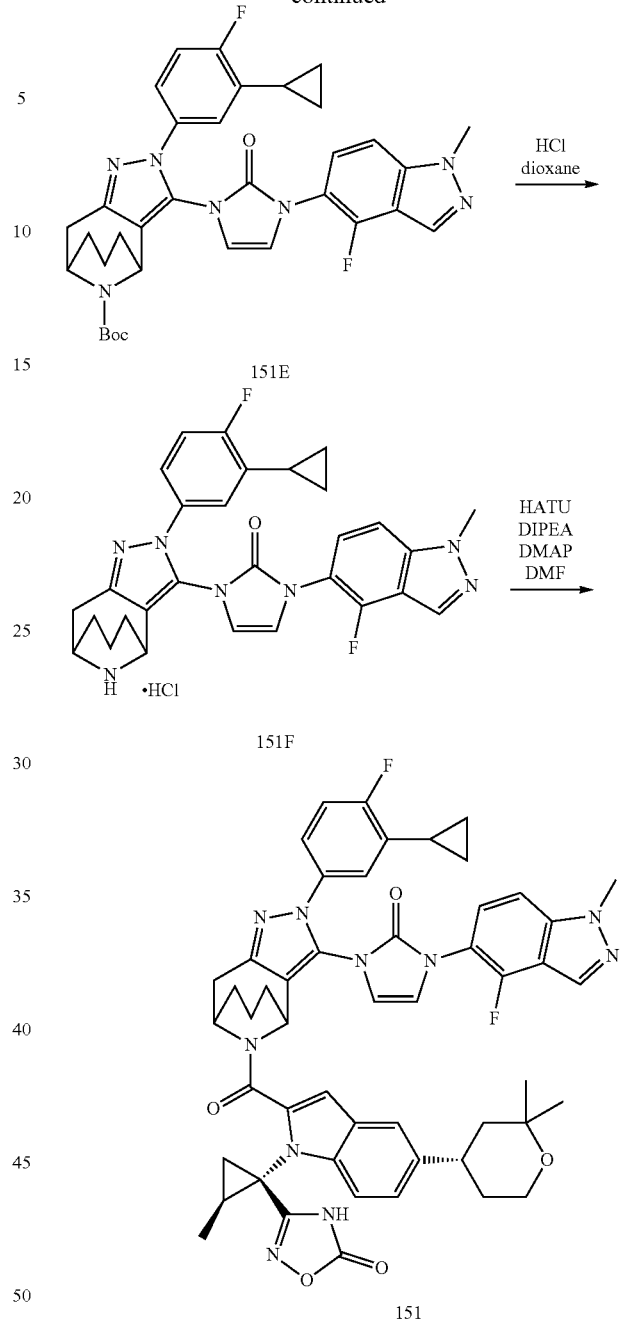

Synthesis of Compound 151A

N-Boc-9-azabicyclo[3.3.1]nonan-3-one (1.0 g, 4.2 mmol) was weighed and dissolved in THF (15 mL). LiHMDS (1M, 8.2 mL, 8.2 mmol) was added in an ice bath, stirred at −70° C. for 30 min, and then a solution of p-toluenesulfonyl cyanide (1.0 g, 5.8 mmol) in THF (6 mL) was added. After stirring for 30 min, the reaction was naturally warmed to room temperature and stirred for 20 min. The reaction was quenched by adding an aqueous citric acid solution. The solution was extracted with ethyl acetate, dried over anhydrous sodium sulfate, and followed by suction filtration. The filtrate was concentrated and then purified by silica gel preparative plate to afford Compound 151A (0.8 g, a colorless oily product). [M+H]⁺=265.

Synthesis of Compound 151

With reference to the preparation method for Compound 1 in Example 1, Compound 151 was synthesized by replacing 1D and 4-fluoro-3,5-dimethylphenylhydrazine hydrochloride with 151A and 3-cyclopropyl-4-fluorophenylhydrazine hydrochloride. [M+H]$^+$=921.

Example 20

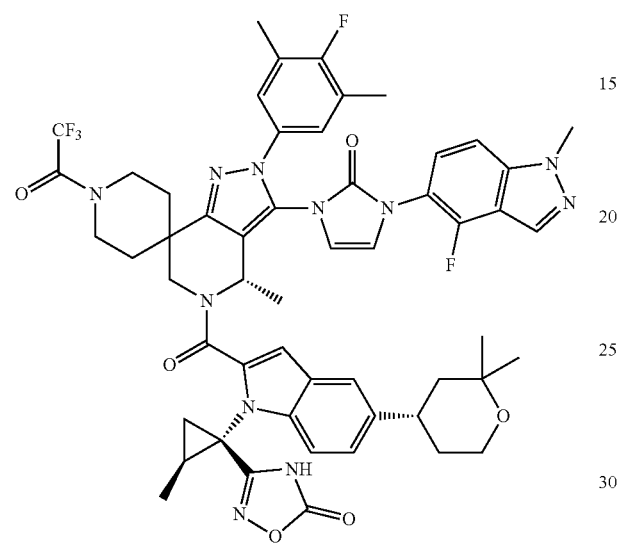

155

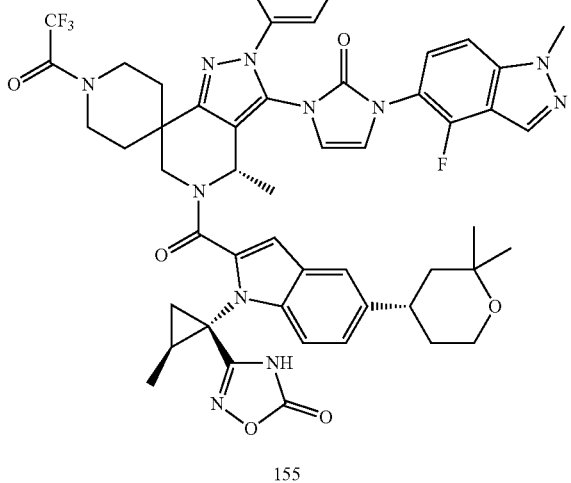

155

Synthesis of Compound 155

57 (9.8 mg, 0.01 mmol) was weighed and added into a 10-mL reaction tube. Dichloromethane (1 mL) was used as a solvent. In an ice bath, pyridine (4.5 mg, 0.05 mmol) and TFAA (6.5 mg, 0.03 mmol) were added in sequence. The ice bath was removed upon addition. The reaction was stirred at room temperature for 4 h. Methanol (0.5 mL) was added in an ice bath to quench the reaction. The solution was concentrated and then purified by silica gel preparative plate to afford Compound 155 (8.4 mg). [M+H]$^+$=1048.

Example 21

156

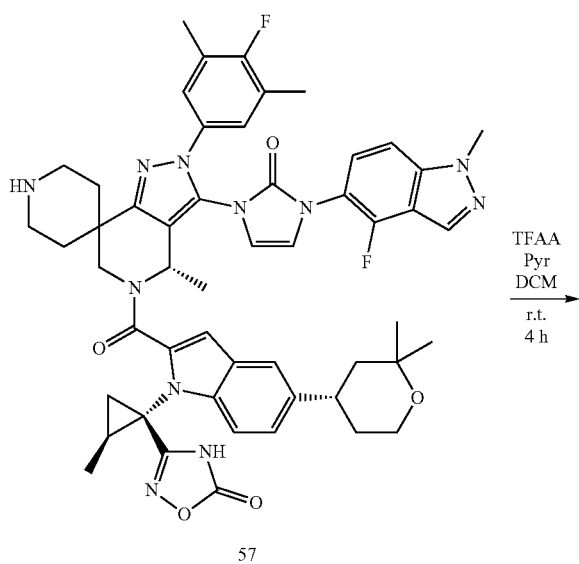

57

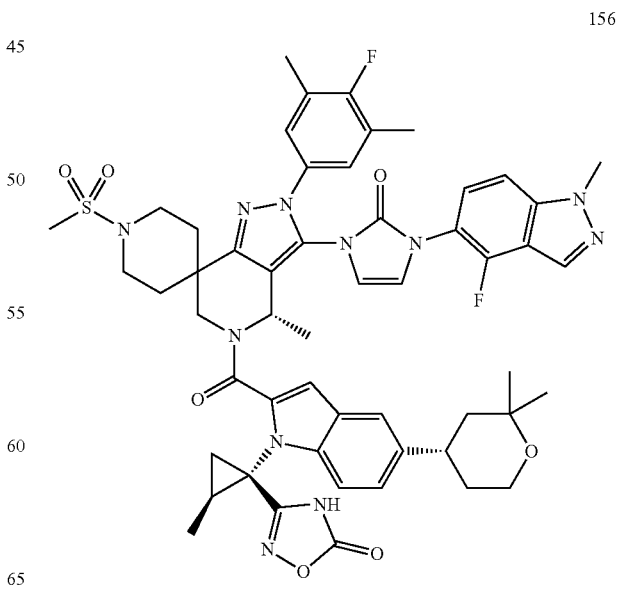

Synthetic Route

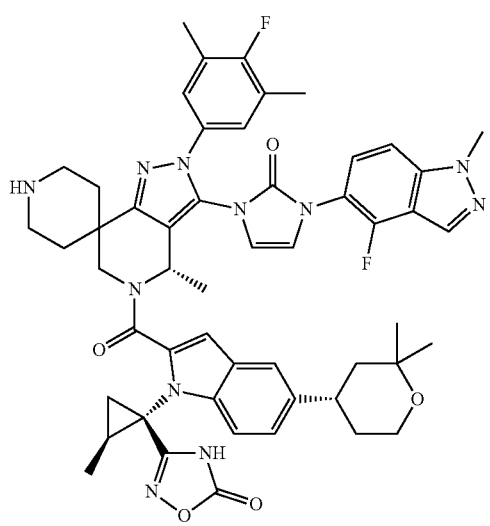

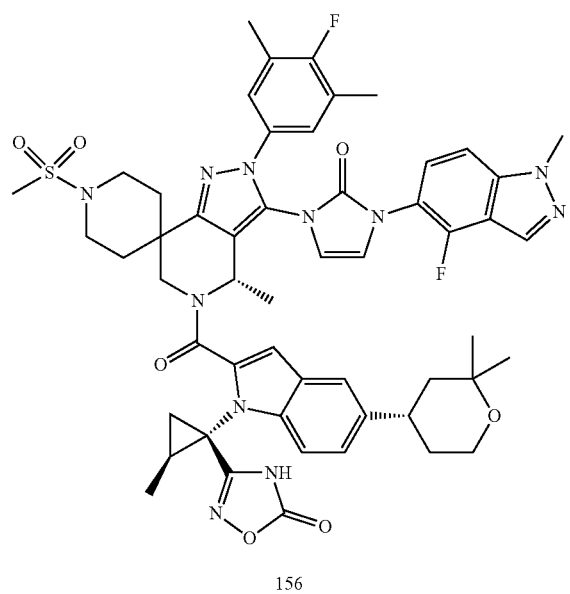

Synthesis of Compound 156

57 (9.8 mg, 0.01 mmol) was weighed and added into a 10-mL reaction tube. Dichloromethane (1 mL) was used as a solvent. Pyridine (8.1 mg, 0.1 mmol) and Ms$_2$O (8.6 mg, 0.05 mmol) were added in sequence and stirred at room temperature for 5 h. Water was added in an ice bath to quench the reaction. The solution was extracted with dichloromethane. The organic phase was dried over anhydrous sodium sulfate and followed by suction filtration. The filtrate was concentrated and then purified by silica gel preparative plate to afford Compound 156 (5.1 mg). [M+H]$^+$=1030.

Example 22

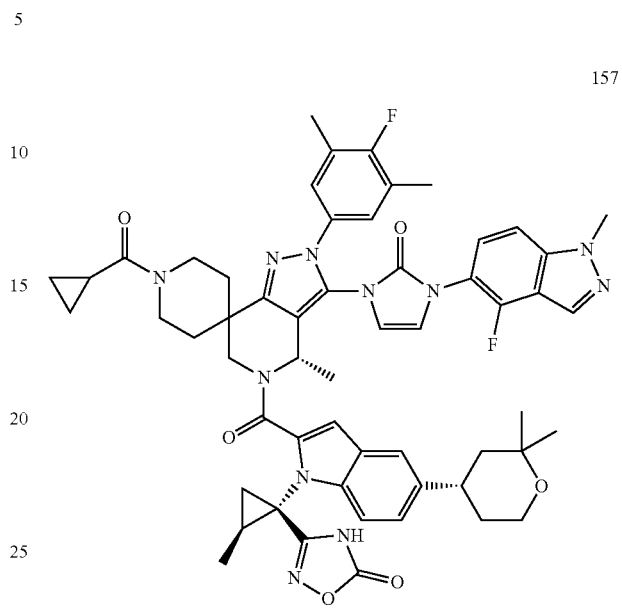

Synthetic Route

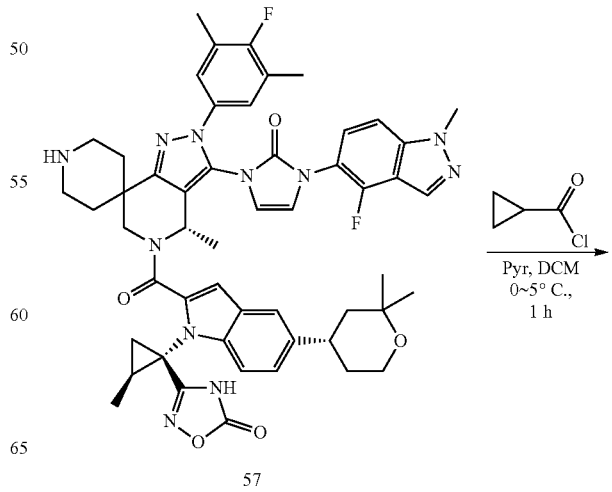

Synthetic Route

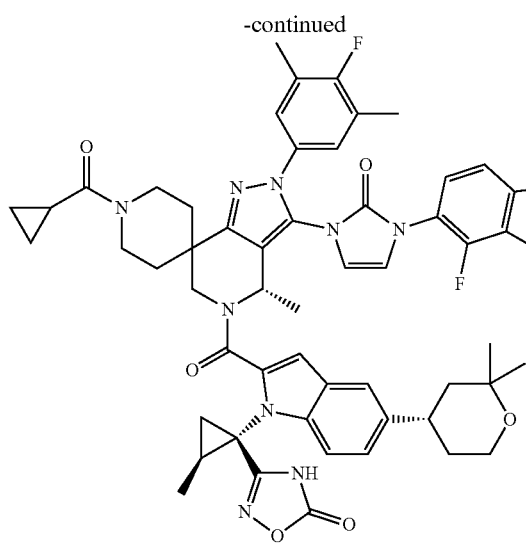

157

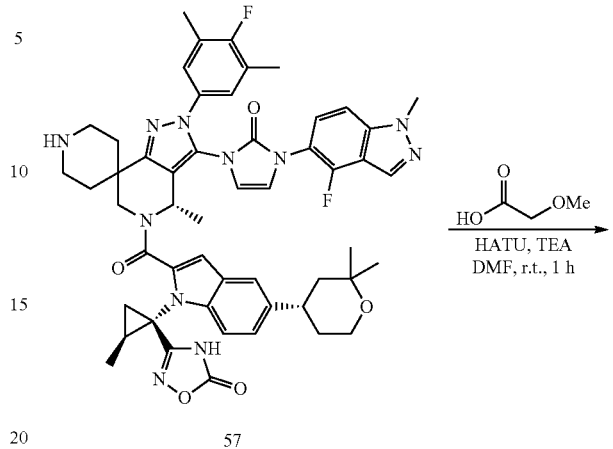

57

Synthesis of Compound 157

57 (5.5 mg, 0.006 mmol) was weighed and added into a 10-mL reaction tube. Dichloromethane (1 mL) was used as a solvent. In an ice bath, pyridine (16.0 mg, 0.2 mmol) and cyclopropanecarbonyl chloride (5.1 mg, 0.048 mmol) were added in sequence, and stirred for 1 h in the ice bath. Water was added in an ice bath to quench the reaction. The solution was extracted with dichloromethane. The organic phase was dried over anhydrous sodium sulfate and followed by suction filtration. The filtrate was concentrated and then purified by silica gel preparative plate to afford Compound 157 (2.8 mg). $[M+H]^+=1020$.

Example 23

158

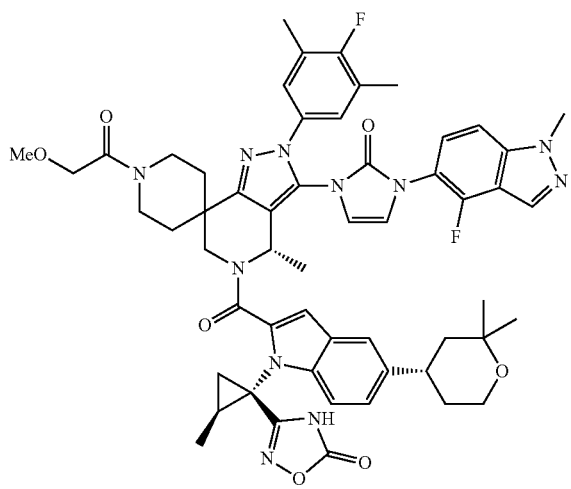

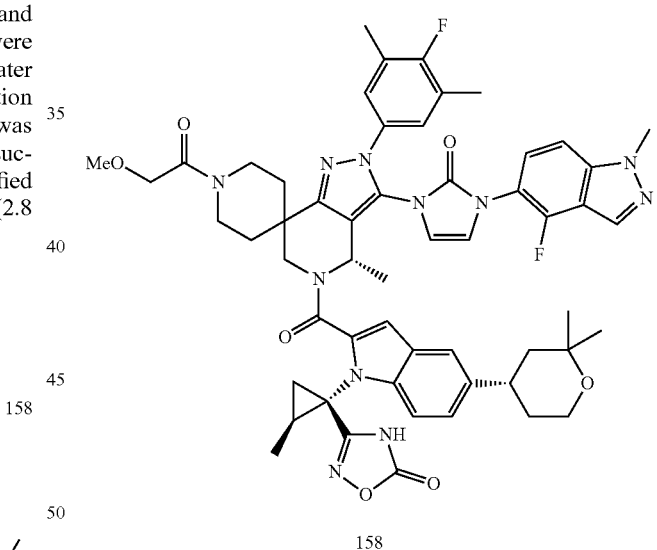

158

Synthesis of Compound 158

57 (5.5 mg, 0.006 mmol) and methoxyacetic acid (4.5 mg, 0.05 mmol) were weighed and added into a 10-mL reaction tube. DMF (0.25 mL) was used as a solvent. Triethylamine (20.0 mg, 0.2 mmol) and HATU (4.5 mg, 0.012 mmol) were added thereto in sequence at room temperature, and stirred at room temperature for 1 h. After the reaction was complete, water was added to quench the reaction. The reaction solution was extracted with ethyl acetate. The organic phase was dried over anhydrous sodium sulfate and followed by suction filtration. The filtrate was concentrated and then purified by a silica gel preparative plate to afford Compound 158 (3.5 mg). $[M+H]^+=1024$.

Example 24
159
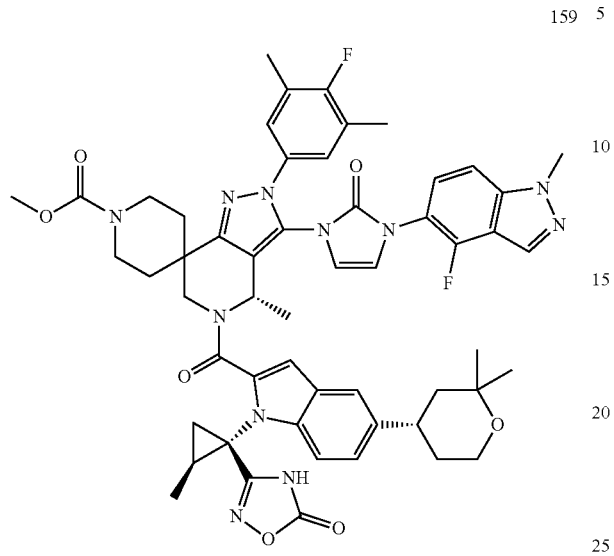
Example 25
160
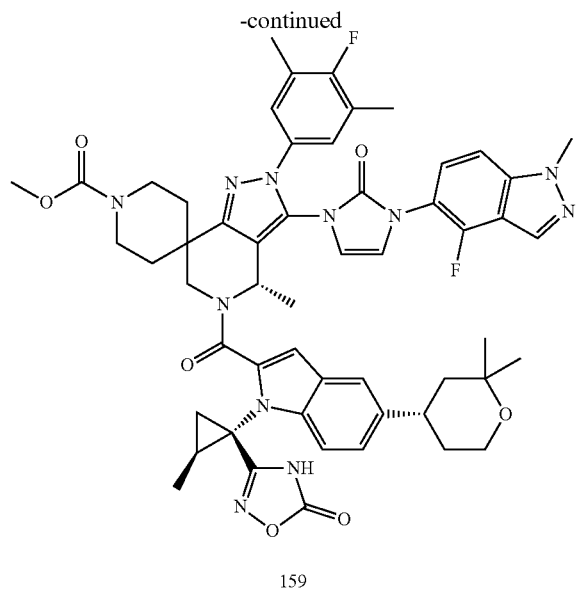
Synthesis of Compound 159
With reference to the preparation method for Compound 91 in Example 18, 159 was synthesized by replacing acetylchloride with methyl chloroformate. [M+H]$^+$=1010.
Synthetic Route
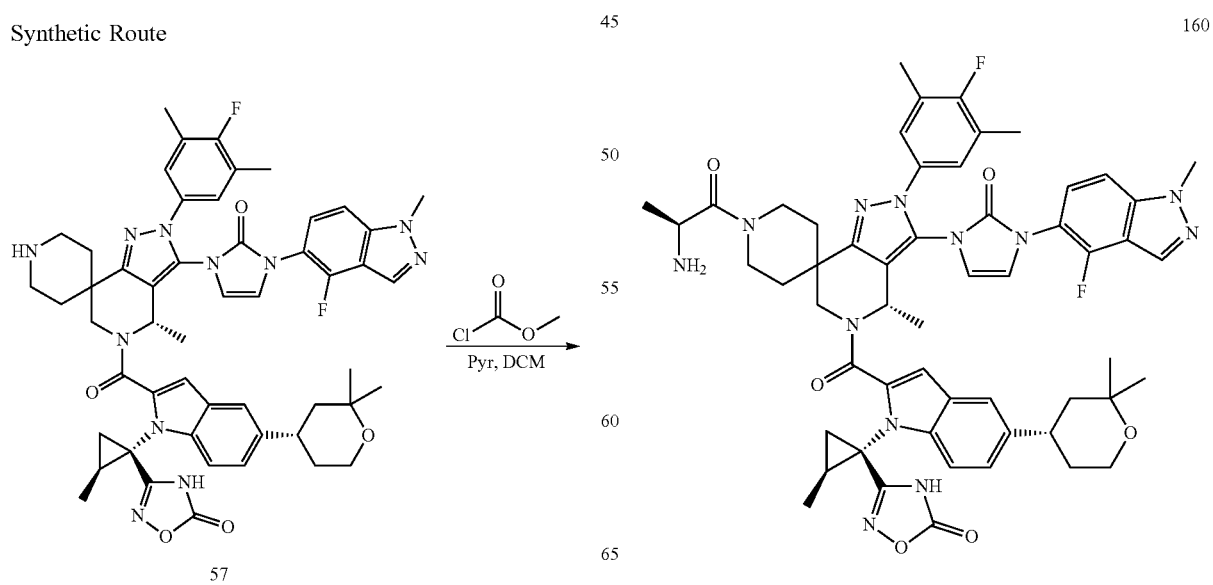

Synthetic Route

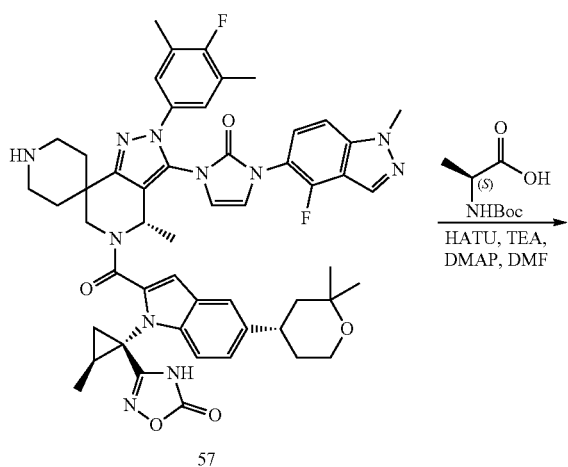

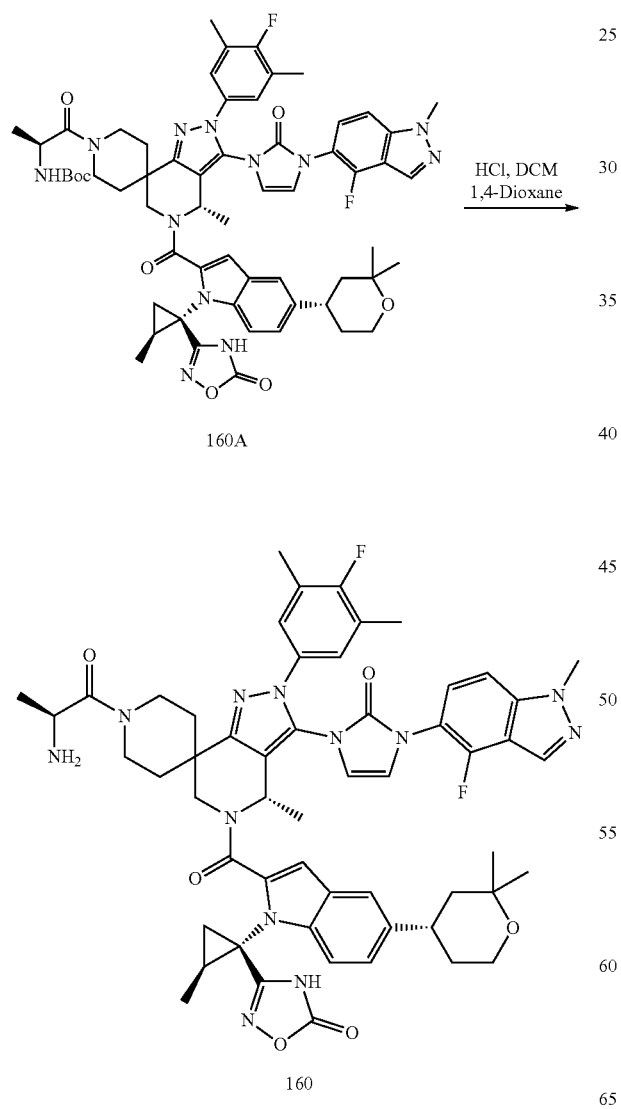

Synthesis of Compound 160A

Compound 57 (6.7 mg, 0.007 mmol) was weighed and dissolved in 1 mL of N,N-dimethylformamide. Thereafter, N-tert-butoxycarbonyl-L-alanine (5.7 mg, 0.030 mmol), HATU (15.3 mg, 0.040 mmol), TEA (10.0 mg, 0.098 mmol), and DMAP (6.0 mg, 0.049 mmol) were added in sequence, and reacted at room temperature for 1 h. Purified water and ethyl acetate were added for extraction. The organic phase was concentrated to afford a crude product of Compound 160A (18.1 mg, an off-white solid), $[M+H]^+=1123$.

Synthesis of Compound 160

The crude product of Compound 160A (18.1 mg) was dissolved in 0.6 mL of dichloromethane. Thereafter, 0.6 mL of a solution (4 mol/L) of hydrogen chloride in dioxane was added, and reacted at room temperature for 1 h. A 1000 potassium phosphate solution was added to quench the reaction. The reaction solution was extracted with ethyl acetate. The organic phase was concentrated and then separated by a silica gel preparative plate to afford Compound 160 (3.1 mg), $[M+H]^+=1023$.

Example 26

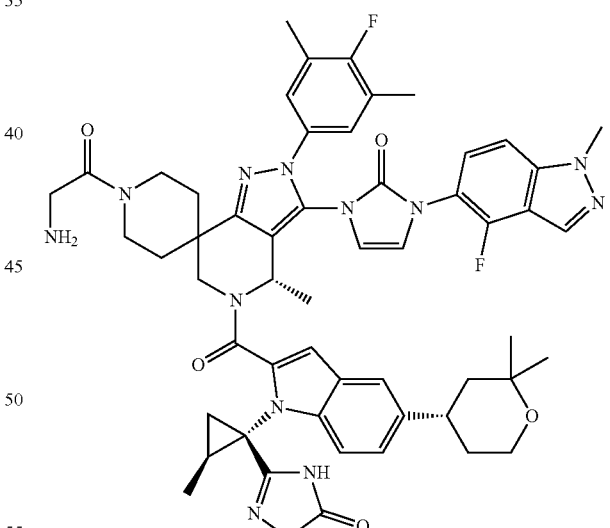

Synthesis of Compound 161

With reference to the preparation method for Compound 160 in Example 25, 161 was synthesized by replacing N-tert-butoxycarbonyl-L-alanine with BOC-glycine. $[M+H]^+=1009$.

Example 27

162

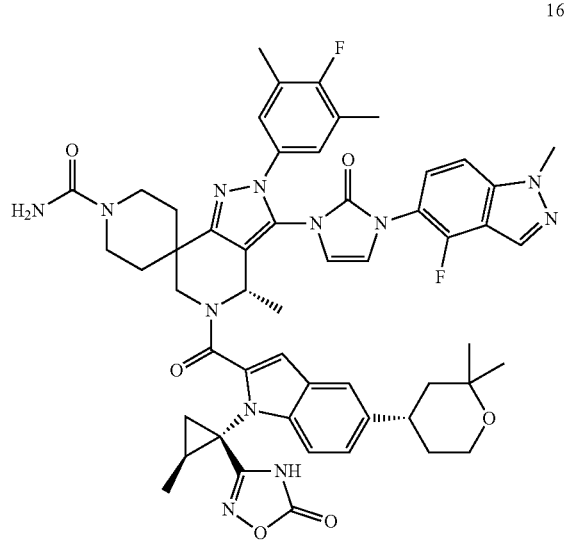

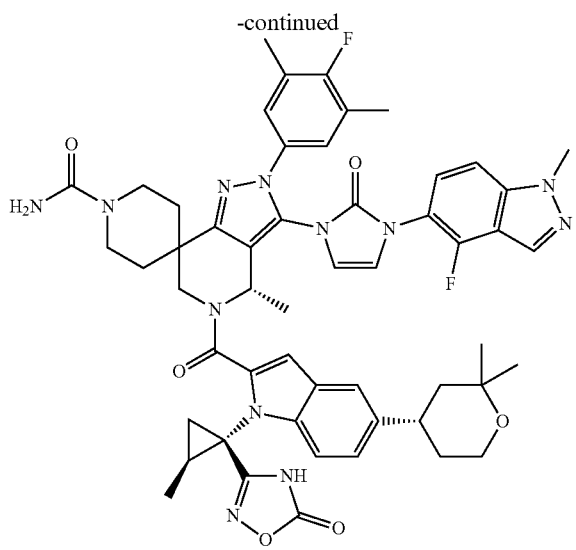

162

Synthesis of Compound 162

57 (9.1 mg, 0.01 mmol), TMSNCO (34.5 mg, 0.2 mmol), and triethylamine (20.1 mg, 0.2 mmol) were weighed and added into a 10-mL reaction tube. DCM (1.5 mL) was used as a solvent. The reaction was stirred at room temperature for 48 h. After the reaction was complete, the solution was concentrated and purified by a silica gel preparative plate to afford Compound 162 (6.1 mg). [M+H]$^+$=995.

Example 28

Synthetic Route

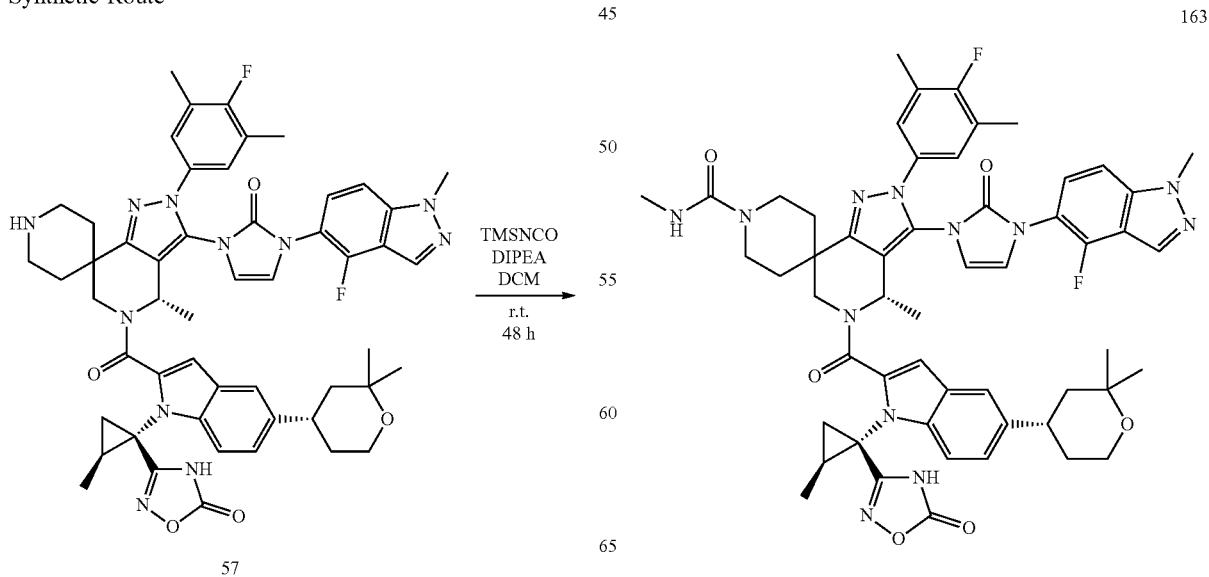

Synthetic Route

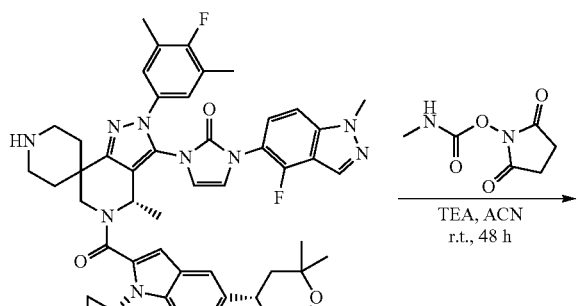

Synthesis of Compound 163

57 (6.0 mg, 0.006 mmol), N-succinimidyl-N-methylcarbamate (3.1 mg, 0.018 mmol), and triethylamine (10.1 mg, 0.1 mmol) were weighed and added into a 10-mL reaction tube. ACN (1.0 mL) was used as a solvent. The reaction was stirred at room temperature for 48 h. After the reaction was complete, the solution was concentrated and purified by a silica gel preparative plate to afford Compound 163 (4.0 mg). $[M+H]^+=1009$.

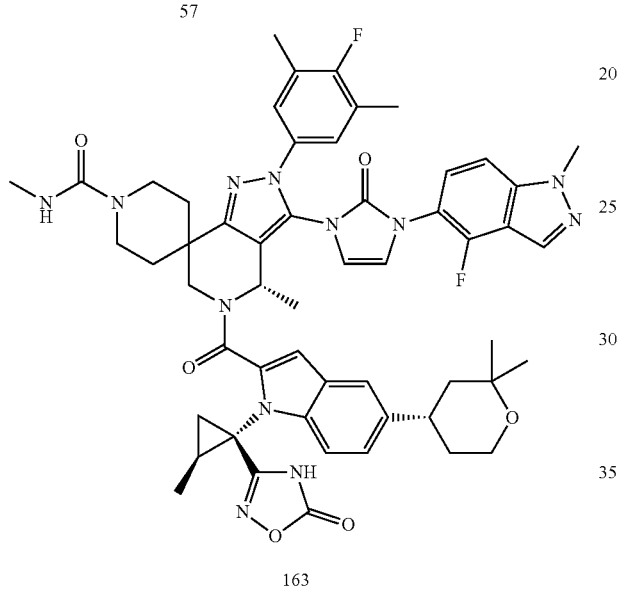

Example 29

Compounds 164-171, 173-177, and 221-224 listed in Table 2 were prepared substantially based on the similar synthetic methods or strategies of Examples 1-28, or prepared using appropriate intermediates that can be readily synthesized by the methods known in the art, and modified if necessary.

TABLE 2

| Cmpd. | Structure | Data |
|---|---|---|
| 164 (Prepared referring to the method in Example 13) | (structure 164) | $[M + H]^+ = 938$ |

TABLE 2-continued

| Cmpd. | Structure | Data |
|---|---|---|
| 165 (Prepared referring to the method in Example 15) | *(structure 165)* | [M + H]⁺ = 952 |
| 166 (Prepared referring to the method in Example 18) | *(structure 166)* | [M + H]⁺ = 966 |

TABLE 2-continued

| Cmpd. | Structure | Data |
|---|---|---|
| 167 (Prepared referring to the method in Example 20) | (structure 167) | $[M + H]^+$ = 1020 |
| 168 (Prepared referring to the method in Example 21) | (structure 168) | $[M + H]^+$ = 1002 |

TABLE 2-continued

| Cmpd. | Structure | Data |
|---|---|---|
| 169 (Prepared referring to the method in Example 1) | 169 | [M + H]⁺ = 895 |
| 170 (Prepared referring to the method in Example 1) | 170 | [M + H]⁺ = 907 |

TABLE 2-continued
| Cmpd. | Structure | Data |
|---|---|---|
| 171 (Prepared referring to the method in Example 1) | 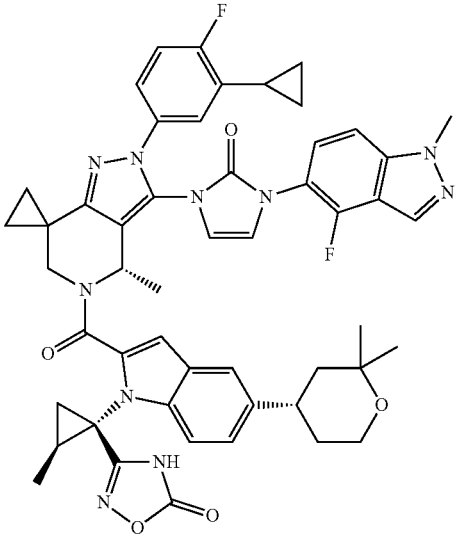 [SMILES: C[C@H]1c2c(nn(-c3ccc(F)c(C4CC4)c3)c2-n2ccn(-c3ccc4c(cnn4C)c3F)c2=O)C2(CC2)CN1C(=O)c1cc2cc([C@H]3CCOC(C)(C)C3)ccc2n1[C@@]1(c2noc(=O)[nH]2)C[C@@H]1C] 171 | [M + H]⁺ = 921 |
| 173 (Prepared referring to the method in Example 1) | 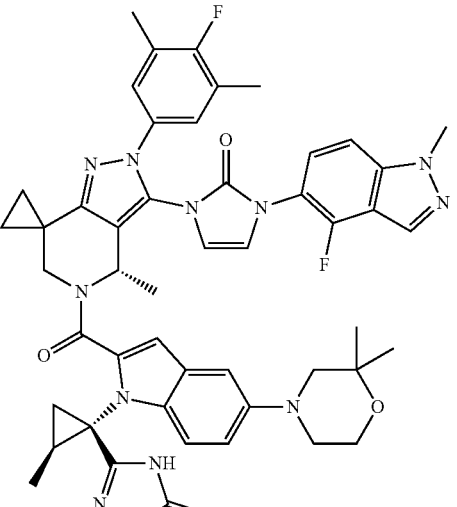 173 | [M + H]⁺ = 910 |

TABLE 2-continued

| Cmpd. | Structure | Data |
|---|---|---|
| 174 (Prepared referring to the method in Example 1) | 174 | [M + H]⁺ = 867 |
| 175 (Prepared referring to the method in Example 1) | 175 | [M + H]⁺ = 881 |

TABLE 2-continued

| Cmpd. | Structure | Data |
|---|---|---|
| 176 (Prepared referring to the method in Example 1) | (structure 176) | [M + H]⁺ = 910 |
| 177 (Prepared referring to the method in Example 1) | (structure 177) | [M + H]⁺ = 896 |

TABLE 2-continued
| Cmpd. | Structure | Data |
|---|---|---|
| 221 (Prepared referring to the method in Example 1) | 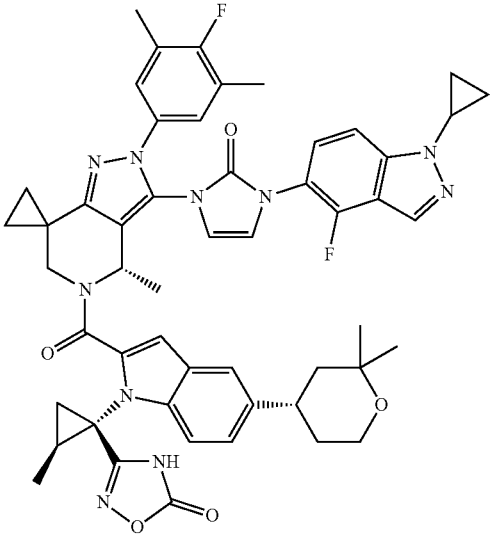 [SMILES: Cc1cc(-n2nc3c(c2-n2ccn(-c4ccc5c(cnn5C5CC5)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC2)cc(C)c1F] 221 | [M + H]⁺ = 935 |
| 222 (Prepared referring to the method in Example 1) | 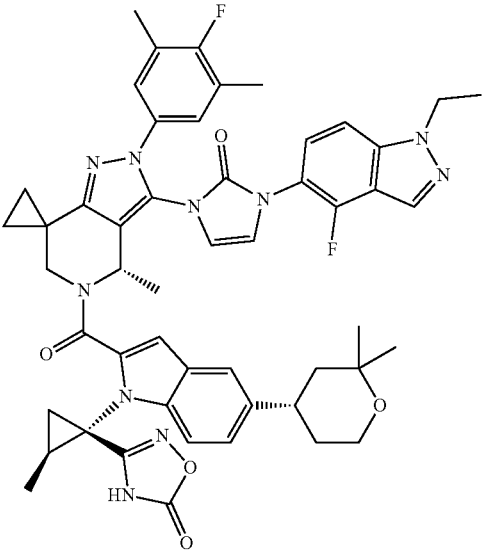 [SMILES: CCn1ncc2c(F)c(-n3ccn(-c4c5c(nn4-c4cc(C)c(F)c(C)c4)C4(CC4)CN(C(=O)c4cc6cc([C@H]7CCOC(C)(C)C7)ccc6n4[C@@]4(c6noc(=O)[nH]6)C[C@@H]4C)[C@H]5C)c3=O)ccc21] 222 | [M + H]⁺ = 923 |

TABLE 2-continued
| Cmpd. | Structure | Data |
|---|---|---|
| 223 (Prepared referring to the method in Example 1) | 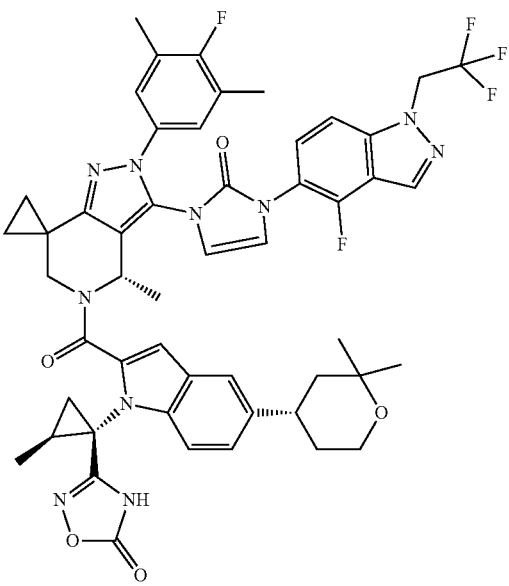 [SMILES: Cc1cc(-n2nc3c(c2-n2ccn(-c4ccc5c(cnn5CC(F)(F)F)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC2)cc(C)c1F]<br>223 | [M + H]+ = 977 |
| 224 (Prepared referring to the method in Example 1) | 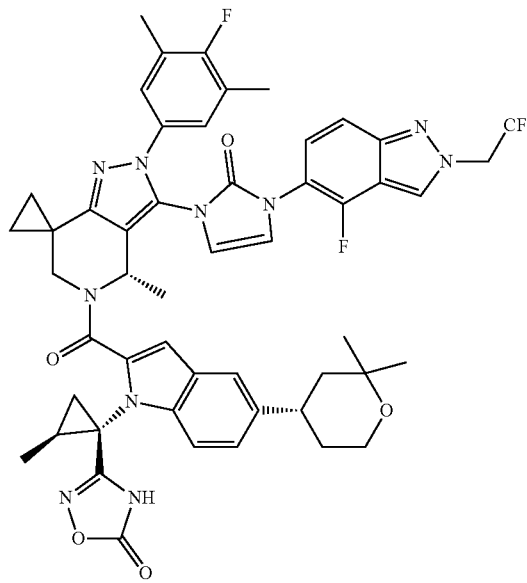 [SMILES: Cc1cc(-n2nc3c(c2-n2ccn(-c4ccc5nn(CC(F)(F)F)cc5c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC2)cc(C)c1F]<br>224 | [M + H]+ = 977 |

Example 30
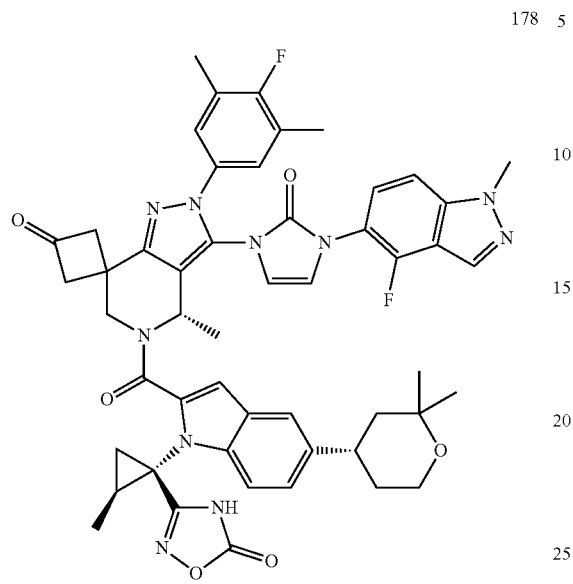
Synthetic Route
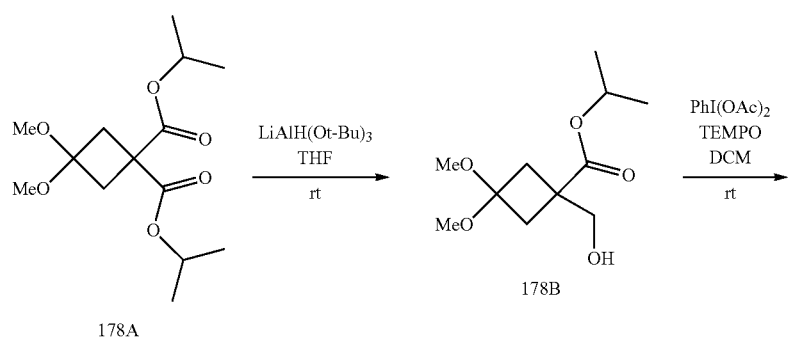
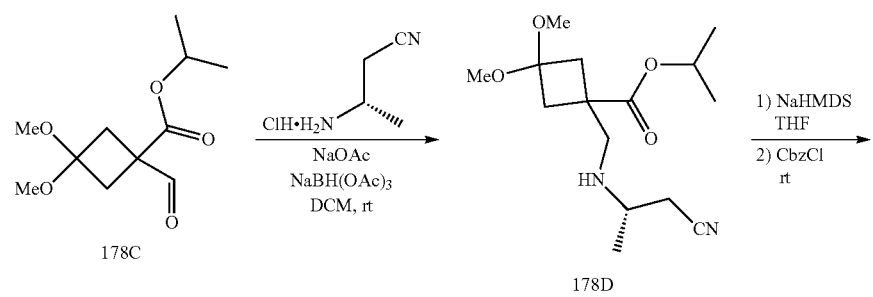

-continued
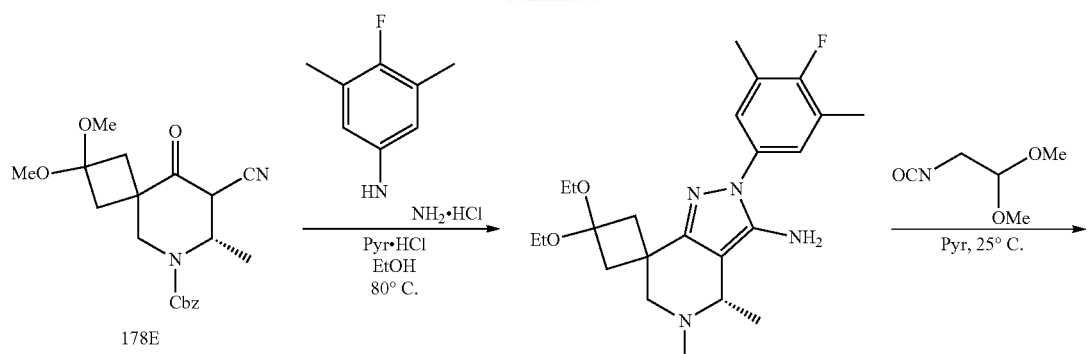
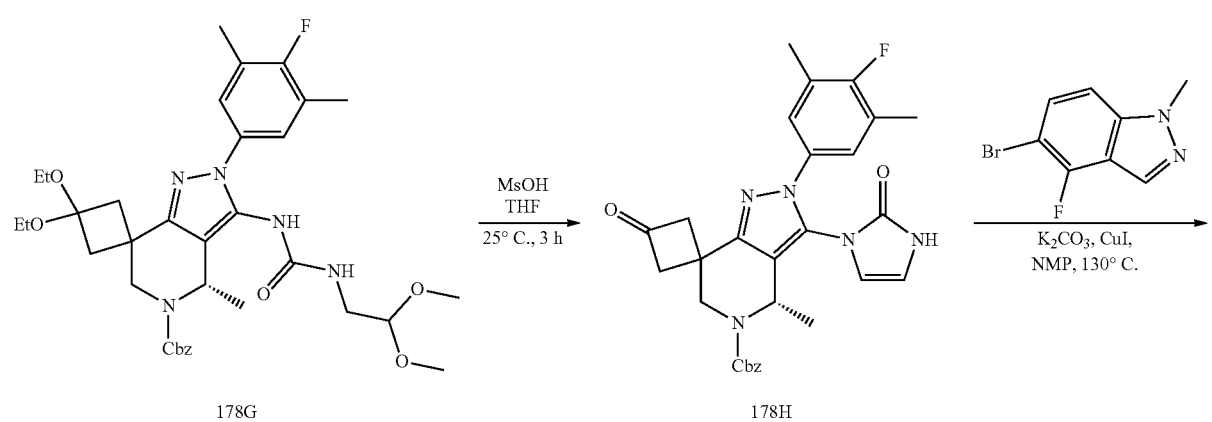
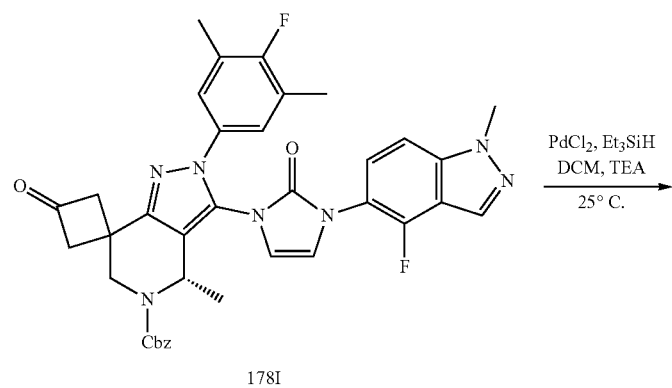
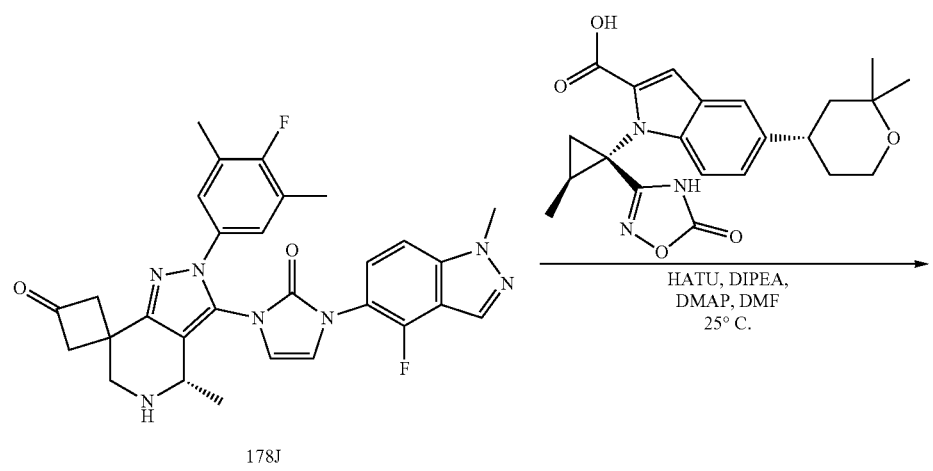

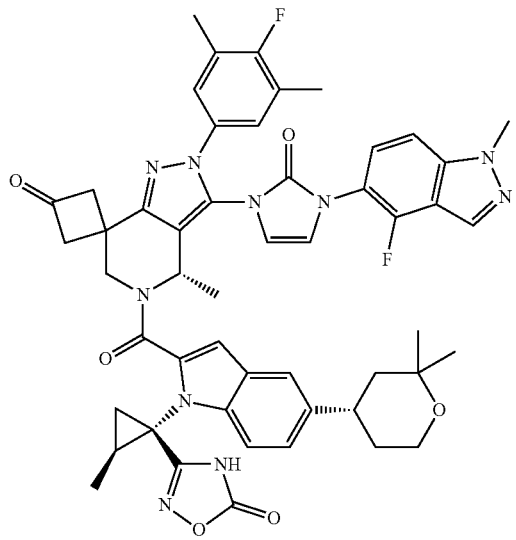

178

Synthesis of Compound 178F

With reference to the preparation method for Compound 25E in Example 8, 178F was synthesized by replacing diethyl 3-cyclopentene-1,1-dicarboxylate with Compound 178A (commercially available). [M+H]⁺=537.

Synthesis of Compound 178

With reference to the preparation method for Compound 57K in Example 3, 178 was synthesized by replacing 57F with Compound 178F. [M+H]⁺=937.

Example 31

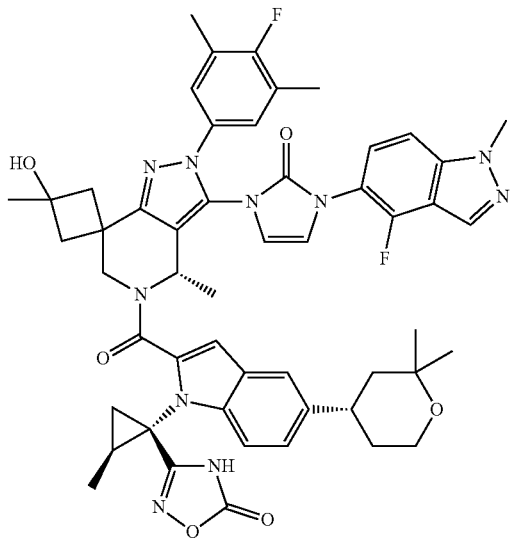

179

Synthetic Route

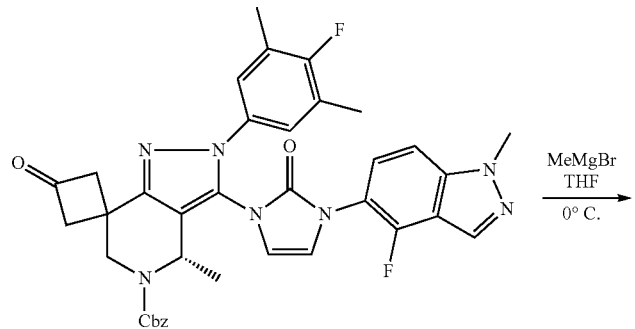

178I

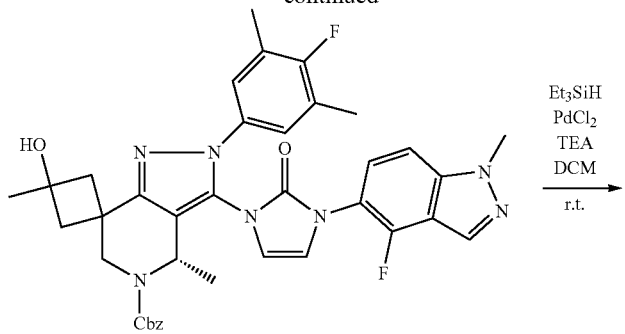

179A

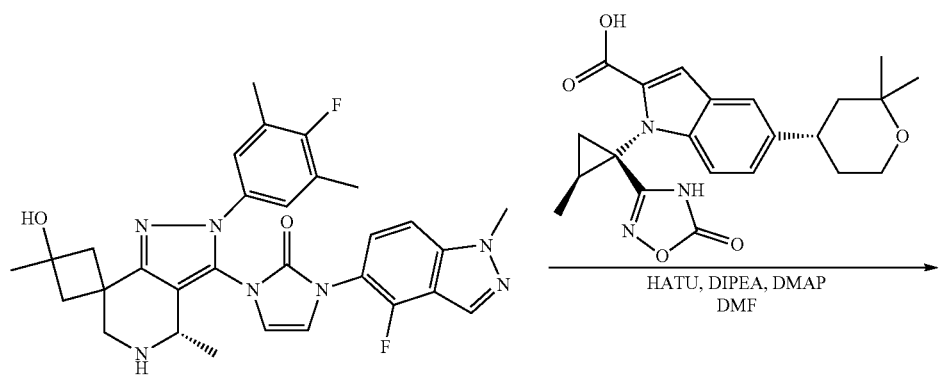

179B

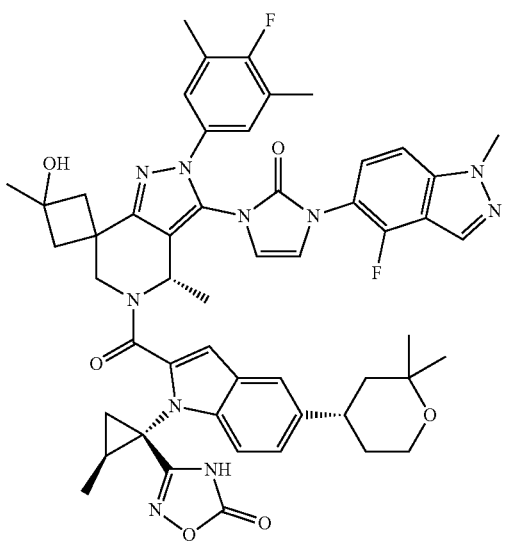

179

Synthesis of Compound 179A 178I (63.2 mg, 0.1 mmol) was weighed and added into a 25-mL round-bottom flask. Tetrahydrofuran (2 mL) was used as a solvent. Methylmagnesium bromide (0.1 mL, 0.3 mmol) was added in an ice bath, and stirred for 1 h in an ice bath. After the reaction was complete, the reaction was quenched with a saturated aqueous ammonium chloride solution in an ice bath. The solution was extracted with ethyl acetate (50 mL). The organic phase was washed with saturated saline (50 mL), dried over anhydrous sodium sulfate, and followed by suction filtration. The filtrate was concentrated and then purified by silica gel column chromatography to afford Compound 179A (38.0 mg). [M+H]$^+$=694.

Synthesis of Compound 179

With reference to the preparation method for Compound 57K in Example 3, 179 was synthesized by replacing 57I with Compound 179A. [M+H]$^+$=953.

Example 32

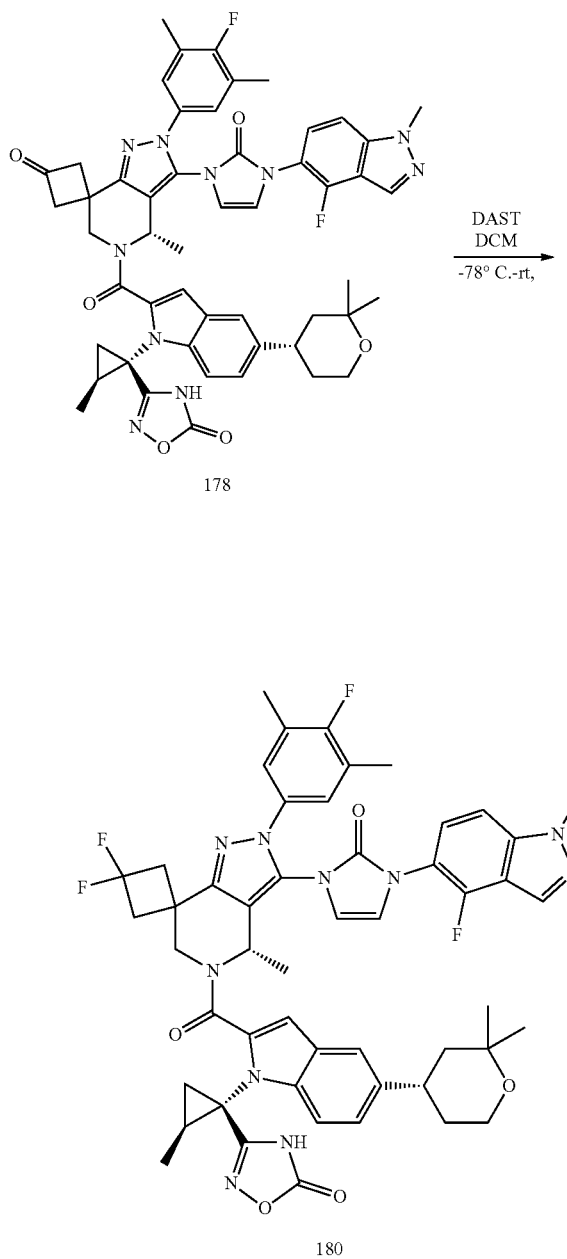

Synthesis of Compound 180

Compound 178 (0.090 g, 0.096 mmol) was dissolved in dichloromethane (3 mL), and DAST (0.015 g, 0.96 mmol) was added dropwise at −78° C., when finished, the temperature was raised to room temperature. The reaction was stirred at room temperature for 12 h. After the reaction was complete, the solution was poured into a sodium bicarbonate solution and extracted with dichloromethane (10 mL*3). The organic phase was washed twice with saline (10 mL), concentrated under reduced pressure, and purified by silica gel column chromatography (eluent: methanol/dichloromethane=1/30, V/V) to afford Compound 180 (0.057 g) with the HPLC purity of 97.80%. [M+H]⁺=959; ¹H NMR (600 MHz, CDCl₃) δ 11.10 (s, 1H), 8.13 (s, 1H), 7.59 (d, J=8.6 Hz, 1H), 7.53 (s, 2H), 7.28 (d, J=10.2 Hz, 1H), 7.23 (s, 1H), 7.14 (dd, J=17.4, 7.4 Hz, 2H), 6.79 (d, J=10.6 Hz, 1H), 6.61 (d, J=3.1 Hz, 1H), 6.29 (d, J=3.0 Hz, 1H), 5.75 (d, J=6.7 Hz, 1H), 4.12 (s, 3H), 3.85-3.80 (m, 2H), 3.41-3.33 (m, 1H), 3.33-3.22 (m, 1H), 2.84 (q, J=13.3 Hz, 1H), 2.28 (d, J=21.9 Hz, 6H), 1.82-1.74 (m, 6H), 1.71 (d, J=6.7 Hz, 3H), 1.65 (d, J=13.2 Hz, 2H), 1.53-1.47 (m, 2H), 1.34 (s, 5H), 1.26 (s, 5H).

Example 33

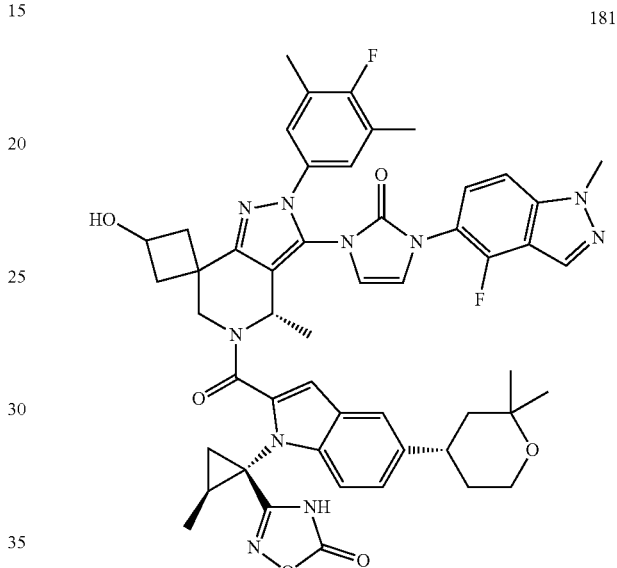

181

Synthetic Route

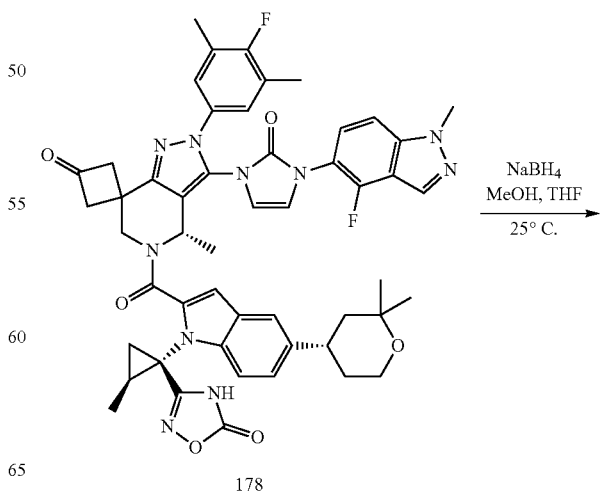

178

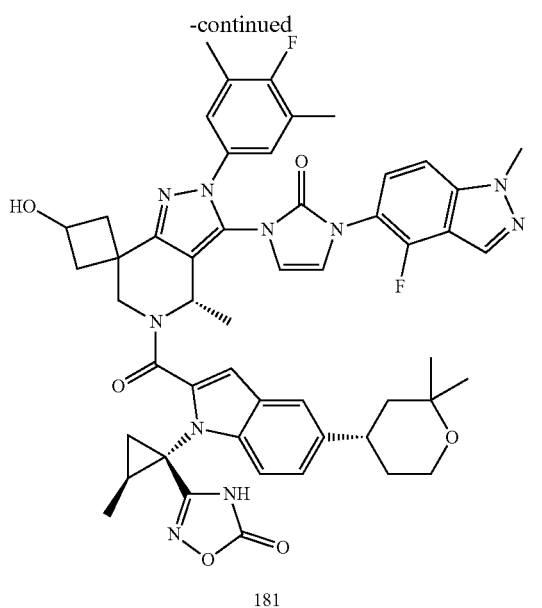

181

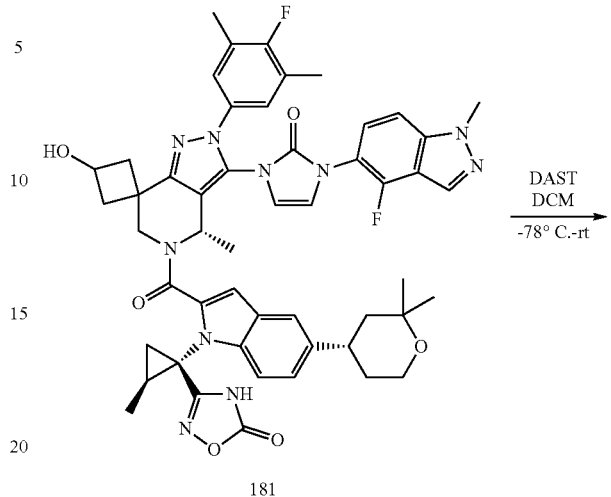

181

Synthesis of Compound 181

Compound 178 (0.043 g, 0.045 mmol) and sodium borohydride (0.009 g, 0.23 mmol) were added into THF (2 mL), and methanol (0.5 mL) was added dropwise at 0° C., when finished, stirred at 25° C. for 1 h. After the reaction was complete, the solution was poured into water. The mixture was extracted with ethyl acetate (20 mL*3). The organic phase was washed twice with saline (60 mL) and concentrated under reduced pressure to afford a crude product. Thereafter, the crude product was purified by silica gel column chromatography (eluent: dichloromethane/methanol=20/1, V/V) to afford Compound 181 (0.025 g). [M+H]$^+$=939.

Example 34

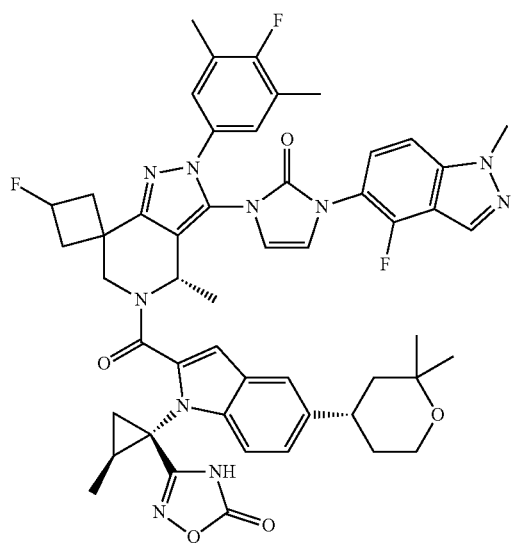

182

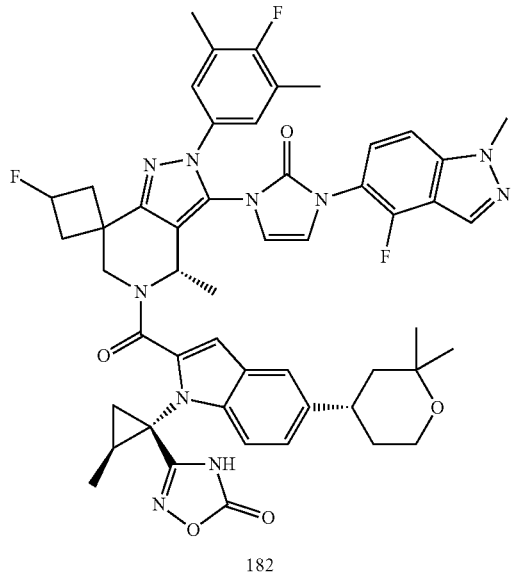

182

Synthesis of Compound 182

Compound 181 (0.009 g, 0.0095 mmol) was dissolved in dichloromethane (1 mL), and DAST (0.015 g, 0.96 mmol) was added dropwise at −78° C., when finished, the temperature was raised to room temperature. The reaction was stirred at room temperature for 5 h. After the reaction was complete, the solution was poured into a sodium bicarbonate solution and extracted with dichloromethane (10 mL*3). The organic phase was washed twice with saline (10 mL), concentrated under reduced pressure, and purified by silica gel column chromatography (eluent: methanol/dichloromethane=1/30, V/V) to afford Compound 182 (0.005 g). [M+H]$^+$=941.

Example 35
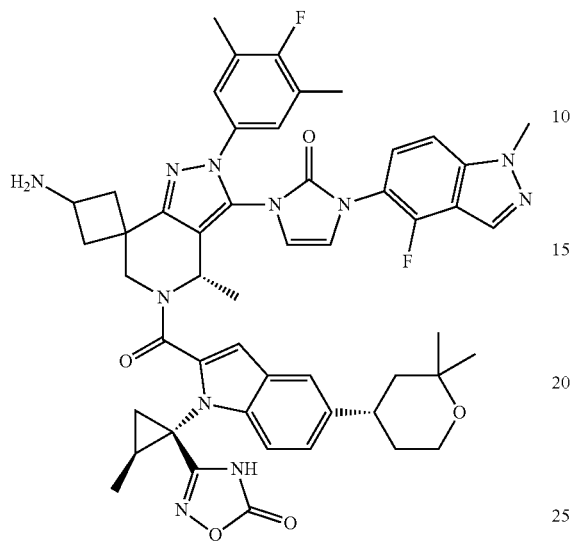
183
Synthetic Route
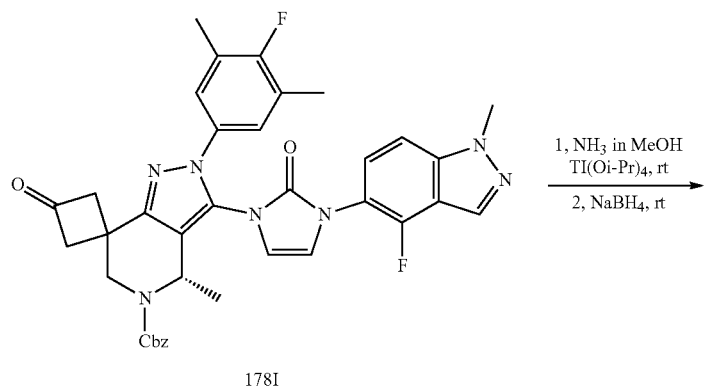
178I
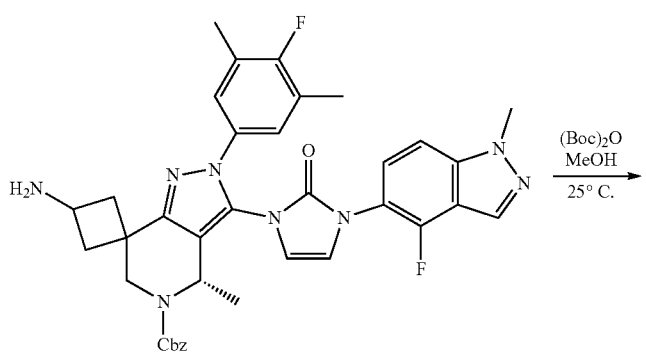
183A

-continued
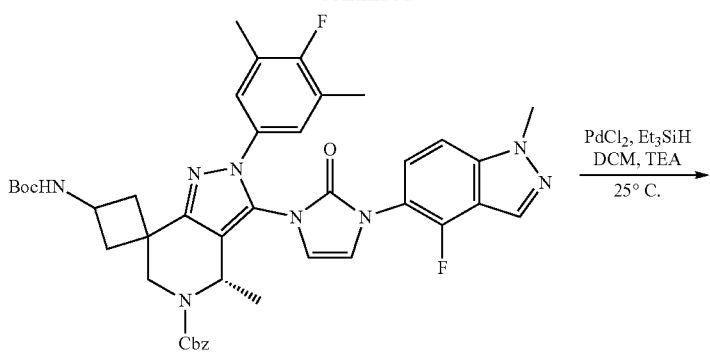
183B
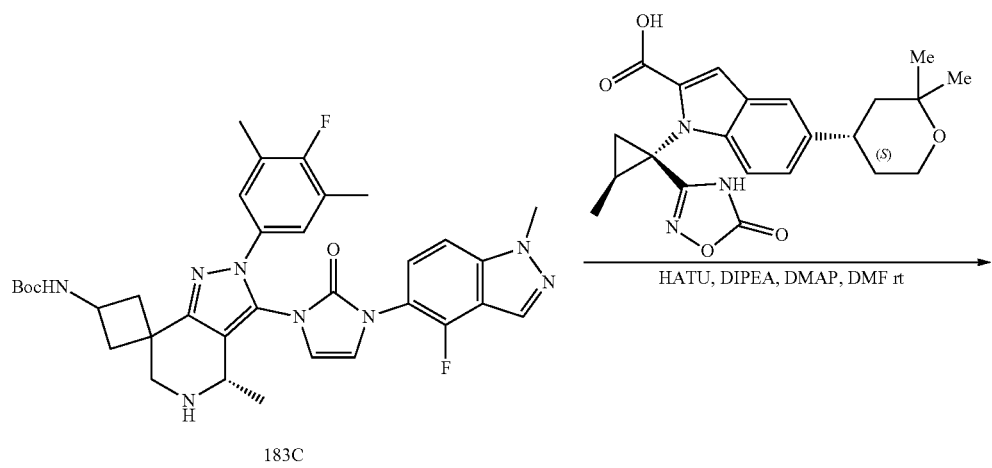
183C
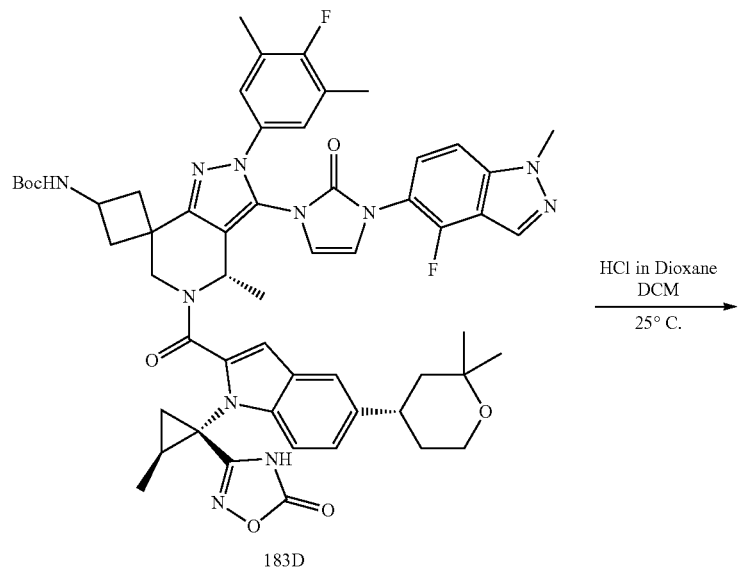
183D

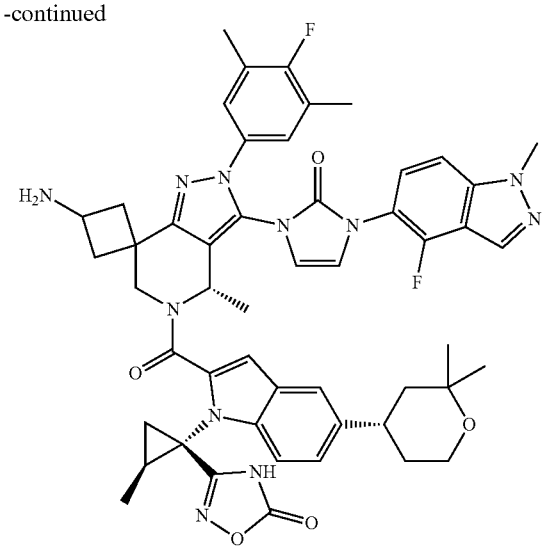

183

Synthesis of Compound 183A

Compound 178I (0.100 g, 0.73 mmol) and titanium tetraisopropanolate (0.042 g, 0.0014 mol) were dissolved in a solution (4 mL) of ammonia in methanol. The reaction was stirred at room temperature for 12 h. After the reaction was complete, the mixture was diluted with dichloromethane (20 mL). The organic phase was washed twice with saline (50 mL) and concentrated under reduced pressure to afford Compound 183A (0.090 g). [M+H]⁺=679.

Synthesis of Compound 183B

Compound 183A (0.090 g, 0.13 mmol), (Boc)₂O (0.144 g, 0.65 mmol), and triethylamine (0.067 g, 0.65 mmol) were dissolved in tetrahydrofuran (1 ml) and dichloromethane (2 ml) and stirred at room temperature for 3 h. After the reaction was complete, the solution was concentrated under reduced pressure, and then purified by silica gel column chromatography (eluent: methanol/dichloromethane=1/40, V/V) to afford Compound 183B (0.092 g). [M+H]⁺=779.

Synthesis of Compound 183

With reference to the preparation method for Compound 57 in Example 3, 183 was synthesized by replacing 57I with Compound 183B. [M+H]⁺=938.

Example 36

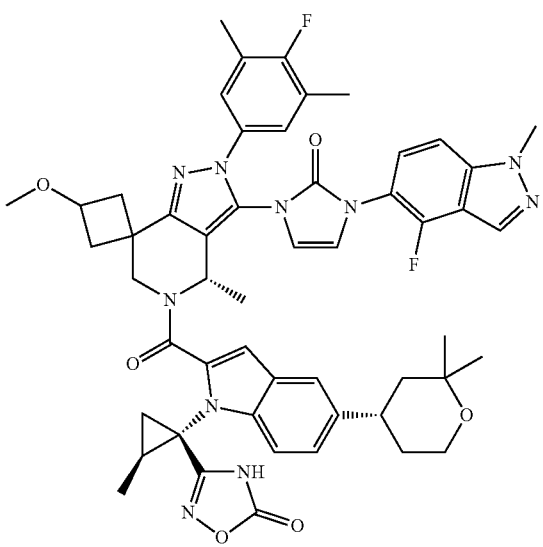

184

Synthetic Route
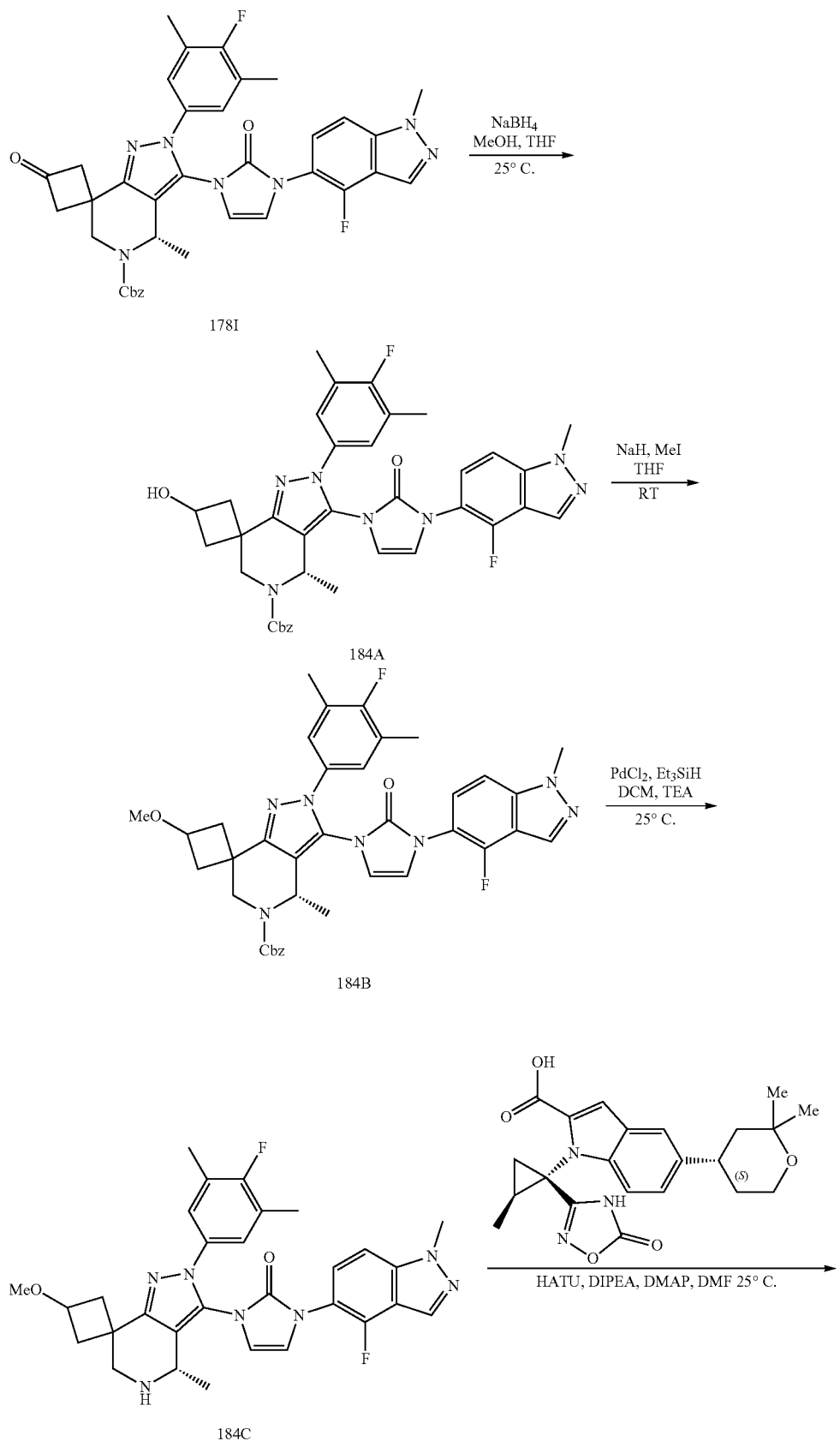

-continued

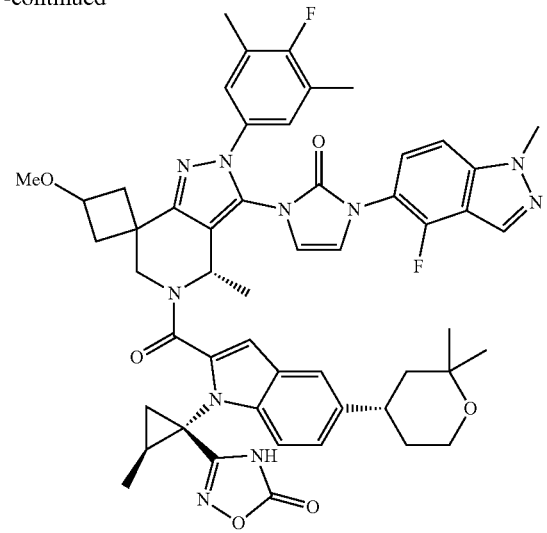

184

Synthesis of Compound 184A

Compound 178I (0.050 g, 0.073 mmol) and sodium borohydride (0.014 g, 0.36 mmol) were added into THF (2 mL), and methanol (0.4 mL) was added dropwise at 0° C., when finished, stirred at 25° C. for 1 h. After the reaction was complete, the solution was poured into water. The mixture was extracted with ethyl acetate (20 mL*3). The organic phase was washed twice with saline (60 mL) and concentrated under reduced pressure to afford a crude product. The crude product was purified by silica gel column chromatography (eluent: dichloromethane/methanol=20/1, V/V) to afford Compound 184A (0.033 g). $[M+H]^+=680$.

Synthesis of Compound 184B

Compound 184A (0.033 g, 0.050 mmol) was added into THF (4 mL), and sodium hydride (0.003 g, 0.075 mmol) was added at 0° C. Upon completion of addition, the reaction was stirred at 25° C. for 30 min, and then iodomethane (0.012 g, 0.090 mmol) was added. The reaction was stirred at 25° C. for 1 h. After the reaction was complete, the solution was poured into water. The mixture was extracted with ethyl acetate (20 mL*3). The organic phase was washed twice with saline (60 mL) and concentrated under reduced pressure to afford a crude product. Afterwards, the crude product was purified by silica gel column chromatography (eluent: dichloromethane/methanol=20/1, V/V) to afford Compound 184B (0.036 g). $[M+H]^+=694$.

Synthesis of Compound 184

With reference to the preparation method for Compound 57K in Example 3, 184 was synthesized by replacing 57I with Compound 183B. $[M+H]^+=953$.

Example 37

Compounds 187, 192-194, 204, 207, and 216-220 listed in Table 3 were prepared substantially based on the similar synthetic method or strategy of Example 36, or prepared using appropriate intermediates that can be readily synthesized by the methods known in the art, and modified if necessary.

TABLE 3

| Cmpd. | Structure | Data |
|---|---|---|
| 187 | 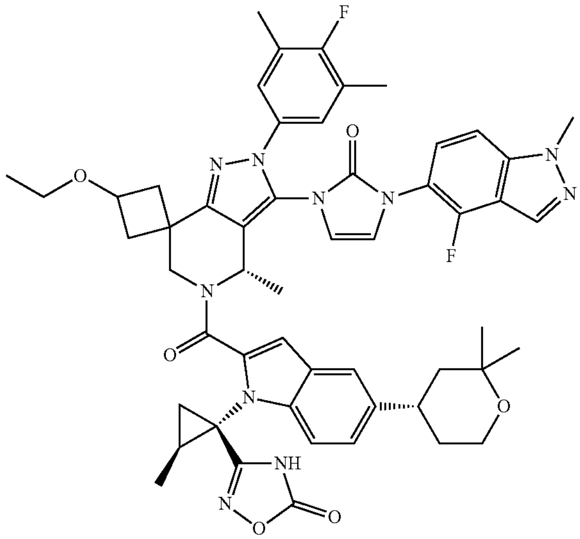 [SMILES: CCOC1CC2(C1)CN(C(=O)c1cc3cc([C@H]4CCOC(C)(C)C4)ccc3n1[C@@]1(c3noc(=O)[nH]3)C[C@@H]1C)[C@@H](C)c1c2nn(-c2cc(C)c(F)c(C)c2)c1-n1ccn(-c2ccc3c(cnn3C)c2F)c1=O] | [M + H]+ = 967 |
| 192 | 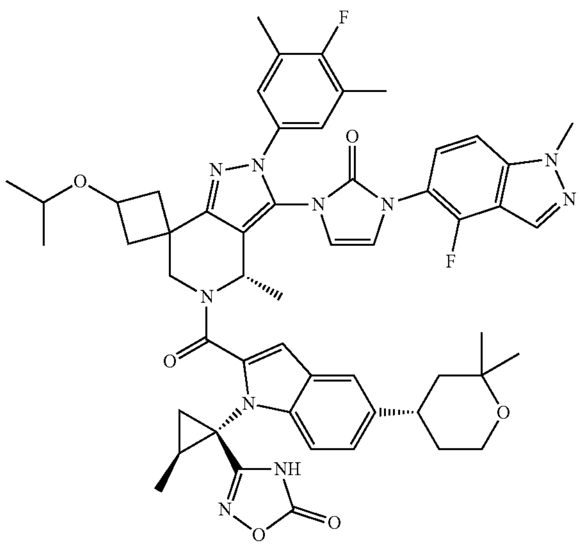 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC(OC(C)C)C2)cc(C)c1F] | [M + H]+ = 981 |
| 193 | 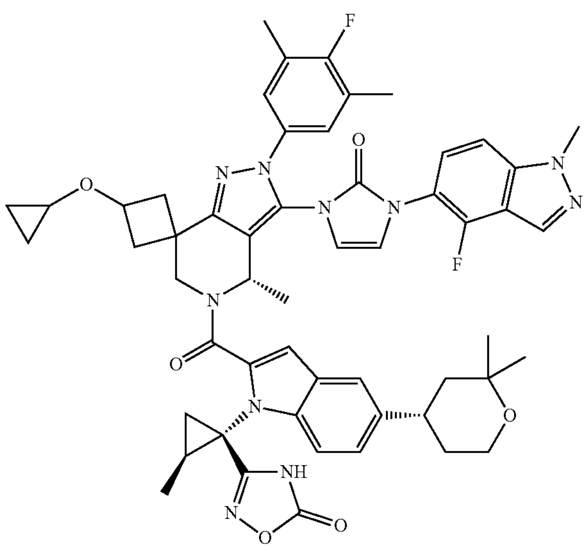 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC(OC3CC3)C2)cc(C)c1F] | [M + H]+ = 979 |

TABLE 3-continued
| Cmpd. | Structure | Data |
|---|---|---|
| 194 | 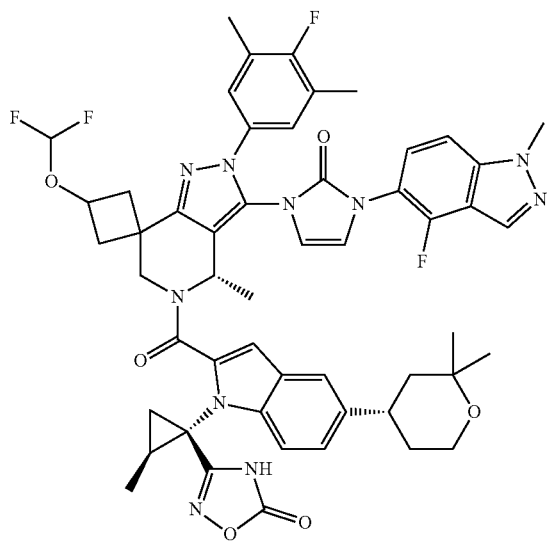 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC(OC(F)F)C2)cc(C)c1F] | [M + H]+ = 989 |
| 204 | 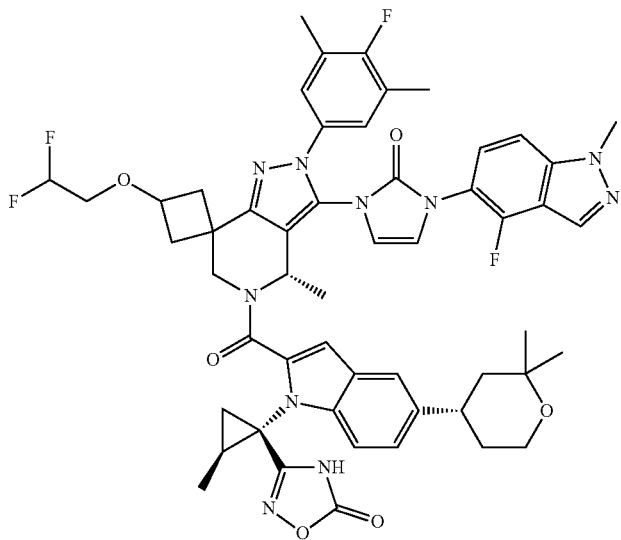 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC(OCC(F)F)C2)cc(C)c1F] | [M + H]+ = 1003 |

TABLE 3-continued

| Cmpd. | Structure | Data |
|---|---|---|
| 207 | 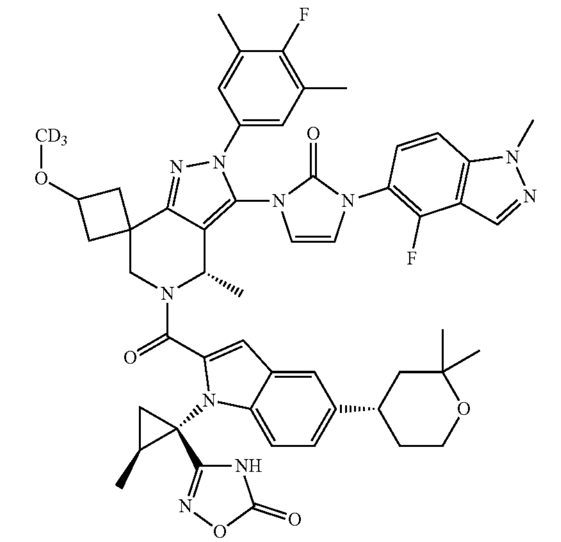 [SMILES: [2H]C([2H])([2H])OC1CC2(C1)CN(C(=O)c1cc3cc([C@H]4CCOC(C)(C)C4)ccc3n1[C@@]1(c3noc(=O)[nH]3)C[C@@H]1C)[C@@H](C)c1c2nn(-c2cc(C)c(F)c(C)c2)c1-n1ccn(-c2ccc3c(cnn3C)c2F)c1=O] | [M + H]⁺ = 956 |
| 216 | 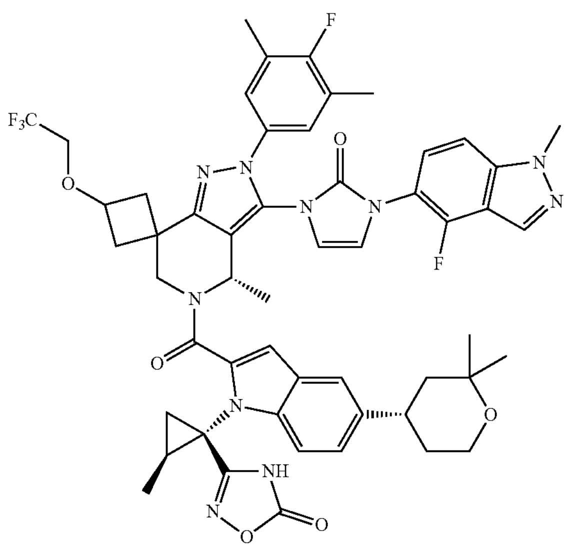 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC(OCC(F)(F)F)C2)cc(C)c1F] | [M + H]⁺ = 1021 |
| 217 | 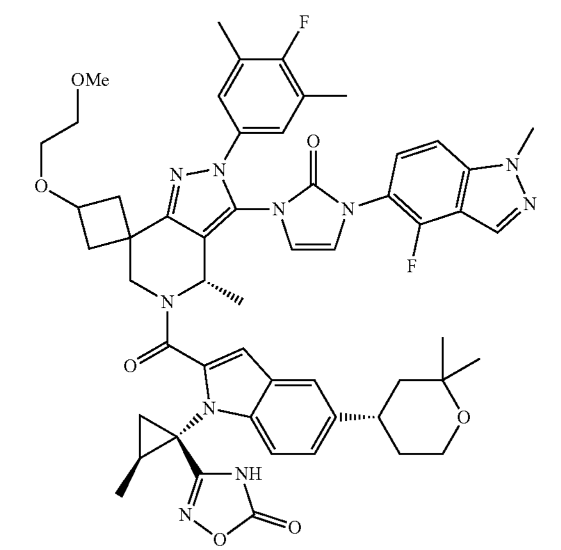 [SMILES: COCCOC1CC2(C1)CN(C(=O)c1cc3cc([C@H]4CCOC(C)(C)C4)ccc3n1[C@@]1(c3noc(=O)[nH]3)C[C@@H]1C)[C@@H](C)c1c2nn(-c2cc(C)c(F)c(C)c2)c1-n1ccn(-c2ccc3c(cnn3C)c2F)c1=O] | [M + H]⁺ = 997 |

TABLE 3-continued
| Cmpd. | Structure | Data |
|---|---|---|
| 218 | 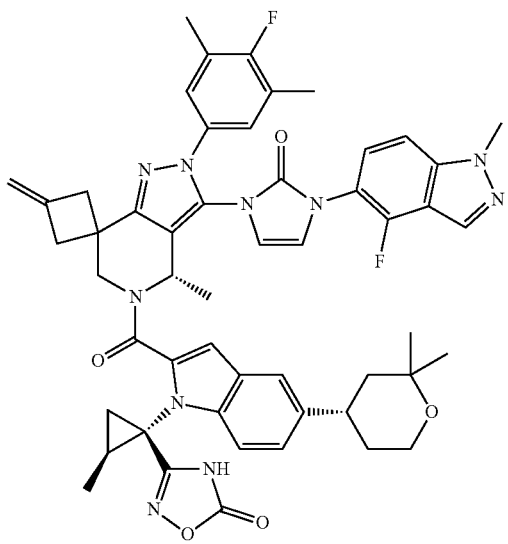 218 | [M + H]+ = 935 |
| 219 | 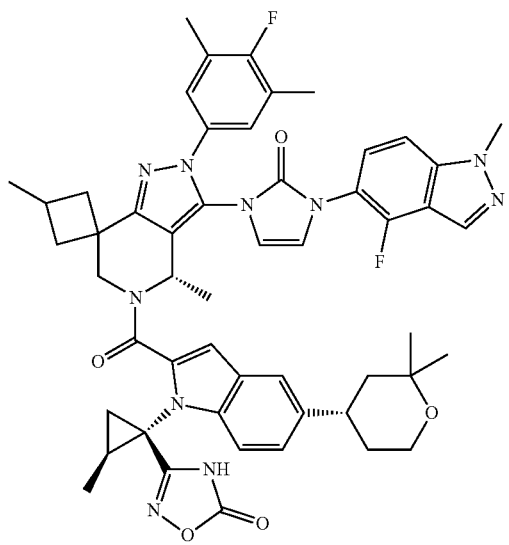 219 | [M + H]+ = 937 |

TABLE 3-continued
| Cmpd. | Structure | Data |
|---|---|---|
| 220 | 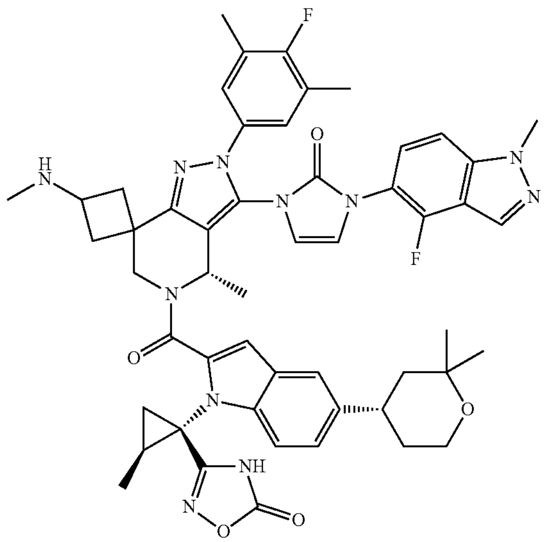 | [M + H]⁺ = 952 |
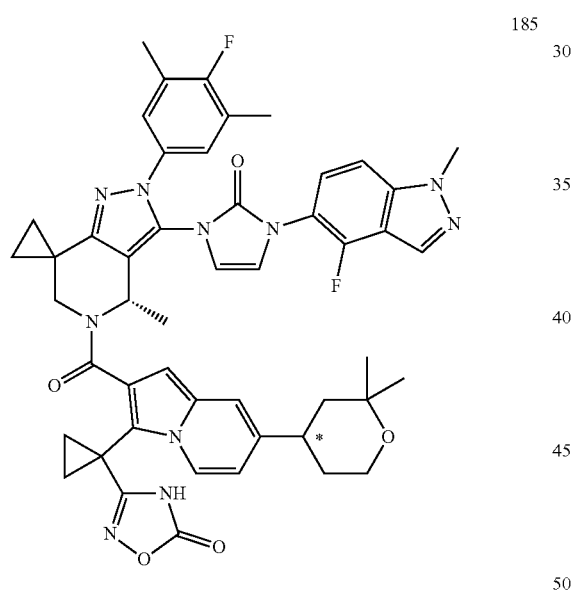
"*" indicated the chiral center with the R or S configuration. 185-A and 185-B were two single stereoisomeric compounds and were collectively represented by Compound 185.

Synthetic Route
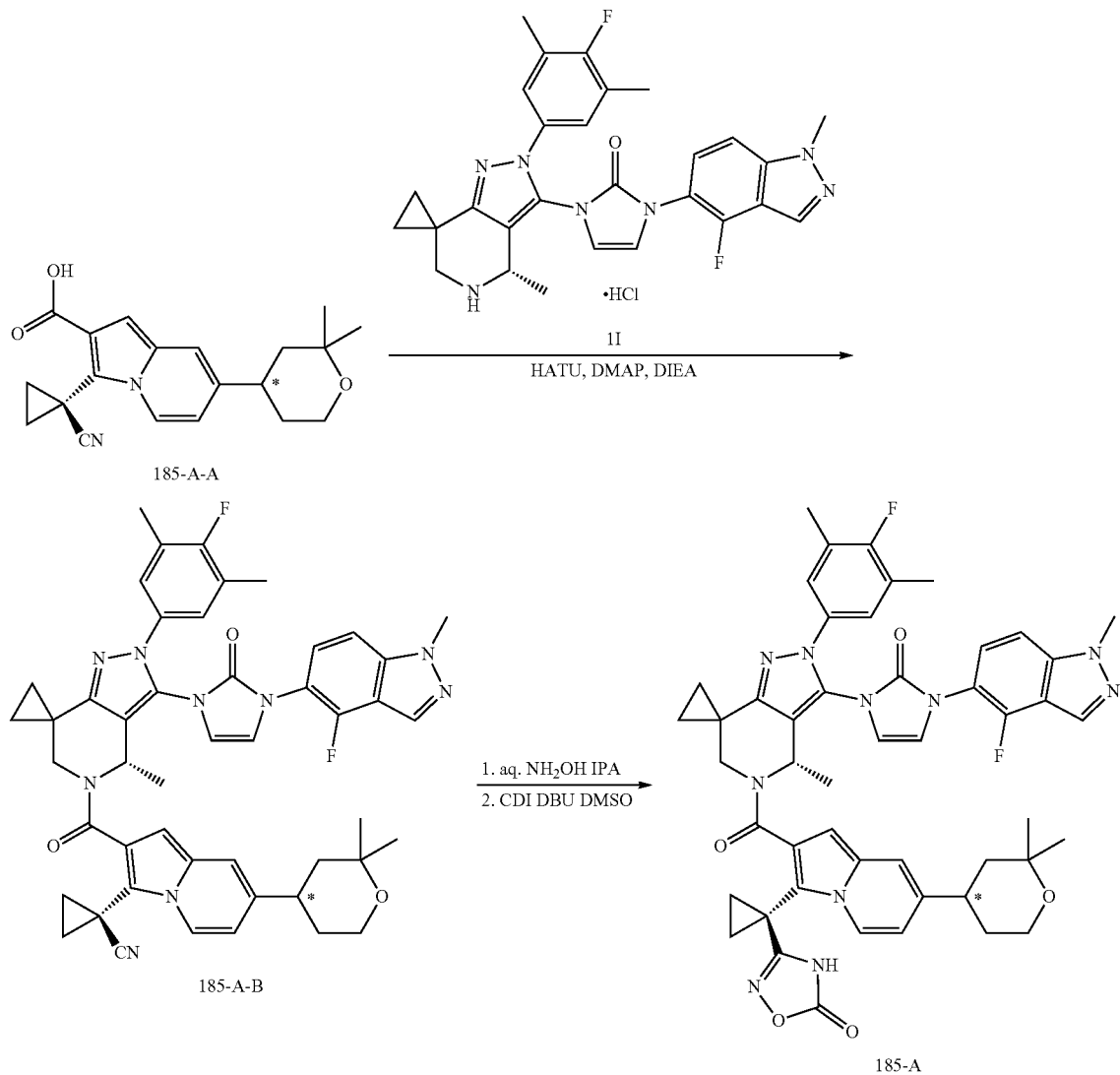
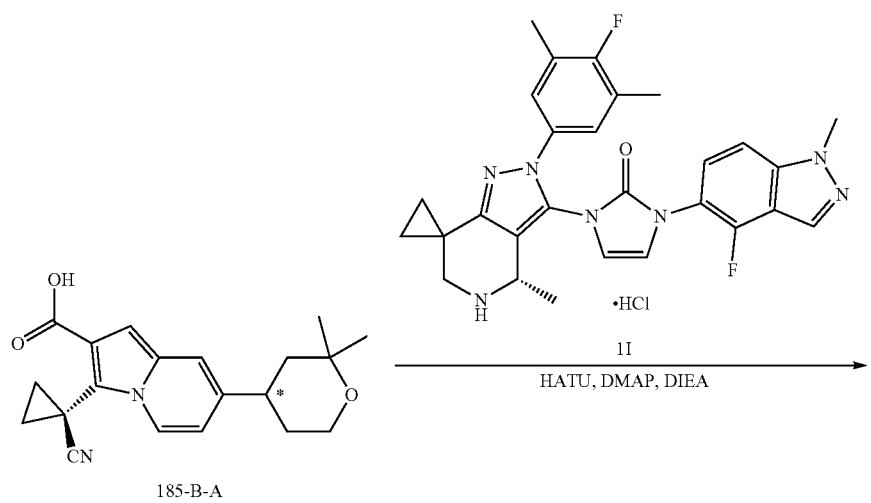

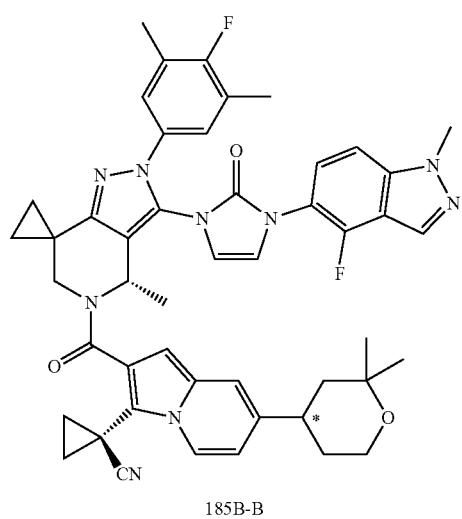

185B-B 1. aq. NH₂OH IPA
2. CDI DBU DMSO

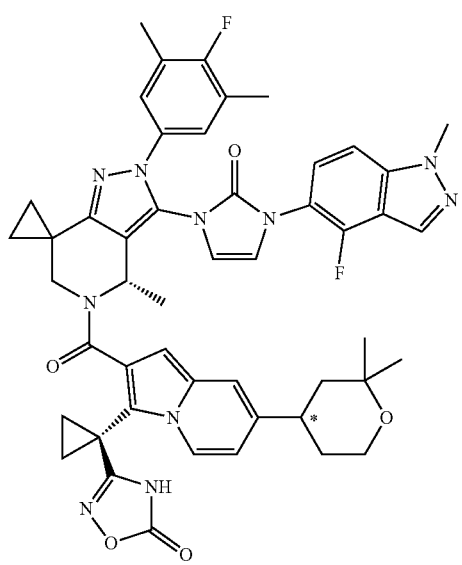

185-B

Synthesis of Compound 185-A-A

Compound 185-A-A was obtained with reference to the preparation method for the intermediate 31-P1 in the patent application WO2022017338A1. [M+H]⁺=339.

Synthesis of Compound 185-A

With reference to the preparation method for Compound 39 in Example 11, 185-A was synthesized by replacing 39L and 39M with 185-A-A and 1I. [M+H]⁺=895.

Synthesis of Compound 185-B-A

Compound 185-B-A was obtained with reference to the preparation method for the intermediate 31-P2 in the patent application WO2022017338A1. [M+H]⁺=339.

Synthesis of Compound 185-B

With reference to the preparation method for Compound 39 in Example 11, 185-B was synthesized by replacing 39L and 39M with 185-B-A and 1I. [M+H]⁺=895.

Example 39

186

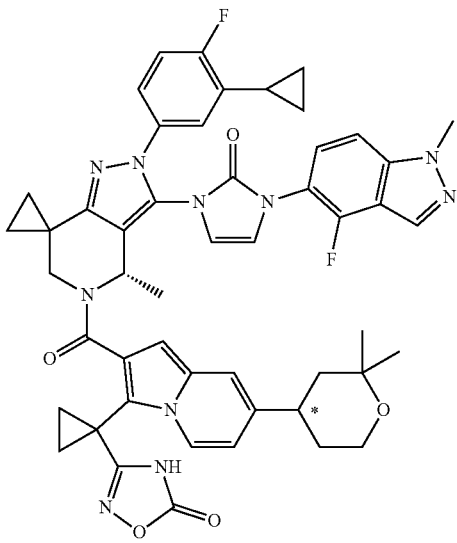

"*" indicated the chiral center with the R or S configuration. 186-A and 186-B were two single stereoisomeric compounds and were collectively represented by Compound 186.

Synthetic Route
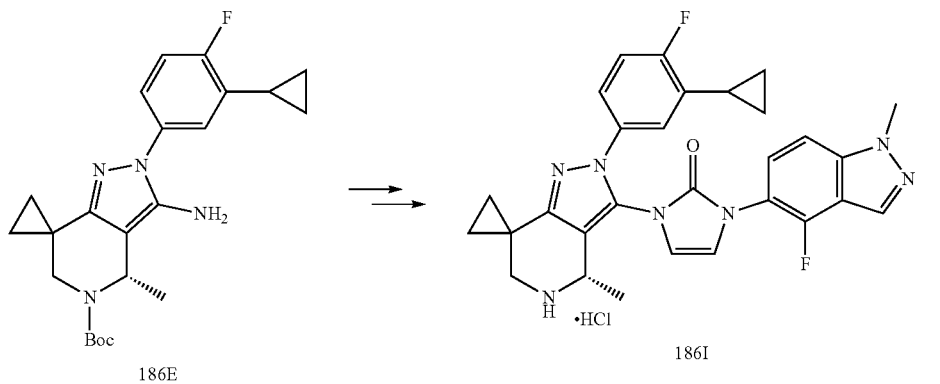
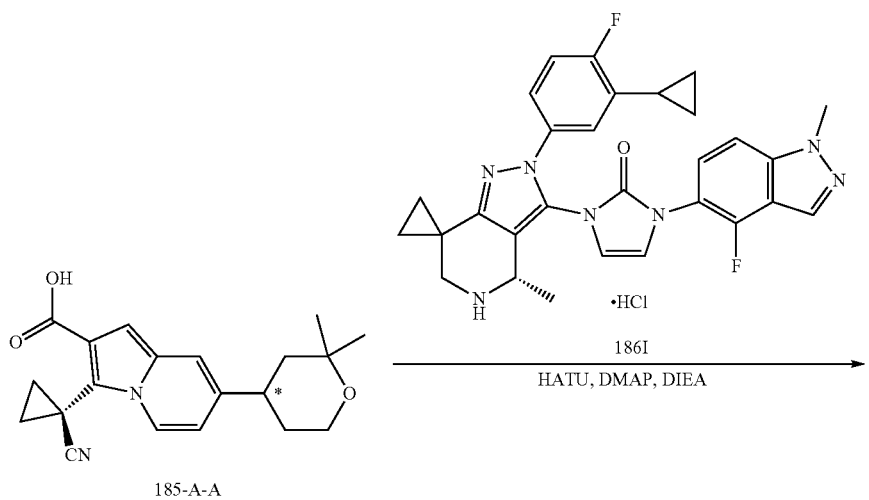
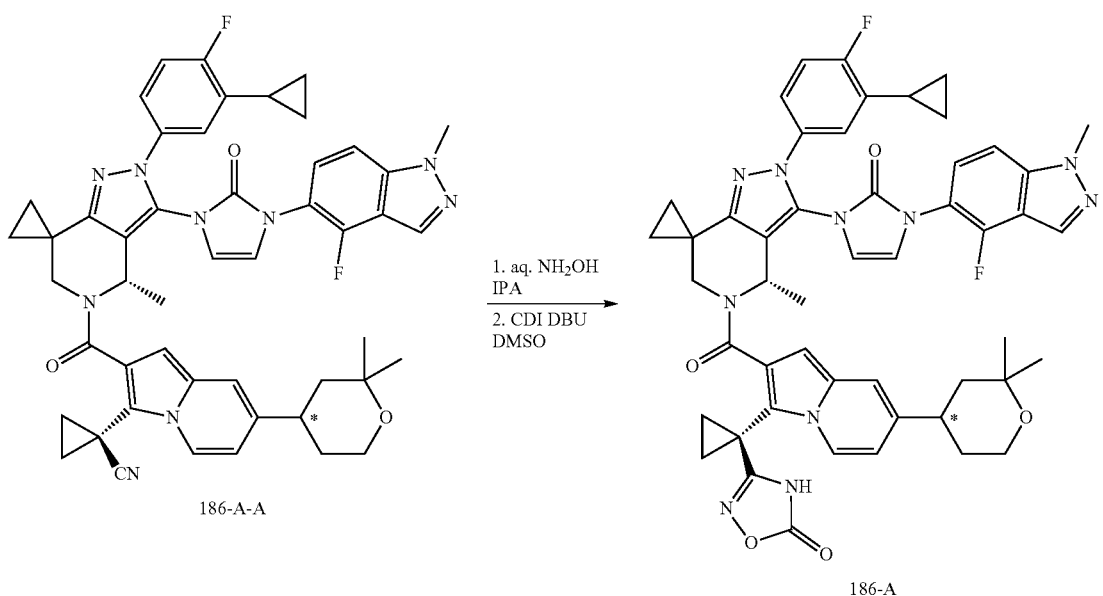

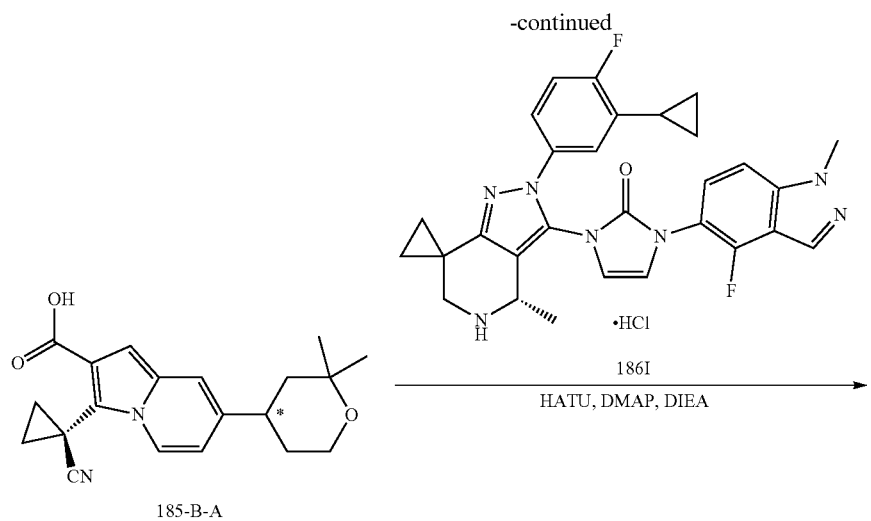

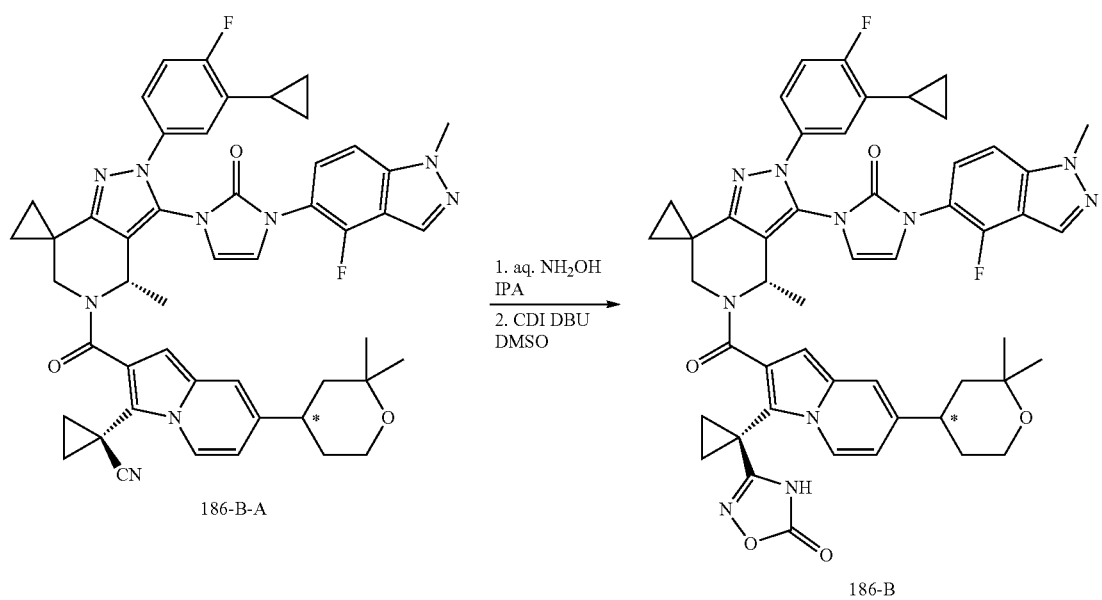

Synthesis of Compound 186E

With reference to the preparation method for Compound 1E in Example 1, 186E was synthesized by replacing 4-fluoro-3,5-dimethylphenylhydrazine hydrochloride with 3-cyclopropyl-4-fluorophenylhydrazine hydrochloride.

Synthesis of Compound 186I

With reference to the preparation method for Compound 1I in Example 1, 186I was synthesized by replacing 1E with 186E.

Synthesis of Compound 186-A

With reference to the preparation method for Compound 185-A in Example 38, 186-A was synthesized by replacing 1I with 186I. [M+H]$^+$=907.

Synthesis of Compound 186-B

With reference to the preparation method for Compound 185-B in Example 38, 186-B was synthesized by replacing 1I with 186I. [M+H]$^+$=907.

Example 40
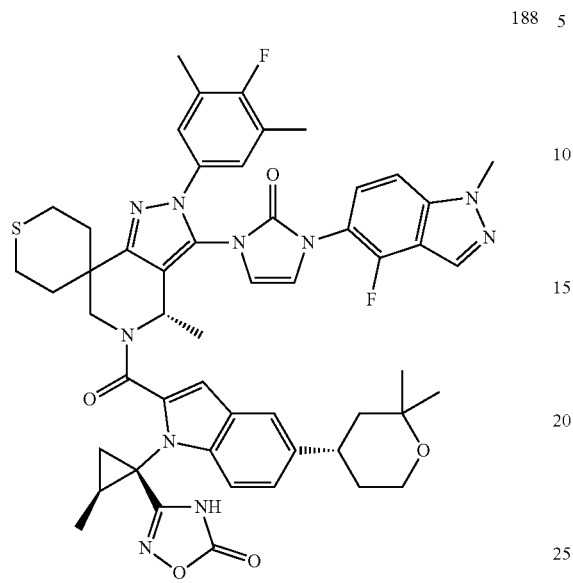
188
Synthetic Route
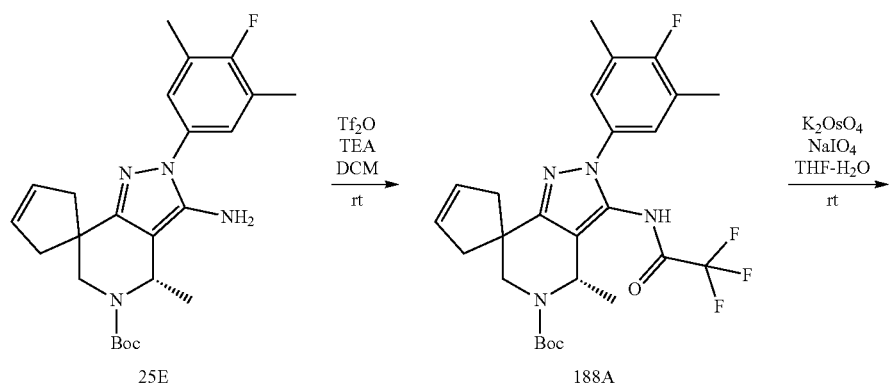
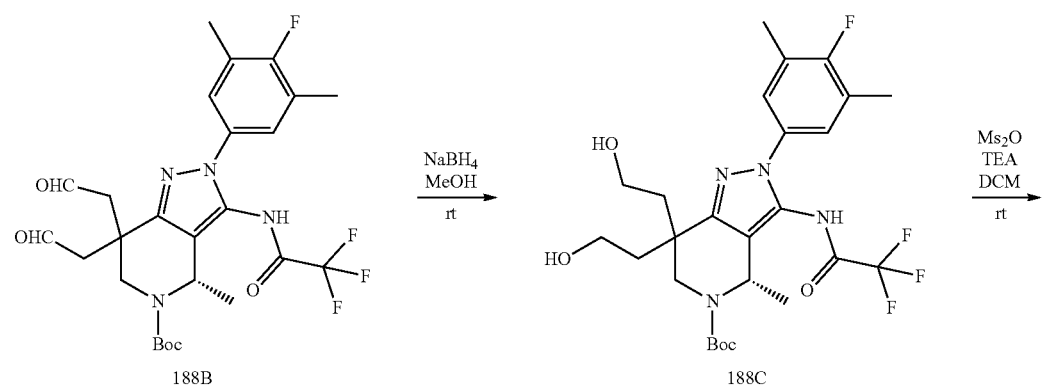

-continued
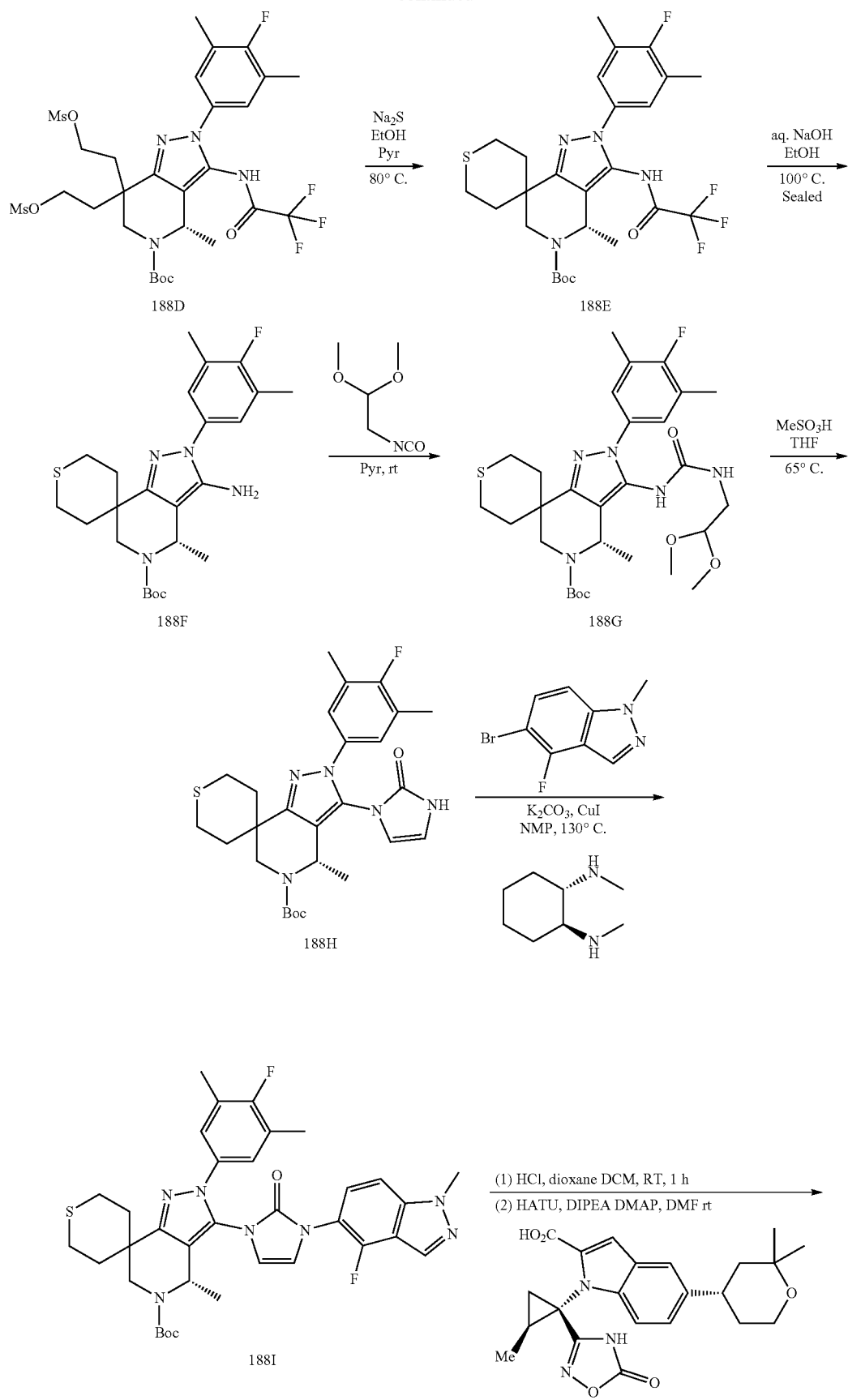

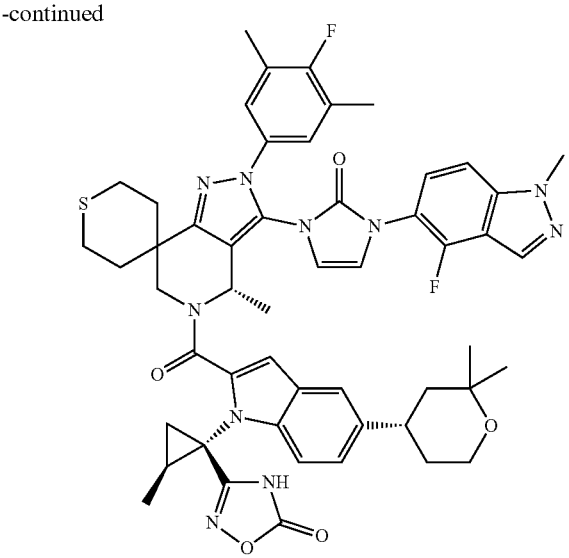

188

Synthesis of Compound 188A 25E (210.2 mg, 0.49 mmol) was weighed and dissolved in 6 mL of DCM, triethylamine (225.7 mg, 2.23 mmol) was added, and a solution of trifluoroacetic anhydride in dichloromethane (205.3 mg, 0.95 mmol, 0.7 mL) was added dropwise. The solution was reacted at room temperature for 0.5 h. Purified water was added dropwise to quenched the reaction. The reaction solution was extracted with ethyl acetate, and the organic phase was washed with a saturated sodium chloride solution, dried over anhydrous sodium sulfate, and filtered. The filtrate was concentrated and then separated by column chromatography to afford Compound 188A (277.6 mg, a light brown solid), $[M+H]^+=523$.

Synthesis of Compound 188B

Compound 188A (277.6 mg, 0.53 mmol) was weighed and added into 8 mL of 1,4-dioxane and 5 mL of pure water, and sodium periodate (568.1 mg, 2.66 mmol) and potassium osmium dihydrate (32 mg, 0.1 mmol) were added, and reacted at room temperature for 2 h. Purified water was added for dilution. The reaction solution was extracted with ethyl acetate, and the organic phase was washed with a saturated sodium chloride solution, dried over anhydrous sodium sulfate, and filtered. The filtrate was concentrated to afford a crude product of 188B (350.6 mg, a brown oily product), $[M+H]^+=555$.

Synthesis of Compound 188C

The crude product of Compound 188B (350.6 mg) was dissolved in 5 mL of methanol, and sodium borohydride (400 mg, 10.57 mmol) was added in batches at room temperature, and reacted at room temperature for 1 h. Purified water was added for dilution. The reaction solution was extracted with ethyl acetate, and the organic phase was washed with a saturated sodium chloride solution, dried over anhydrous sodium sulfate, and filtered. The filtrate was concentrated and then separated by column chromatography to afford Compound 188C (216.1 mg, a light yellow solid), $[M+H]^+=559$.

Synthesis of Compound 188D

Compound 188C (183.8 mg, 0.33 mmol) was weighed and dissolved in 5 mL of DCM, triethylamine (390.1 mg, 3.86 mmol) was added, and a solution of methanesulfonic anhydride in dichloromethane (230.5 mg, 1.32 mmol, 1.5 mL) was added dropwise. The solution was reacted at room temperature for 0.5 h. Purified water was added dropwise to quench the reaction. The solution was extracted with ethyl acetate, and the organic phase was washed with a saturated sodium chloride solution, dried over anhydrous sodium sulfate, and filtered. The filtrate was concentrated and then separated by column chromatography to afford Compound 188D (54.7 mg, a light brown solid), $[M+H]^+=715$.

Synthesis of Compound 188E

Compound 188D (54.7 mg, 0.076 mmol) was dissolved in 2 mL of ethanol, and 0.2 mL of pyridine and anhydrous sodium sulfide (49.8 mg, 0.64 mmol) were added, and reacted at 80° C. for 2 h. Purified water was added dropwise to quench the reaction. The reaction solution was extracted with ethyl acetate, and the organic phase was washed with a saturated sodium chloride solution, dried over anhydrous sodium sulfate, and filtered. The filtrate was concentrated and separated by column chromatography to afford Compound 188E (29.5 mg, a white solid), $[M+H]^+=557$.

Synthesis of Compound 188F

Compound 188E (39.2 mg, 0.07 mmol) was weighed and dissolved in 5 mL of ethanol, and 1.0 mL of 5 mol/L sodium hydroxide solution was added. The solution was reacted at 100° C. for 30 h with the tube sealed. Purified water was added dropwise to dilute the reaction, then adjusted with a 10% citric acid solution until pH is approximately equal to 7 and extracted with ethyl acetate, and the organic phase was washed with a saturated sodium bicarbonate solution, dried over anhydrous sodium sulfate, and filtered. The filtrate was concentrated to afford Compound 188F (38.1 mg, a light yellow solid), $[M+H]^+=461$.

Synthesis of Compound 188

With reference to the preparation method for Compound 1 in Example 1, 188 was synthesized by replacing 1E with 188F. $[M+H]^+=969$.

Example 41
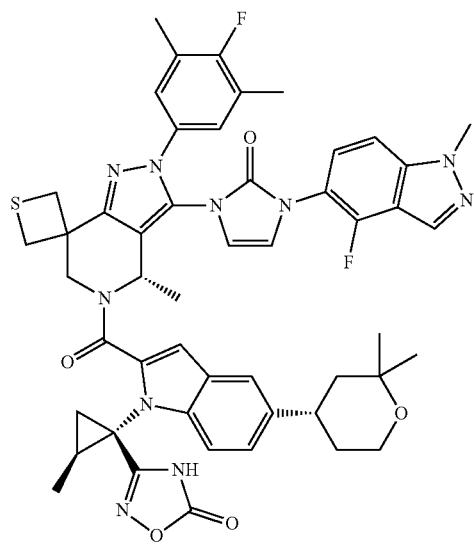
189
Synthetic Route
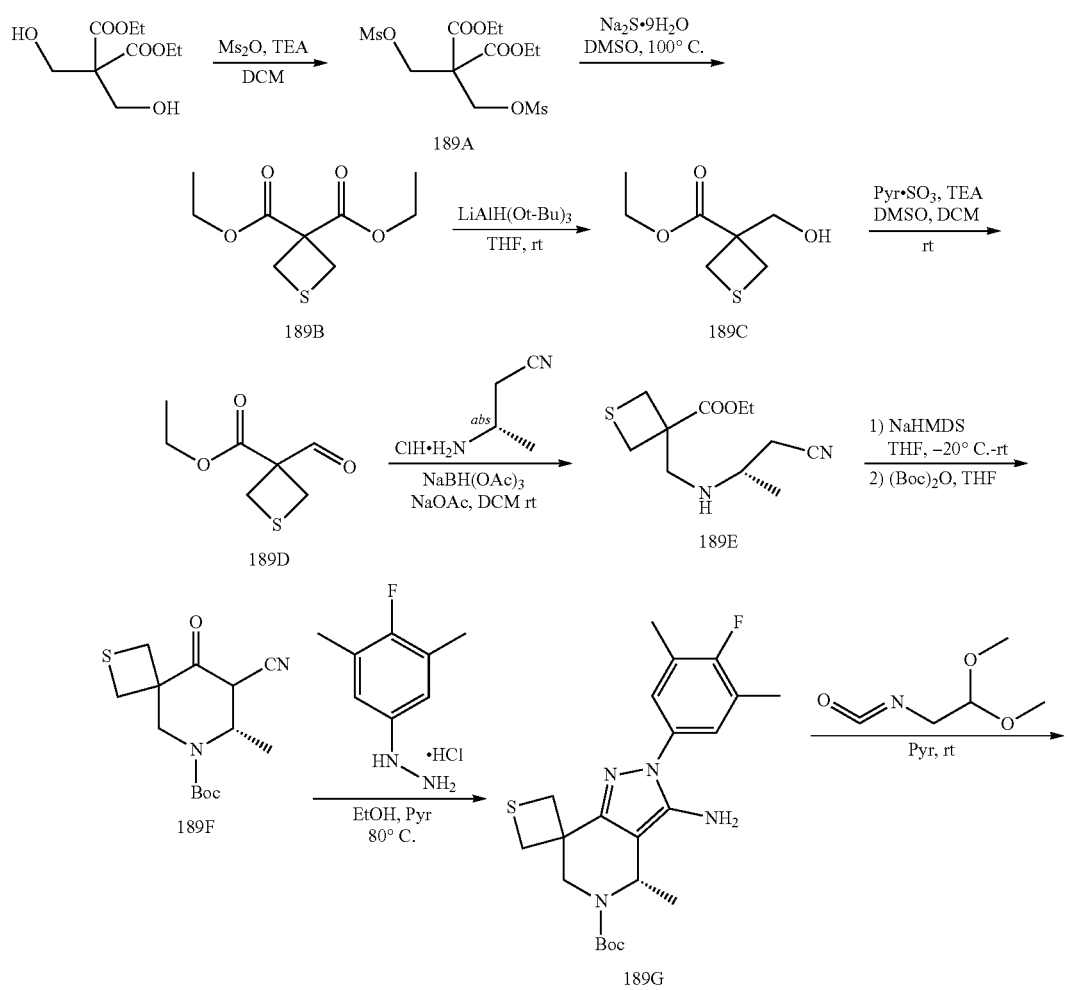

-continued
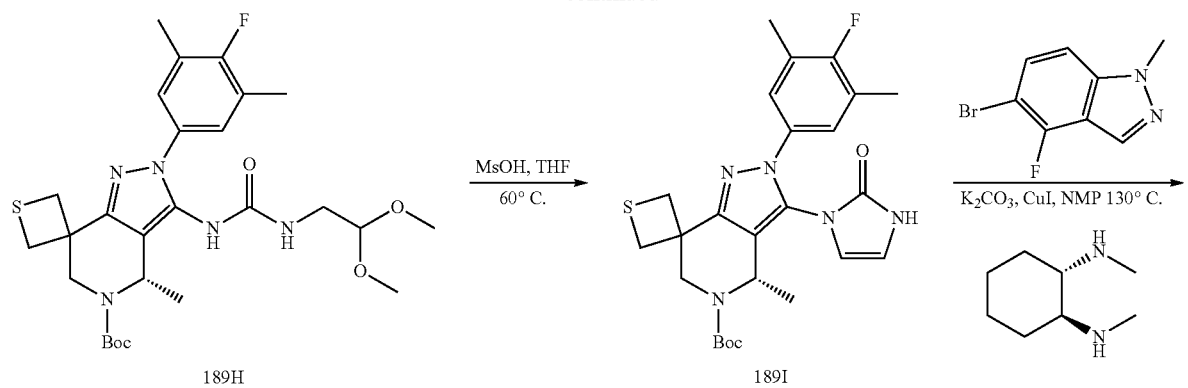
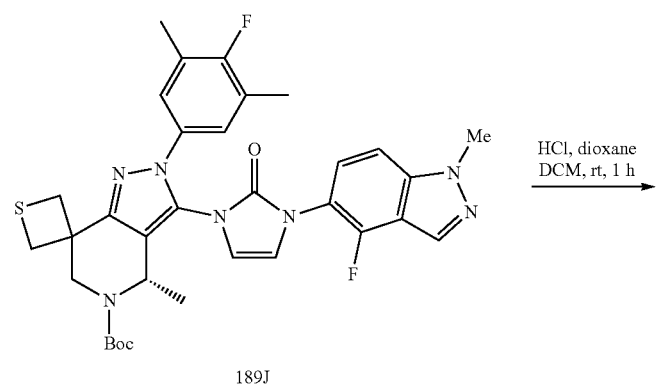
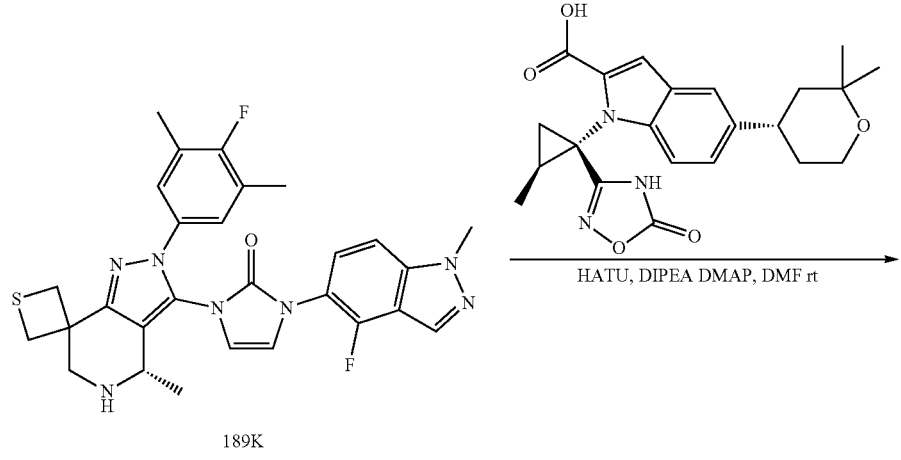

-continued

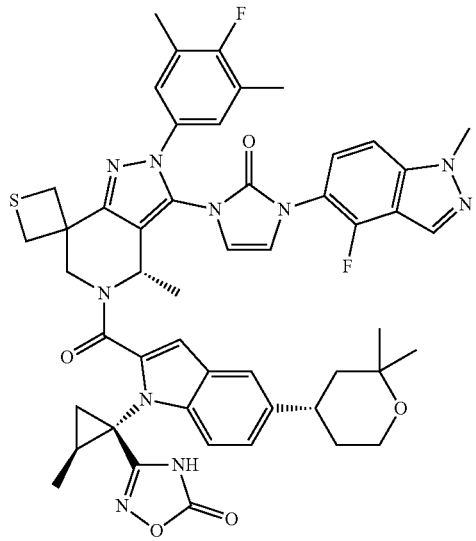

189

Synthesis of Compound 189A

Diethyl bis(hydroxymethyl) malonate (2.2 g, 10 mmol) was weighed and added into dichloromethane (35 mL) for dissolution. Afterwards, TEA (8.4 mL, 60 mmol) was added. The reaction was cooled to 0° C. to 5° C. in an ice-water bath. A solution of Ms$_2$ (5.23 g, 30 mmol) in dichloromethane (15 mL) was added dropwise, and stirred overnight at room temperature. After the reaction was complete, the solution was washed twice with 1000 citric acid. The organic phase was dried over anhydrous sodium sulfate and followed by suction filtration. The filtrate was concentrated to afford Compound 189A (3.8 g). [M+H]$^+$=377.

Synthesis of Compound 189B

Compound 189A (1.5 g, 4.0 mmol) and Na$_2$S 9H$_2$ (1.05 g, 4.4 mmol) were weighed and dissolved in 30 mL of DMSO, heated to 100° C. and reacted for 6 h. Water was added dropwise to quench the reaction. The solution was extracted with ethyl acetate, and the organic phase was washed with a saturated sodium chloride solution, dried over anhydrous sodium sulfate, and filtered. The filtrate was concentrated and then separated by column chromatography to afford Compound 189B, [M+H]$^+$=219.

Synthesis of Compound 189C

With reference to the preparation method for Compound 25A in Example 8, 189C was synthesized by replacing diethyl 3-cyclopentene-1,1-dicarboxylate with 189B. [M+H]$^+$=177.

Synthesis of Compound 189

With reference to the preparation method for Compound 57K in Example 3, 189 was synthesized by replacing 57B with 189C. [M+H]$^+$=941.

Example 42

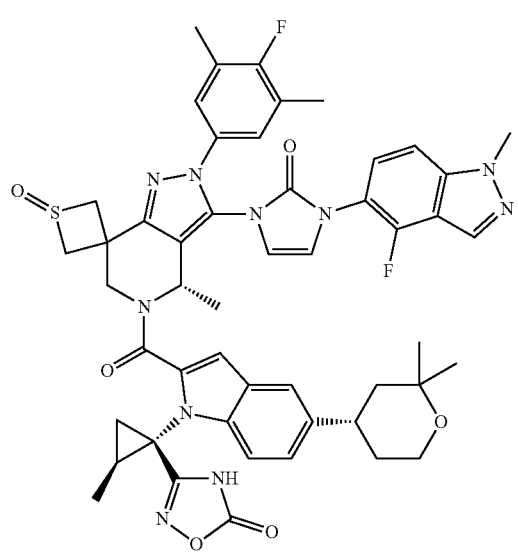

190

-continued

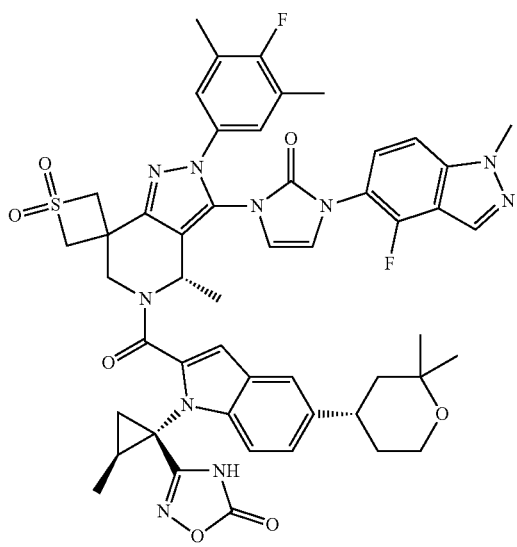

191

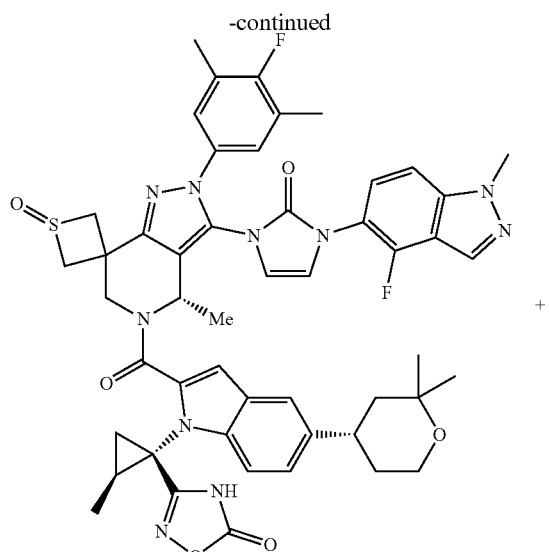

190

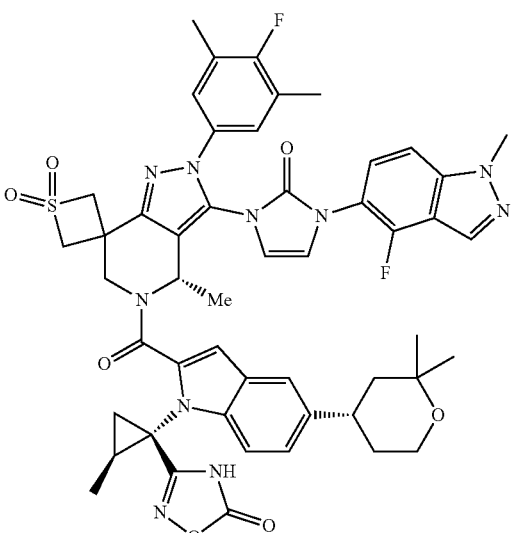

191

Synthetic Route

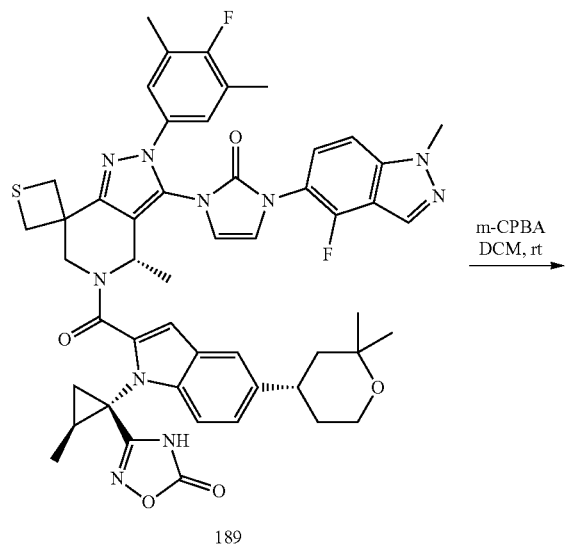

189

→ m-CPBA
DCM, rt

Synthesis of Compounds 190 and 191

Compound 189 (17.6 mg, 0.0187 mmol) and m-CPBA (11.4 mg, 0.0561 mmol) were weighed and dissolved in 2.5 mL of dichloromethane, and reacted at room temperature for 6 h. Water was added dropwise to quench the reaction. The solution was extracted with ethyl acetate, and the organic phase was washed with a saturated sodium chloride solution, dried over anhydrous sodium sulfate, and filtered. The filtrate was concentrated and separated by column chromatography. Among the separated products, the compound with lower polarity was 191, and the compound with higher polarity was 190. $[M+H]^+=973$ and $[M+H]^+=957$.

Example 43

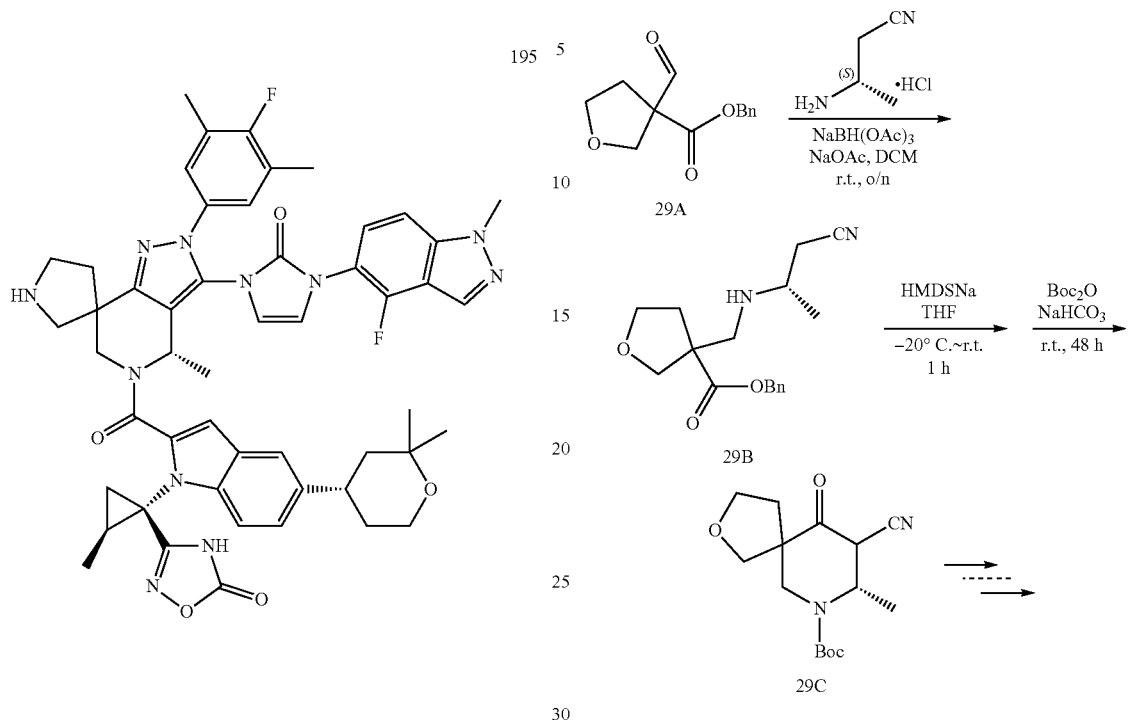

Synthesis of Compound 195

With reference to the preparation method for Compound 31 in Example 9, Compound 195 was synthesized by replacing Boc-L-proline-methyl ester with methyl 1-Boc-pyrrolidine-3-carboxylate (commercially available). [M+H]$^+$=938.

Example 44

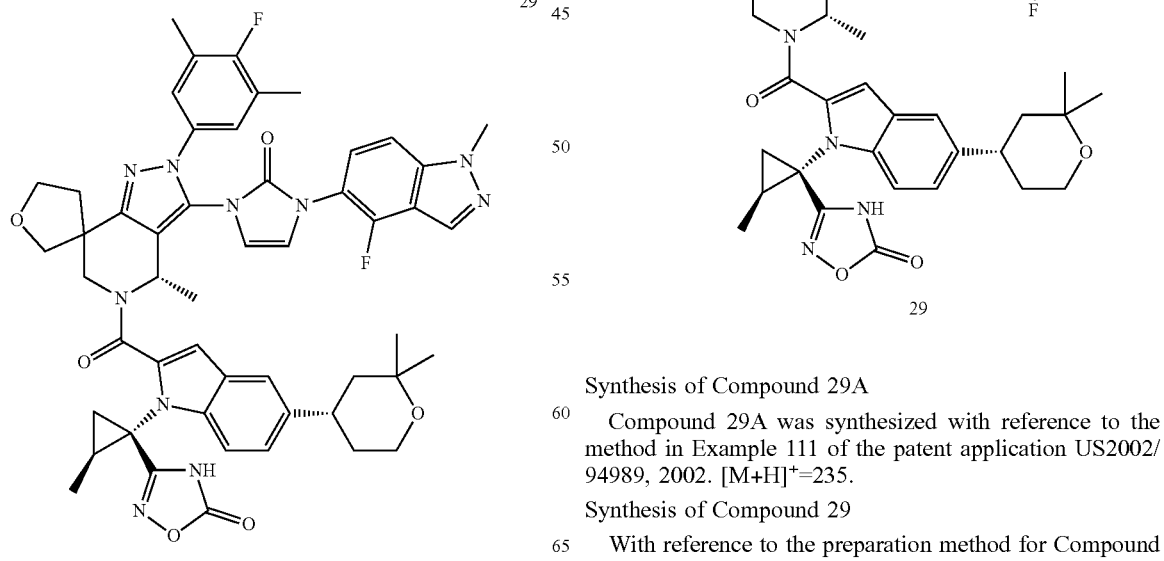

Synthesis of Compound 29A

Compound 29A was synthesized with reference to the method in Example 111 of the patent application US2002/94989, 2002. [M+H]$^+$=235.

Synthesis of Compound 29

With reference to the preparation method for Compound 1 in Example 1, Compound 29 was synthesized by replacing 1A with 29A. [M+H]$^+$=939.

Example 45
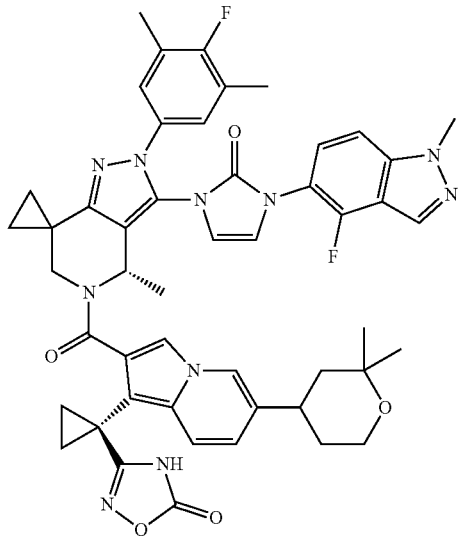
196
Synthesis of Compound 196
With reference to the preparation method for Compound 185-A in Example 39, 196 was synthesized by replacing 185-A-A with 1-(1-cyanocyclopropyl)-6-(2,2-dimethyltetrahydro-2H-pyran-4-yl)indolizine-2-carboxylic acid (the intermediate 28-P1 in WO2022017338A1). [M+H]$^+$=895.
Example 46
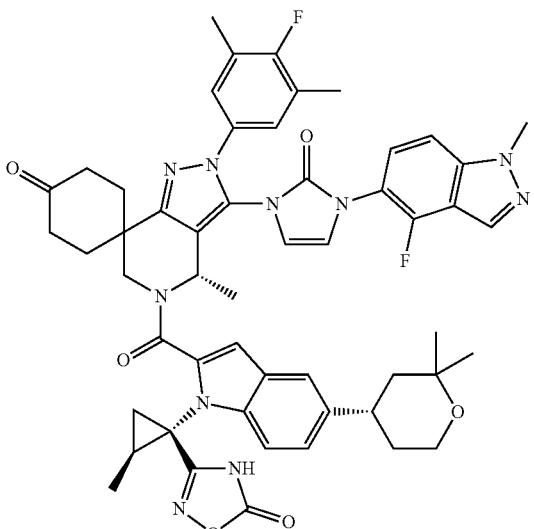
198
Synthetic Route
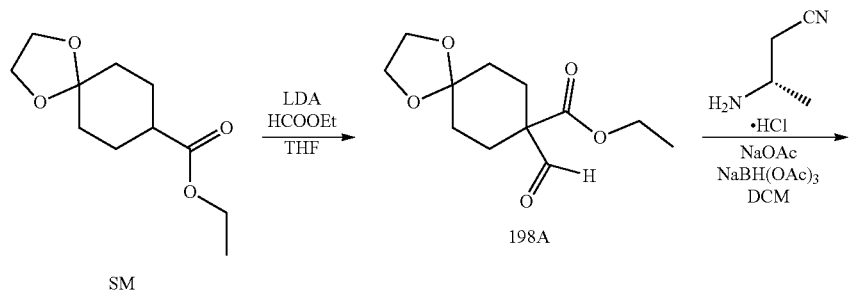
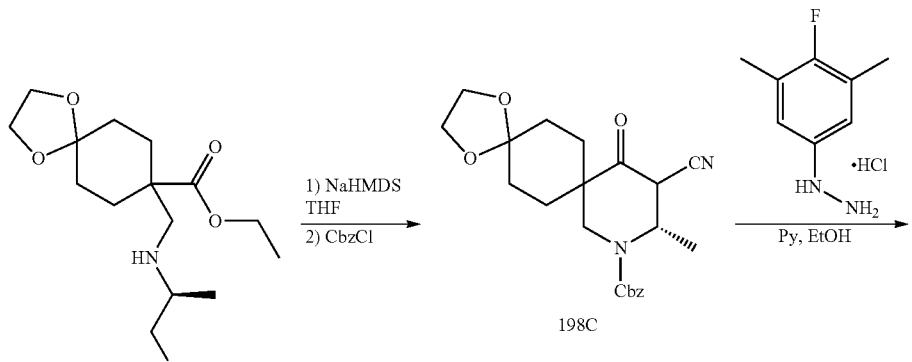

-continued
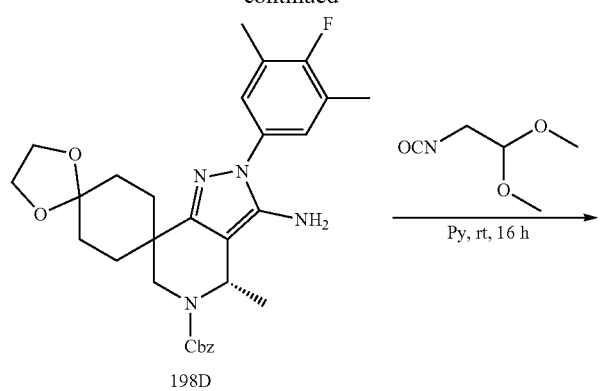
198D
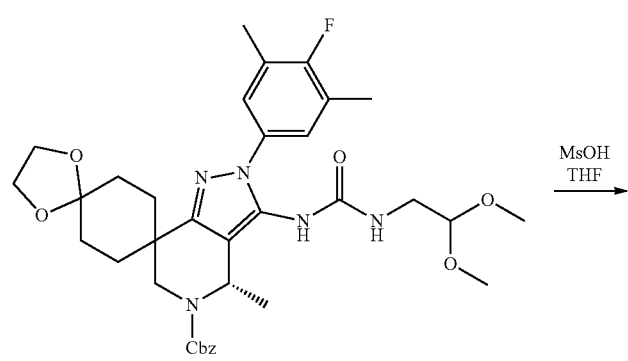
198E
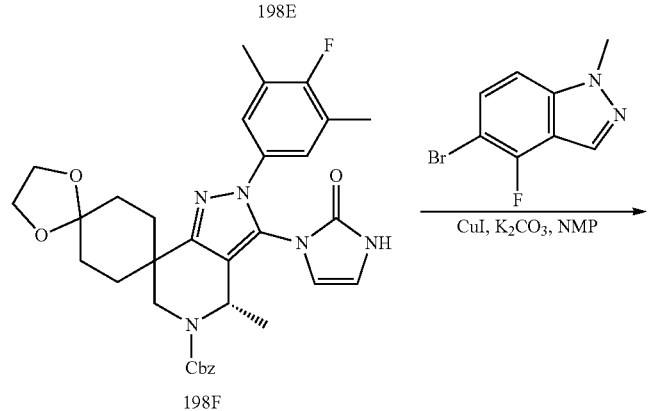
198F
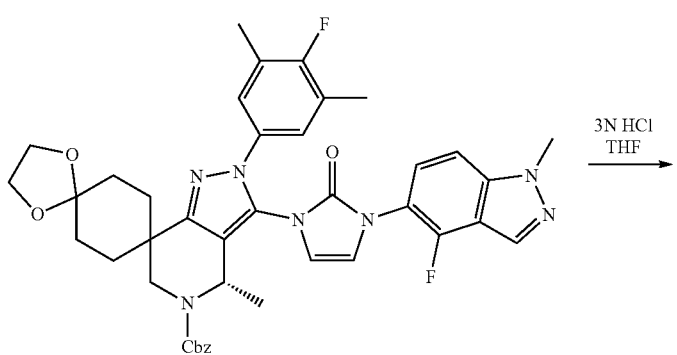
198G

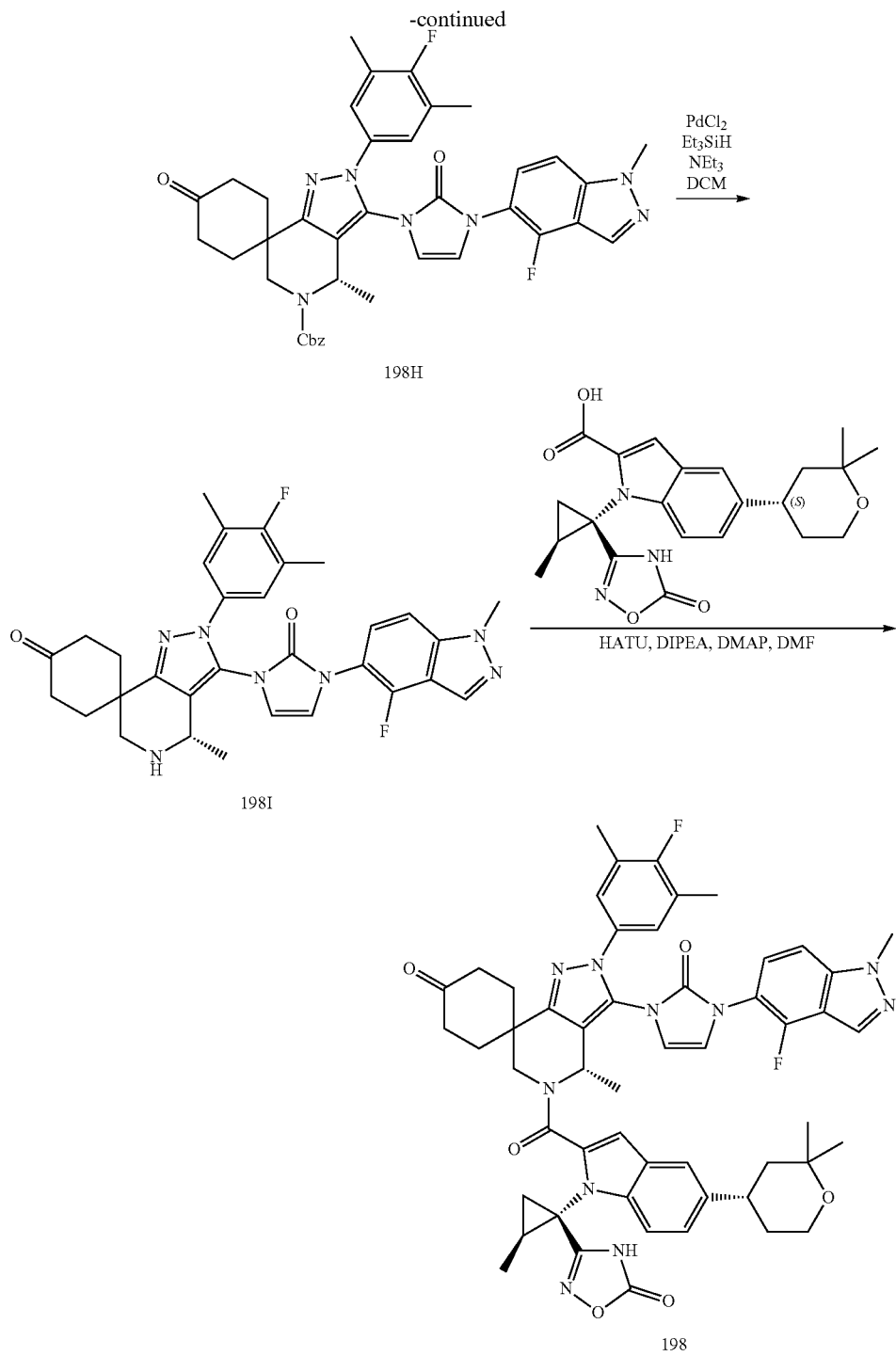

Synthesis of Compound 198A

Ethyl 1,4-dioxaspiro[4.5]decane-8-carboxylate (2.02 g, 9.41 mmol) was weighed and dissolved in THF (20 ml). The air was purged with nitrogen for three times. The temperature of reaction was lowered to −70° C. LDA (2.0M, 6.1 mL) was slowly added dropwise, when finished, stirred at −70° C. for 1 h, and then stirred at 0° C. for 1 h. The temperature of reaction was lowered again to −70° C. A solution of ethyl formate (1.05 g, 14.19 mmol) in THF (4 mL) was added dropwise, when finished, stirred at −70° C. for 1 h, and further stirred at room temperature for 30 min. The reaction was quenched with a saturated aqueous ammonium chloride solution (30 mL). The reaction was stirred at room temperature for 30 min, then added with purified water (30 mL), and extracted with ethyl acetate (30 mL*3). The organic phases were combined, washed with 0.5N HCl (20 mL), washed with water (30 mL), washed with saturated saline (30 mL), dried over anhydrous sodium sulfate, and filtered. The filtrate was concentrated to afford a crude product of 198A (2.21 g, a yellow oily product). The crude product was not further purified and was used directly for the next reaction step.

Synthesis of Compound 198B 198A (2.21 g, 4.13 mmol) and (S)-3-aminobutanenitrile hydrochloride (0.55 g, 4.54 mmol) were weighed and added into dichloromethane (20 mL). Thereafter, anhydrous sodium acetate (0.37 g, 4.54 mmol) and sodium triacetoxyborohydride (1.31 g, 6.19 mmol) were added at 0° C., and reacted overnight under nitrogen protection at room temperature. The reaction was quenched with a saturated sodium bicarbonate solution. The reaction solution was adjusted to pH 8 to 9, and extracted with dichloromethane (30 mL*3). The organic phases were combined, washed with water (30 mL), washed with saturated saline (30 mL), dried over anhydrous sodium sulfate, and filtered. The filtrate was concentrated to afford a crude product. The crude product was purified by silica gel column chromatography (eluent: methanol/dichloromethane=1/100 to 1/50, V/V) to afford product 198B (1.15 g, yield: 39%). LC/MS (ESI) m/z: 311 (M+H)+.

Synthesis of Compound 198C 198B (1.00 g, 3.23 mmol) was weighed and dissolved in tetrahydrofuran (20 mL), and NaHMDS (2.0M THF solution, 3.2 mL, 6.45 mmol) was added dropwise at −20° C. under nitrogen protection, during which the internal temperature was kept at no higher than −10° C., when finished, slowly warmed to room temperature and stirred for 30 min. The reaction was quenched by 10% aqueous citric acid solution, and the pH was adjusted to 9 to 10. Benzyl chloroformate (0.66 g, 3.87 mmol) was added dropwise in an ice-water bath, when finished, stirred at room temperature for 30 min. 30 mL of water was added, and the pH was adjusted with 3N HCl to 5 to 6. The reaction solution was extracted with ethyl acetate (20 mL*3). The organic phases were combined, washed with water (20 mL*2), washed with saturated saline (20 mL), dried over anhydrous sodium sulfate, and filtered. The filtrate was concentrated to afford a crude product. The crude product was purified by silica gel column chromatography (eluent: ethyl acetate/n-heptane=1/4 to 1/2, V/V) to afford product 198C (0.58 g, yield: 45%). LC/MS (ESI) m/z: 399 (M+H)+.

Synthesis of Compound 198D

Compound 198C (0.58 g, 1.46 mmol), 4-fluoro-3,5-dimethylphenylhydrazine trifluoroacetate (0.83 g, 4.37 mmol), and pyridine (1.41 g, 17.82 mmol) were weighed and dissolved in 20 mL of ethanol, and heated to 80° C. and reacted for 5 h under nitrogen protection. The solution was concentrated to remove the solvent. Ethyl acetate (30 mL) was added. The solution was washed with a saturated sodium bicarbonate solution (20 mL). The organic phase was dried over anhydrous sodium sulfate, and filtered. The filtrate was concentrated to afford a crude product. The crude product was purified by silica gel column chromatography (eluent: ethyl acetate/n-heptane=1/4 to 1/2, V/V) to afford product 198D (0.33 g, yield: 42%). LC/MS (ESI) m/z: 535 (M+H)+.

Synthesis of Compound 198E

Compound 198D (1.07 g, 2.00 mmol) was weighed and dissolved in 10 mL of pyridine, to which 2-isocyanato-1,1-dimethoxyethane (1.62 g, 12.46 mmol) was added in an ice-water bath, and stirred overnight at room temperature. Methanol (5 mL) was added to the system, and stirred for 30 min. The solution was concentrated to remove the solvent. Ethyl acetate (30 mL) was added. The solution was washed with a 10% aqueous citric acid solution (15 mL), washed with a saturated aqueous sodium bicarbonate solution (15 mL), and washed with saturated saline (15 mL). The organic phase was dried over anhydrous sodium sulfate, and filtered. The filtrate was concentrated to afford a crude product. The crude product was purified by silica gel column chromatography (eluent: ethyl acetate/n-heptane=1/3 to 1/1.5, V/V) to afford product 198E (1.05 g, yield: 79%). LC/MS (ESI) m/z: 666 (M+H)+.

Synthesis of Compound 198F

Compound 198E (1.05 g, 1.58 mmol) was weighed and dissolved in 20 mL of tetrahydrofuran, and methanesulfonic acid (0.19 g, 1.90 mmol) was added, and stirred at 60° C. for 2 h under nitrogen protection. After cooling to room temperature, a saturated sodium bicarbonate solution (10 mL) was added to adjust the pH to 8 to 9. The solution was extracted with ethyl acetate (20 mL*3). The organic phases were combined, washed with water (20 mL*2), washed with saturated saline (20 mL), dried over anhydrous sodium sulfate, and filtered. The filtrate was concentrated to afford a crude product. The crude product was purified by silica gel column chromatography (eluent: ethyl acetate/n-heptane=1/4 to 1/2, V/V) to afford product 198F (1.00 g, yield: 100%). LC/MS (ESI) m/z: 602 (M+H)+.

Synthesis of Compound 198G

Compound 198F (1.00 g, 1.67 mmol) was weighed and dissolved in 14 mL of N-methylpyrrolidone. Thereafter, 5-bromo-4-fluoro-1-methylindazole (0.76 g, 3.34 mmol), potassium carbonate (0.69 g, 5.00 mmol), cuprous iodide (0.37 g, 1.92 mmol), and (1S,2S)-(+)—N,N'-dimethyl-1,2-cyclohexanediamine (0.55 g, 3.83 mmol) were added in sequence, and reacted at 130° C. for 2 h under nitrogen protection. After the reaction was cooled to room temperature, purified water (100 mL) was added, and the reaction solution was extracted with ethyl acetate (50 mL*2). The organic phases were combined, washed with water (30 mL*2), washed with saturated saline (30 mL), dried over anhydrous sodium sulfate, and filtered. The filtrate was concentrated to afford a crude product of 198G (1.63 g, a brown oily product). The crude product was not further purified and was used directly for the next reaction step. LC/MS (ESI) m/z: 750 (M+H)+.

Synthesis of Compound 198H

Compound 198G (1.63 g) was weighed and added into THF (10 mL), and then 3N HCl (20 mL) was added and stirred at 50° C. for 2 h. In an ice-water bath, a saturated sodium bicarbonate solution was added to adjust the pH to 7 to 8. The reaction solution was extracted with ethyl acetate (20 mL*3). The organic phases were combined, washed with water (20 mL), washed with saturated saline (20 mL), dried over anhydrous sodium sulfate, and filtered. The filtrate was concentrated to afford a crude product. The cured product was purified by silica gel column chromatography (eluent: ethyl acetate/n-heptane=1/2 to 1/1, V/V) to afford product 198H (0.70 g, yield: 62.7%). LC/MS (ESI) m/z: 706 (M+H)+.

Synthesis of Compound 198I 198H (91.8 mg, 0.013 mmol) was weighed and added into dichloromethane (2.0 mL), and then palladium chloride (46.5 mg, 0.026 mmol) and triethylamine (53.5 mg, 0.052 mmol) were added. The reaction was purged with nitrogen three times. In an ice-water bath, triethylsilane (45.9 mg, 0.039 mmol) was added dropwise, when finished, the reaction was stirred at room temperature for 2 h. Methanol (2 mL) was added and stirred for 30 min. The solution was filtered through diatomite, and the diatomite was rinsed with methanol (10 mL). The filtrate was concentrated to afford a crude product. The crude product was purified by silica gel column chromatography (eluent: ethyl acetate/n-heptane=1/4 to 3/1, V/V) to afford product 198I (52.4 mg, yield: 70%). LC/MS (ESI) m/z: 572 (M+H)⁺.

Synthesis of Compound 198

Compound 198I (52.4 mg, 0.092 mmol) was weighed and dissolved in N,N-dimethylformamide (2 mL). Thereafter, 5-[(S)-2,2-dimethyltetrahydro-2H-pyran-4-yl]-1-[(1S,2S)-2-methyl-1-(5-oxo-4,5-dihydro-1,2,4-oxadiazol-3-yl)cyclopropyl]-1H-indole-2-carboxylic acid (37.7 mg, 0.092 mmol), HATU (45.3 mg, 0.119 mmol), DIPEA (35.6 mg, 0.275 mmol), and DMAP (3.9 mg, 0.028 mmol) were added in sequence, and stirred overnight at room temperature. Purified water (10 mL) was added. The solution was extracted with ethyl acetate (10 mL*3). The organic phases were combined, washed with water (20 mL*2), washed with saturated saline (20 mL), dried over anhydrous sodium sulfate, and filtered. The filtrate was concentrated to afford a crude product. The crude product was purified by preparative TLC (developing solvent: methanol/dichloromethane/ethyl acetate=1/50/5, V/V) to afford product 198 (18.3 mg, yield: 21%). LC/MS (ESI) m/z: 965 (M+H)⁺.

Example 47

Compounds 199 to 203 listed in Table 4 were prepared using 198H as a starting material, readily synthesized by the similar synthetic methods in Examples 32 to 36 or the methods known in the art, and modified if necessary.

TABLE 4

| Cmpd. | Structure | Data |
|---|---|---|
| 199 | 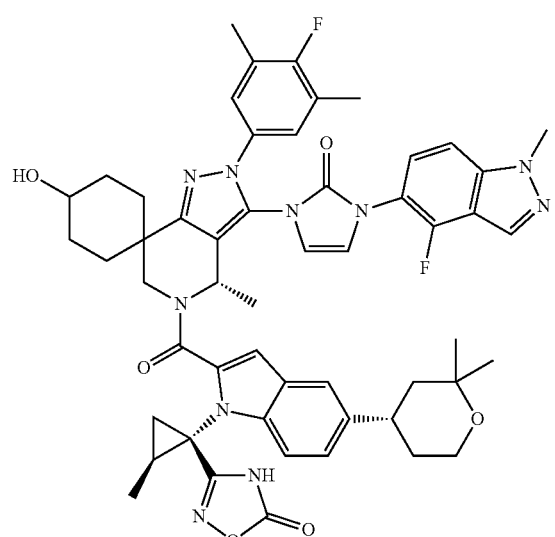 | [M + H]⁺ = 967 |
| 200 | 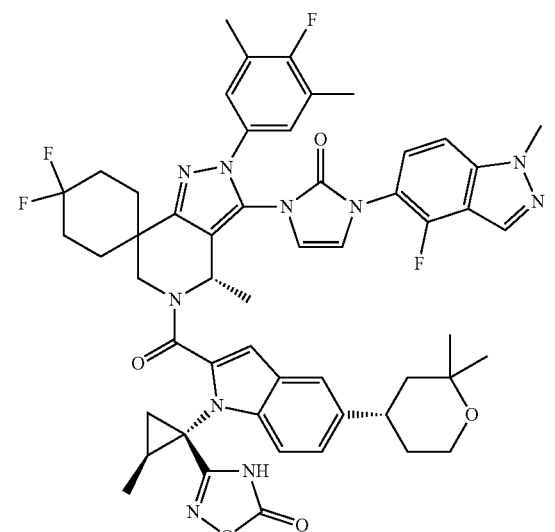 | [M + H]⁺ = 987 |

TABLE 4-continued
| Cmpd. | Structure | Data |
|---|---|---|
| 201 | 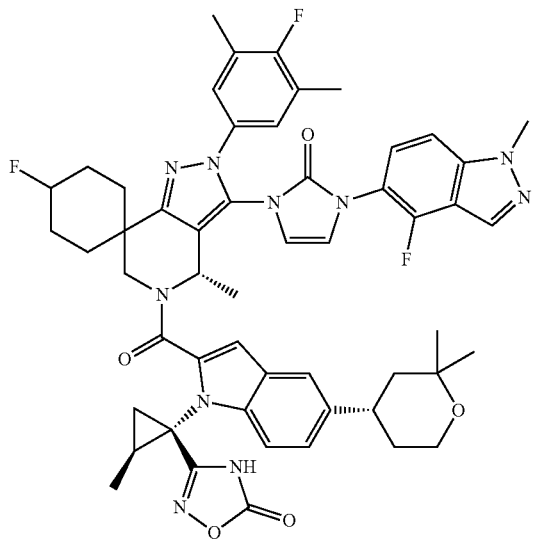 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CCC(F)CC2)cc(C)c1F] | [M + H]⁺ = 969 |
| 202 | 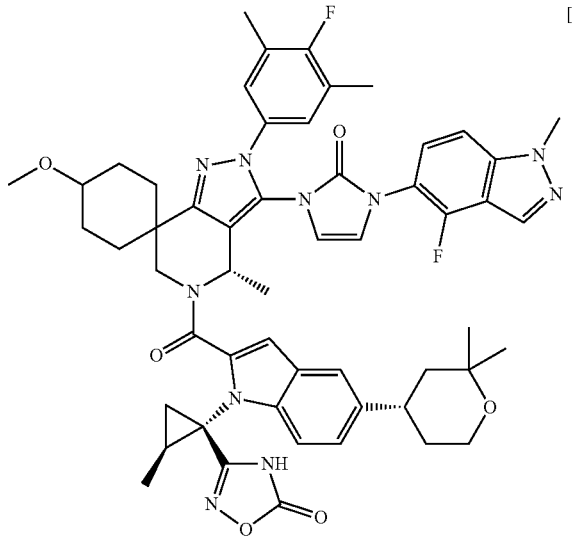 | [M + H]⁺ = 981 |

TABLE 4-continued

| Cmpd. | Structure | Data |
|---|---|---|
| 203 | 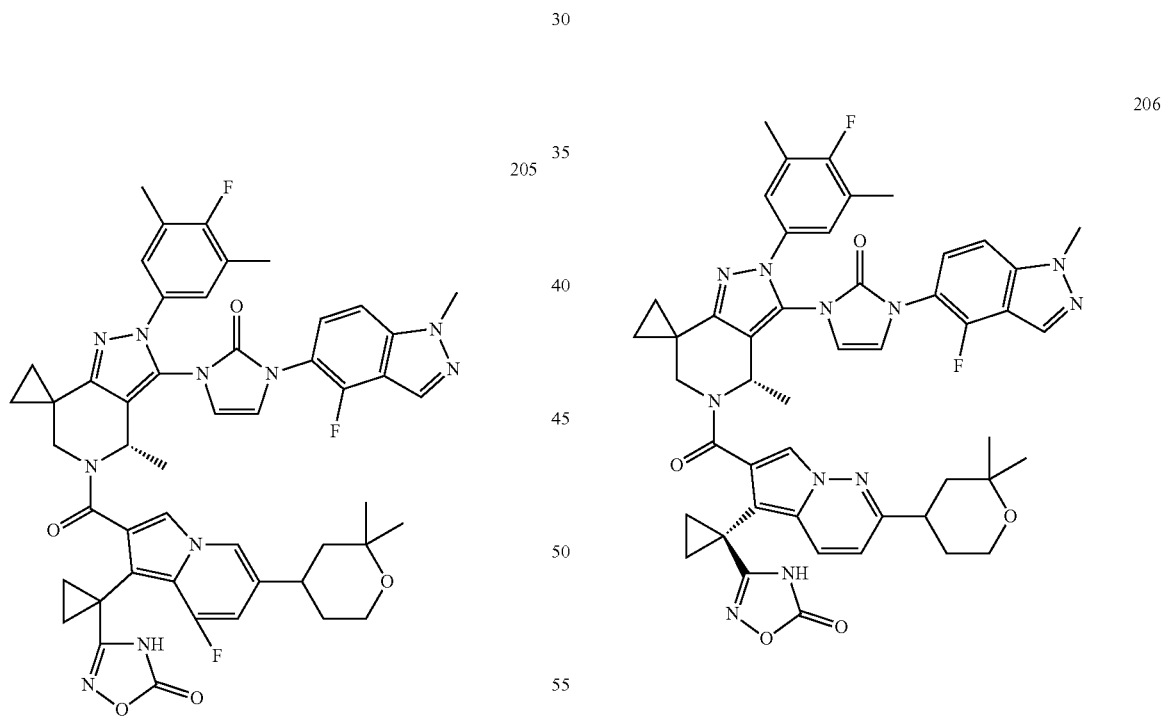 | [M + H]⁺ = 949 |

Example 48

205

Example 49

206

Synthesis of Compound 205

With reference to the preparation method for Compound 185-A in Example 38, 205 was synthesized by replacing 185-A-A with 1-(1-cyanocyclopropyl)-6-(2,2-dimethyltetrahydro-2H-pyran-4-yl)-8-fluoroindolizine-2-carboxylic acid (intermediate 73 in WO2022017338A1). [M+H]⁺=913.

Synthesis of Compound 206

With reference to the preparation method for Compound 185-A in Example 38, 206 was synthesized by replacing 185-A-A with 5-(1-cyanocyclopropyl)-2-(2,2-dimethyltetrahydro-2H-pyran-4-yl)pyrrolo[1,2-b]pyridazine-6-carboxylic acid (intermediate 70 in WO2022017338A1). [M+H]⁺=896.

Example 50
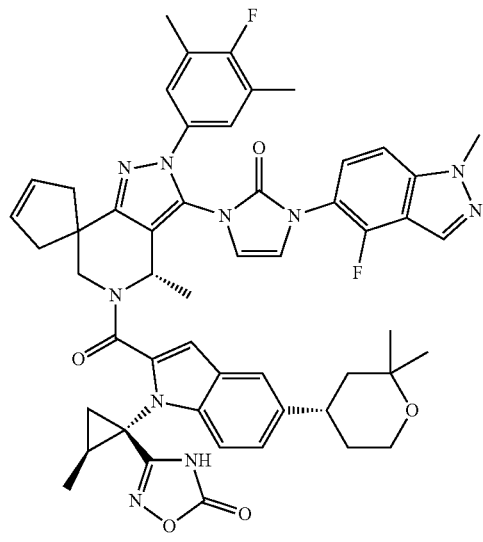
172
Synthetic Route
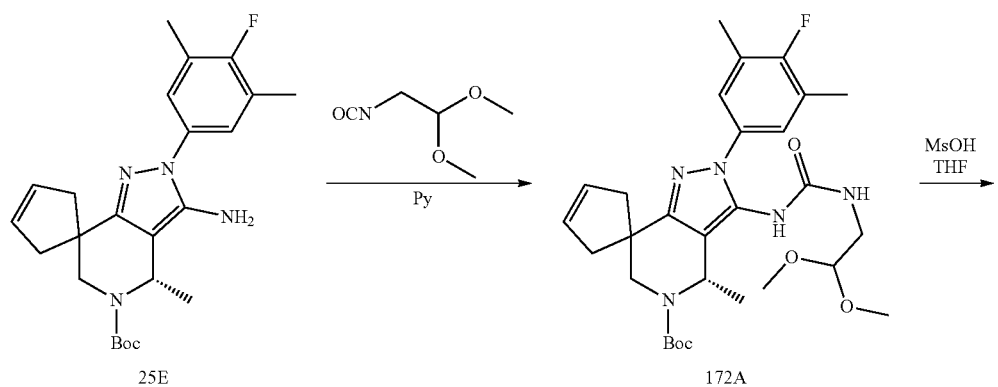
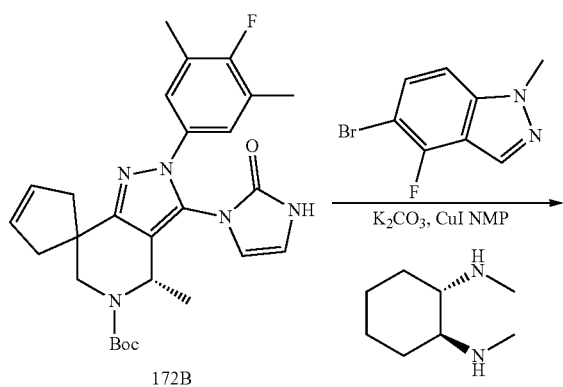

-continued
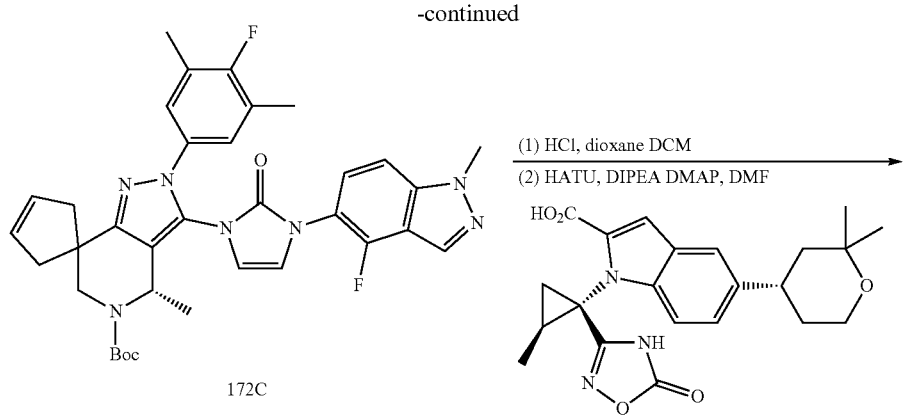
172C
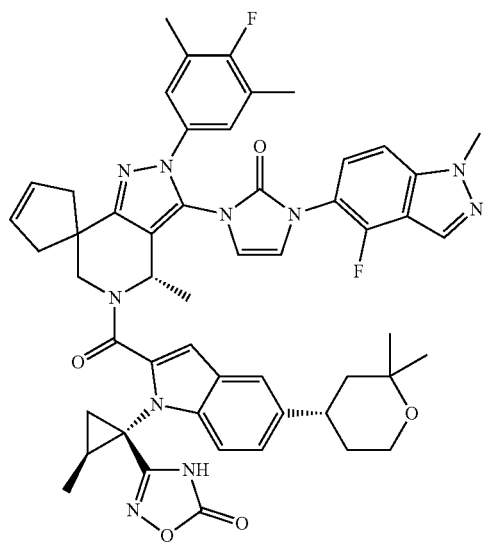 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32C=CCC2)cc(C)c1F]
172
Synthesis of Compound 172
With reference to Example 2, Compound 172 was prepared by replacing 43G with 25E. [M+H]⁺=935.

Example 51
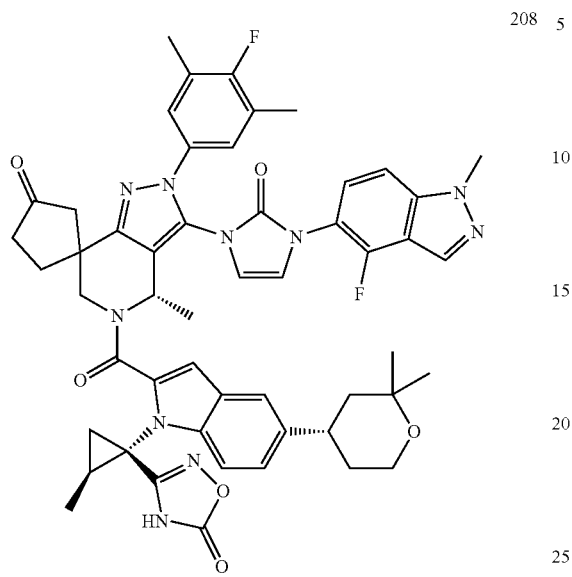
208
Synthetic Route
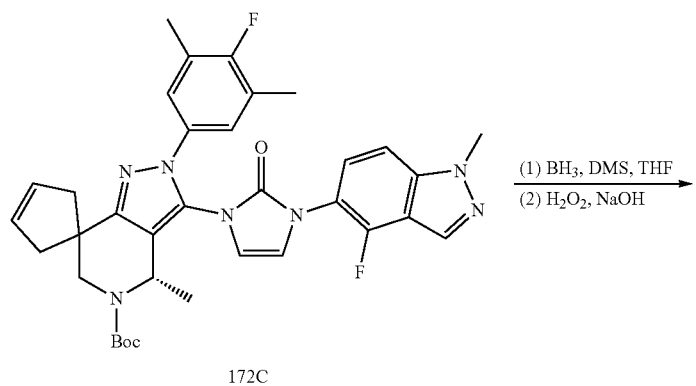
172C
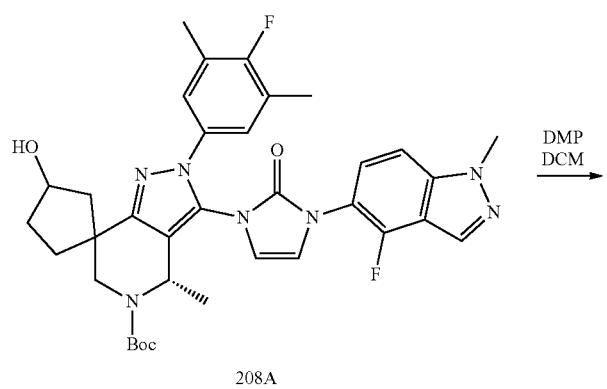
208A

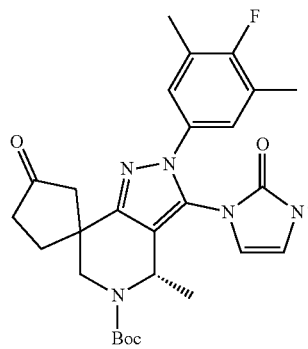

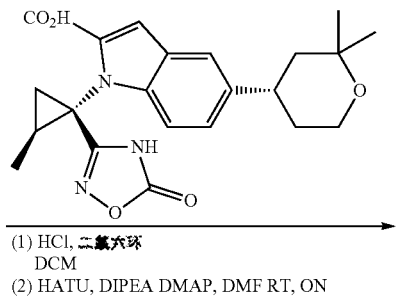

208B (1) HCl, 二氧六环 DCM
(2) HATU, DIPEA DMAP, DMF RT, ON

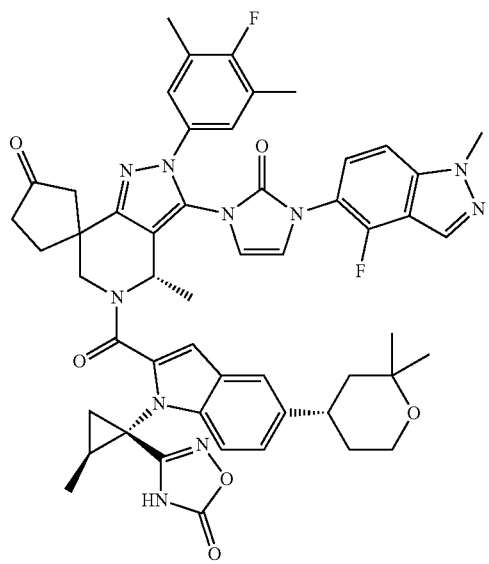

208

Synthesis of Compound 208A

Compound 172C (400 mg, 0.62 mmol) was dissolved in 20 mL of tetrahydrofuran, and cooled to 0° C. to 5° C. in an ice-water bath. A solution of borane-dimethyl sulfide complex in tetrahydrofuran (0.25 mL, 10 mol/L, 2.50 mmol) was added dropwise, when finished, reacted at 0° C. to 5° C. for 1 h. 1 mL of 10% sodium hydroxide solution was added dropwise, and then 0.5 mL of 30% hydrogen peroxide solution was added dropwise and reacted at 0° C. to 5° C. for 2 h. Water and ethyl acetate were added for extraction. The organic phase was washed with a saturated sodium chloride solution, dried over anhydrous sodium sulfate, and filtered. The filtrate was concentrated and then separated by column chromatography to afford Compound 208A (400 mg, a light yellow solid), [M+H]$^+$=660.

Synthesis of Compound 208B

Compound 208A (179 mg, 0.27 mmol) was dissolved in 5 mL of dichloromethane, and Dess-Martin periodinane (230 mg, 0.54 mmol) was added in batches at room temperature. Upon completion of addition, the reaction was reacted at room temperature for 0.5 h. A saturated sodium bicarbonate solution was added dropwise to quench the reaction and the reaction was stirred for 10 min. Water and ethyl acetate were added for extraction. The organic phase was washed with a saturated sodium chloride solution, dried over anhydrous sodium sulfate, and filtered. The filtrate was concentrated and separated by column chromatography to afford Compound 208B (75 mg, a white solid), [M+H]$^+$=658.

Synthesis of Compound 208

With reference to Example 1, Compound 208 was prepared by replacing 1H with 208B. [M+H]$^+$=951.

Example 52

Compounds 197, 209-215, and 229 listed in Table 5 were readily synthesized using 172C as a starting material with reference to the preparation methods for 208A and 208B in Example 51 in conjunction with the similar synthetic methods in Examples 30 to 36 or the methods known in the art, and modified if necessary.

TABLE 5
| Cmpd. | Structure | Data |
|---|---|---|
| 197 | 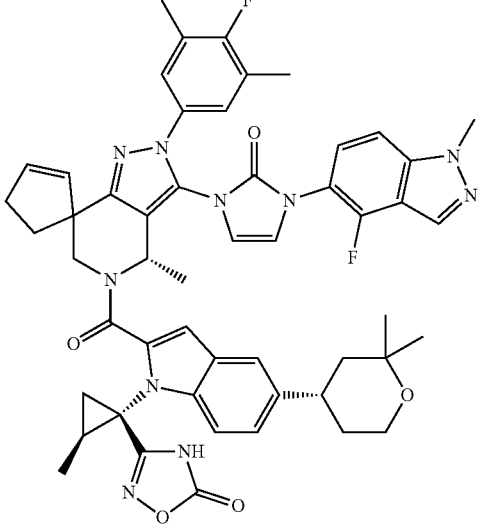 197 | [M + H]⁺ = 935 |
| 209 | 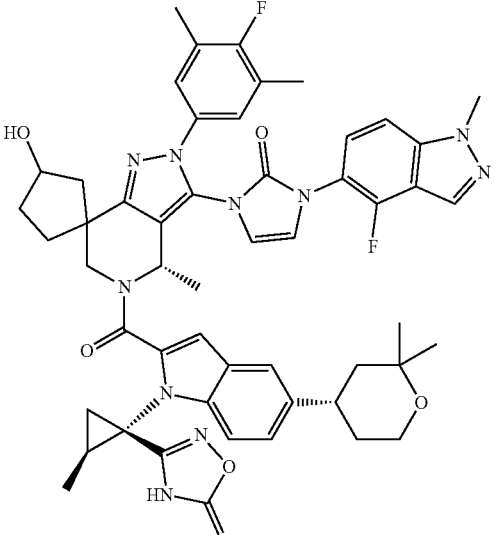 209 | [M + H]⁺ = 953 |

TABLE 5-continued

| Cmpd. | Structure | Data |
|---|---|---|
| 210 | (structure) | [M + H]+ = 967 |
| 211 | (structure) | [M + H]+ = 955 |

TABLE 5-continued
| Cmpd. | Structure | Data |
|---|---|---|
| 212 | 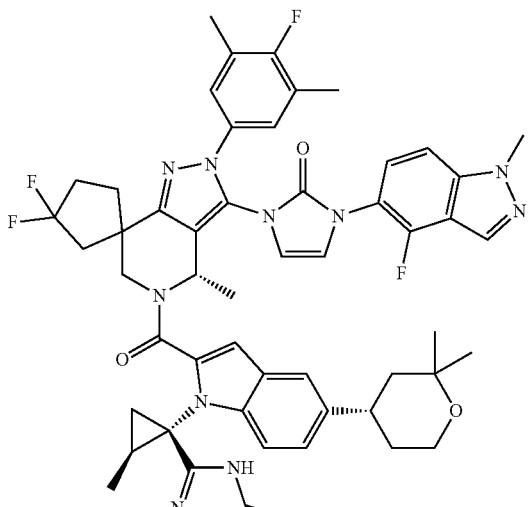 212 | [M + H]⁺ = 973 |
| 213 | 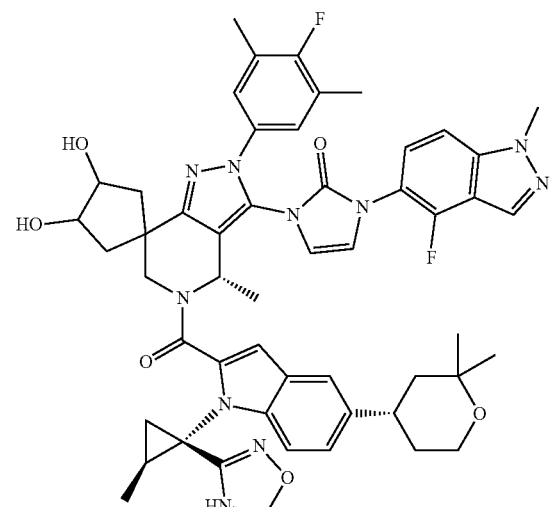 213 | [M + H]⁺ = 969 |

TABLE 5-continued
| Cmpd. | Structure | Data |
|---|---|---|
| 214 | 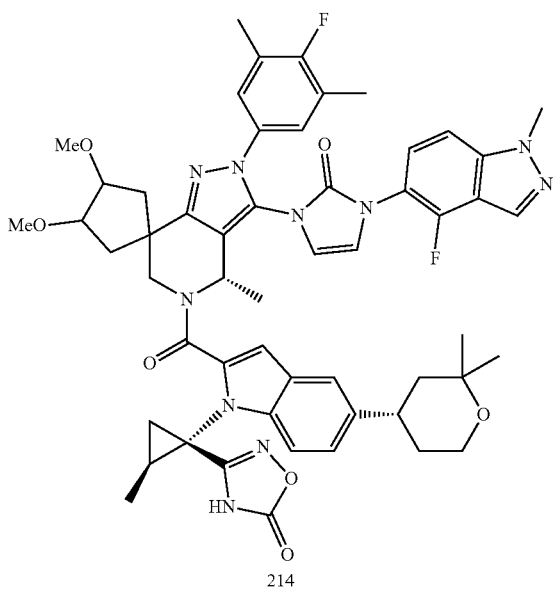 | [M + H]+ = 997 |
| 215 | 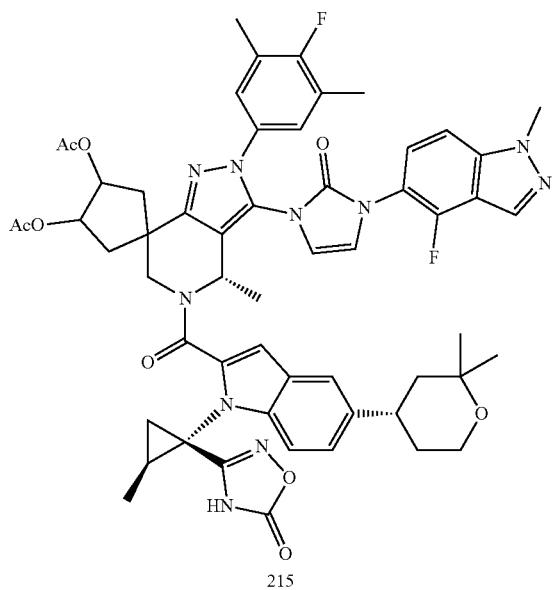 | [M + H]+ = 1053 |

TABLE 5-continued

| Cmpd. | Structure | Data |
|---|---|---|
| 229 | 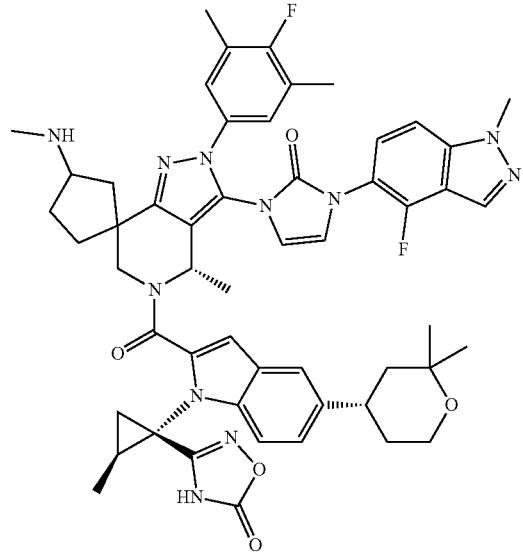 [SMILES: CNC1CCC2(C1)CN(C(=O)c1cc3cc([C@H]4CCOC(C)(C)C4)ccc3n1[C@@]1(c3noc(=O)[nH]3)C[C@@H]1C)[C@@H](C)c1c2nn(-c2cc(C)c(F)c(C)c2)c1-n1ccn(-c2ccc3c(cnn3C)c2F)c1=O]<br>229 | [M + H]⁺ = 966 |

Example 53

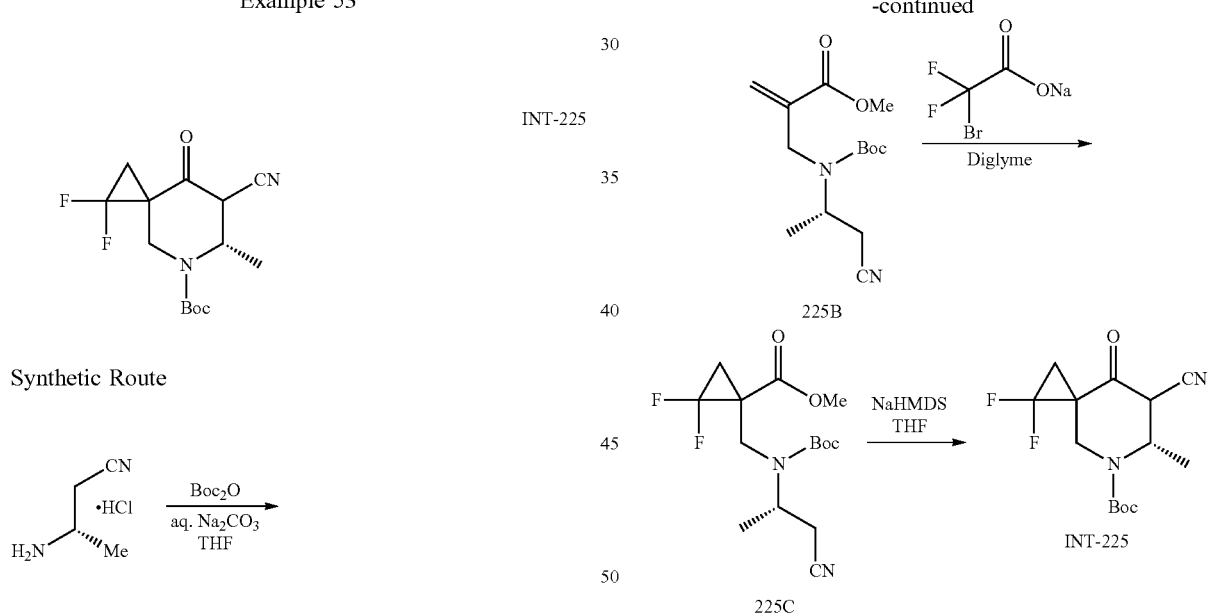

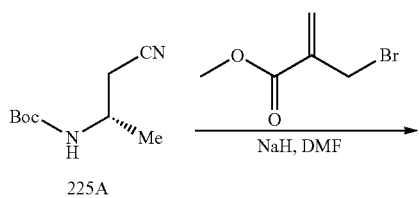

Synthesis of Compound 225A

At room temperature, compound (S)-3-aminobutanenitrile hydrochloride (2.05 g, 17.0 mmol) was weighed and dissolved in THF (20 mL) and water (20 mL). Sodium carbonate (3.56 g, 33.6 mmol) and Boc₂O (4.56 g, 20.9 mmol) were added. The reaction was reacted at room temperature for 2 h. The reaction solution was added with water and ethyl acetate and subjected to liquid separation. The organic phase was washed once with a saturated NaCl solution, dried over anhydrous sodium sulfate, and filtered. The filtrate was concentrated under reduced pressure to afford a crude product. The residue was purified by silica gel column chromatography (eluent: dichloromethane/ethyl acetate=1/0 to 1/1, V/V) to afford product 225A (2.36 g, yield: 77%). [M+H]⁺=185.

Synthesis of Compound 225B

At room temperature, 225A (0.31 g, 1.6 mmol) was weighed and dissolved in DMF (5 mL), and cooled to 0° C. to 5° C. in an ice-water bath. 60% sodium hydride (0.096 g, 2.4 mmol) was added and stirred for 0.5 h. Methyl 2-bromomethacrylate (0.52 g, 2.90 mmol) was added and reacted for 5 min. The solution was added with water and ethyl acetate and subjected to liquid separation. The organic phase was washed once with a saturated NaCl solution, dried over anhydrous sodium sulfate, and filtered. The filtrate was concentrated under reduced pressure to afford a crude product. The residue was purified by silica gel column chromatography (eluent: n-heptane/ethyl acetate=1/50 to 1/5, V/V) to afford product 225B (0.35 g, yield: 70%). $[M+H]^+=283$.

Synthesis of Compound 225C

At room temperature, 225B (0.100 g, 0.35 mmol) was weighed and dissolved in Diglyme (1 ml), and heated to 150° C. A solution of sodium bromodifluorosulfonate (0.300 g, 1.39 mmol) in Diglyme (1 ml) was slowly added dropwise into the mixture, when finished, reacted for 1 h at the constant temperature. The solution was concentrated under reduced pressure to afford a crude product. The residue was purified by silica gel column chromatography (eluent: ethyl acetate/n-heptane=1/5, V/V) to afford product 225C (0.110 g). $[M+H]^+=333$ $(M+H)^+$.

Synthesis of Compound INT-225

At room temperature, 225C (0.110 g, 0.38 mmol) was weighed and added with THF (60 mL). Thereafter, the reaction system was purged with nitrogen three times. The system was cooled to −40° C., and NaHMDS (0.2 mL, 0.49 mmol) was added dropwise, when finished, the temperature of reaction was raised to room temperature and reacted for 2 h. 1 mL of water was dropped into the system. The reaction solution was extracted with ethyl acetate (10 ml*2). The organic phase was washed with saline, dried over sodium sulfate, and filtered. The filtrate was concentrated under reduced pressure to afford a crude product. The residue was purified by silica gel column chromatography (eluent: dichloromethane/methanol=40/1, V/V) to afford product INT-225 (0.092 g, yield: 80%). $[M+H]^+=301$.

Example 54

INT-226

Synthetic Route

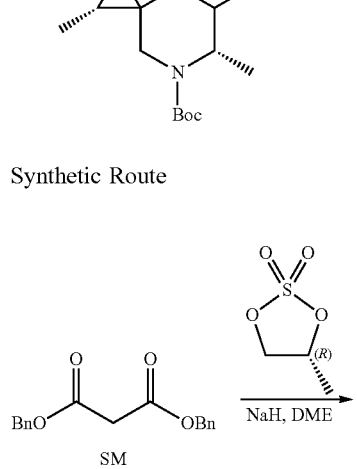

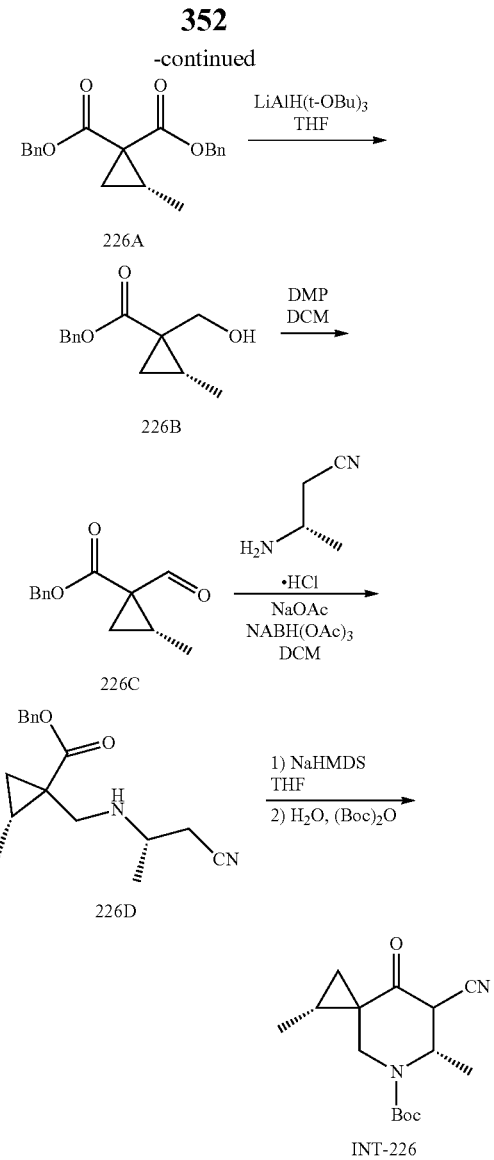

Synthesis of Compound 226A

Sodium hydride (0.62 g, 15.48 mmol) was added into ethylene glycol dimethyl ether (20 mL). The reaction was purged with nitrogen and cooled to 0° C. to 5° C. in an ice bath. Thereafter, a mixed solution of dibenzyl malonate (2.00 g, 7.04 mmol) and (4R)-4-methyl-1,3,2-dioxathiolane 2,2-dioxide (0.97 g, 7.04 mmol) in ethylene glycol dimethyl ether (6 mL) was added dropwise, when finished, stirred for 30 min at room temperature, and then stirred at 40° C. for 30 min. The reaction was poured into ice water (50 mL) and extracted with ethyl acetate (30 mL*2). The organic phases were combined, washed with purified water, washed with saturated saline, dried over anhydrous sodium sulfate, and filtered. The filtrate was concentrated to afford a crude product. The crude product was separated by column chromatography to afford Compound 226A (1.78 g, colorless liquid), $[M+H]^+=325$.

Synthesis of Compound INT-226

With reference to the synthetic method for Compound 39F in Example 11, Compound INT-226 was prepared by replacing 39B with 226A. $[M+H]^+=279$.

Example 55

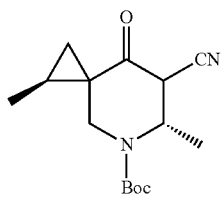

Synthetic Route

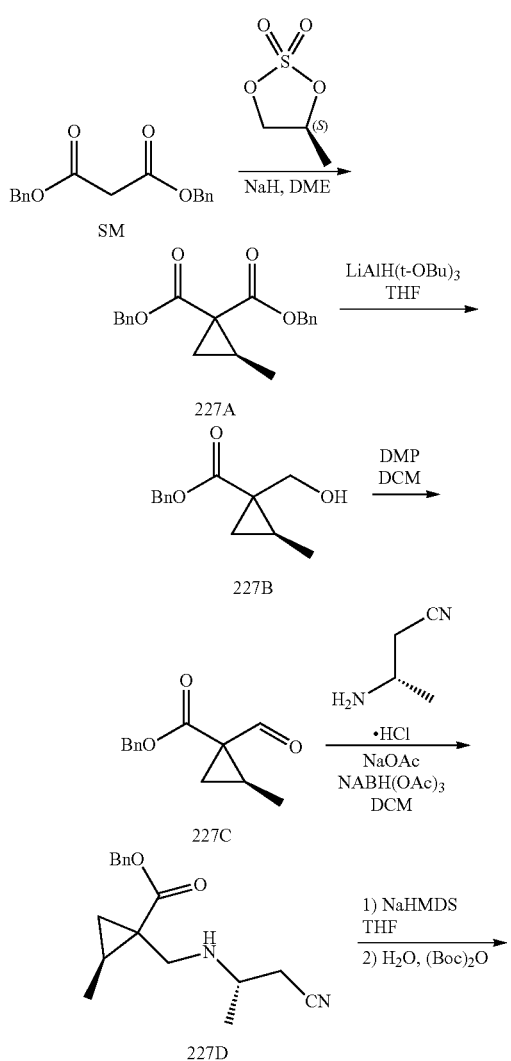

With reference to the synthetic method in Example 54, Compound INT-226 was prepared by replacing (4R)-4-methyl-1,3,2-dioxathiolane 2,2-dioxide with (4S)-4-methyl-1,3,2-dioxathiolane 2,2-dioxide. [M+H]$^+$=279.

Example 56

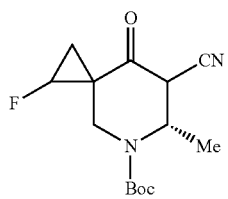

Synthetic Route

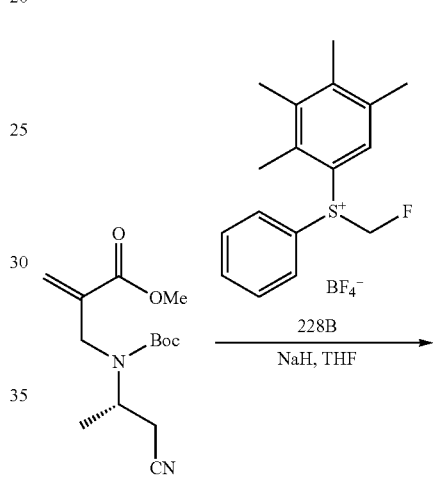

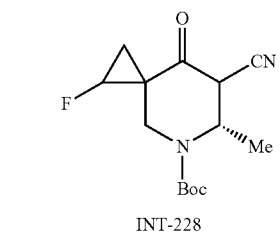

Synthesis of Compound 228A

At room temperature, 225B (485.4 mg, 1.7 mmol) was weighed and dissolved in THF (8 mL). 228B (*J. Org. Chem.* 2021, 86, 3196-3212) (915.7 mg, 2.5 mmol) was added and cooled to 0° C. to 5° C. in an ice-water bath. 60% Sodium hydride (343.8 mg, 8.6 mmol) was slowly added and reacted for 0.5 h. The reaction solution was added with water and ethyl acetate, and subjected to liquid separation. The organic phase was washed once with a saturated NaCl solution, dried over anhydrous sodium sulfate, and filtered. The filtrate was

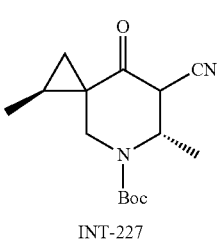

concentrated under reduced pressure to afford a crude product. The residue was purified by silica gel column chromatography (eluent: n-heptane/ethyl acetate=1/10 to 1/1, V/V) to afford product 228A (468.2 mg, yield: 87.5%). [M+H]$^+$=315.

Synthesis of Compound INT-228

Compound 228A (468.2 mg, 1.48 mmol) was dissolved in 20 mL of tetrahydrofuran, and cooled to 0° C. to 5° C. in an ice-water bath under nitrogen protection. NaHMDS (2.0M THF solution, 1.6 mL, 3.20 mmol) was added dropwise, and stirred for 30 min after the dropwise addition was finished. The reaction was quenched by 10% aqueous citric acid solution. The solution was extracted with ethyl acetate, and the organic phase was dried over anhydrous sodium sulfate, and filtered. The filtrate was concentrated and then separated by column chromatography to afford Compound INT-228 (448.7 mg, 107%), [M−H]$^-$=281.

Example 57

Compounds 225 to 228 listed in Table 6 were prepared using INT-225 to INT-228 as starting materials, readily synthesized by the similar synthetic method in Example 1 or the methods known in the art, and modified if necessary.

TABLE 6

| Cmpd. | Structure | Data |
|---|---|---|
| 225 | 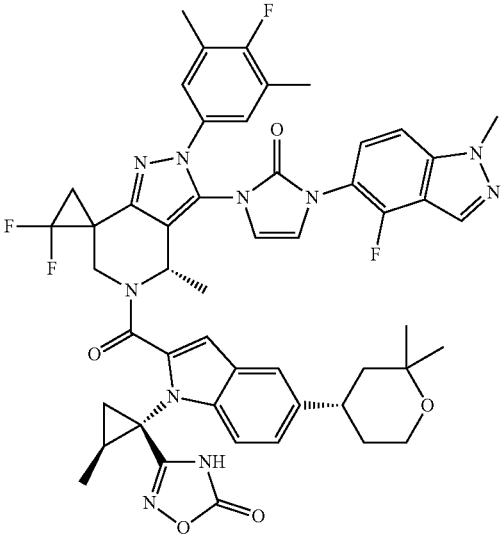 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC2(F)F)cc(C)c1F] | [M + H]$^+$ = 945 |
| 226 | 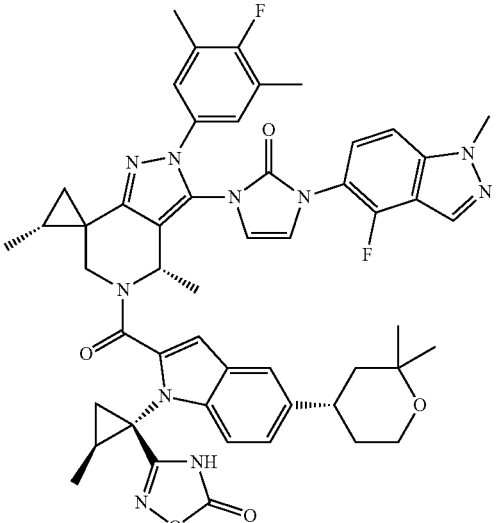 | [M + H]$^+$ = 923; HPLC purity: 98.01% |

TABLE 6-continued

| Cmpd. | Structure | Data |
|---|---|---|
| 227 | 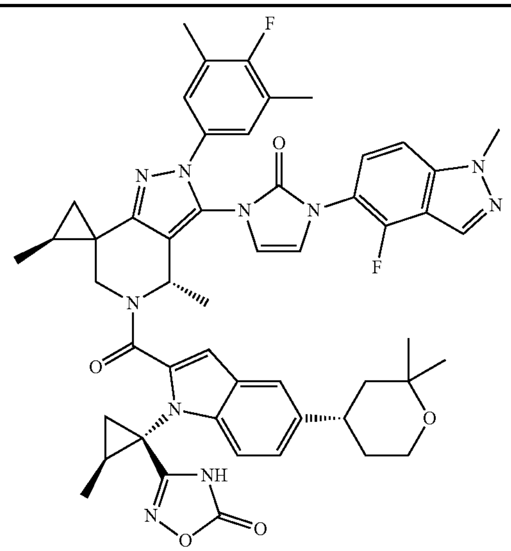 | [M + H]⁺ = 923 |
| 228 | 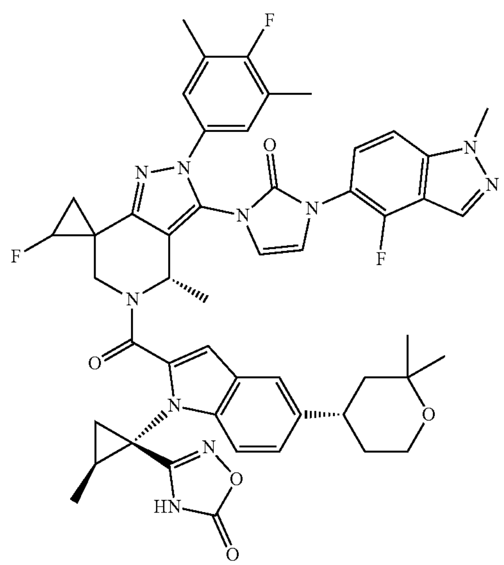 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC32CC2F)cc(C)c1F] | [M + H]⁺ = 927; HPLC purity: 97.86% |

Example 58 Biological Evaluation

The agonistic activities of the compounds of the present disclosure on GLP-1R were evaluated by detecting the generation of cAMP.

1. Cells and Reagents
   (1) Cell line: HEK293-GLP-1R-luc Stable Cell Line (Cobioer, CBP71117);
   (2) Culture medium: DMEM+10% FBS (Gibco);
   (3) Kit: cAMP detection kit (PerkinElmer).
2. Experimental Procedures
   (1) HEK293-GLP1R cells were inoculated in a 384-well plate at a density of 2000 cells per well;
   (2) 4× working solution of each compound was formulated;
   (3) 5 μL of 4× working solution of each compound was added to corresponding well and incubated at 37° C. for 30 min;
   (4) 10 μL of Eu-cAMP tracer diluted with Lysis Buffer (1/50) was added to each well;
   (5) 10 μL of Ulight-anti-cAMP diluted with Lysis Buffer (1/150) was added to each well;
   (6) The plate was incubated at room temperature for 1 h;
   (7) The plate was read by a multimode microplate reader (excitation wavelength: 320 nm; emission wavelength: 665 nm and 620 nm).
3. Data Analysis
   (1) % Activity was calculated by the following formula:

$$\% \text{ Activity} = 100 - (\text{Signal}_{cmpd} - \text{Signal}_{Ave\text{-}PC}) / (\text{Signal}_{Ave\text{-}VC} - \text{Signal}_{Ave\text{-}PC}) \times 100$$

(2) The dose-response curve was plotted to calculate $EC_{50}$:

$$Y=\text{Bottom}+(\text{Top}-\text{Bottom})/(1+10^{\wedge}(\text{Log } EC_{50}-X)*\text{Hill-Slope}))$$

X: log of agonist concentration; Y: Activity.

4. Experimental Results

TABLE 7

| Cmpd. No. | cAMP $EC_{50}$ |
|---|---|
| Example Compound 67 in WO2018056453 | A |
| 1 | A |
| 43 | A |
| 57 | A |
| 59 | A |

Notes:
A indicated $EC_{50} \leq 0.1$ nM;
B indicated 0.1 nM < $EC_{50} \leq 1$ nM;
C indicated 1 nM < $EC_{50} \leq 10$ nM.

Example 59 Biological Evaluation

The agonistic activities of the compounds of the present disclosure on GLP-1R were evaluated by detecting the generation of cAMP.

1. Cells and Reagents
   (1) Cell line: HEK293-GLP-1R-luc Stable Cell Line (Cobioer, CBP71117);
   (2) Culture medium: DMEM+10% FBS (Gibco);
   (3) Kit: One-Lite™ kit Luciferase Assay System (Vazyme).
2. Experimental Procedures
   (1) HEK293-GLP1R cells were inoculated in a 96-well plate at a density of 30000 cells per well;
   (2) 10× working solution of each compound was formulated;
   (3) 10 µL of 10× working solution of each compound was added to corresponding well and incubated at 37° C. for 6 h;
   (4) 100 µL of One-Lite Luciferase Assay Substrate formulated using One-Lite Luciferase Assay Buffer was added to each well;
   (5) The plate was incubated at room temperature for 3 min;
   (6) The plate was read by a multimode microplate reader to detect chemiluminescence.
3. Data Analysis
   (1) % Activity was calculated by the following formula:

$$\% \text{ Activity}=100-(\text{Signal}_{cmpd}-\text{Signal}_{Ave-PC})/(\text{Signal}_{Ave-VC}-\text{Signal}_{Ave-PC})\times 100$$

(2) The dose-response curve was plotted to calculate $EC_{50}$:

$$Y=\text{Bottom}+(\text{Top}-\text{Bottom})/(1+10^{\wedge}(\text{Log } EC_{50}-X)*\text{Hill-Slope}))$$

X: log of agonist concentration; Y: Activity.

4. Experimental Results

TABLE 8

| Cmpd. No. | cAMP $EC_{50}$ |
|---|---|
| Example Compound 67 in WO2018056453 | ++++ |
| 1 | ++++ |
| 15 | ++++ |
| 21 | ++++ |
| 23 | ++++ |
| 25 | ++++ |
| 29 | ++++ |
| 31 | ++++ |
| 37 | +++ |
| 39 | ++++ |
| 43 | ++++ |
| 51-A | ++++ |
| 51-B | ++++ |
| 53-A | ++++ |
| 53-B | ++ |
| 53-C | +++ |
| 53-D | ++++ |
| 55-A | ++++ |
| 55-B | ++++ |
| 57 | ++++ |
| 59 | ++++ |
| 64 | ++++ |
| 79 | ++++ |
| 83 | ++++ |
| 91 | ++++ |
| 151 | ++++ |
| 155 | ++++ |
| 156 | ++++ |
| 157 | ++++ |
| 158 | ++++ |
| 159 | ++++ |
| 160 | ++++ |
| 161 | ++++ |
| 162 | ++++ |
| 163 | ++++ |
| 164 | ++++ |
| 165 | ++++ |
| 166 | ++++ |
| 167 | ++++ |
| 168 | ++++ |
| 169 | ++++ |
| 170 | ++++ |
| 171 | ++++ |
| 172 | ++++ |
| 173 | +++ |
| 174 | ++ |
| 175 | +++ |
| 177 | ++++ |
| 179 | ++++ |
| 180 | ++++ |
| 181 | ++++ |
| 182 | ++++ |
| 183 | ++++ |
| 184 | ++++ |
| 185-A | + |
| 185-B | +++ |
| 186-A | + |
| 186-B | +++ |
| 187 | ++++ |
| 188 | ++++ |
| 189 | ++++ |
| 190 | ++++ |
| 191 | ++++ |
| 192 | ++++ |
| 193 | ++++ |
| 194 | ++++ |
| 195 | ++++ |
| 196 | ++++ |
| 197 | ++++ |
| 198 | ++++ |
| 199 | ++++ |
| 200 | +++ |
| 201 | +++ |
| 202 | ++++ |
| 203 | ++++ |
| 207 | ++++ |
| 208 | ++++ |
| 209 | ++++ |
| 210 | ++++ |
| 211 | ++++ |
| 212 | ++++ |

TABLE 8-continued

| Cmpd. No. | cAMP EC$_{50}$ |
|---|---|
| 213 | ++++ |
| 214 | ++++ |
| 218 | ++++ |
| 219 | ++++ |
| 220 | ++++ |
| 221 | ++++ |
| 222 | ++++ |
| 223 | ++++ |
| 224 | +++ |
| 225 | ++++ |
| 226 | ++++ |
| 227 | +++ |
| 228 | ++++ |
| 229 | ++++ |
| / | / |

Notes:

++++ indicated EC$_{50}$ ≤ 20 nM; +++ indicated 20 nM < EC$_{50}$ ≤ 100 nM; ++ indicated 100 nM < EC$_{50}$ ≤ 300 nM; + indicated EC$_{50}$ > 300 nM.

The above results suggested that the compounds in the Examples of the present disclosure exhibited good agonistic activities on GLP-1R.

Example 60 In Vivo Evaluation of Pharmacokinetics in Rats

The compounds of the present disclosure were formulated with 1000 PEG 400+90% 100 mM glycine-64 mM NaOH, and orally administered to fasted SD rats at a dose of 1 mg/kg or 5 mg/kg, respectively. At different time points (0.25, 0.5, 1.0, 2.0, 4.0, 5.0, 6.0, 7.0, 8.0, and 24 h) after administration, about 50 μL of blood samples were collected from veins into anticoagulant tubes containing EDTA-K2, and centrifuged to separate plasma. The plasma concentrations of the compounds were determined by LC-MS/MS. WinNonlin was used to calculate the pharmacokinetic parameters by using the non-compartmental analysis, and the experimental results were listed in Table 9.

TABLE 9

| Route of Administration | Cmpd. No. | Dose (mg/kg) | T$_{1/2}$ (h) | C$_{max}$ (ng/ml) | AUC$_{last}$ (h * ng/ml) |
|---|---|---|---|---|---|
| PO | Example compound 67 in WO2018056453 | 1 | 6.8 | 145 | 1421 |
| | | 5 | 5.5 | 260 | 2376 |
| | 1 | 1 | 10.0 | 213 | 2298 |
| | | 5 | 12.9 | 1083 | 11844 |
| | 180 | 1 | 6.4 | 129 | 1116 |
| | 218 | 1 | 11.6 | 110 | 990 |
| | 226 | 1 | 9.3 | 160 | 1475 |
| | 228 | 1 | 13.0 | 216 | 2405 |

The above test results of pharmacokinetics in rats indicated that some of the representative compounds of the present disclosure had a longer half-life T$_{1/2}$ than that of the control compound (example compound 67 in WO2018056453), and meanwhile, Compound 1 and Compound 228 had higher oral exposure AUC and a higher maximum plasma concentration C$_{max}$, indicating that the example compounds of the present disclosure showed better pharmacokinetic properties and oral administration characteristics and are more suitable for development as drugs.

Example 61 In Vivo Evaluation of Pharmacokinetics in *Macaca fascicularis*

A clear solution of "example compound 67 in WO2018056453" in 10% PEG/90% 100 mM glycine-NaOH and a clear solution of "Compound 1" in 10% PEG/90% 100 mM glycine-NaOH were prepared. The above solutions were injected into subcutaneous veins of the fore limbs of male *Macaca fascicularis* (n=2) at a dose of 0.12 mg/kg, respectively. At different time points (0.083, 0.25, 0.5, 1.0, 2.0, 4.0, 8.0, 24.0, and 36 h) after administration, blood samples were collected from veins into anticoagulant tubes containing EDTA-K2, and centrifuged to separate plasma.

The drug concentrations in the plasma were determined by the LC-MS/MS method, and the pharmacokinetic software (e.g., winNonlin Version 6.3) was used to calculate the related pharmacokinetic parameters as shown in Table 10 by using the log-linear trapezoidal rule of the non-compartmental analysis.

TABLE 10

| Route of Administration | Cmpd. No. | Dose (mg/kg) | T$_{1/2}$ (h) | Cl (ml/h/kg) | AUC$_{last}$ (h * ng/ml) |
|---|---|---|---|---|---|
| IV | Example compound 67 in WO2018056453 | 0.12 | 3.67 | 629 | 190 |
| | 1 | 0.12 | 6.08 | 158 | 754 |

The above test results of pharmacokinetics in *Macaca fascicularis* indicated that, as compared to the control compound (example compound 67 in WO2018056453), the representative Compound 1 of the present disclosure had a lower clearance (Cl), a longer half-life (T$_{1/2}$), a higher exposure (AUC), and better pharmacokinetic properties, and was more suitable for development as a drug.

Example 62 In Vivo Evaluation of Efficacy in Mice

1. Experimental Purpose

The effects of long-term administration of the compounds of the present disclosure on the weight and food intake of GLP-1R humanized C57BL/6N mice fed with high-fat diets were evaluated.

2. Experimental Reagents and Instruments five-week-old male C57BL/6N hGLP-1R mice;

60% high-fat diet (HFD); electronic balance.

3. Experimental Method
(1) C57BL/6N_hGLP-1R mice were fed with 60% high-fat diets until the end of the experiment.
(2) At the $10^{th}$ week of HFD feeding, the model mice were randomly divided into groups according to their body weight, with 6 to 7 mice in each group. Subsequently, the single-caged mice were adaptively fed for 2 weeks. The first group was Vehicle group (Vehicle: 10% PEG 400+10% propylene glycol+80% glycine-NaOH buffer), and administered with the Vehicle; the remaining groups were drug treatment groups; the duration of administration was 27 days.
(3) The day of drug administration was defined as Day 0. At each administration, the animals were weighed and the data were recorded, and the mice were treated depending upon their body weight.
(4) The food intake of the mice in each group was measured once a day from Day 0 of the experiment. Specifically, the diets were changed after each weighing and administration, and the addition amounts and residual amounts thereof were recorded.

4. Experimental Data Processing and Statistical Analysis

The rates of change in the body weight of mice after administration were summarized and statistically analyzed.

The rate of change in the body weight corrected by Vehicle was calculated: $(((BW_t/BW_0)-1)-(BW_{t\text{-}vec\text{-}avg}))*100\%$;

$BW_t$ represented the body weight of mouse in drug treatment group on Day t; $BW_0$ represented the body weight of mouse in drug treatment group on Day 0; $BW_{t\text{-}vec\text{-}avg}$ represented the average body weight of mice in Vehicle group on Day t for drug treatment groups.

The cumulative food intake of mice after drug administration was summarized and statistically analyzed.

Cumulative food intake was calculated: addition amounts (g)—residual amounts (g).

The cumulative food intake was the sum of daily food intake of each animal during the period of administration.

5. Experimental Results

TABLE 11

| No. | Groups | Dose | Dosing Volume | Route of Administration | Dosing Frequency | Change Rate of Body Weight on Day 27 (%) | Cumulative Food Intake on Day 27 (g) |
| --- | --- | --- | --- | --- | --- | --- | --- |
| 1 | Vehicle | — | 5 mL/kg | Gavage | Once daily | — | 86.72 ± 3.74 |
| 2 | Example compound 67 in WO2018056453 | 0.3 mpk | | Gavage | Once daily | −11.89 ± 1.27 | 75.41 ± 7.20 |
| 3 | | 1.5 mpk | | Gavage | Once daily | −13.71 ± 1.72 | 74.78 ± 3.64 |
| 4 | Compound 1 | 0.3 mpk | | Gavage | Once daily | −15.04 ± 1.90 | 73.91 ± 6.71 |
| 5 | | 1.5 mpk | | Gavage | Once daily | −18.46 ± 1.98 | 70.01 ± 5.88 |
| 6 | | 3.0 mpk | | Gavage | Once daily | −23.78 ± 1.61 | 62.75 ± 6.97 |

The above experimental results showed that long-term administration of Example Compound 1 of the present disclosure had excellent effects on reduction of the body weight and inhibition of the food intake for GLP-1R humanized C57BL/6 mice fed with high-fat diets, which were better than those of the control compound at both the doses of 0.3 mpk and 1.5 mpk, exhibiting reduction of the body weight and inhibition of the food intake in mice in a dose-dependent manner within the dose range of 0.3 to 3 mpk.

The above descriptions of the Examples are merely intended to help with comprehension of the methods of the present disclosure and its core idea. It should be indicated that for those skilled in the art, several improvements and modifications can further be made to the present disclosure without departing from the principles thereof, and these improvements and modifications also fall within the scope of the appended claims.

What is claimed is:

1. A compound, wherein the compound is selected from the group consisting of:

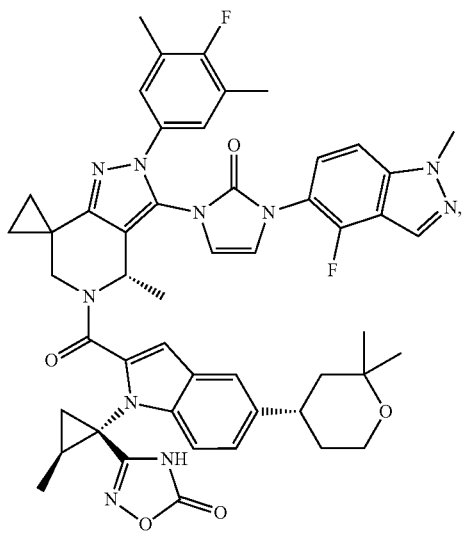

1

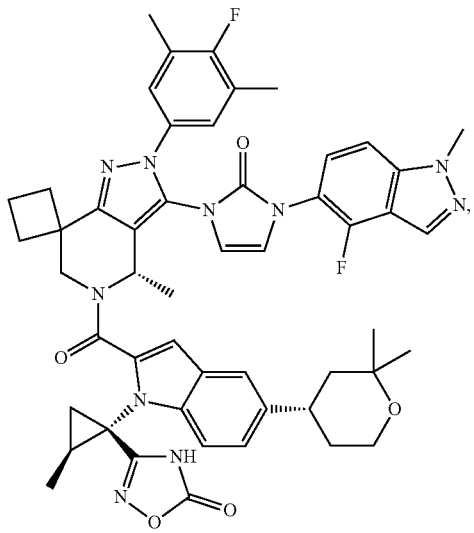

23

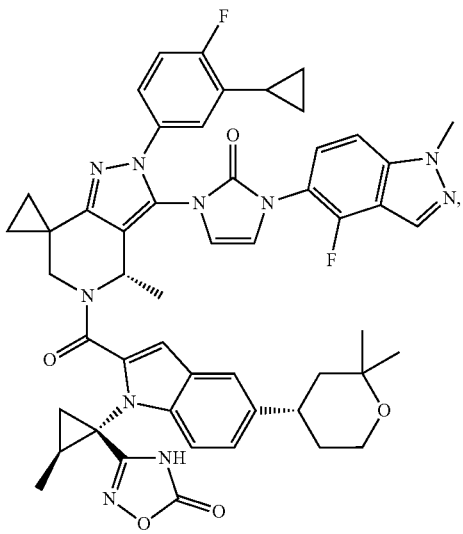

171

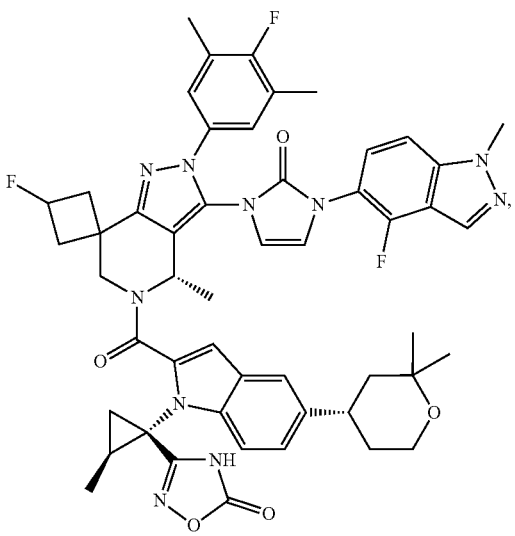

182

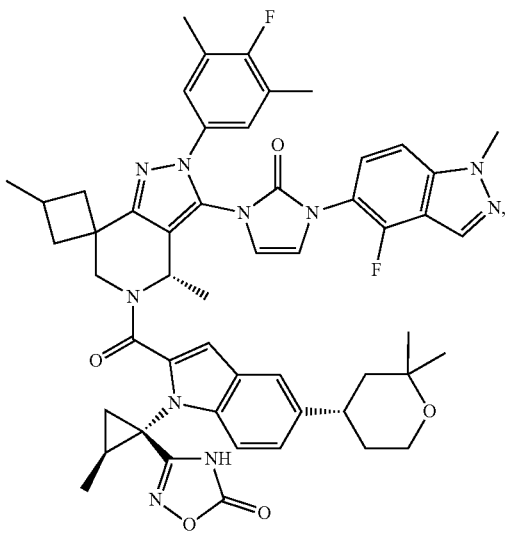

219

222
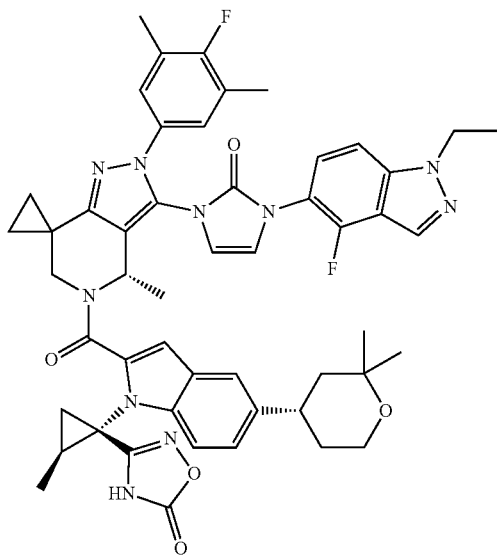
226
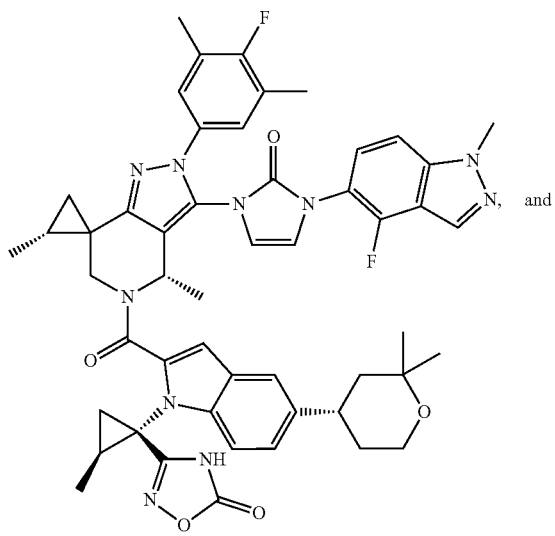
228
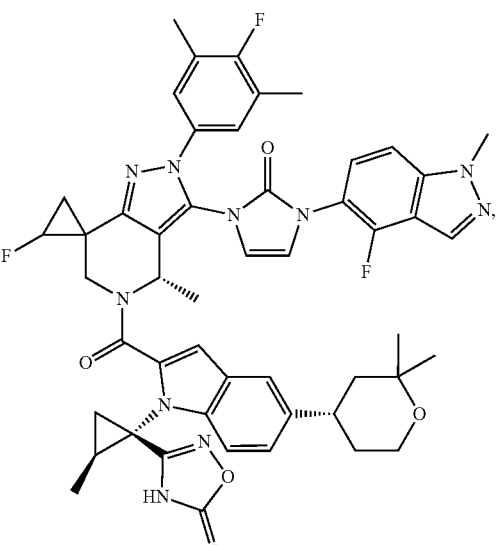
or an isotopic compound or stereoisomer thereof, or a pharmaceutically acceptable salt thereof.
2. The compound according to claim 1, wherein the compound is:
23
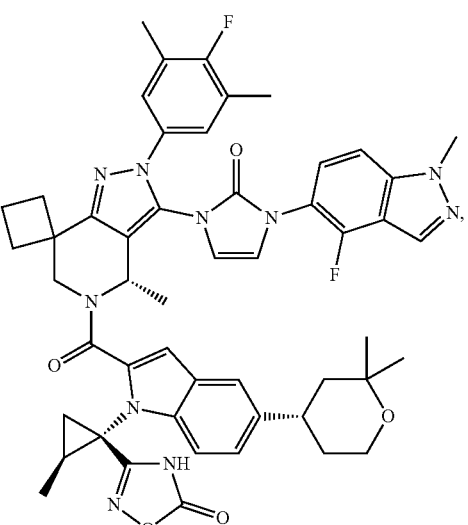
or the isotopic compound or stereoisomer thereof, or the pharmaceutically acceptable salt thereof.

3. The compound according to claim 1, wherein the compound is:

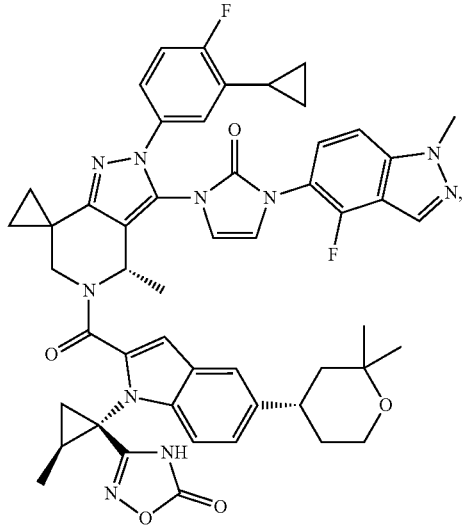

or the isotopic compound or stereoisomer thereof, or the pharmaceutically acceptable salt thereof.

4. The compound according to claim 1, wherein the compound is:

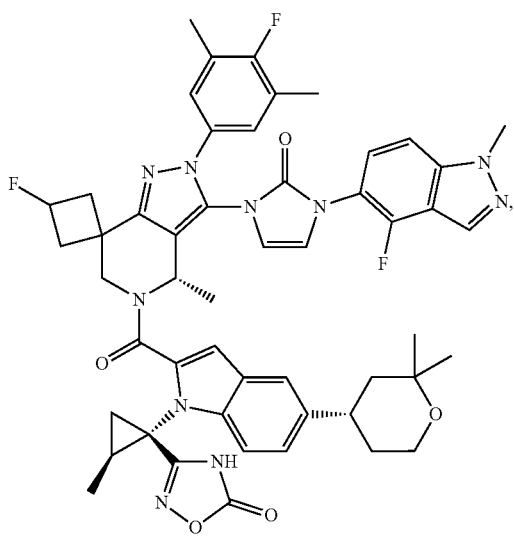

or the isotopic compound or stereoisomer thereof, or the pharmaceutically acceptable salt thereof.

5. The compound according to claim 1, wherein the compound is:

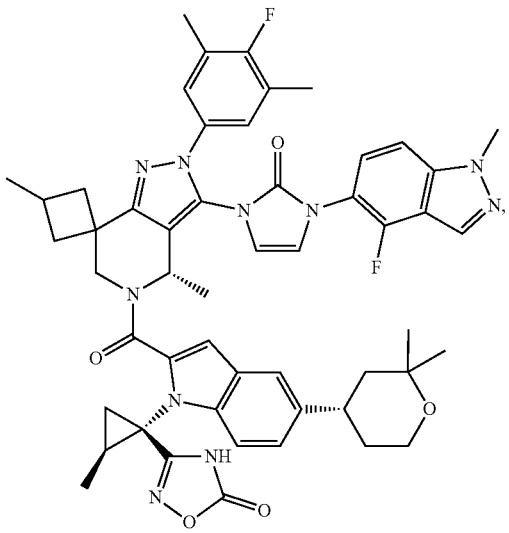

or the isotopic compound or stereoisomer thereof, or the pharmaceutically acceptable salt thereof.

6. The compound according to claim 1, wherein the compound is:

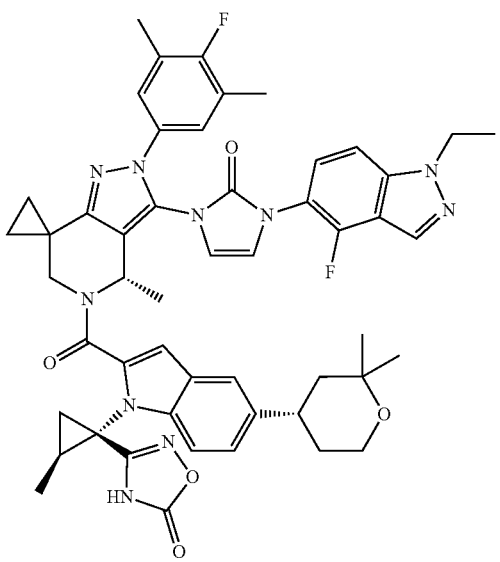

or the isotopic compound or stereoisomer thereof, or the pharmaceutically acceptable salt thereof.

7. The compound according to claim 1, wherein the compound is:

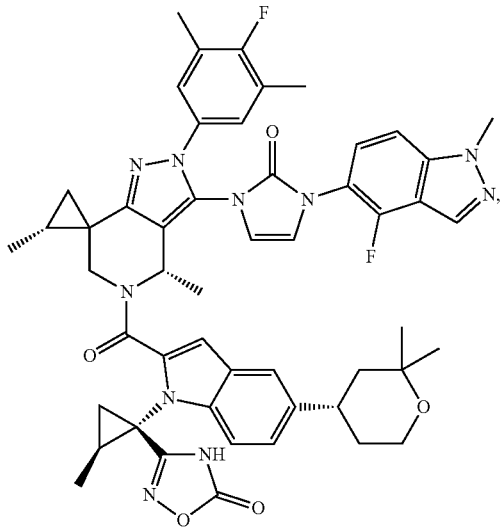

226 or the isotopic compound or stereoisomer thereof, or the pharmaceutically acceptable salt thereof.

8. A pharmaceutical composition, comprising the compound of claim 1, or the isotopic compound or stereoisomer thereof, or the pharmaceutically acceptable salt thereof, and at least one pharmaceutically acceptable carrier.

9. A pharmaceutical composition, comprising the compound of claim 3, or the isotopic compound or stereoisomer thereof, or the pharmaceutically acceptable salt thereof, and at least one pharmaceutically acceptable carrier.

10. A pharmaceutical composition, comprising the compound of claim 4, or the isotopic compound or stereoisomer thereof, or the pharmaceutically acceptable salt thereof, and at least one pharmaceutically acceptable carrier.

11. A pharmaceutical composition, comprising the compound of claim 5, or the isotopic compound or stereoisomer thereof, or the pharmaceutically acceptable salt thereof, and at least one pharmaceutically acceptable carrier.

12. A pharmaceutical composition, comprising the compound of claim 6, or the isotopic compound or stereoisomer thereof, or the pharmaceutically acceptable salt thereof, and at least one pharmaceutically acceptable carrier.

13. A pharmaceutical composition, comprising the compound of claim 7, or the isotopic compound or stereoisomer thereof, or the pharmaceutically acceptable salt thereof, and at least one pharmaceutically acceptable carrier.

14. A method for treating disease or condition in a subject in need thereof, the method comprising: administering to the subject an effective amount of the compound of claim 1, or the isotopic compound or stereoisomer thereof, or the pharmaceutically acceptable salt thereof, wherein the disease or condition is diabetes or obesity.

15. A compound having the structure of:

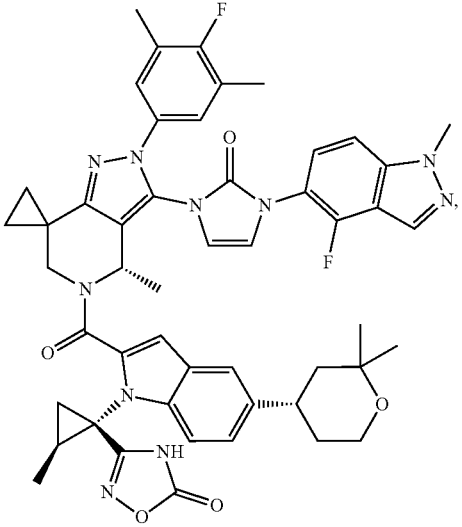

1 or an isotopic compound or stereoisomer thereof, or a pharmaceutically acceptable salt thereof.

16. A pharmaceutical composition, comprising the compound of claim 15 or the isotopic compound or stereoisomer thereof, or the pharmaceutically acceptable salt thereof, and at least one pharmaceutically acceptable carrier.

17. A method for treating disease or condition in a subject in need thereof, the method comprising: administering to the subject an effective amount of the compound of claim 15, or the isotopic compound or stereoisomer thereof, or the pharmaceutically acceptable salt thereof, wherein the disease or condition is diabetes or obesity.

18. A compound having the structure of:

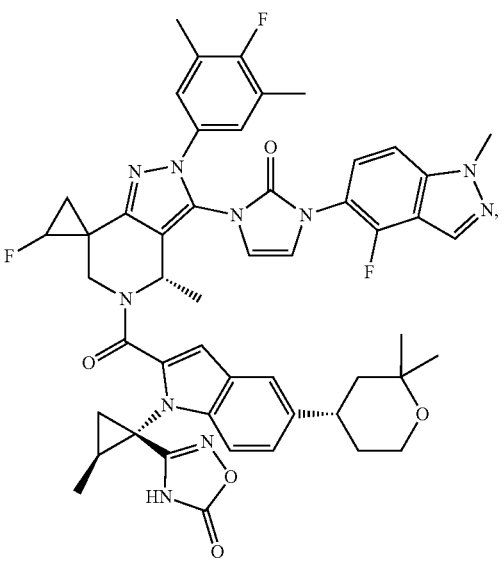

228 or an isotopic compound or stereoisomer thereof, or a pharmaceutically acceptable salt thereof.

19. A pharmaceutical composition, comprising the compound of claim 18, or the isotopic compound or stereoisomer thereof, or the pharmaceutically acceptable salt thereof, and at least one pharmaceutically acceptable carrier.

20. A method for treating disease or condition in a subject in need thereof, the method comprising: administering to the subject an effective amount of the compound of claim 18, or the isotopic compound or stereoisomer thereof, or the pharmaceutically acceptable salt thereof, wherein the disease or condition is diabetes or obesity.

\* \* \* \* \*